United States Patent
Carniato et al.

(10) Patent No.: US 8,519,188 B2
(45) Date of Patent: Aug. 27, 2013

(54) COMPOUNDS WHICH CAN BE USED FOR THE TREATMENT OF CANCERS

(75) Inventors: Denis Carniato, Marcoussis (FR); Karine Jaillardon, Saint Michel S/orge (FR); Olivier Busnel, Lille (FR); Mathieu Gutmann, Vaugrigneuse (FR); Jean-Francois Briand, Orsay (FR); Benoit Deprez, Lille (FR); Dominique Thomas, Gif S/yvette (FR); Cécile Bougeret, Le Vesinet (FR)

(73) Assignee: Marc-Henry Pitty, Boulogne (FR)

( * ) Notice: Subject to any disclaimer, the term of this patent is extended or adjusted under 35 U.S.C. 154(b) by 259 days.

(21) Appl. No.: 12/997,764

(22) PCT Filed: Jun. 15, 2009

(86) PCT No.: PCT/EP2009/057371
§ 371 (c)(1), (2), (4) Date: Dec. 13, 2010

(87) PCT Pub. No.: WO2009/150248
PCT Pub. Date: Dec. 17, 2009

(65) Prior Publication Data
US 2011/0104162 A1      May 5, 2011

Related U.S. Application Data

(60) Provisional application No. 61/076,984, filed on Jun. 30, 2008.

(30) Foreign Application Priority Data

Jun. 13, 2008   (FR) ..................... 08 53944
Apr. 17, 2009   (FR) ..................... 09 52520

(51) Int. Cl.
C07C 233/05   (2006.01)
A61K 31/16    (2006.01)
A61K 31/381   (2006.01)
A61K 31/433   (2006.01)
C07D 333/24   (2006.01)
C07D 417/12   (2006.01)

(52) U.S. Cl.
USPC ........... 564/153; 544/146; 544/165; 544/333; 544/379; 544/400; 546/163; 546/244; 546/337; 548/127; 548/253; 548/259; 548/315.1; 548/365.7; 548/568; 558/414; 514/231.5; 514/252.12; 514/252.13; 514/256; 514/329; 514/357; 514/361; 514/438; 514/492

(58) Field of Classification Search
USPC ......... 544/146, 165, 333, 379, 400; 546/163, 546/244, 337; 548/127, 253, 259, 315.1, 548/365.7, 568; 558/414; 564/155; 514/231.5, 514/252.12, 252.13, 256, 329, 357, 361, 514/438, 492, 616
See application file for complete search history.

(56) References Cited

U.S. PATENT DOCUMENTS 4,205,168 A    5/1980  Chan
4,944,796 A    7/1990  Wee
5,200,426 A    4/1993  Hersh et al.
8,188,277 B2 * 5/2012  Fukushima et al. .......... 544/344
2009/0176756 A1 7/2009  Haurand et al.

FOREIGN PATENT DOCUMENTS

DE   10 2005 062 991 A1   7/2007
WO   WO 03/016335 A2      2/2003
WO   WO 2007/025249 A2    3/2007
WO   WO 2008/008022 A1    1/2008

OTHER PUBLICATIONS

Carter et al., Chemotherapy of Cancer, second edition, John Wiley & Sons, N.Y., N.Y., 1981, pp. 362-365.*
Gatti et al., "Overview of Tumor Cell Chemoresistance Mechanisms", Methods in Molecular Medicine, vol. 111: Chemosensitivity: vol. 2: In Vivo Models, Imaging, and Molecular Regulators, 2005, pp. 127-148.
Longley et al., "Molecular Mechanisms of Drug Resistance", J. Pathol 2005; 205: pp. 275-292.
Kohno et al., "Transcription Factors and Drug Resistance", European Journal of Cancer 41, 2005, pp. 2577-2586.
Heymann et al., "Bisphosphonates: New Therapeutic Agents for the Treatment of Bone Tumors", TRENDS in Molecular Medicine, vol. 10, No. 7, 2004, pp. 337-343.
Neo et al., Studies on Isocyanides. A Facile Synthesis of 4,5-dihydro-1,4-Benzothiazepin-3(2H)-ones via Post-Condensation Modifications of the Ugi Reaction, Tetrahedron Letters 46, 2005, pp. 7977-7979.
International Search Report dated Sep. 24, 2009 (four (4) sheets).
Wright et al., "Studies on the Sequential Multi-Component Coupling/Diels-Alder Cycloaddition Reaction", Tetrahedron Letters, 2002, pp. 943-946, vol. 43, No. 6 (four (4) sheets).
Akritopoulou-Zanze et al., "A Versatile Synthesis of Fused Triazolo Derivatives by Sequential Ugi/Alkyne-Azide Cycloaddition Reactions", Tetrahedron Letters, 2004, pp. 8439-8441, vol. 45, No. 46 (three (3) sheets).
Kati et al., "Inhibition of 3C Protease from Human Rhinovirus Strain 1B by Peptidyl Bromomethylketonehydrazides", Archives of Biochemistry and Biophysics, 1999, pp. 363-375, vol. 362, No. 2, (thirteen (13) sheets).
Written Opinion dated Dec. 14, 2010 (eight (8) sheets).

* cited by examiner

*Primary Examiner* — Shailendra Kumar
(74) *Attorney, Agent, or Firm* — Crowell & Moring LLP

(57) ABSTRACT

The present invention relates to a compound of general formula (I): and also to the pharmaceutically acceptable salts thereof, to the isomers or isomer mixtures thereof in all proportions, in particular to an enantiomer mixture, and especially to a racemic mixture. The present invention also relates to the use of these compounds as a medicament, and in particular for the treatment of cancer, and also to the compositions containing them.

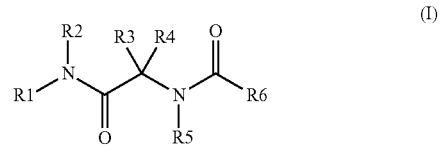

(I)

28 Claims, No Drawings

COMPOUNDS WHICH CAN BE USED FOR THE TREATMENT OF CANCERS

This application is a national stage of PCT International Application No. PCT/EP2009/057371, filed Jun. 15, 2009, which claims priority to French Patent Application No. 0853944, filed Jun. 13, 2008, U.S. Patent Application No. 61/076,984, filed Jun. 30, 2008, and French Patent Application No. 0952520, filed Apr. 17, 2009.

The present invention relates to new compounds which can be used for the treatment of cancer, and to the compositions containing them.

An increasing life expectancy means that cancer, the leading cause of mortality in France, is affecting more and more people; yet it remains difficult to treat.

The development of resistance to chemotherapeutic agents is a serious problem representing a considerable obstacle to the treatment of many types of cancer. Tolerance to one agent is frequently accompanied by cross-resistance to a variety of other agents. This multidrug resistance, MDR, is the result of numerous mechanisms, only a small number of which have been well described. They include an increase in drug efflux, an increase in the cell's detoxification capabilities, a change in a drug's target, changes in the DNA repair system, and changes to the apototic pathways (Gatti et al. *Methods Mol. Med.* 2005, 111, 127-148; Longley et al. *J. Pathol.* 2005, 205, 275-292; Kohno et al. *Eur. J. Cancer* 2005, 41, 2577-2586).

Numerous attempts have been made to inhibit these mechanisms, but as yet no substance has demonstrated convincing inhibitory activity.

There therefore remains a real need to develop new anticancer compounds which are able in particular to resolve the problems of multidrug resistance.

The present invention concerns more particularly a compound of general formula (I):

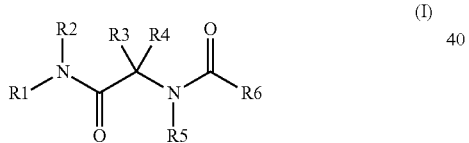
(I)

as well as the pharmaceutically acceptable salts thereof, the isomers or isomer mixtures thereof in all proportions, in particular an enantiomer mixture, and especially a racemic mixture, for which:
R1 represents a hydrogen atom or a $(C_1-C_6)$alkyl, $(C_3-C_0)$cycloalkyl, $(C_1-C_{10})$cycloalkenyl, aryl, heteroaryl, aryl-$(C_1-C_6)$alkyl, heteroaryl-$(C_1-C_6)$alkyl group, said group being optionally substituted by one or more groups selected from a halogen atom, $(C_1-C_6)$alkoxy, $-NH_2$, $-COOH$, $-CN$, $-OH$, $-NR^7R^8$, $-O-(C_1-C_6)$alkyl-$NR^7R^8$, benzyloxy, aryloxy, $-C(O)O-(C_1-C_6)$alkyl, $-NH-C(O)O-(C_1-C_6)$alkyl, $-C(O)NH_2$, $-C(O)NR^9R^{10}$, $-S-(C_1-C_6)$alkyl, $-S(O)-(C_1-C_6)$alkyl, $-SO_2-(C_1-C_6)$alkyl, $-SO_2NH_2$, $-SO_2NR^{11}R^{12}$, $-NR^{13}SO_2R^{14}$ and a $(C_1-C_6)$alkyl group optionally substituted by one or more halogen atoms, R2 represents a hydrogen atom or a $(C_1-C_6)$alkyl, advantageously $(C_1-C_4)$ alkyl group, or R1 and R2 together form, with the nitrogen atom carrying them:

a heteroaryl optionally substituted by one or more groups selected from a halogen atom, a $-CN$, $-NH_2$, $-NR^{40}R^{41}$, $-NO_2$, $-OH$, $(C_1-C_6)$alkoxy, aryloxy, benzyloxy, $-O(C_1-C_6)$alkyl-$NR^{42}R^{43}$, $-C(O)O-(C_1-C_6)$alkyl, $-NHC(O)O-(C_1-C_6)$alkyl, $-C(O)NH_2$, $-C(O)NR^{44}R^{45}$, $-SO_2NH_2$, $-SO_2NR^{46}R^{47}$ and $-NR^{48}SO_2R^{49}$, or a 3 to 7-membered heterocycle optionally substituted by one or more groups selected from a halogen atom, a $(C_3-C_{10})$cycloalkyl, $(C_3-C_{10})$cycloalkenyl, aryl, heteroaryl, aryl-$(C_1-C_6)$alkyl, heteroaryl-$(C_1-C_6)$alkyl, heterocycloalkyl-$(C_1-C_6)$alkyl, $-OH$, $-NH_2$, $-C(O)OH$, $-C(O)NH_2$, $-C(S)NH_2$, $-OR^{50}$, $-OC(O)R^{51}$, $-C(O)R^{52}$, $-C(O)OR^{53}$, $-NHC(O)R^{54}$, $-NHC(O)OR^{55}$, $-SO_2R^{56}-(C_1-C_6)$alkyl-$C(O)OR^{57}$, $-NR^{58}R^{59}$, $-C(O)NR^{60}R^{61}$, $-C(O)N(R^{62})$(aryl), $C(O)N(R^{63})$(heteroaryl), $-C(O)NHNR^{64}R^{65}$, $-C(S)NR^{66}R^{67}$, $-C(S)N(R^{68})$(aryl), $-C(S)N(R^{69})$(heteroaryl), $-C(S)NHNR^{70}R^{71}$, $-OC(O)-NR^{72}R^{73}$, $-(C_1-C_6)$alkyl-$C(O)-NR^{74}R^{75}$, $-(C_1-C_6)$alkyl-$NR^{103}-C(O)-OR^{104}$, $-(C_1-C_6)$alkyl-$NR^{76}R^{77}$, $-C(NOR^{78})$-aryl radical, and a $(C_1-C_6)$alkyl group optionally substituted with one or more halogen atoms, the aryl and heteroaryl unit of said radical, when present, being optionally substituted by one or more groups selected from a halogen atom, and a $-CN$, $-OH$, $(C_1-C_6)$alkyl, $(C_1-C_6)$alkoxy, $-NR^{79}R^{80}$, $-(C_1-C_6)$alkyl-$NR^{81}R^{82}$ and $-O-(C_1-C_6)$alkyl-$NR^{83}R^{84}$ group, R3 represents a hydrogen atom or a $(C_1-C_6)$alkyl group, advantageously $(C_1-C_4)$alkyl, or $-(C_1-C_4)$alkyl-$NR^{15}R^{16}$, R4 represents a hydrogen atom or a $(C_1-C_6)$alkyl, $(C_3-C_{10})$cycloalkyl, aryl, advantageously phenyl, heteroaryl, advantageously thiophenyl, group, said group being optionally substituted by one or more groups selected from a halogen atom, a $-C(CF_3)_2OH$, $-CN$, $-NH_2$, $-OPO_3H_2$, $-NR^{17}R^{18}$, $-NO_2$, $-COOH$, $-OH$, $-O(C_1-C_6)$alkyl-$OPO_3H_2$, $-O-(C_1-C_6)$alkyl-$O-(C_1-C_6)$alkyl, $-O(C_1-C_6)$alkyl-$NR^{19}R^{20}$, $-NR^{81}(C_1-C_6)$alkyl-$NR^{85}R^{86}$, benzyloxy, $-C(O)O-(C_1-C_6)$alkyl, $-NHC(O)O-(C_1-C_6)$alkyl, $-C(O)NH_2$, $-C(O)NR^{21}R^{22}$, $-S-(C_1-C_6)$alkyl, $-S(O)-(C_1-C_6)$alkyl, $-SO_2-(C_1-C_6)$alkyl, $-SO_2NH_2$, $-SO_2NR^{23}R^{24}$, $-NR^{25}SO_2R^{26}$, 3 to 7-membered heterocycloalkyl, aryloxy radical, a $(C_1-C_6)$alkyl group optionally substituted by one or more halogen atoms and a $(C_1-C_6)$alkoxy optionally substituted by one or more fluorine atoms, and the aryl and heteroaryl unit of said radical, when present, being optionally fused to a 5 or 6-membered heterocycle, or R3 and R4 form with the carbon carrying them a ring selected from a $(C_3-C_{10})$cycloalkyl and a 3 to 7-membered heterocycloalkyl, said ring being optionally substituted by a $(C_1-C_6)$alkyl, $-C(O)-(C_1-C_6)$alkyl, $-C(O)O-(C_1-C_6)$alkyl group, R5 represents a $(C_1-C_6)$alkyl, $(C_3-C_{10})$cycloalkyl, $(C_3-C_{10})$cycloalkenyl, aryl (advantageously phenyl), heteroaryl, aryl-$(C_1-C_6)$alkyl, heteroaryl-$(C_1-C_6)$alkyl, $(C_3-C_{10})$cycloalkyl-$(C_1-C_6)$alkyl, (3 to 7-membered hetero-cycloalkyl)-$(C_1-C_6)$alkyl group, said group being optionally substituted by one or more groups selected from a halogen atom, a $-NH_2$, $-COOH$, $-CN$, $-OH$, $-NO_2$, $-B(OH)_2$, $(C_1-C_6)$alkoxy, $-O-(C_1-C_6)$alkyl-$NR^{27}R^{28}$, $-O-(C_1-C_6)$ alkyl-O—(C$_1$-C$_6$)alkyl, aryloxy, —C(O)O—(C$_1$-C$_6$) alkyl, (C$_2$-C$_6$)alkynyl, —NR$^{29}$R$^{30}$, —NHC(O)O—(C$_1$-C$_6$)alkyl, —C(O)NH$_2$, —C(O)NR$^{31}$R$^{32}$, —S—(C$_1$-C$_6$) alkyl, —S(O)—(C$_1$-C$_6$)alkyl, —SO$_2$—(C$_1$-C$_6$)alkyl, —SO$_2$NH$_2$, —SO$_2$NR$^{33}$R$^{34}$, —NR$^{35}$SO$_2$R$^{36}$, aryl, heteroaryl, (C$_1$-C$_6$)alkyl-heteroaryl 3 to 7-membered heterocycloalkyl, (3 to 7-membered heterocycloalkyl)-(C$_1$-C$_6$)alkoxy radical and a (C$_1$-C$_6$)alkyl group optionally substituted by one or more halogen atoms, the aryl or heteroaryl unit of said radical, when present, being optionally fused to a 5 or 6-membered heterocycle, and R6 represents a —CHR$^{37}$Hal or —C≡CR$^{38}$ group, with Hal representing a halogen atom, advantageously chlorine or bromine, wherein:

R$^7$ to R$^{13}$, R$^{15}$ to R$^{18}$, R$^{21}$ to R$^{25}$, R$^{27}$ to R$^{35}$, R$^{37}$, R$^{40}$ to R$^{48}$, R$^{58}$ to R$^{84}$, R$^{89}$ to R$^{103}$, represent, independently of one another, a hydrogen atom or a (C$_1$-C$_6$)alkyl group, and preferably a (C$_1$-C$_6$)alkyl group or, if two groups are carried by the same nitrogen, the two groups form with the nitrogen atom carrying them a 3 to 7-membered heterocycloalkyl, R$^{14}$, R$^{26}$, R$^{36}$ and R$^{49}$ represent, independently of one another, a (C$_1$-C$_6$)alkyl group, R$^{38}$ and R$^{49}$ represent, independently of one another, a (C$_1$-C$_6$)alkyl group, R$^{38}$ represents a hydrogen atom, a (C$_1$-C$_6$)alkyl group, preferably a methyl, or a phenyl group, R$^{50}$ to R$^{57}$, R$^{87}$, R$^{88}$ and R$^{104}$ represent, independently of one another, a (C$_1$-C$_6$)alkyl, aryl, heteroaryl, aryl-(C$_1$-C$_6$)alkyl, heteroaryl-(C$_1$-C$_6$)alkyl, (C$_1$-C$_6$)alkyl-aryl or (C$_1$-C$_6$)alkyl-heteroaryl group, and R$^{19}$, R$^{20}$, R$^{85}$ and R$^{86}$ represent, independently of one another, a (C$_1$-C$_6$)alkyl group, or (R$^{19}$ and R$^{20}$) and/or (R$^{85}$ and R$^{86}$) together form, with the nitrogen atom carrying them, a 3 to 7-membered heterocycle optionally substituted by one or more groups selected from a halogen atom, a (C$_3$-C$_{10}$)cycloalkyl, aryl, heteroaryl, aryl-(C$_1$-C$_6$)alkyl, heteroaryl-(C$_1$-C$_6$)alkyl, —C(O)OR$^{87}$, —SO$_2$R$^{88}$, —OH, (C$_1$-C$_6$)alkoxy, —OC(O)—(C$_1$-C$_6$)alkyl, —OC(O)—NR$^{89}$R$^{90}$, —NHC(O)O—(C$_1$-C$_6$)alkyl, —C(O)NH$_2$, —C(O)NR$^{91}$R$^{92}$, —C(S)NR$^{93}$R$^{94}$, —C(O)NHNR$^{95}$R$^{96}$, —C(S)NHNR$^{97}$R$^{98}$ radical and a (C$_1$-C$_6$)alkyl group optionally substituted by one or more atoms of halogen, the aryl and heteroaryl unit of said radical, when present, being optionally substituted with one or more groups selected from a halogen atom and a (C$_1$-C$_6$)alkyl, —CN, —OH, NR$^{99}$R$^{100}$, (C$_1$-C$_6$)alkoxy, —O—(C$_1$-C$_6$)alkyl-NR$^{11}$R$^{102}$ group, for use thereof as a medicament—

Compounds of formula (I), for which R6═—C≡CR$^{38}$ and R1 is an optionally substituted 1,3-thiazol-2-yl group, are preferably not claimed as compounds suitable for use as a medicament. Indeed, these compounds are described in DE10 2005 062 991 as inhibitors of the mGluR5 receptor, but not as anticancer agents.

The present invention will therefore similarly relate to compounds of formula (I) such as those described above, including compounds for which R6═—C≡CR$^{38}$ and R1 is an optionally substituted 1,3-thiazol-2-yl group, for use thereof as a medicament intended to treat or prevent a cancer, and in particular a cancer resistant to chemotherapy.

The term <<halogen>> refers in the sense of the present invention to a fluorine, bromine, chlorine or iodine atom. Advantageously, it is a fluorine, bromine or chlorine atom.

The term <<alkyl>> group refers in the sense of the present invention to any saturated linear or branched hydrocarbon group, comprising preferably 1 to 6 carbon atoms, and advantageously 1 to 4 carbon atoms for the groups R2 and R3, in particular, the methyl, ethyl, n-propyl, isopropyl, n-butyl, isobutyl, sec-butyl, ten-butyl, n-pentyl, neopentyl or n-hexyl groups. Advantageously it is a methyl, isopropyl, tert-butyl, isobutyl or neopentyl group.

The alkyl group can be substituted by one or more halogen atoms, in particular bromine, chlorine and fluorine and advantageously fluorine. It will in particular in this case be the —CF$_3$ group.

The term <<alkynyl>> group refers in the sense of the present invention to any linear or branched hydrocarbon group, comprising at least one triple bond and comprising preferably 2 to 6 carbon atoms. Advantageously it is a —C≡CH group.

The term <<alkoxy>> group refers in the sense of the present invention to an —O—(C$_1$-C$_6$)alkyl group, i.e. an alkyl group as defined hereinbefore bound to the molecule via an oxygen atom. Examples of an alkoxy group include the methoxy, ethoxy or else tert-butoxy group. Advantageously, it is methoxy or tert-butoxy, and even more advantageously, it is methoxy.

The alkoxy group can be substituted by one or more fluorine atoms. In this case, it will advantageously be the —OCHF$_2$ or —OCF$_3$ group.

The term <<aryl>> group refers in the sense of the present invention to an aromatic group, comprising preferably 5 to 10 carbon atoms and comprising one or more fused rings. Advantageously, it is phenyl or naphthyl, and more advantageously, phenyl (Ph).

The term <<heteroaryl>> group refers in the sense of the present invention to any aryl group as defined hereinbefore in which one or more carbon atoms have been replaced by one or more heteroatoms, advantageously 1 to 4 and, even more advantageously 1 to 2, such as for example sulphur, nitrogen or oxygen atoms. Advantageously, it is a furyl, thiophenyl, pyridinyl, pyrimidinyl, tetrazolyl, quinolinyl, 1,2,3-thiadiazolyl, benzoimidazolyl, indazolyl or 1,2,3-benzotriazolyl group. Also advantageously, it is a thiophenyl, and in particular, a thiophen-2-yl.

The term <<aryloxy>> group refers in the sense of the present invention to an —O-(aryl) group, i.e. an aryl group as defined hereinbefore bound to the molecule via an oxygen atom. It is advantageously a phenyloxy group.

The term <<cycloalkyl>> group refers in the sense of the present invention to a saturated hydrocarbon ring comprising 3 to 10 carbon atoms, advantageously 3 to 7 carbon atoms, also advantageously 3 to 7 carbon atoms and even more advantageously 5 to 6 carbon atoms, in particular the cyclopropyl, cyclohexyl or cyclopentyl group. Advantageously, it is a cyclopentyl or a cyclohexyl, and more particularly a cyclohexyl. Also advantageously, it is a cyclopropyl.

The term <<cycloalkenyl>> group refers in the sense of the present invention to a hydrocarbon ring comprising at least one double bond and comprising 3 to 10 carbon atoms, advantageously 3 to 7 carbon atoms, also advantageously 3 to 6 carbon atoms and even more advantageously 5 to 6 carbon atoms. Advantageously, it is a cyclohexenyl.

The term <<heterocycloalkyl>> group refers in the sense of the present invention to any cycloalkyl group as defined hereinbefore, comprising advantageously 3 to 7 members, in which one or more carbon atoms have been replaced by one or more heteroatoms, advantageously 1 to 4 and, even more advantageously 1 to 2, such as for example sulphur, nitrogen or oxygen atoms. Advantageously, it is a tetrahydrofuranyl, piperidinyl, pyrrolidinyl or else morpholinyl group.

The term <<heterocycle>> refers in the sense of the present invention to a 5 or 6-membered non-aromatic hydrocarbon ring (unless otherwise stated) which can comprise one or more unsaturation and comprising one or more heteroatoms, advantageously 1 to 4 and, even more advantageously 1 to 2, such as for example sulphur, nitrogen or oxygen atoms.
When it is fused to an aryl or heteroaryl group, this will advantageously be a group of the following structure:

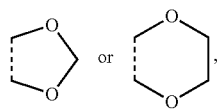

the bond indicated by broken lines representing the bond common with the aryl or heteroaryl ring.
When the group is $NR^1R^2$, $NR^{19}R^{20}$ or $NR^{85}R^{86}$, the heterocycle will advantageously be a 5 or 6-membered ring, preferably saturated or comprising a double bond, and optionally comprising a heteroatom in addition to the nitrogen atom already present, this heteroatom advantageously being an oxygen or nitrogen atom. The heterocycle can be in particular a morpholine, piperidine, piperazine, pyrrolidine, 2,5-dihydropyrrole and 1,2,5,6-tetrahydropyridine group. It will preferably be a piperazine group.

The term <<aryl-$(C_1-C_6)$alkyl>> group refers in the sense of the present invention to an aryl group as defined hereinbefore bound to the molecule via an alkyl group as defined hereinbefore. Advantageously, it is a benzyl or 1-phenylethyl group, and even more advantageously a phenyl.

The term <<heteroaryl-$(C_1-C_6)$alkyl>> group refers in the sense of the present invention to a heteroaryl group as defined hereinbefore bound to the molecule via an alkyl group as defined hereinbefore. Advantageously, it will be a heteroarylmethyl group, the heteroaryl group being advantageously a pyridinyl group, especially bound in position 2 or 3, or a furanyl group, especially bound in position 2.

The term <<$(C_3-C_{10})$cycloalkyl-$(C_1-C_6)$alkyl>> group refers in the sense of the present invention to a cycloalkyl group as defined hereinbefore bound to the molecule via an alkyl group as defined hereinbefore. Advantageously, the alkyl unit will be a methyl, and also advantageously, the cycloalkyl unit will be a cyclopropyl.

The term <<(3 to 7-membered heterocycloalkyl)-$(C_1-C_6)$alkyl>> group refers in the sense of the present invention to a heterocycloalkyl group as defined hereinbefore bound to the molecule via an alkyl group as defined hereinbefore. Advantageously, the alkyl unit will be a methyl, and also advantageously, the heterocycloalkyl unit will be 5 or 6-membered, especially will be a tetrahydrofuranyl group.

The term <<(3 to 7-membered heterocycloalkyl)-$(C_1-C_6)$alkoxy>> group refers in the sense of the present invention to a heterocycloalkyl group as defined hereinbefore bound to the molecule via an alkoxy group as defined hereinbefore. Advantageously, the alkoxy unit will comprise 1 to 3 carbon atoms, and also advantageously will be a linear propoxy. Advantageously, the heterocycloalkyl unit will be 5 or 6-membered, preferably 6-membered, and especially will be a morpholinyl group.

The term <<$(C_1-C_6)$alkyl-heteroaryl group>> refers in the sense of the present invention to an alkyl group as defined hereinbefore bound to the molecule via a heteroaryl group as defined hereinbefore. Advantageously, it will be a methylpyridine or methylimidazole group.

The term <<(3 to 7-membered heterocycloalkyl)-$(C_1-C_6)$alkoxy group>> refers in the sense of the present invention to a heterocycloalkyl group as defined hereinbefore bound to the molecule via an alkoxy group as defined hereinbefore. Advantageously, the alkoxy unit will be an n-propoxy and the heterocycloalkyl unit will be a morpholinyl bound by its nitrogen atom to the alkoxy group.

In the present invention, the term <<pharmaceutically acceptable>> refers to that which can be used in the preparation of a pharmaceutical composition which to is generally safe, non-toxic and neither biologically nor otherwise undesirable and which is acceptable both for veterinary and for human pharmaceutical use.

The term <<pharmaceutically acceptable salts>> of a compound refers in the present invention to salts which are pharmaceutically acceptable, as defined in the present document, and which have the desired pharmacological activity of the parent compound. Such salts include (1) hydrates and solvates,
(2) acid addition salts formed with inorganic acids such as hydrochloric acid, hydrobromic acid, sulphuric acid, nitric acid, phosphoric acid and the like; or formed with organic acids such as acetic acid, benzenesulphonic acid, benzoic acid, camphorsulphonic acid, citric acid, ethanesulphonic acid, fumaric acid, glucoheptonic acid, gluconic acid, glutamic acid, glycolic acid, hydroxynaphthoic acid, 2-hydroxyethanesulphonic acid, lactic acid, maleic acid, malic acid, mandelic acid, methanesulphonic acid, muconic acid, 2-naphthalenesulphonic acid, propionic acid, salicylic acid, succinic acid, dibenzoyl-L-tartaric acid, tartaric acid, p-toluenesulphonic acid, trimethylacetic acid, trifluoroacetic acid and the like, advantageously, this will be hydrochloric acid; and
(3) the salts formed when an acidic proton present in the parent compound either is replaced by a metal ion, for example an alkali metal ion ($Na^+$, $K^+$ or $Li^+$ for example), an alkaline earth metal ion (like $Ca^{2+}$ or $Mg^{2+}$) or an aluminium ion; or is coordinated with an organic or inorganic base. Acceptable organic bases include diethanolamine, ethanolamine, N-methylglucamine, triethanolamine, tromethamine and the like. Acceptable inorganic bases include aluminium hydroxide, calcium hydroxide, potassium hydroxide, sodium carbonate and sodium hydroxide.

In the present invention, the term <<isomers>> refers in the sense of the present invention to diastereoisomers or enantiomers. They are therefore optical isomers also known as <<stereoisomers>>. Stereoisomers which are not mirror images of one another are thus referred to as <<diastereoisomers>>, and stereoisomers which are non-superimposable mirror images are referred to as <<enantiomers>>.

A carbon atom bound to four non-identical substituents is called a <<chiral centre>>.

An equimolar mixture of two enantiomers is called a racemic mixture.

When the NR1R2 group represents a heteroaryl or heterocycle, it is of course possible for said cycle to comprise one or more other heteroatoms, preferably zero or one another, heteroatom(s) in addition to the nitrogen atom carrying R1 and R2 which is already present, said heteroaryl or heterocycle advantageously having 5 to 6 members. Said heteroatom will therefore be advantageously selected from O, S and N, and preferably from O and N. Advantageously, it will be a piperidine, morpholine or piperazine group, and preferably piperazine.

The same comment also applies to the groups $NR^{19}R^{20}$ and $NR^{85}R^{86}$, when they form heterocycles.

Advantageously, R1 does not represent a hydrogen atom.

Advantageously, R1 and/or R4 do(es) not represent a hydrogen atom.

Even more advantageously, R1 and R4 do not represent a hydrogen atom.

According to a particular embodiment of the invention, R1:
represents a hydrogen atom or a $(C_1\text{-}C_6)$alkyl, $(C_3\text{-}C_{10})$cycloalkyl, $(C_3\text{-}C_{10})$cycloalkenyl, aryl, heteroaryl, aryl-$(C_1\text{-}C_6)$alkyl, heteroaryl-$(C_1\text{-}C_6)$alkyl group, said group being optionally substituted by one or more groups selected from a halogen atom, a $(C_1\text{-}C_6)$alkoxy, —$NH_2$, —COOH, —CN, —OH, —$NR^7R^8$, —O—$(C_1\text{-}C_6)$alkyl-$NR^7R^8$, benzyloxy, —C(O)O—$(C_1\text{-}C_6)$alkyl, —NH—C(O)O—$(C_1\text{-}C_6)$alkyl, —C(O)$NH_2$, —C(O)$NR^9R^{10}$, —S—$(C_1\text{-}C_6)$alkyl, —S(O)—$(C_1\text{-}C_6)$alkyl, —$SO_2$—$(C_1\text{-}C_6)$alkyl, —$SO_2NH_2$, —$SO_2NR^{11}R^{12}$, —$NR^{13}SO_2R^{14}$ radical and a $(C_1\text{-}C_6)$alkyl group optionally substituted by one or more halogen atoms, or forms, with R2 and the nitrogen atom carrying them, a 3 to 7-membered heterocycloalkyl, said heterocycloalkyl being optionally substituted by one or more groups selected from a halogen atom and a $(C_1\text{-}C_6)$alkyl group optionally substituted by one or more halogen atoms.

Advantageously, R1 represents a hydrogen atom or a $(C_1\text{-}C_6)$alkyl, aryl, heteroaryl, aryl-$(C_1\text{-}C_6)$alkyl, heteroaryl-$(C_1\text{-}C_6)$alkyl, $(C_1\text{-}C_{10})$cycloalkyl group, said group being optionally substituted by one or more groups selected from —$NH_2$, —COOH, benzyloxy, —C(O)O($(C_1\text{-}C_6)$alkyl), —NHC(O)O(($C_1\text{-}C_6)$alkyl).

Also advantageously, R1 represents a $(C_1\text{-}C_6)$alkyl, aryl, aryl-$(C_1\text{-}C_6)$alkyl, $(C_1\text{-}C_{10})$cycloalkyl group, said group being optionally substituted by one or more groups selected from —$NH_2$, —COOH, benzyloxy, —C(O)O(($C_1\text{-}C_6)$alkyl), —NHC(O)O(($C_1\text{-}C_6)$alkyl), and advantageously from benzyloxy and —C(O)O(($C_1\text{-}C_6)$alkyl).

Also advantageously, R1 represents a $(C_1\text{-}C_6)$alkyl group optionally substituted by a —C(O)O(($C_1\text{-}C_6)$alkyl) group; an aryl group optionally substituted by a —C(O)O(($C_1\text{-}C_6)$alkyl) or benzyloxy group; an aryl-$(C_1\text{-}C_6)$alkyl group; or a $(C_3\text{-}C_{10})$cycloalkyl group.

Even more advantageously, R1 represents a cyclohexyl, cyclopentyl, benzyl, —$C_6H_4$—C(O)OMe, —$C_6H_4$—OBn, —$CH_2CH_2$—$CO_2$Me or —$CH_2CH_2$—$CO_2$tBu group.

Also advantageously, R1 represents a cyclohexyl, cyclopentyl or benzyl, and also advantageously cyclohexyl group.

In one particular embodiment, R2 represents a hydrogen atom.

According to a first preferred embodiment of the invention, R1 represents a $(C_3\text{-}C_{10})$cycloalkyl or aryl-$(C_1\text{-}C_6)$alkyl group, and preferably cyclohexyl, cyclopentyl or benzyl, said group being optionally substituted by one or more groups selected from a halogen atom, a $(C_1\text{-}C_6)$alkoxy, —$NH_2$, —COOH, —CN, —OH, —$NR^7R^8$, —O—$(C_1\text{-}C_6)$alkyl-$NR^7R^8$, benzyloxy, aryloxy, —C(O)O—$(C_1\text{-}C_6)$alkyl, —NH—C(O)O—$(C_1\text{-}C_6)$alkyl, —C(O)$NH_2$, —C(O)$NR^9R^{10}$, —S—$(C_1\text{-}C_6)$alkyl, —S(O)—$(C_1\text{-}C_6)$alkyl, —$SO_2$—$(C_1\text{-}C_6)$alkyl, —$SO_2NH_2$, —$SO_2NR^{11}R^{12}$, —$NR^{13}SO_2R^{14}$ radical and a $(C_1\text{-}C_6)$alkyl group optionally substituted by one or more groups selected from a halogen atom, a $(C_1\text{-}C_6)$alkoxy, —$NH_2$, —COOH, benzyloxy, aryloxy, —C(O)O(($C_1\text{-}C_6)$alkyl), —NHC(O)O(($C_1\text{-}C_6)$alkyl) group.

Advantageously, R1 represents a $(C_3\text{-}C_{10})$cycloalkyl or aryl-$(C_1\text{-}C_6)$alkyl group, preferably cyclohexyl, cyclopentyl or benzyl, said group being optionally substituted by one or more groups from a halogen atom, —OH and $(C_1\text{-}C_6)$alkoxy.

In this case, R1 advantageously represents a $(C_3\text{-}C_{10})$cycloalkyl group, and preferably cyclohexyl, preferably unsubstituted, and R2 advantageously represents a hydrogen atom.

According to a second preferred embodiment of the invention, R1 forms, with R2 and the nitrogen atom carrying them, a 3 to 7-membered heterocycle optionally substituted by one or more groups selected from a halogen atom, a $(C_3\text{-}C_{10})$cycloalkyl, $(C_3\text{-}C_{10})$cycloalkenyl, aryl, heteroaryl, aryl-$(C_1\text{-}C_6)$alkyl, heteroaryl-$(C_1\text{-}C_6)$alkyl, heterocycloalkyl-$(C_1\text{-}C_6)$alkyl, —OH, —$NH_2$, —C(O)OH, —C(O)$NH_2$, —C(S)$NH_2$, —$OR^{50}$, —OC(O)$R^{51}$, —C(O)$R^{52}$, —C(O)$OR^{53}$, —NHC(O)$R^{54}$, —NHC(O)$OR^{55}$, —$SO_2R^{56}$, —$(C_1\text{-}C_6)$alkyl-C(O)$OR^{57}$, —$NR^{58}R^{59}$, —C(O)$NR^{66}R^{61}$, —C(O)N($R^{62}$)(aryl), —C(O)N($R^{63}$)(heteroaryl), —C(O)$NHNR^{64}R^{65}$, —C(S)$NR^{66}R^{67}$, —C(S)N($R^{68}$)(aryl), —C(S)N($R^{69}$)(heteroaryl), —C(S)$NHNR^{70}R^{71}$, —OC(O)—$NR^{72}R^{73}$, —$(C_1\text{-}C_6)$alkyl-C(O)—$NR^{74}R^{75}$, —$(C_1\text{-}C_6)$alkyl-$NR^{103}$—C(O)—$OR^{104}$, —$(C_1\text{-}C_6)$alkyl-$NR^{76}R^{77}$, —C(N$OR^{78}$)-aryl radical, and a $(C_1\text{-}C_6)$alkyl group optionally substituted by one or more halogen atoms, the aryl and heteroaryl unit of said radical, when present, being optionally substituted by one or more groups selected from a halogen atom, a —CN, —OH, $(C_1\text{-}C_6)$alkyl, $(C_1\text{-}C_6)$alkoxy, —$NR^{79}R^{80}$, —$(C_1\text{-}C_6)$alkyl-$NR^{81}R^{82}$ and —O—$(C_1\text{-}C_6)$alkyl-$NR^{83}R^{84}$ group.

In this case the heterocycle will advantageously be 5 or 6-membered and preferably saturated. It will advantageously be piperazine.

Thus, —NR1R2 will advantageously represent the following piperazine cycle:

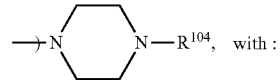

$R^{104}$ representing a hydrogen atom, a $(C_3\text{-}C_{10})$cycloalkyl, $(C_3\text{-}C_{10})$cycloalkenyl, aryl, heteroaryl, aryl-$(C_1\text{-}C_6)$alkyl, heteroaryl-$(C_1\text{-}C_6)$alkyl, heterocycloalkyl-$(C_1\text{-}C_6)$alkyl, —C(O)$R^{52}$, —C(O)$OR^{53}$, —C(O)$NH_2$, —C(S)$NH_2$, —C(O)$NR^{60}R^{61}$, —C(S)$NR^{66}R^{67}$, —$SO_2R^{56}$, —C(O)$NHNR^{64}R^{65}$, —C(S)$NHNR^{70}R^{71}$ radical, and a $(C_1\text{-}C_6)$alkyl group optionally substituted by one or more halogen atoms, the aryl and heteroaryl unit of said radical, when present, being optionally substituted with one or more groups selected from a halogen atom, a —CN, —OH, $(C_1\text{-}C_6)$alkoxy, —$NR^{79}R^{80}$, and —O—$(C_1\text{-}C_6)$alkyl-$NR^{83}R^{84}$ group.

Advantageously, $R^{104}$ represents a $(C_3\text{-}C_{10})$cycloalkyl, aryl-$(C_1\text{-}C_6)$alkyl, heteroaryl-$(C_1\text{-}C_6)$alkyl, —C(O)$R^{52}$, —C(O)$OR^{53}$, —C(O)$NH_2$, —C(O)$NR^{60}R^{61}$, —$SO_2R^{56}$ or —C(O)$NHNR^{64}R^{65}$ group, and preferably a represents a $(C_3\text{-}C_{10})$cycloalkyl, aryl-$(C_1\text{-}C_6)$alkyl, heteroaryl-$(C_1\text{-}C_6)$alkyl, —C(O)$R^{52}$, —C(O)$OR^{53}$, —C(O)$NR^{60}R^{61}$ or —$SO_2R^{56}$ group.

According to a particular embodiment of the invention, $R^4$:
represents a hydrogen atom or a $(C_1\text{-}C_6)$alkyl, $(C_3\text{-}C_{10})$cycloalkyl, aryl advantageously phenyl, or heteroaryl, advantageously thiophenyl, group, said group being optionally substituted by one or more groups selected from a halogen atom, a —C($CF_3$)$_2$OH, —CN, —$NH_2$, —$OPO_3H_2$, —$NR^{17}R^{18}$, —$NO_2$, —COOH, —OH, —O—$(C_1\text{-}C_6)$alkyl-O—$(C_1\text{-}C_6)$alkyl, —O$(C_1\text{-}C_6)$alkyl-$NR^{19}R^{20}$ (with $R^{19}$ and $R^{20}$ each representing a $(C_1\text{-}C_6)$alkyl), benzyloxy, —C(O)

O—($C_1$-$C_6$)alkyl, —NHC(O)O—($C_1$-$C_6$)alkyl, —C(O)NH$_2$, —C(O)NR$^{21}$R$^{22}$, —S—($C_1$-$C_6$)alkyl, —S(O)—($C_1$-$C_6$)alkyl, —SO$_2$—($C_1$-$C_6$)alkyl, —SO$_2$NH$_2$, —SO$_2$NR$^{23}$R$^{24}$, —NR$^{25}$SO$_2$R$^{26}$ group, a 3 to 7-membered heterocycloalkyl, aryloxy radical, a ($C_1$-$C_6$)alkyl optionally substituted by one or more halogen atoms, and a ($C_1$-$C_6$)alkoxy optionally substituted by one or more fluorine atoms, and said group, when it is an aryl or heteroaryl, being optionally fused to a 5 or 6-membered heterocycle, or forms, with R3 and the carbon carrying them, a ring selected from a ($C_3$-$C_{10}$)cycloalkyl and a 3 to 7-membered heterocycloalkyl, said cycle being optionally substituted by a ($C_1$-$C_6$)alkyl, —C(O)—($C_1$-$C_6$)alkyl, —C(O)O—($C_1$-$C_6$)alkyl group.

Advantageously, R3 represents a hydrogen atom or a methyl, and advantageously a hydrogen atom, and R4 represents a hydrogen atom or a ($C_1$-$C_6$)alkyl, aryl, advantageously phenyl, or heteroaryl, advantageously thiophenyl, group, said group being optionally substituted by one or more groups selected from a halogen atom, a —CF$_3$, —B(OH)$_2$, —CN, —OH, —NR$^{17}$R$^{18}$ (R$^{17}$ and R$^{18}$ being as defined hereinbefore), —NO$_2$, —COOH, 3 to 7-membered heterocycloalkyl, ($C_1$-$C_6$)alkyl, —S—($C_1$-$C_6$)alkyl, aryloxy radical and a ($C_1$-$C_6$)alkoxy optionally substituted by one or more fluorine atoms, and said group, if it is an aryl or heteroaryl, being optionally fused to a 5 or 6-membered heterocycle, or R3 and R4 form with the carbon carrying them a ring selected from a ($C_3$-$C_{10}$)cycloalkyl and a 3 to 7-membered heterocycloalkyl, said ring being optionally substituted by a —C(O)O(($C_1$-$C_6$)alkyl group).

Also advantageously, R3 represents a hydrogen atom or a methyl, and advantageously a hydrogen atom, and R4 represents a hydrogen atom or an aryl, advantageously phenyl, or heteroaryl, advantageously thiophenyl group, said group being optionally substituted by one or more groups selected from a halogen atom, a —CF$_3$, —B(OH)$_2$, —CN, —OH, —NR$^{17}$R$^{18}$, —NO$_2$, —COOH, 3 to 7-membered heterocycloalkyl, ($C_1$-$C_6$)alkyl, —S—($C_1$-$C_6$)alkyl, aryloxy radical and a ($C_1$-$C_6$)alkoxy optionally substituted by one or more fluorine atoms, and said group being optionally fused to a 5 or 6-membered heterocycle, or R3 and R4 form with the carbon carrying them a ring selected from a ($C_3$-$C_{10}$)cycloalkyl and a 3 to 7-membered heterocycloalkyl, advantageously a 3 to 7-membered heterocycloalkyl, said ring being optionally substituted by a —C(O)O(($C_1$-$C_6$)alkyl) group, R$^{17}$ and R$^{18}$ being as defined hereinbefore.

Advantageously, R3 represents a hydrogen atom or a methyl, and advantageously a hydrogen atom, and R4 represents a hydrogen atom; a heteroaryl, preferably thiophenyl, group optionally substituted by a ($C_1$-$C_6$)alkyl group; or an aryl, preferably phenyl, group optionally fused to a 5 or 6-membered heterocycle comprising preferably two oxygen atoms, and optionally substituted by one or more groups selected from a halogen atom and a —CN, —NR$^{17}$R$^{18}$, —NO$_2$, ($C_1$-$C_6$)alkyl, ($C_1$-$C_6$)alkoxy, ($C_5$-$C_6$)heterocycloalkyl, —S—($C_1$-$C_6$)alkyl and aryloxy group, or R3 and R4 form with the carbon carrying them a ($C_5$-$C_6$) cycloalkyl or 5 or 6-membered heterocycloalkyl ring, advantageously a 5 or 6-membered heterocycloalkyl, said ring being optionally substituted by a —C(O)O(($C_1$-$C_6$)alkyl) group, R$^{17}$ and R$^{18}$ being as defined hereinbefore.

Advantageously, R3 represents a hydrogen atom or a methyl, and advantageously a hydrogen atom, and R4 represents a hydrogen atom; or a heteroaryl, preferably thiophenyl, group optionally substituted by a ($C_1$-$C_6$)alkyl group; or an aryl, preferably phenyl, group optionally fused to a 5 or 6-membered heterocycle comprising preferably two oxygen atoms, and optionally substituted by one or more groups selected from a halogen atom and a —CN, —NR$^{17}$R$^{12}$, —NO$_2$, ($C_1$-$C_6$)alkyl, ($C_1$-$C_6$)alkoxy, ($C_5$-$C_6$)heterocycloalkyl, —S—($C_1$-$C_6$)alkyl and aryloxy group, R$^{17}$ and R$^{18}$ being as defined hereinbefore.

Even more advantageously, R4 does not represent a hydrogen atom.

Advantageously, R3 represents a hydrogen atom or a methyl, and advantageously a hydrogen atom.

Also advantageously, R3 represents a hydrogen atom or a methyl, and advantageously a hydrogen atom, and R4 represents a thiophenyl group optionally substituted by a methyl; a 1,3-benzodioxolyl; group or a phenyl group optionally substituted by one or more groups selected from a halogen atom and a —CN, —NR$^{17}$R$^{18}$, preferably —NMe$_2$, —NO$_2$, ($C_1$-$C_6$)alkyl, preferably methyl or isopropyl, ($C_1$-$C_6$)alkoxy, preferably methoxy, pyrrolidinyl, —S—($C_1$-$C_6$)alkyl, preferably thiomethoxy, and phenoxy group, or R3 and R4 form with the carbon carrying them a ring of formula

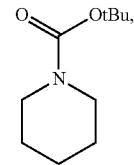

R$^{17}$ and R$^{18}$ being as defined hereinbefore.

Also advantageously, R3 represents a hydrogen atom or a methyl, and advantageously a hydrogen atom, and R4 represents a thiophenyl group optionally substituted by a methyl, a 1,3-benzodioxolyl group or a phenyl group optionally substituted by one or more groups selected from a halogen atom and a —CN, —NR$^{17}$R$^{18}$, preferably —NMe$_2$, —NO$_2$, ($C_1$-$C_6$) alkyl, preferably methyl or isopropyl, ($C_1$-$C_6$)alkoxy, preferably methoxy, pyrrolidinyl, —S—($C_1$-$C_6$)alkyl, preferably thiomethoxy, and phenoxy group, R$^7$ and R$^8$ being as defined hereinbefore.

Also advantageously, R3 represents a hydrogen atom or a methyl, and advantageously a hydrogen atom, and R4 represents a thiophenyl, advantageously thiophen-2-yl group.

According to a first preferred embodiment of the invention, R3 and R4 each represent, independently of each other, a ($C_1$-$C_6$)alkyl group, such as methyl.

According to a second preferred embodiment of the invention, R3 represents a hydrogen atom, and R4 represents an aryl, advantageously phenyl or heteroaryl, advantageously thiophenyl, group, said group being optionally substituted by one or more groups selected from a halogen atom, a —C(CF$_3$)$_2$OH, —CN, —NH$_2$, —OPO$_3$H$_2$, —NR$^{17}$R$^{18}$, —NO$_2$, —COOH, —OH, —O(C$_1$-C$_6$)alkyl-OPO$_3$H$_2$, —O—(C$_1$-C$_6$)alkyl-O—(C$_1$-C$_6$)alkyl, —O(C$_1$-C$_6$)alkyl-NR$^{19}$R$^{20}$, —NR$^{81}$(C$_1$-C$_6$)alkyl-NR$^{85}$R$^{86}$, benzyloxy, —C(O)O—(C$_1$-C$_6$)alkyl, —NHC(O)O—(C$_1$-C$_6$)alkyl, —C(O)NH$_2$, —C(O)NR$^{21}$R$^{22}$, —S—(C$_1$-C$_6$)alkyl, —S(O)—(C$_1$-C$_6$)alkyl, —SO$_2$—(C$_1$-C$_6$)alkyl, —SO$_2$NH$_2$, —SO$_2$NR$^{23}$R$^{24}$, —NR$^{25}$SO$_2$R$^{26}$, 3 to 7-membered heterocycloalkyl, aryloxy radical, a (C$_1$-C$_6$)alkyl optionally substituted by one or more halogen atoms, and a (C$_1$-C$_6$)alkoxy optionally substituted by one or more fluorine atoms, and said group being optionally fused to a 5 or 6-membered heterocycle.

In this case, R4 advantageously represents an aryl, advantageously phenyl, or heteroaryl, advantageously thiophenyl, group, said group being optionally substituted by one or more groups selected from a halogen atom, a —CF$_3$, —B(OH)$_2$, —CN, —OH, —NR$^{17}$R$^{18}$ (R$^{17}$ and R$^{18}$ being as defined above), —NO$_2$, —COOH, 3 to 7-membered heterocycloalkyl, (C$_1$-C$_6$)alkyl, —S—(C$_1$-C$_6$)alkyl, aryloxy, —O(C$_1$-C$_6$)alkyl-NR$^{19}$R$^{20}$ radical and a (C$_1$-C$_6$)alkoxy optionally substituted by one or more fluorine atoms, and said group being optionally fused to a 5 or 6-membered heterocycle R4 preferably represents an unsubstituted thiophenyl group, preferably thiophen-2-yl; or a phenyl group optionally substituted by one or more groups selected from a halogen atom and a —CF$_3$, —B(OH)$_2$, —CN, —OH, —NR$^{17}$R$^{18}$ group (R$^{17}$ and R$^{18}$ being as defined above), —NO$_2$, —COOH, 3 to 7-membered heterocycloalkyl, (C$_1$-C$_6$)alkyl, —S—(C$_1$-C$_6$)alkyl, aryloxy, —O(C$_1$-C$_6$)alkyl-NR$^{19}$R$^{20}$ radical and a (C$_1$-C$_6$)alkoxy optionally substituted by one or more fluorine atoms, and optionally fused to

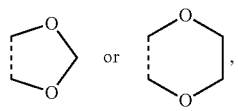

the bond shown as a dotted line representing the bond common with phenyl.

Advantageously, R5 represents a (C$_1$-C$_6$)alkyl, aryl, heteroaryl, aryl-(C$_1$-C$_6$)alkyl, heteroaryl-(C$_1$-C$_6$)alkyl, (C$_1$-C$_{10}$)cycloalkyl-(C$_1$-C$_6$)alkyl, (3 to 7-membered heterocycloalkyl)-(C$_1$-C$_6$)alkyl group, said group being optionally substituted by one or more groups selected from a halogen atom, a —CF$_3$, —CN, —OH, —NR$^{29}$R$^{30}$, —NO$_2$, —C(CF$_3$)$_2$OH, (C$_1$-C$_6$)alkoxy, aryloxy, —S—(C$_1$-C$_6$)alkyl, —C(O)O((C$_1$-C$_6$)alkyl), (C$_2$-C$_6$)alkynyl, aryl, heteroaryl, (C$_1$-C$_6$)alkyl-heteroaryl, 3 to 7-membered heterocycloalkyl, (3 to 7-membered heterocycloalkyl)-(C$_1$-C$_6$)alkoxy radical and a (C$_1$-C$_6$) alkyl optionally substituted by one or more fluorine atoms, and the aryl or heteroaryl core of said group, when present, being optionally fused to a 5 or 6-membered heterocycle, R$^{29}$ and R$^{30}$ being as defined hereinbefore.

Also advantageously, R5 represents a (C$_1$-C$_6$)alkyl, heteroaryl, (C$_3$-C$_{10}$)cycloalkyl-(C$_1$-C$_6$)alkyl, aryl-(C$_1$-C$_6$)alkyl, or aryl group, the aryl core of the aryl or aryl-(C$_1$-C$_6$)alkyl group being optionally fused to a 5 or 6-membered heterocycle, comprising preferably two oxygen atoms, and being optionally substituted by one or more groups selected from a halogen atom, a —CF$_3$, —CN, —OH, —NR$^{29}$R$^{30}$, —NO$_2$, —C(CF$_1$)$_2$OH, (C$_1$-C$_6$)alkoxy, aryloxy, —S—(C$_1$-C$_6$)alkyl, —C(O)O((C$_1$-C$_6$)alkyl), (C$_2$-C$_6$)alkynyl, aryl, heteroaryl, (C$_1$-C$_6$)alkylheteroaryl, 3 to 7-membered heterocycloalkyl, (3 to 7-membered heterocycloalkyl)-(C$_1$-C$_6$)alkoxy radical, and a (C$_1$-C$_6$)alkyl optionally substituted by one or more fluorine atoms, R$^{29}$ and R$^{30}$ being as defined hereinbefore.

Advantageously, R5 represents a (C$_1$-C$_6$)alkyl, heteroaryl, (C$_3$-C$_{10}$)cycloalkyl-(C$_1$-C$_6$)alkyl, aryl-(C$_1$-C$_6$)alkyl, or aryl group, the aryl core of the aryl or aryl-(C$_1$-C$_6$)alkyl group being optionally fused to a 5 or 6-membered heterocycle, comprising preferably two oxygen atoms, and being optionally substituted by one or more groups selected from a halogen atom, a —CF$_3$, —CN, —NR$^{29}$R$^{30}$, —NO$_2$, —C(CF$_3$)$_2$OH, (C$_1$-C$_6$)alkoxy, aryloxy, (C$_1$-C$_6$)alkyl, (C$_2$-C$_6$)alkynyl, aryl and 5 or 6-membered heterocycloalkyl group, R$^{29}$ and R$^{30}$ being as defined hereinbefore.

Also advantageously, R5 represents a (C$_1$-C$_6$)alkyl, preferably methyl or isobutyl; indazolyl; phenyl-(C$_1$-C$_6$)alkyl, preferably benzyl; cyclopropyl-(C$_1$-C$_6$)alkyl, preferably, cyclopropylmethyl; 1,3-benzodioxolyl; 1,3-benzodioxolyl-methyl; naphthyl; or phenyl group, said phenyl group being optionally substituted by one or more groups selected from a halogen atom, preferably a fluorine or chlorine atom, a —CF$_3$, —CN, —NR$^{29}$R$^{30}$, preferably —NMe$_2$ or -NEt$_2$, —NO$_2$, —C(CF$_3$)$_2$OH, (C$_1$-C$_6$)alkoxy, preferably methoxy, phenoxy, (C$_1$-C$_6$)alkyl, preferably methyl, isopropyl or tert-butyl, (C$_2$-C$_6$)alkynyl, preferably —C≡CH, phenyl and morpholinyl group, R$^{29}$ and R$^{30}$ being as defined hereinbefore.

Also advantageously, R5 represents a phenyl group, being optionally fused to a 5 or 6-membered heterocycle, comprising preferably two oxygen atoms, and being optionally substituted by one or more groups selected from a halogen atom, a —NH$_2$, —COOH, —CN, —OH, —NO$_2$, —B(OH)$_2$, (C$_1$-C$_6$)alkoxy, —O—(C$_1$-C$_6$)alkyl-NR$^{27}$R$^{28}$, —O—(C$_1$-C$_6$)alkyl-O—(C$_1$-C$_6$)alkyl, aryloxy, —C(O)O—(C$_1$-C$_6$)alkyl, (C$_2$-C$_6$)alkynyl, —NR$^{29}$R$^{30}$, —NHC(O)O—(C$_1$-C$_6$)alkyl, —C(O)NH$_2$, —C(O)NR$^{31}$R$^{32}$, —S—(C$_1$-C$_6$)alkyl, —S(O)—(C$_1$-C$_6$)alkyl, —SO$_2$—(C$_1$-C$_6$)alkyl, —SO$_2$NH$_2$, —SO$_2$NR$^{33}$R$^{34}$, —NR$^{35}$SO$_2$R$^{36}$, aryl, heteroaryl, (C$_1$-C$_6$)alkylheteroaryl, 3 to 7-membered heterocycloalkyl, (3 to 7-membered heterocycloalkyl)-(C$_1$-C$_6$)alkoxy radical and a (C$_1$-C$_6$)alkyl group optionally substituted by one or more halogen atoms, R$^{29}$ to R$^{36}$ being as defined hereinbefore.

Even more advantageously, R5 represents a 1,3-benzodioxolyl or phenyl group, said phenyl group being optionally substituted by one or more groups selected from a halogen atom, preferably a fluorine or chlorine atom, a —CF$_3$, —CN, —NR$^{29}$R$^{30}$, preferably —NMe$_2$ or —NEt$_2$, —NO$_2$, —C(CF$_3$)$_2$OH, (C$_1$-C$_6$)alkoxy, preferably methoxy, phenoxy, (C$_1$-C$_6$)alkyl, preferably methyl, isopropyl or tert-butyl, (C$_2$-C$_6$)alkynyl, preferably —C≡CH, phenyl and morpholinyl group, R$^{29}$ and R$^{30}$ being as defined hereinbefore.

Also advantageously, R6 represents a —CH$_2$Hal or —C≡CR$^{12}$ group, with Hal and R$^{12}$ as defined hereinbefore.

Even more advantageously, R6 is selected from —CH₂Cl, —CH₂Br, —CH₂F, —C≡CH, —C≡CMe and —C≡CPh, and advantageously R6 is selected from —CH₂Cl and —C≡CH.

In one particular embodiment, R6 represents the —CH₂Cl group.

In another particular embodiment, R6 represents the —C≡CH group.

In one particular embodiment, the compounds according to the invention will be selected from the compounds of formula (I) for which R1 represents a cyclohexyl, R2 and R3 represent a hydrogen atom, R4 represents a thiophenyl, R6 represents a —CH₂Cl or —C≡CH group and R5 represents a phenyl group, said phenyl group being optionally fused to a 5 or 6-membered heterocycle, comprising preferably two oxygen atoms, and being optionally substituted by one or more groups selected from a halogen atom, a —NH₂, —COOH, —CN, —OH, —NO₂, —B(OH)₂, (C₁-C₆)alkoxy, —O—(C₁-C₆)alkyl-NR²⁷R²⁸, —O—(C₁-C₆)alkyl-O—(C₁-C₆)alkyl, aryloxy, —C(O)O—(C₁-C₆)alkyl, (C₂-C₆)alkynyl, —NR²⁹R³⁰, —NHC(O)O—(C₁-C₆)alkyl, —C(O)NH₂, —C(O)NR³¹R³², —S—(C₁-C₆)alkyl, —S(O)—(C₁-C₆)alkyl, —SO₂—(C₁-C₆)alkyl, —SO₂NH₂, —SO₂NR³³R³⁴, —NR³⁵SO₂R³⁶, aryl, heteroaryl, (C₁-C₆)alkylheteroaryl, 3 to 7-membered heterocycloalkyl, (3 to 7-membered heterocycloalkyl)-(C₁-C₆)alkoxy radical and a (C₁-C₆)alkyl group optionally substituted by one or more halogen atoms, R²⁹ to R³⁶ being as defined hereinbefore.

In another particular embodiment, the compounds according to the invention will be selected from the compounds of formula (I) for which R1 represents a cyclohexyl, R2 and R3 represent a hydrogen atom, R4 represents a thiophenyl, R6 represents a —CH₂Cl or group and R5 represents a 1,3-benzodioxolyl or phenyl group, said phenyl group being optionally substituted by one or more groups selected from a halogen atom, preferably a fluorine or chlorine atom, a —CF₃, —CN, —NR²⁹R³⁰, preferably —NMe₂ or -NEt₂, —NO₂, —C(CF₃)₂OH, (C₁-C₆)alkoxy, preferably methoxy, phenoxy, (C₁-C₆)alkyl, preferably methyl, isopropyl or tert-butyl, (C₂-C₆)alkynyl, preferably —C≡CH, phenyl and morpholinyl group,
R²⁹ and R³⁹ being as defined hereinbefore.

In one particular embodiment, the compound of the invention is selected from the following molecules:

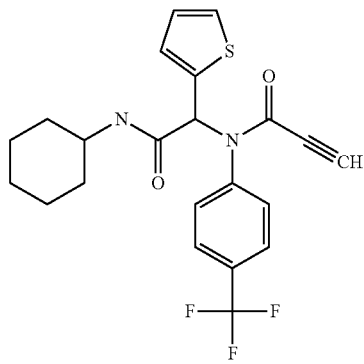

1

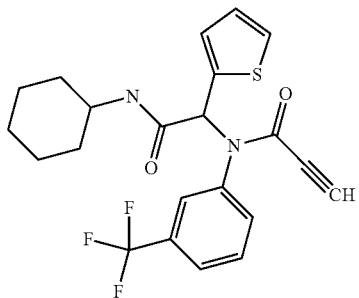

2

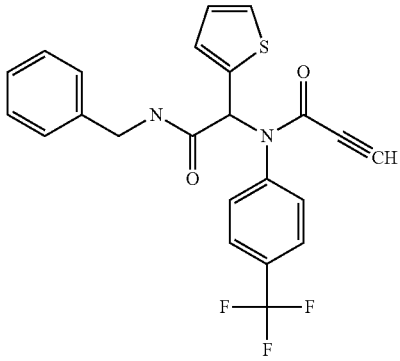

3

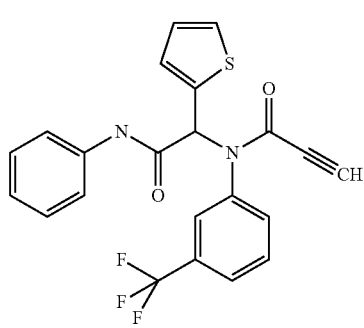

4

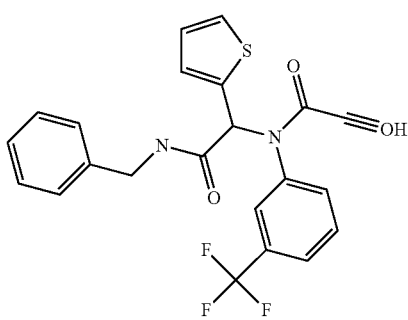

5

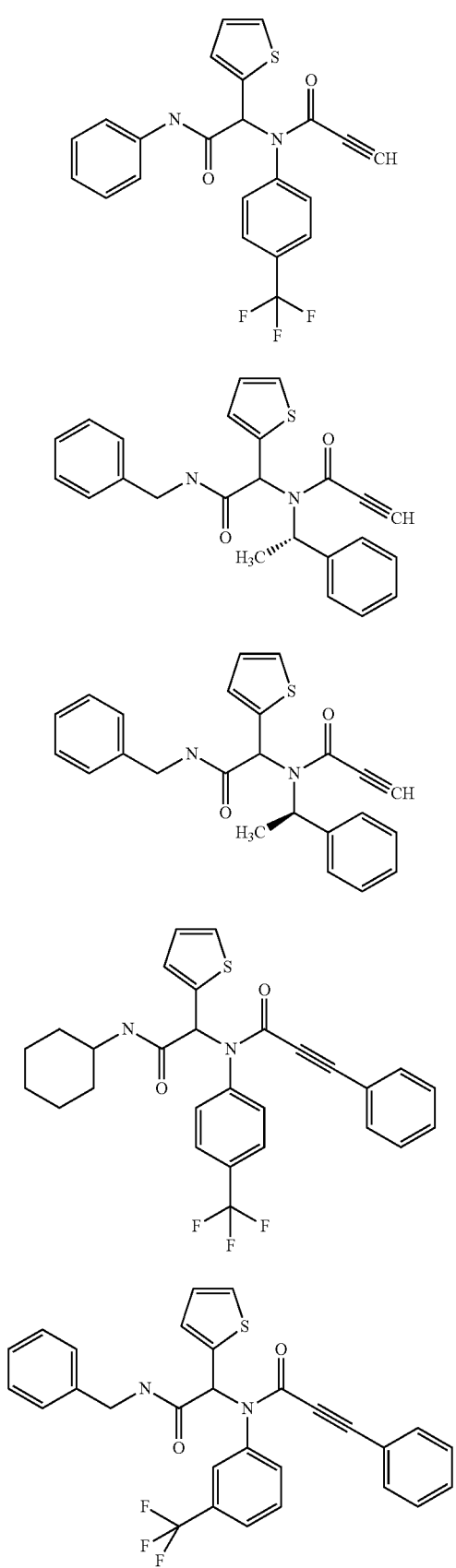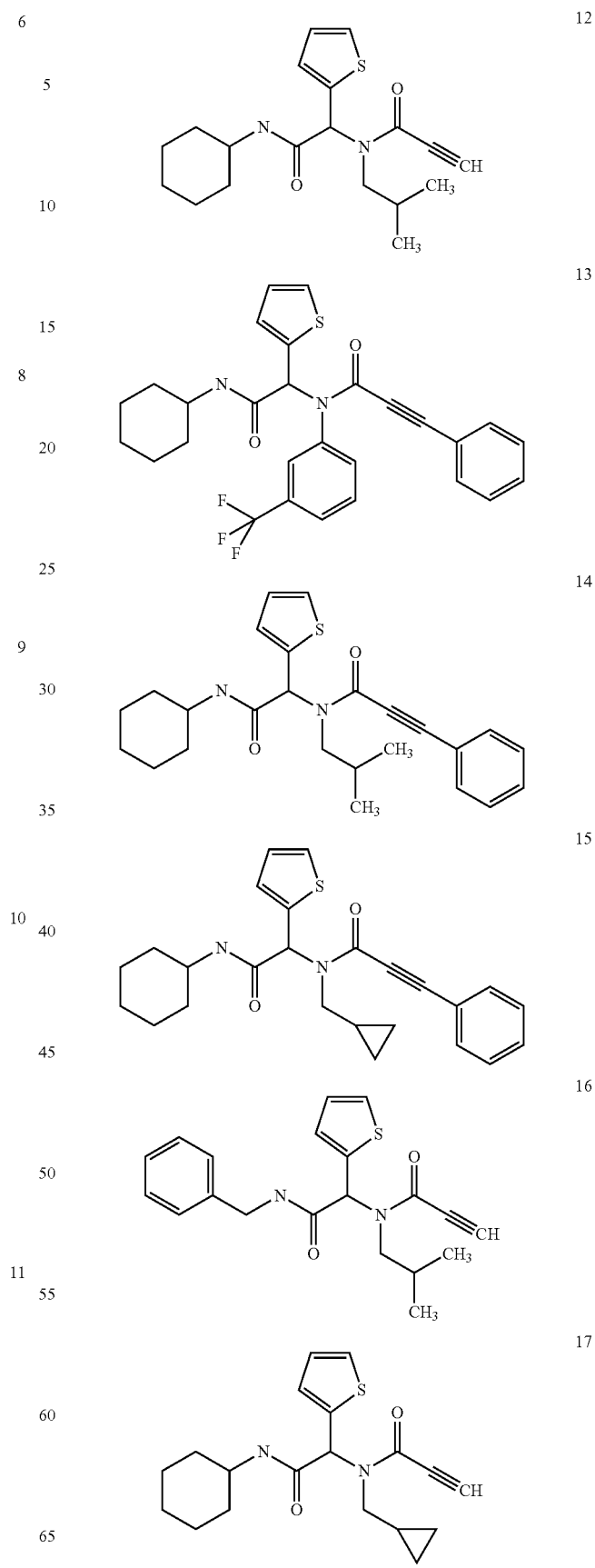

18
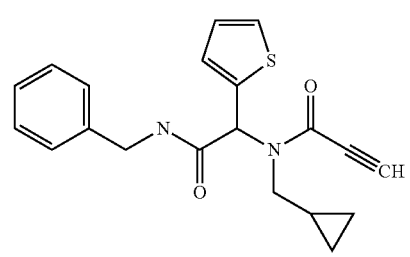
19
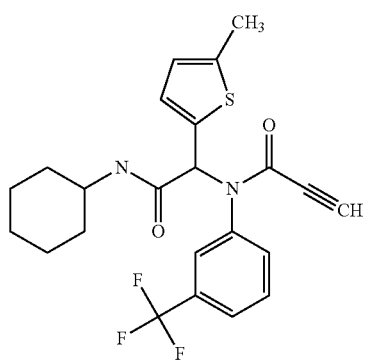
20
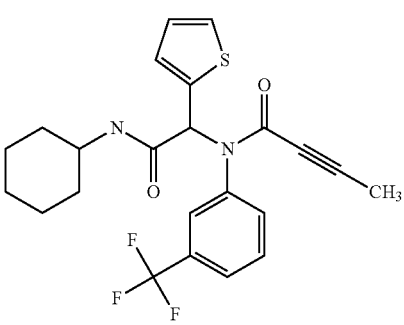
21
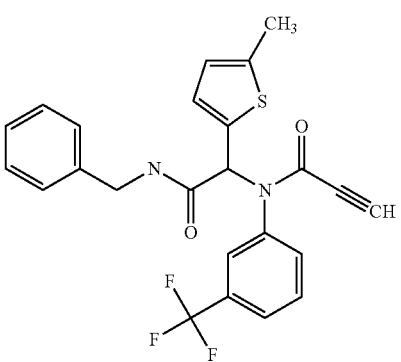
22
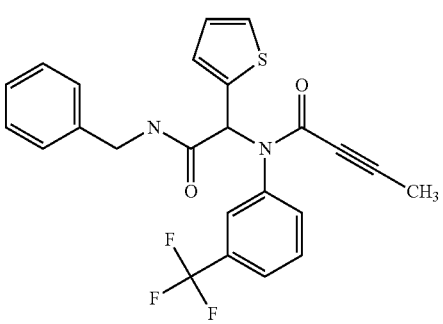
23
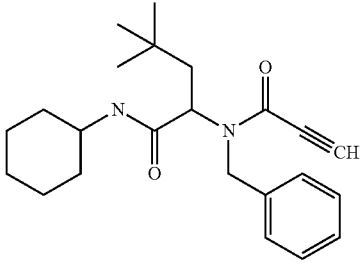
24
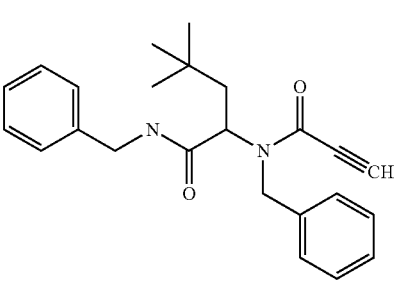
25
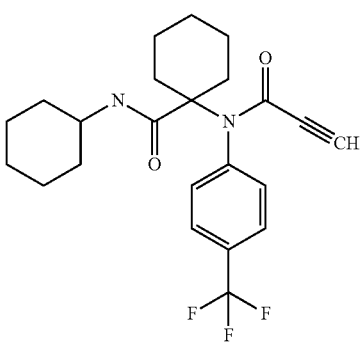
26
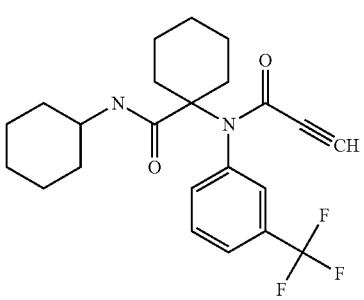
27
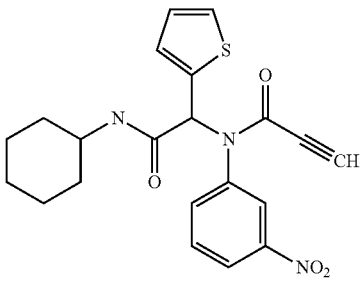

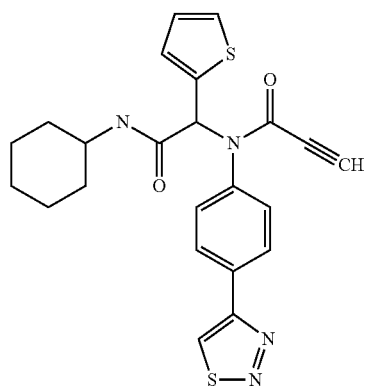
28
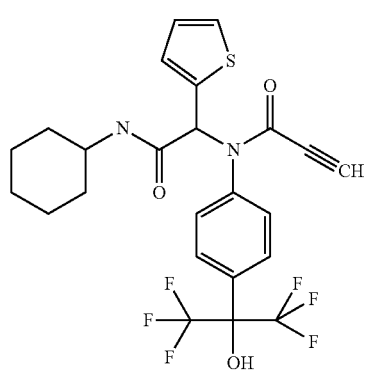
29
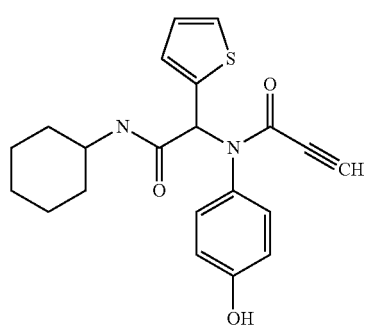
30
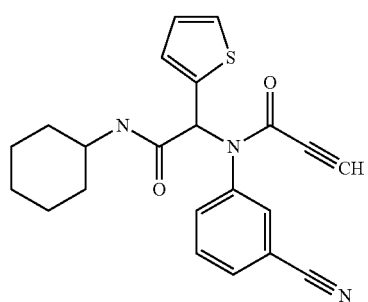
31
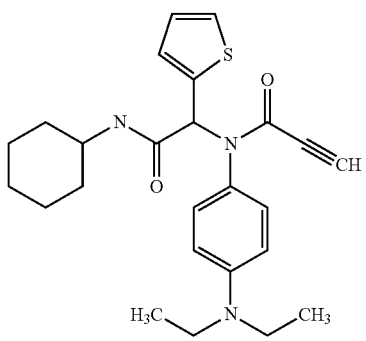
32
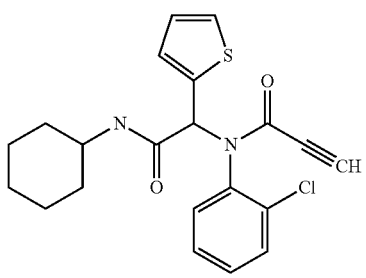
33
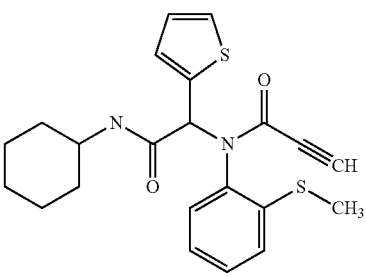
34
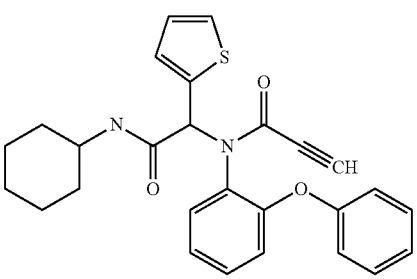
35
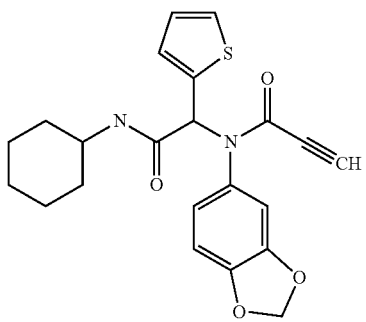
36

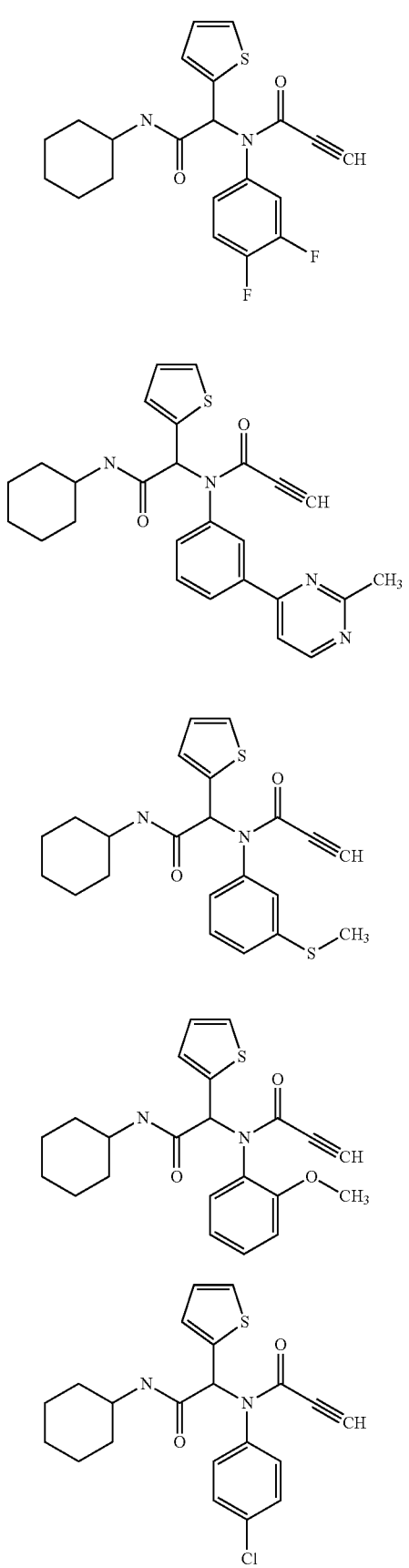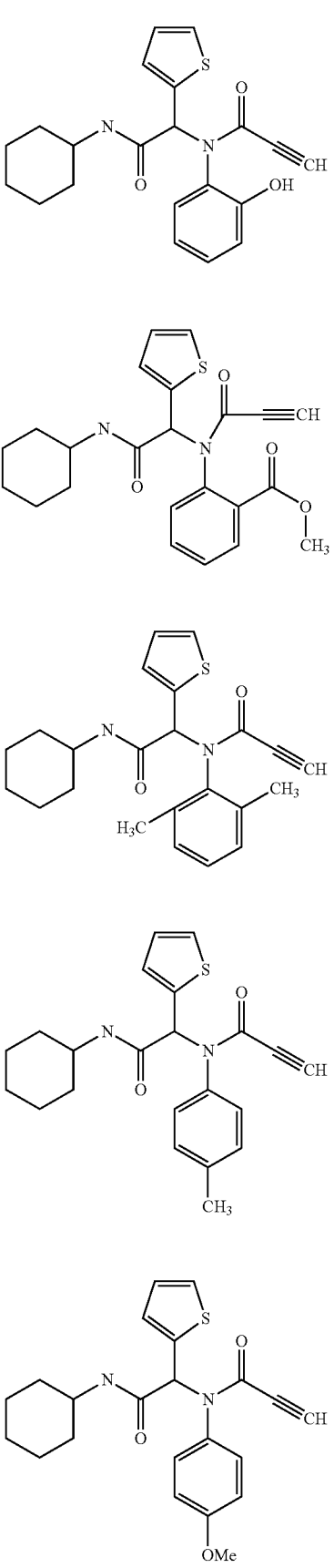

47
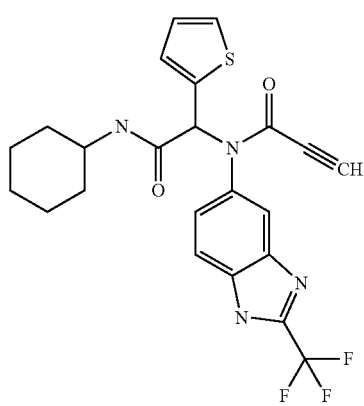
48
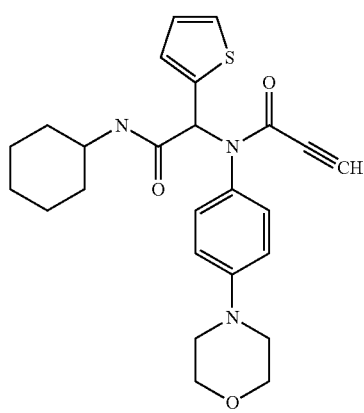
49
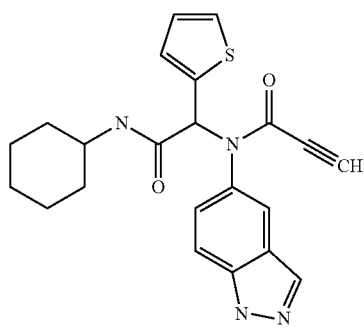
50
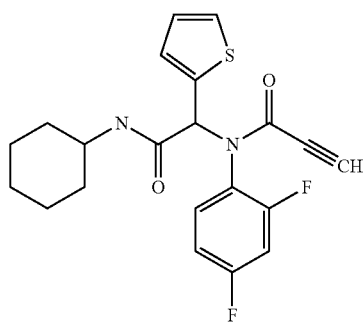
51
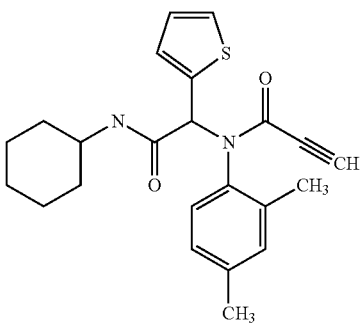
52
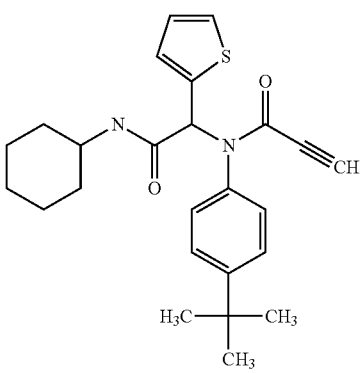
53
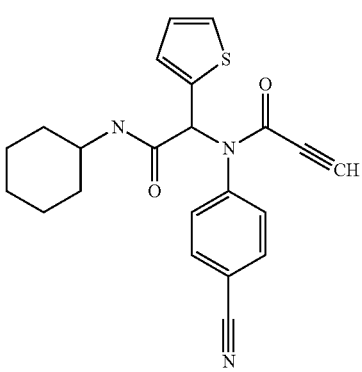
54
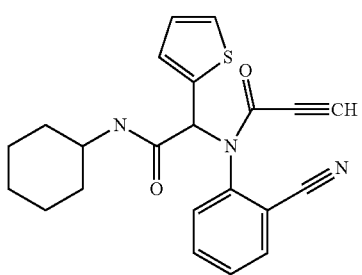

55
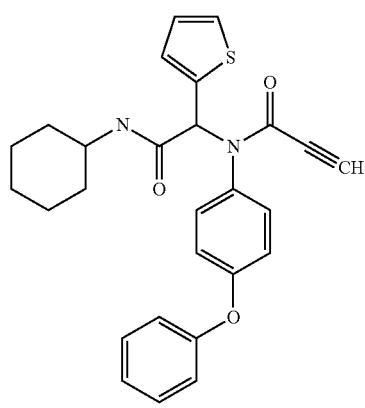
56
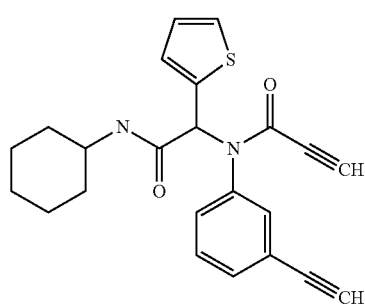
57
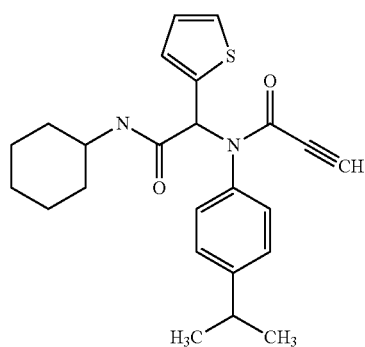
58
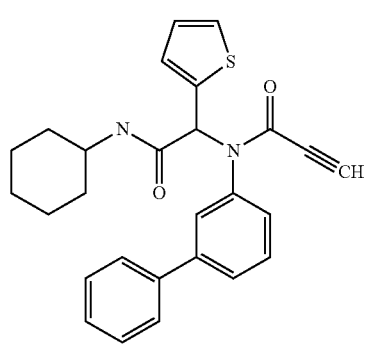
59
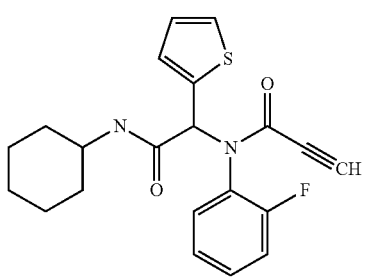
60
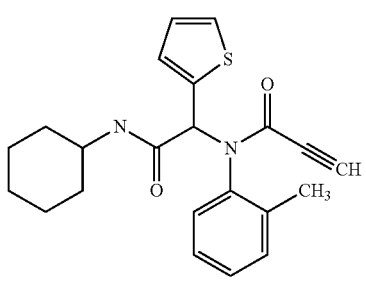
61
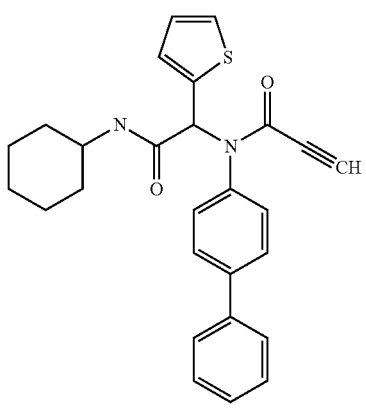
62
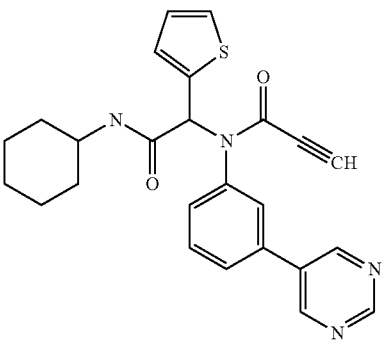

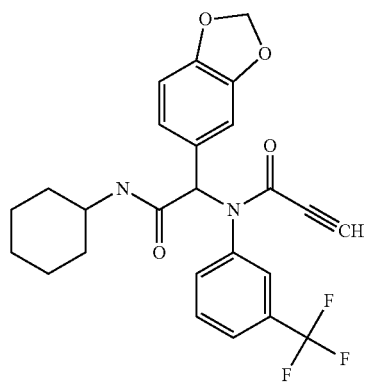
63
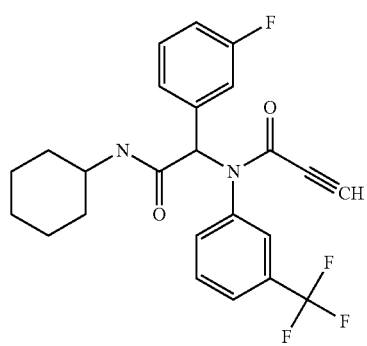
64
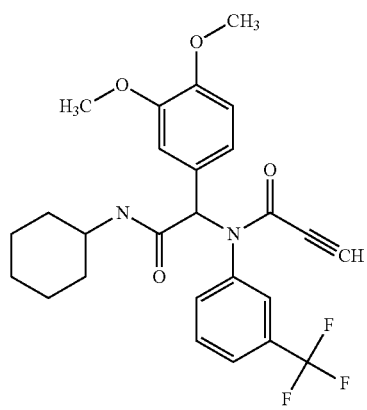
65
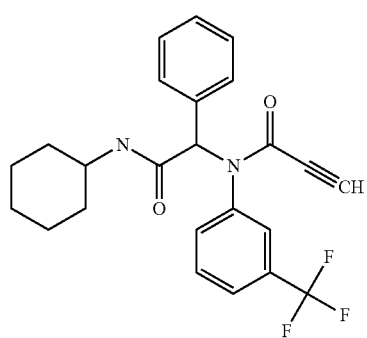
66
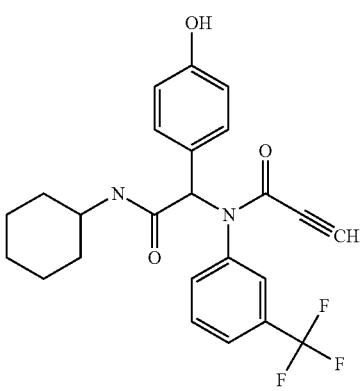
67
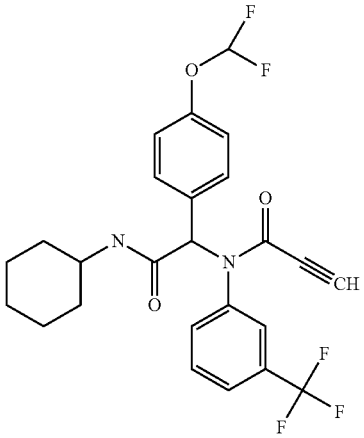
68
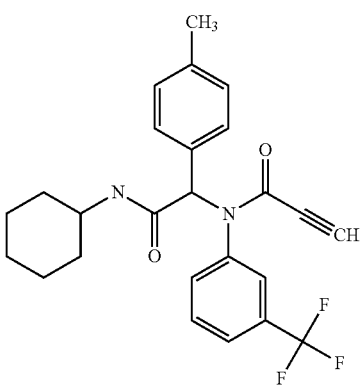
69
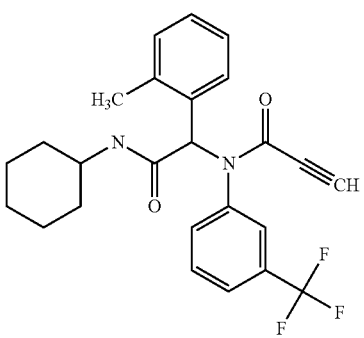
70

71 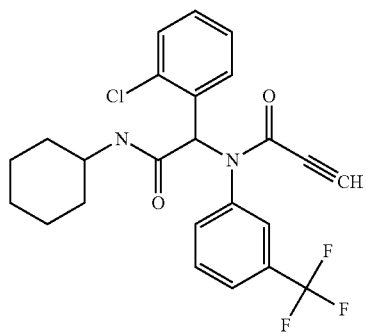
72 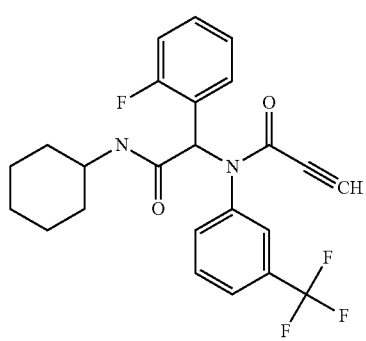
73 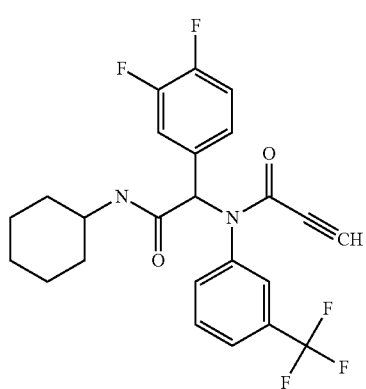
74 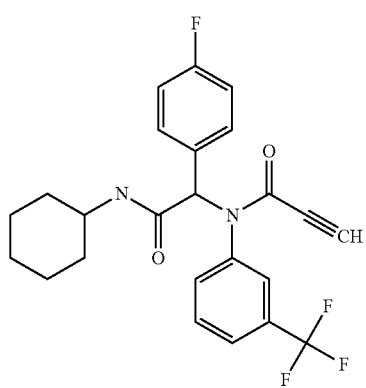
75 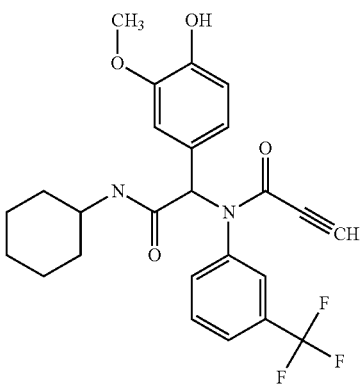
76 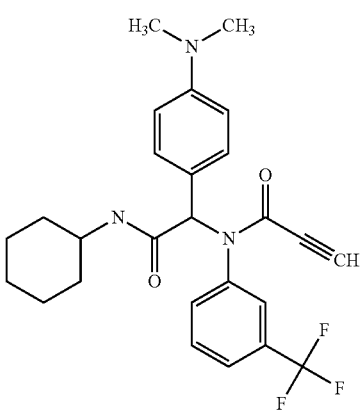
77 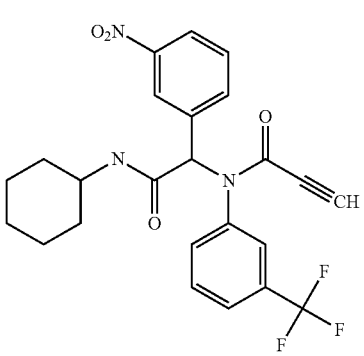
78 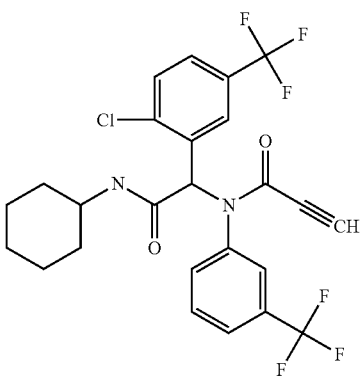

79
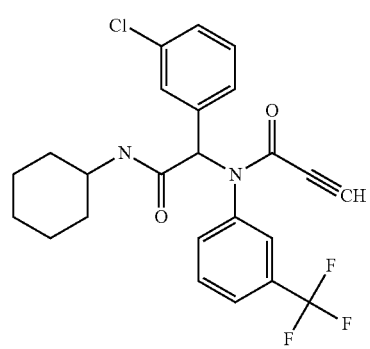
80
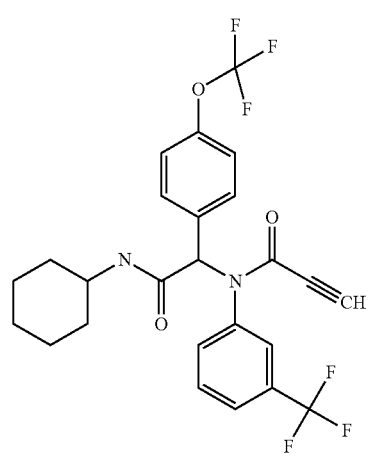
81
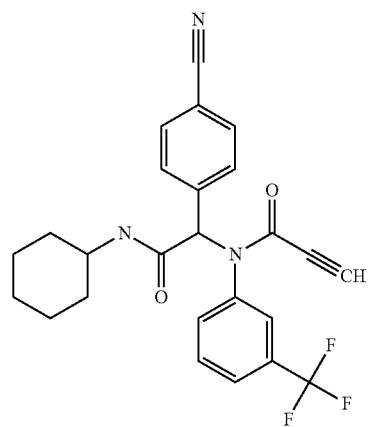
82
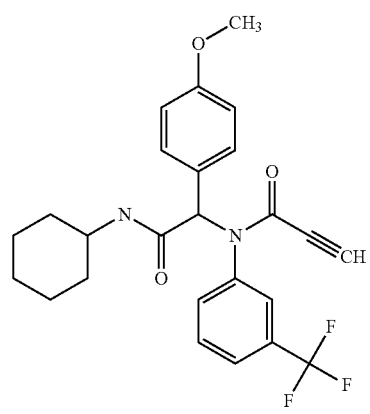
83
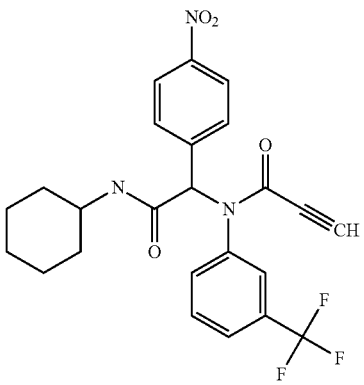
84
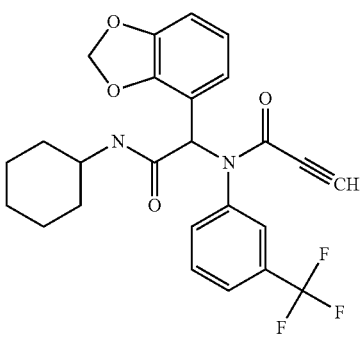
85
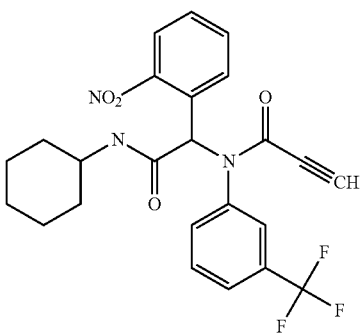
86
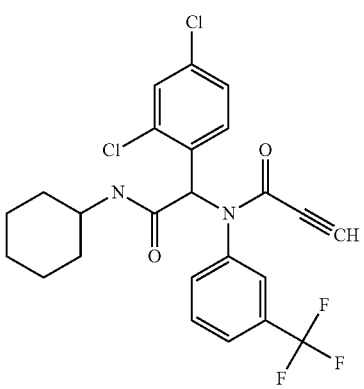

87 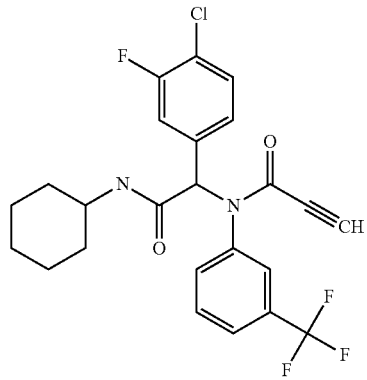
88 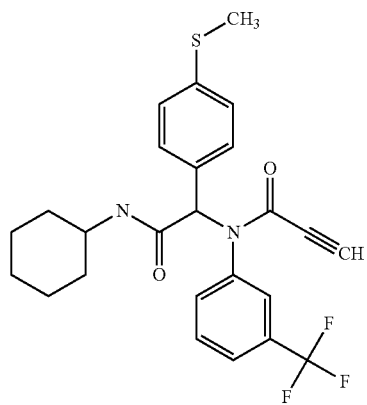
89 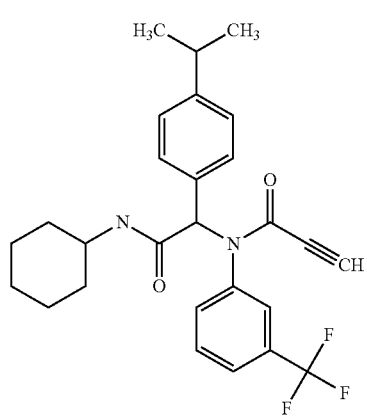
90 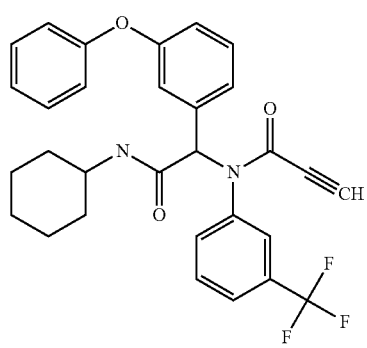
91 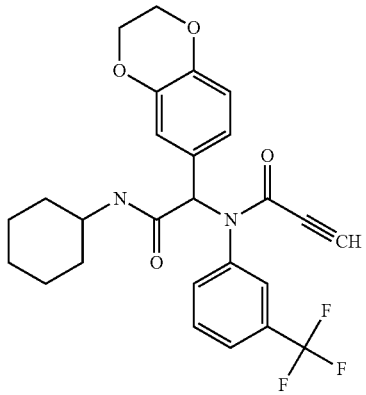
92 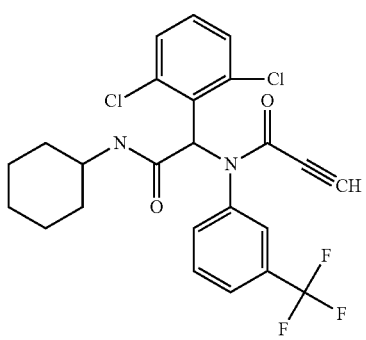
93 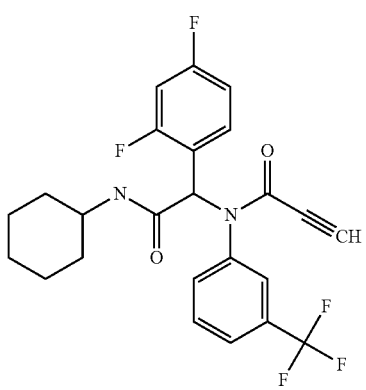
94 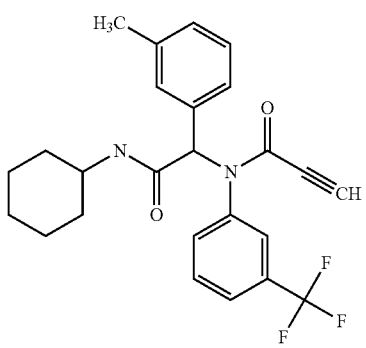

95 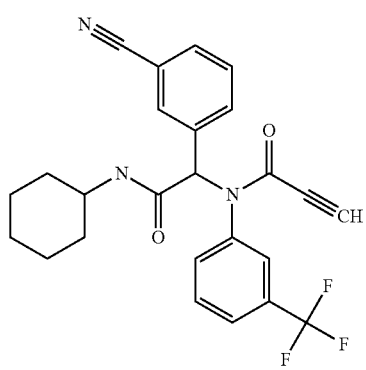
96 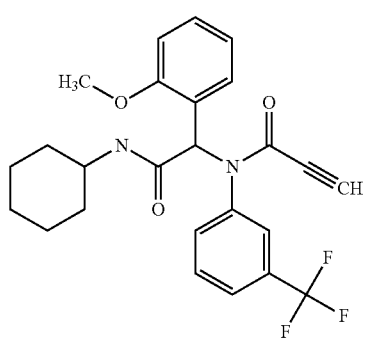
97 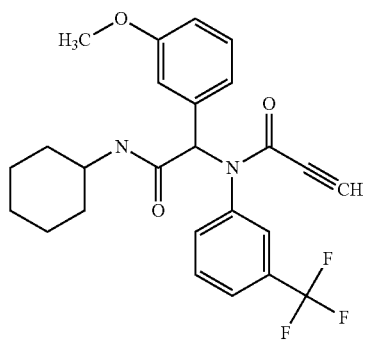
98 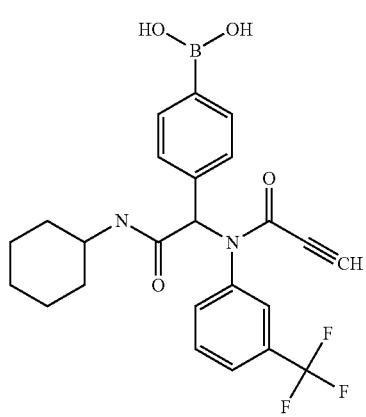
99 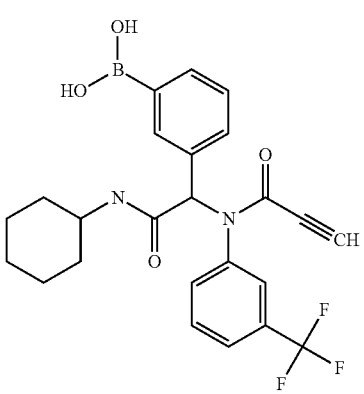
100 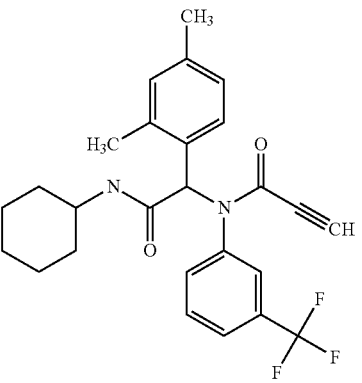
101 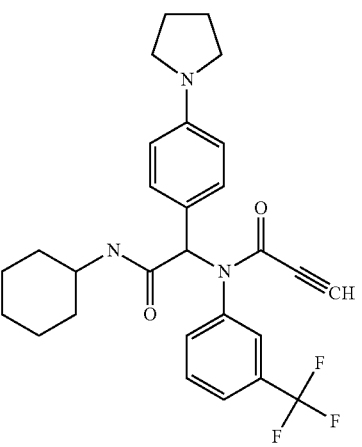
102 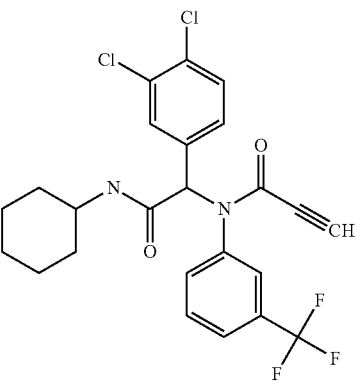

103 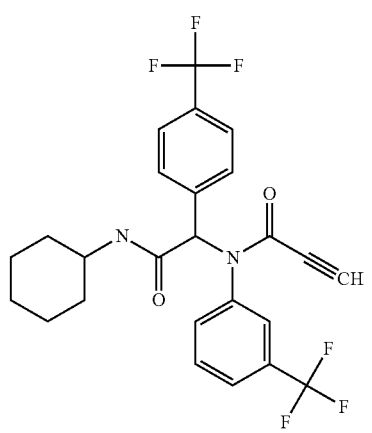
104 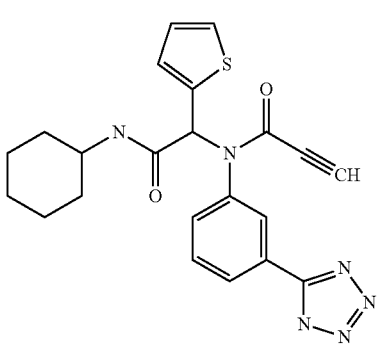
105 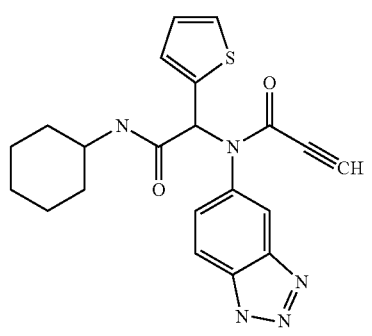
106 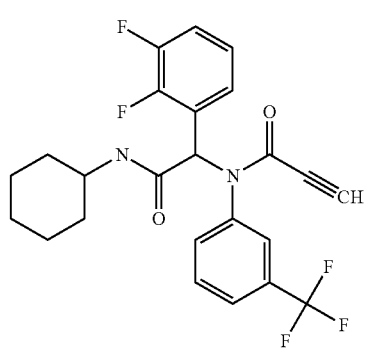
107 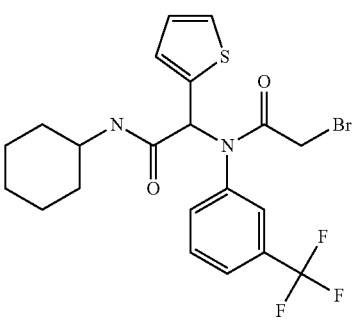
108 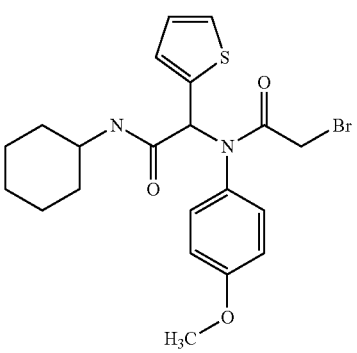
109 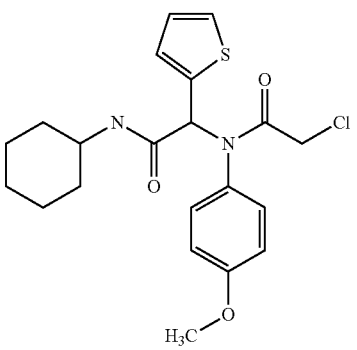
110 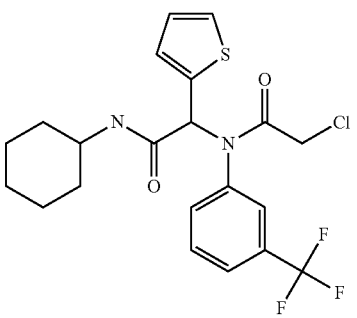
111 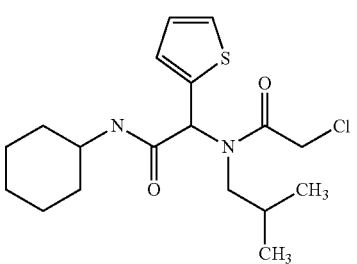

112 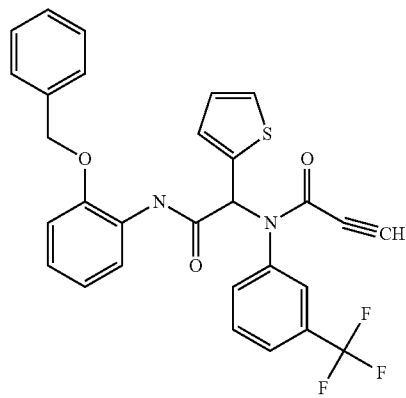
113 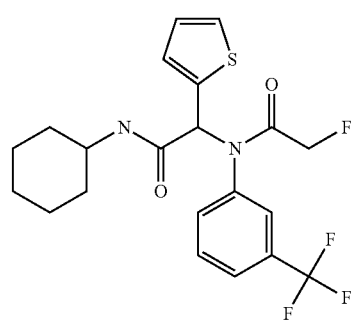
114 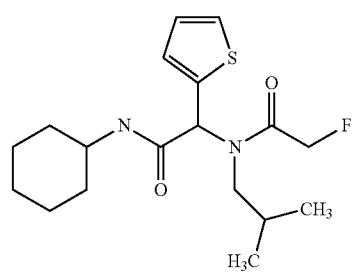
115 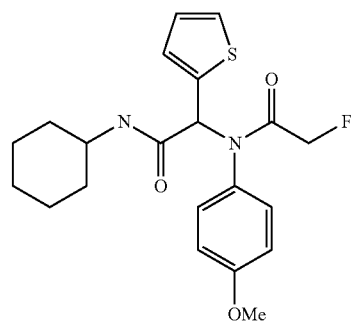
116 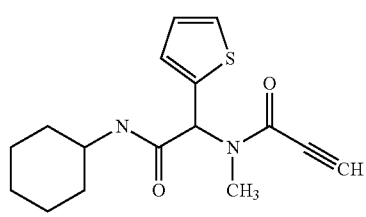
117 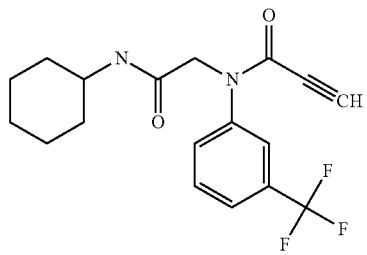
118 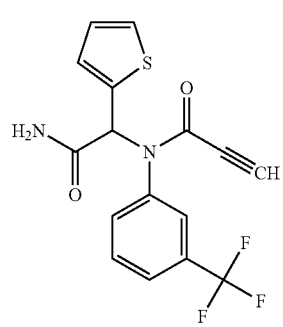
119 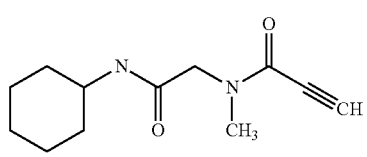
120 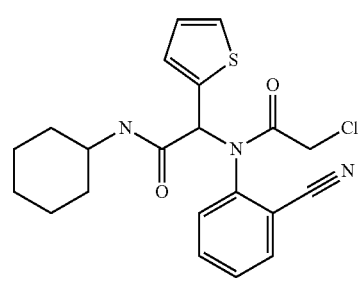
121 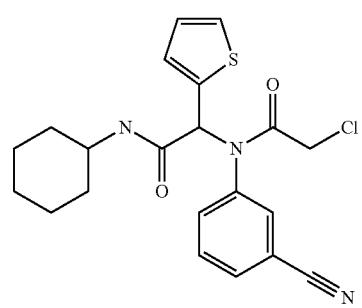

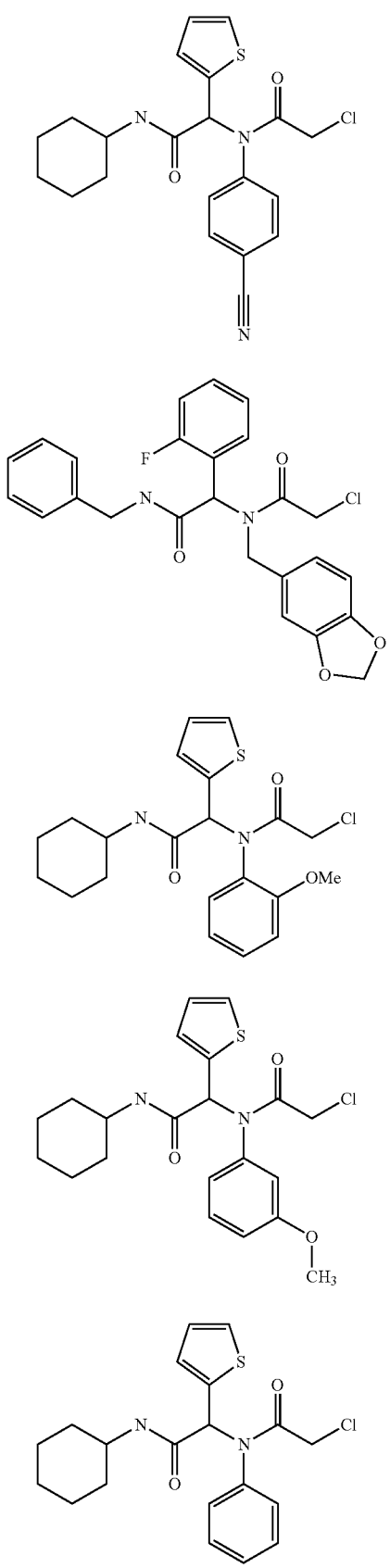
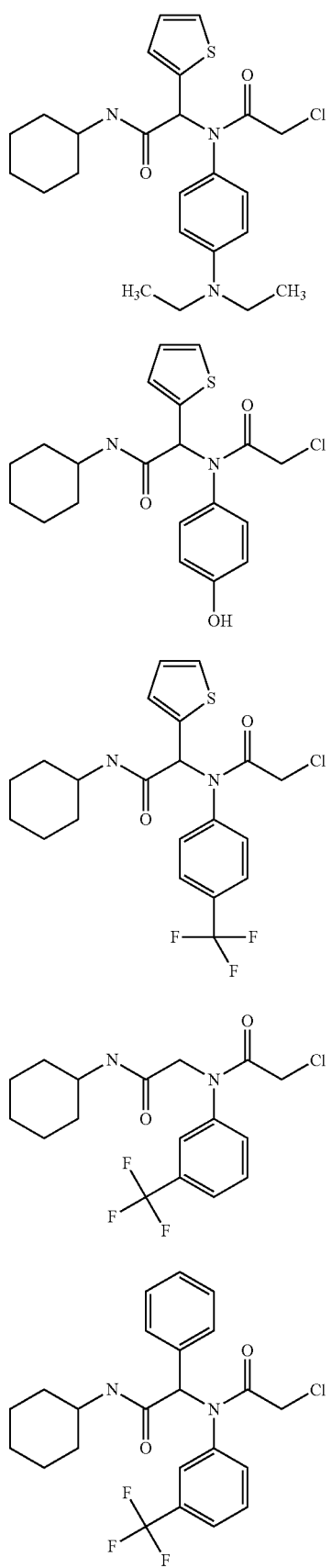

| | |
|---|---|
| 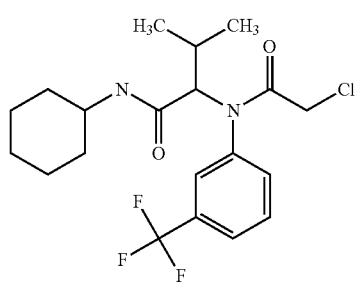 132 | 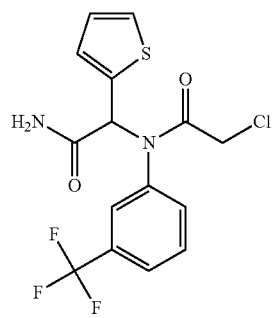 137 |
| 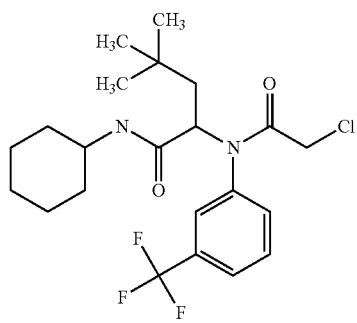 133 | 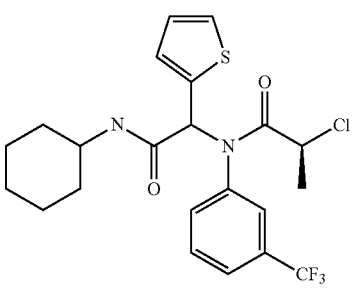 138 |
| 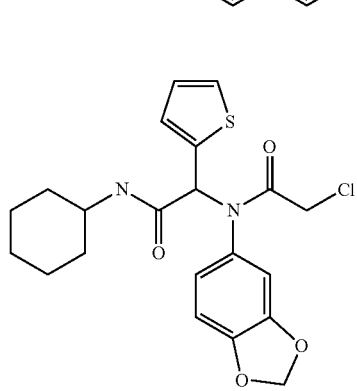 134 | 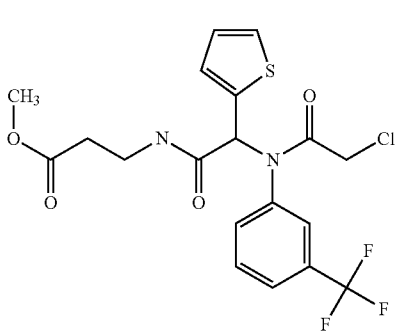 139 |
| 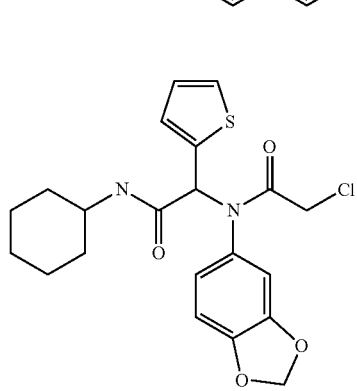 135 | 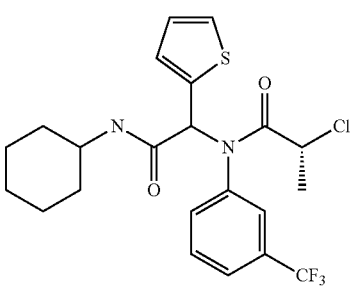 140 |
| 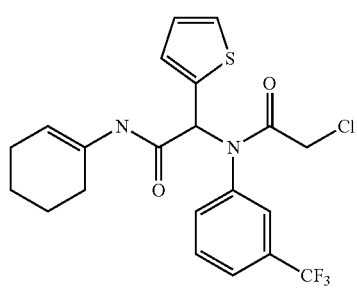 136 | 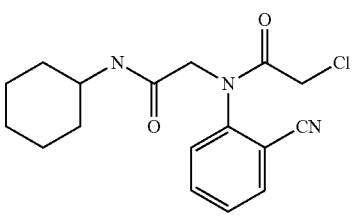 141 |

142
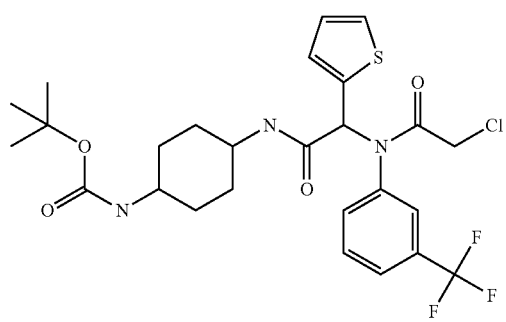
143
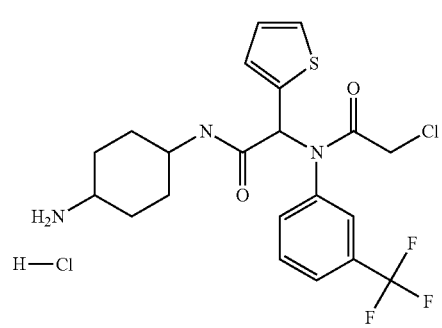
144
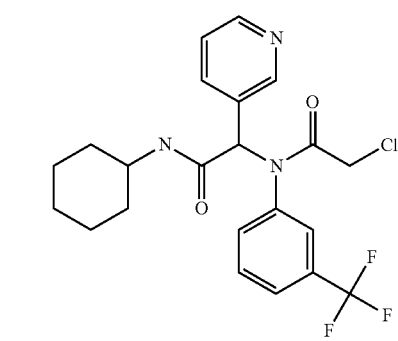
145
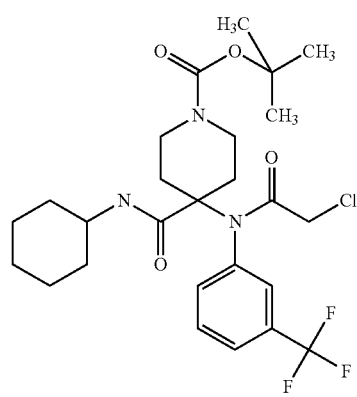
146
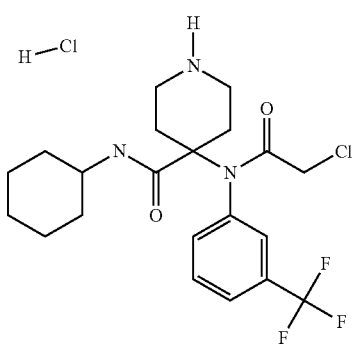
147
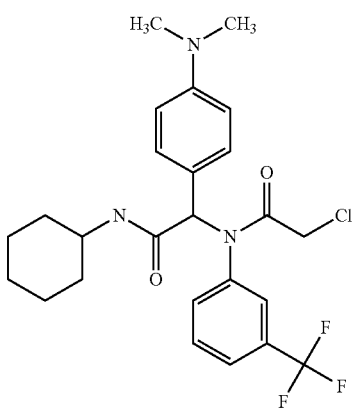
148
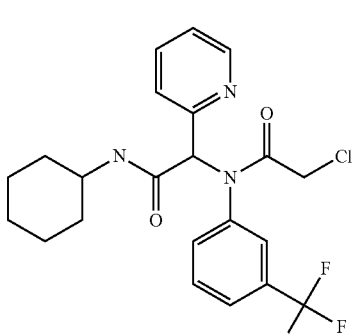
149
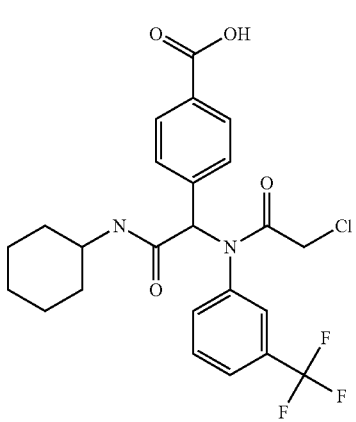

-continued
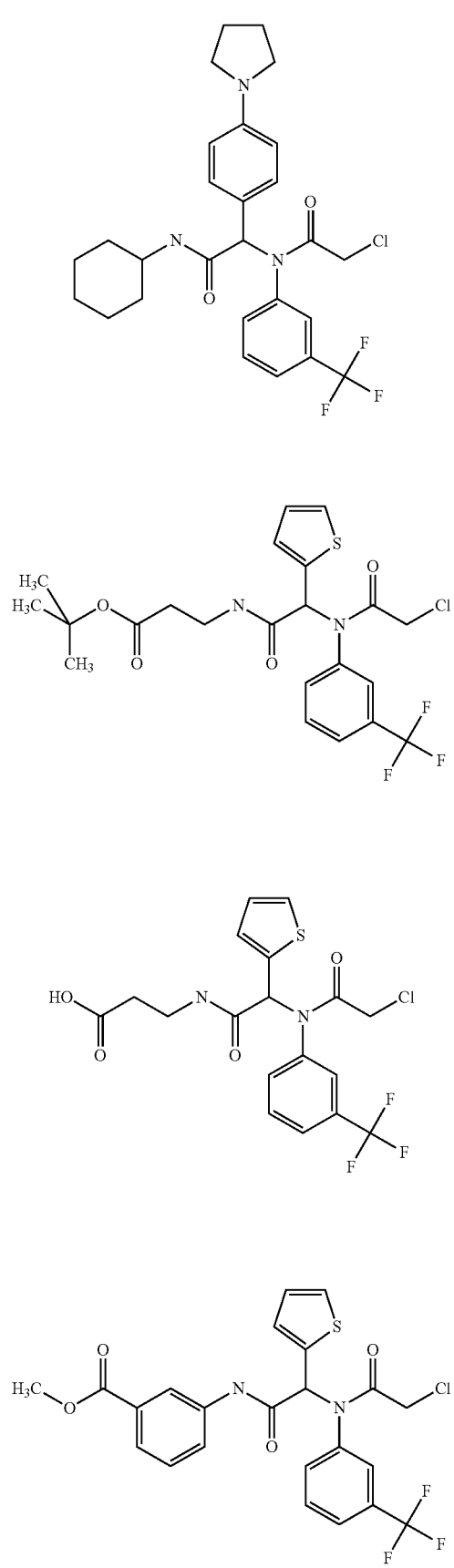
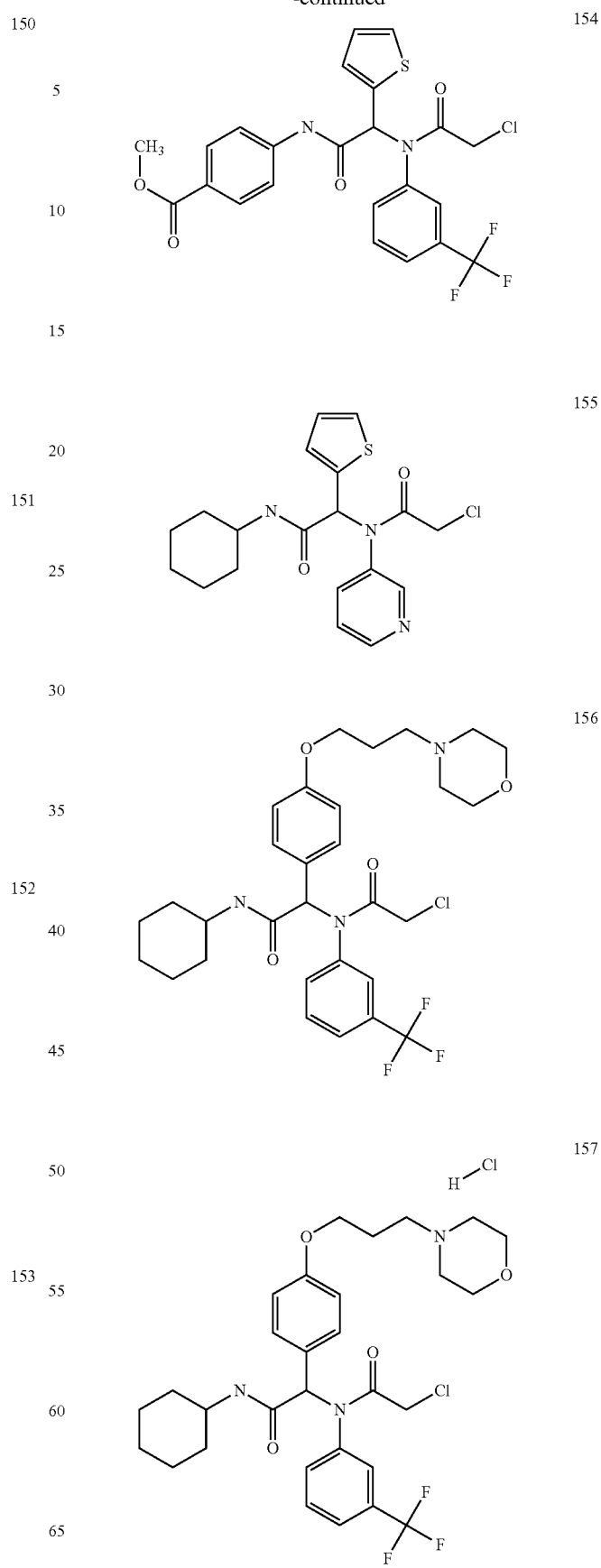

158
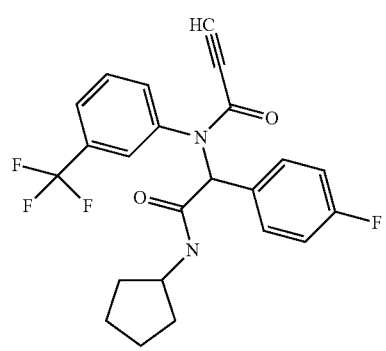
159
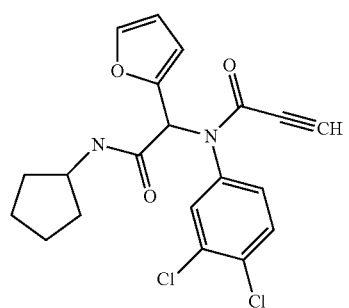
160
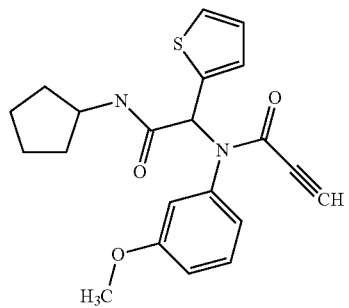
161
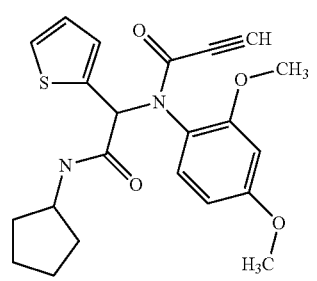
162
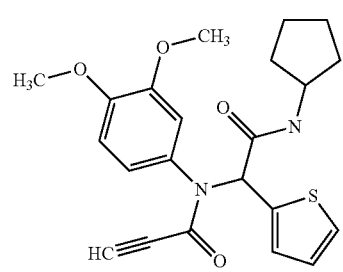
163
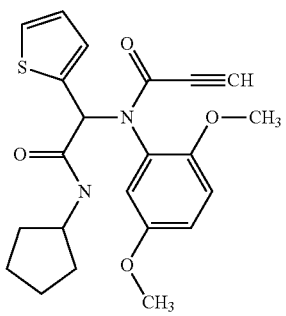
164
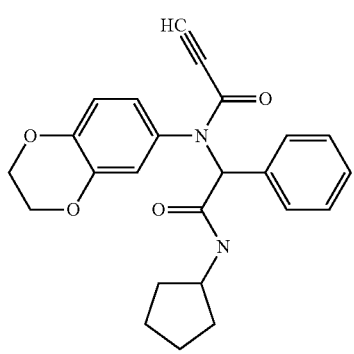
165
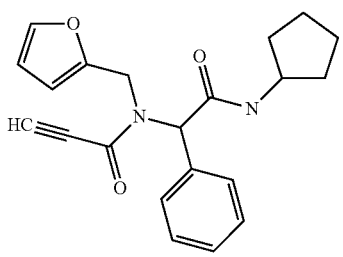
166
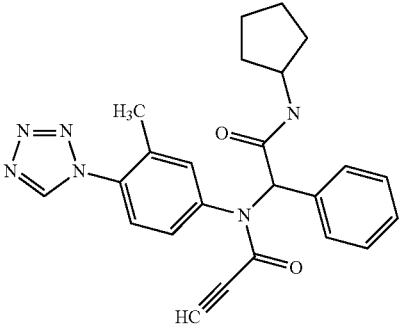
167
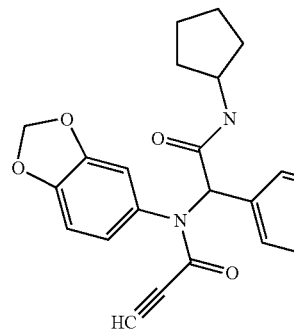

168 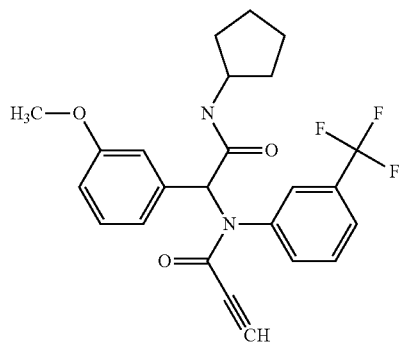
169 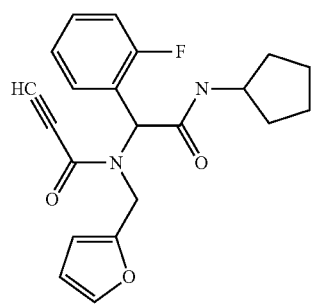
170 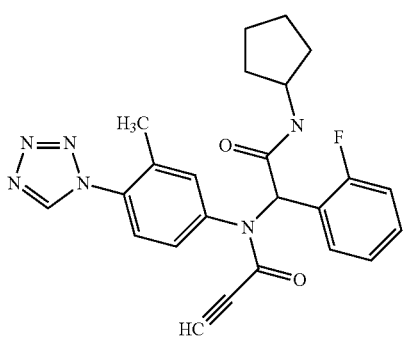
171 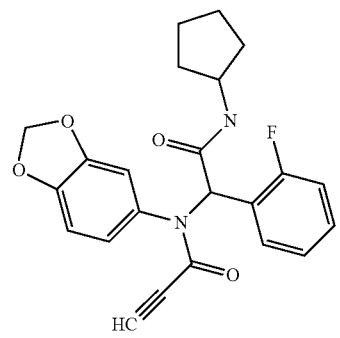
172 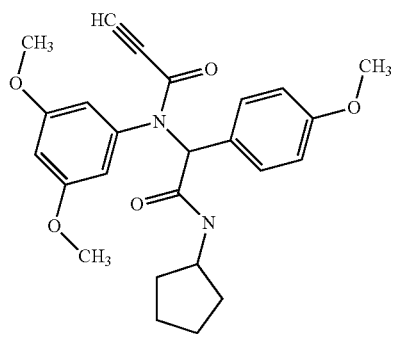
173 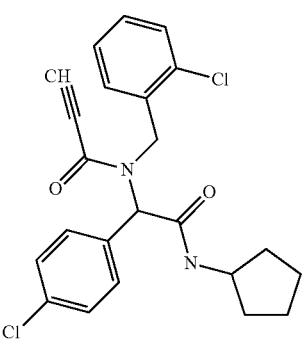
174 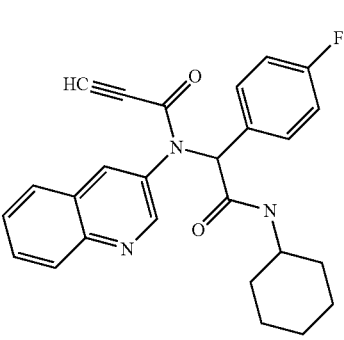
175 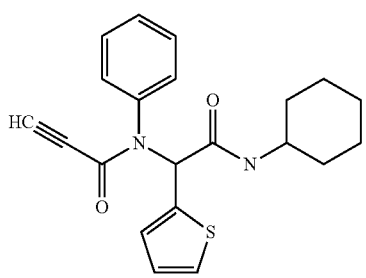
176 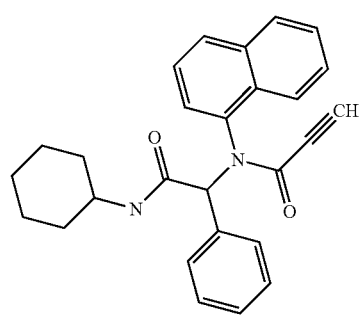
177 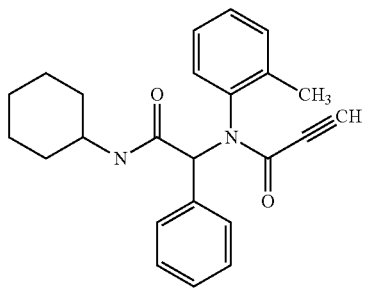

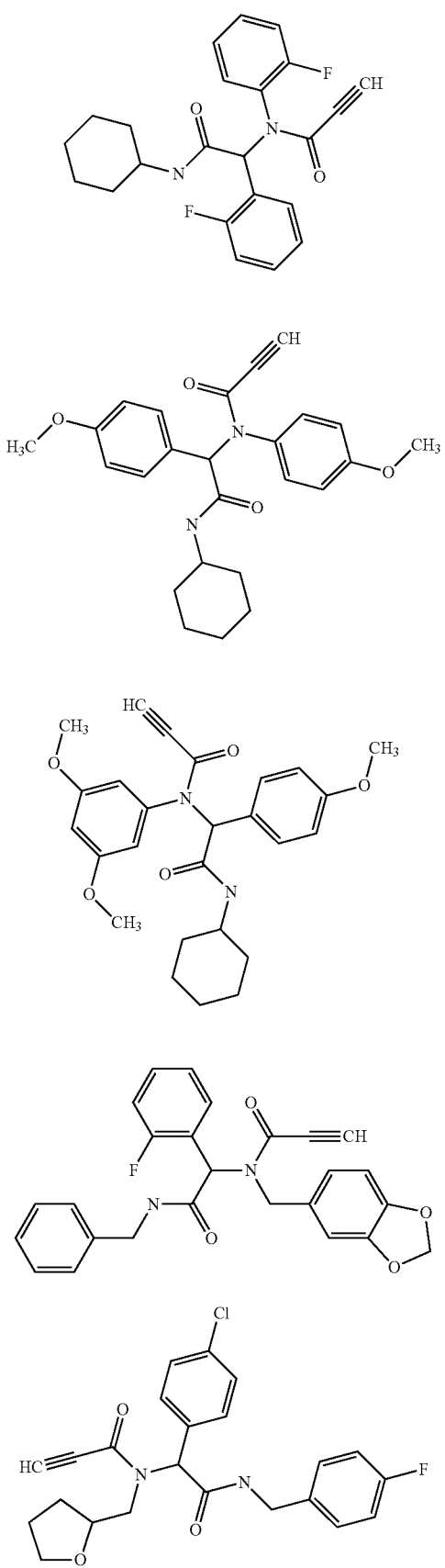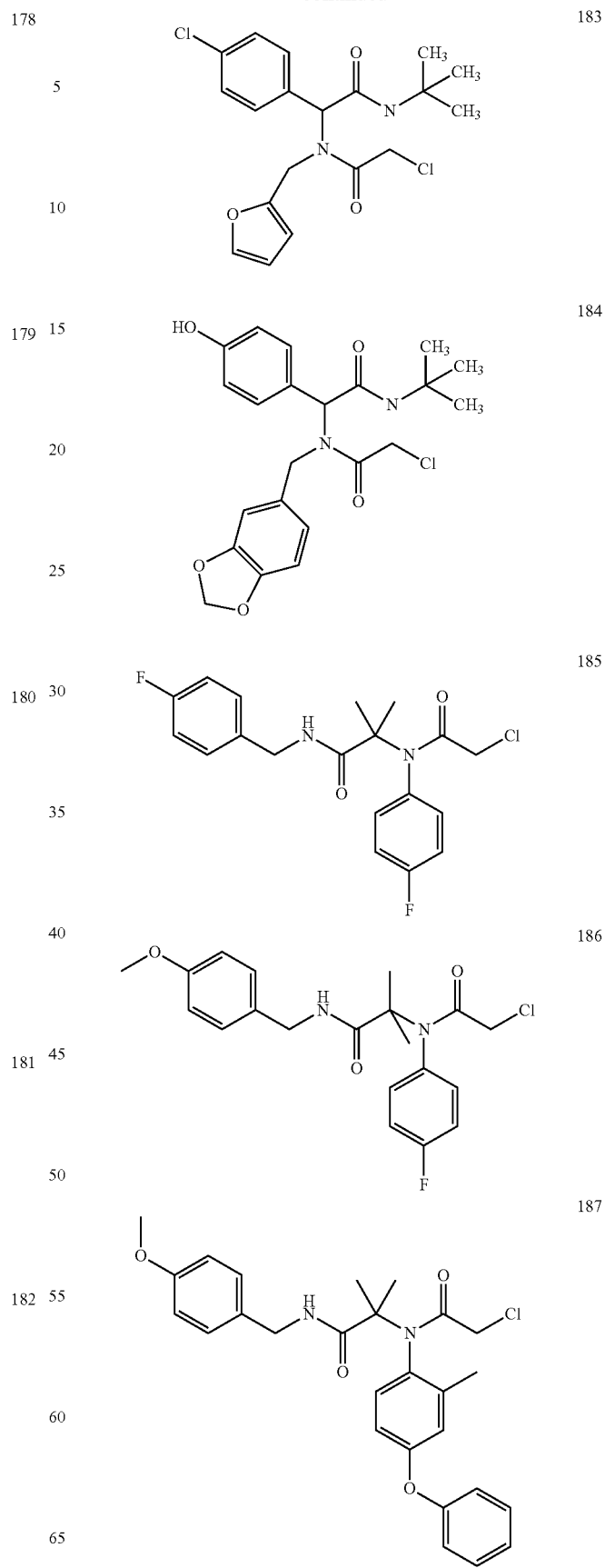

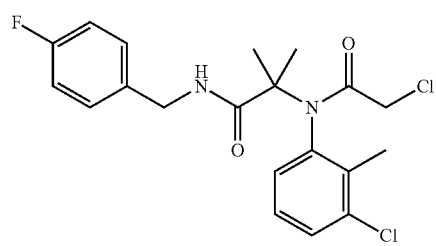
188
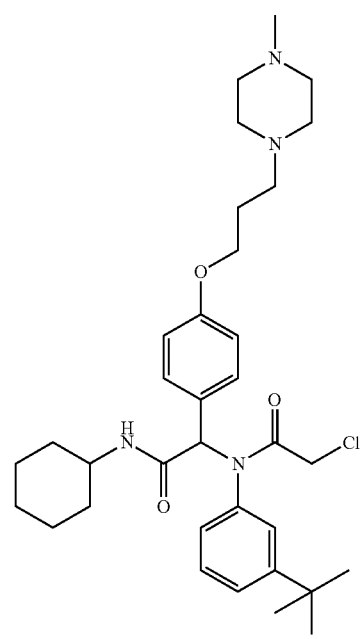
189
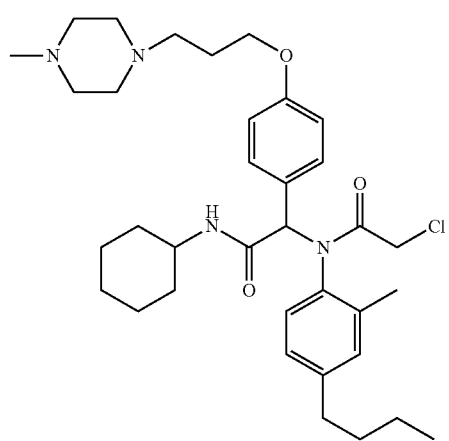
190
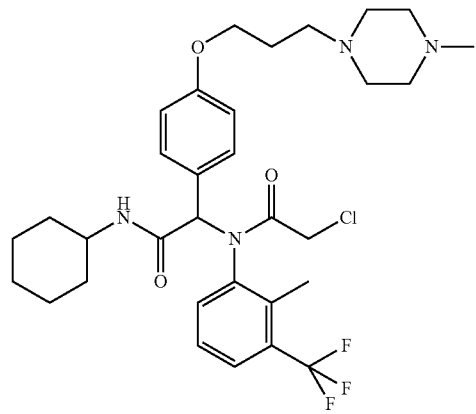
191
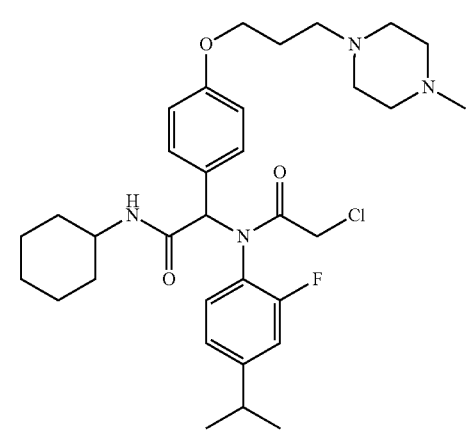
192
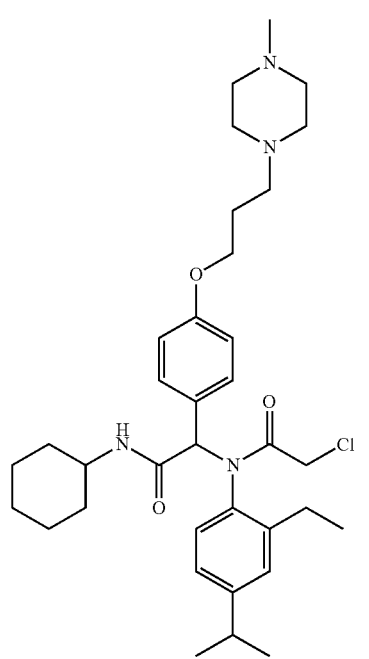
193

57
-continued
194
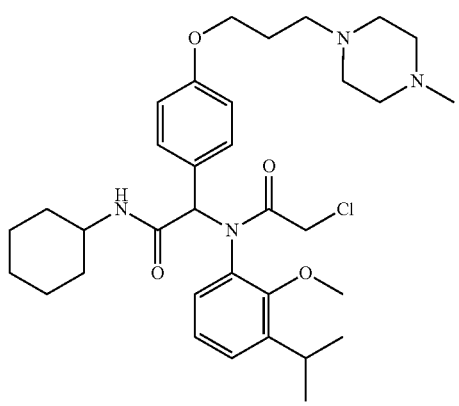
195
196
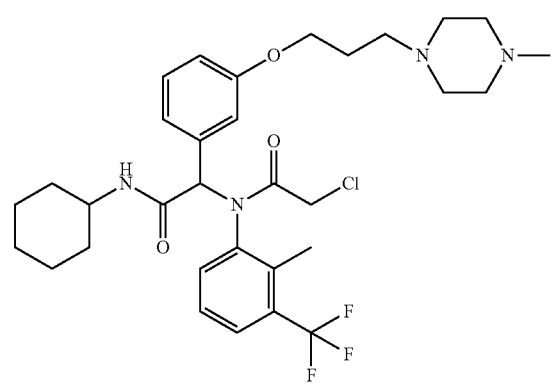
58
-continued
197
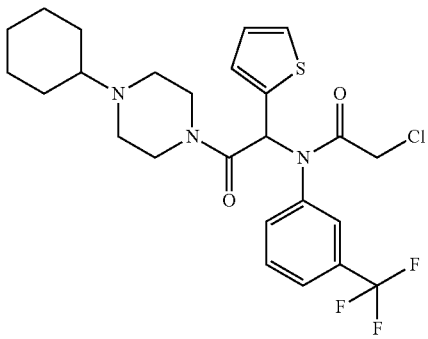
198
199
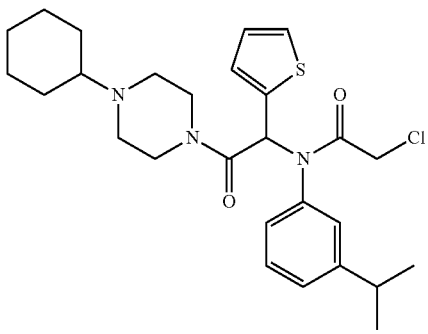
200
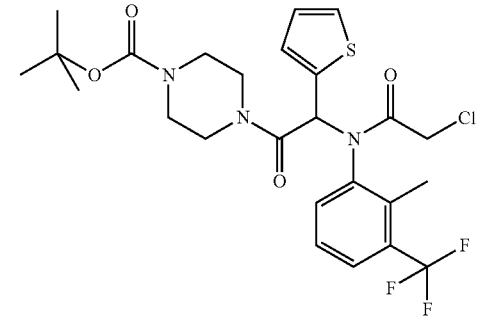

201

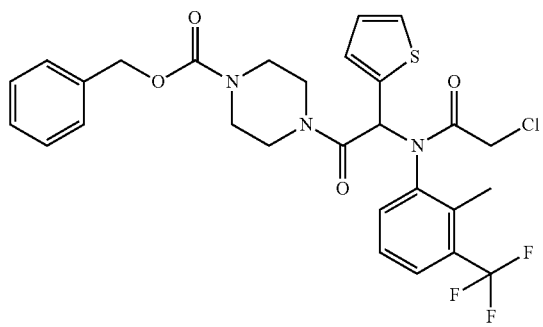

205

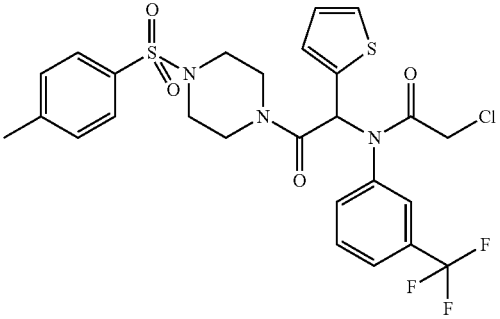

206

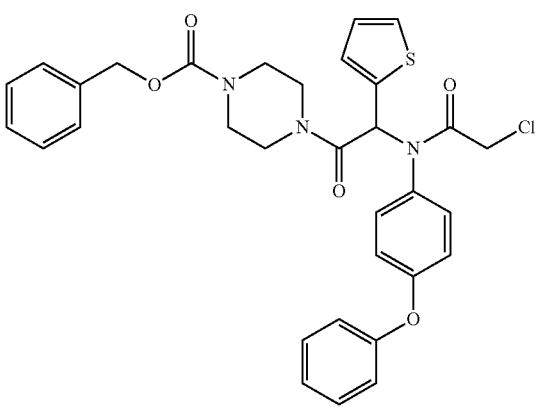

202

203

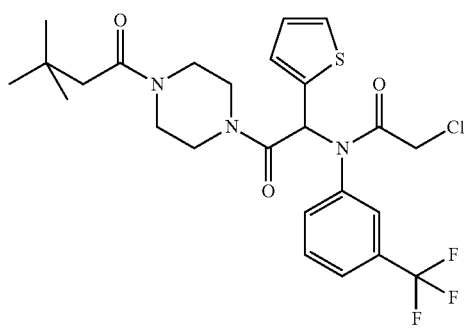

204

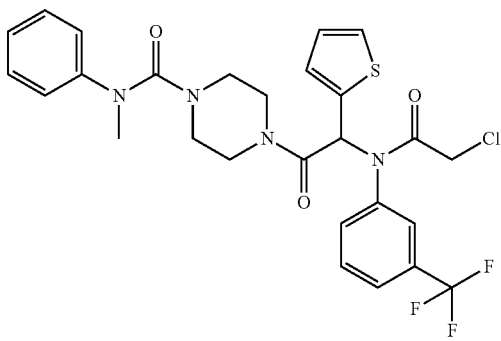

N.B. It should be noted that when nitrogen atoms present only 2 substituents on the above molecules, the 3$^{rd}$ substituent is, of course, a hydrogen atom.

The present invention also relates to the use of a compound of formula (I) as defined hereinbefore for the production of a medicament, in particular intended to treat or prevent a cancer, and in particular a cancer resistant to chemotherapy.

The present invention also relates to a method for the treatment or prevention of cancer comprising the administration of an effective quantity of a compound of formula (I) as defined hereinbefore to a patient In need thereof.

The present invention also concerns a pharmaceutical composition comprising at least one compound of formula (I) as defined hereinbefore, in association with one or more pharmaceutically acceptable excipients.

The compounds of formula (I) for which R6=—C≡CR$^{38}$ and R1 is an optionally substituted 1,3-thiazol-2-yl group will preferably be excluded from the pharmaceutical compositions not comprising another active principle, such as an anticancer agent.

In one particular embodiment, this composition may comprise at least one other active principle.

In particular, this/these active principle(s) may be anticancer agents conventionally used in the treatment of cancer. These anticancer agents may be selected in particular from cisplatin and the derivatives thereof such as carboplatin and oxaliplatin taxanes such as taxol, taxotere, paclitaxel and docetaxel vinca alkaloids such as vinblastine, vincristine and vinorelbine; purine analogues such as mercaptopurine, thioguanine, pentostatin and 2-chlorodeoxyadenosine; topoisomerase I inhibitors such as compounds of camptothecin, like irinotecan and topotecan topoisomerase II inhibitors such as epipodophyllotoxin, podophyllotoxin and the derivatives thereof like etoposide and teniposide; antitumoural nucleoside derivatives such as 5-fluorouracil, leucovorin, gemcitabine or capecitabine; alkylating agents such as nitrogen mustards like cyclophosphamide, mechlorethamine, chlorambucil and melphalan, nitrosoureas like carmustine, lomustine and streptozocin, alkyl sulphonates like busulphan, ethyleneimines and methylmelamines like thiotepa and hexamethylmelamine, and tetrazines like dacarbazine; antitumoural anthracycline derivatives such as daunorubicin, adriamycin, doxil, idarubicin and mitoxantrone; molecules targeting the IGF-I receptor such as picropodophyllin; tetracarcin derivatives such as tetrocarcin A; corticosteroids such as prednisone; antibodies such as trastuzumab (anti-HER2 antibody), rituximab (anti-CD20 antibody), gemtuzamab, cetuximab, pertuzumab and bevacizumab; selective oestrogen receptor antagonists or modulators such as tamoxifen, fulvestrant, toremifene, droloxifene, faslodex and raloxifene; aromatase inhibitors such as exemestane, anastrozole, letrozole and vorozole; differentiating agents such as retinoids like retinoic acid and vitamin D and retinoic acid metabolism blocking agents such as accutane; DNA methyltransferase inhibitors such as azacytidine and decitabine; antifolates such as disodium permetrexed; antibiotics such as antinomycin D, bleomycin, mitomycin C, actinomycin D, caminomycin, daunomycin and plicamycin; antimetabolites such as chlofarabine, aminopterin, cytosine arabinoside, floxuridine and methotrexate; apoptosis inducing agents and Bcl-2 inhibitor antiangiogenic agents such as YC 137, BH 312, ABT 737, gossypol, HA 14-1, TW 37 and decanoic acid; agents binding to tubulin such as combrestatin, colchicine derivatives and nocodazole; kinase inhibitors such as flavoperidol, imatinib mesylate, erlotinib and gefitinib; farnesyltransferase inhibitors such as tipifarnib; histone deacetylase inhibitors such as sodium butyrate, suberoylanilide hydroxamic acid, depsipeptide, NVP-LAQ824, R306465, JNJ-26481585 and trichostatin A; inhibitors of the ubiquitin proteasome system such as MLN 0.41, bortezomib and yondelis; and telomerase inhibitors such as telomestatin.

The compounds according to the invention can be administered orally, sublingually, parenterally, subcutaneously, intramuscularly, intravenously, transdermally, locally or rectally.

In the pharmaceutical compositions of the present invention for oral, sublingual, parenteral, subcutaneous, intramuscular, intravenous, transdermal, local or rectal administration, the active ingredient can be administered in unitary forms of administration, in a mixture with conventional pharmaceutical carriers, to animals or to human beings. Appropriate unitary forms of administration include forms to be administered orally such as tablets, capsules, powders, granules and oral solutions or suspensions, forms to be administered sublingually and buccally, forms to be administered parenterally, subcutaneously, intramuscularly, intravenously, intranasally or intraocularly and forms to be administered rectally.

During preparation of a solid composition in the form of tablets, the main active ingredient is mixed with a pharmaceutical vehicle such as gelatin, starch, lactose, magnesium stearate, talc, gum arabic or the like. Tablets made of sucrose or other suitable materials can be coated or else treated in such a way that they display prolonged or delayed activity and that they continuously release a predetermined quantity of active principle.

A capsule preparation is obtained by mixing the active ingredient with a diluent and by pouring the mixture obtained into soft or hard capsules.

A preparation in the form of a syrup or elixir can contain the active ingredient in conjunction with a sweetening agent, an antiseptic, and also a flavour-imparting agent and an appropriate dye.

Water-dispersible powders or granules can contain the active ingredient in a mixture with dispersing agents or wetting agents, or suspending agents, and also with taste modifiers or sweetening agents.

For rectal administration, use is made of suppositories prepared with binders which melt at rectal temperature, for example cocoa butter or polyethylene glycols.

For parenteral, intranasal or intraocular administration, use is made of aqueous suspensions, isotonic saline solutions or sterile and injectable solutions containing pharmacologically compatible dispersing agents and/or wetting agents.

The active principle can also be formulated in the form of microcapsules, optionally with one or more additive carriers.

The compounds of the invention can be used at doses of between 0.01 mg and 1,000 mg per day, given in a single dose once per day or administered in a plurality of doses over the course of the day, for example twice per day in equal doses. The daily administered dose is advantageously comprised between 5 mg and 500 mg, even more advantageously between 10 mg and 200 mg. It may be necessary to use doses outside these ranges; a person skilled in the art will be able to take account of this himself.

The present invention also concerns a pharmaceutical composition comprising:

(i) at least one compound of formula (I) as defined hereinbefore, and (ii) at least one other active principle, as combination products for use simultaneously, separately or spread over time.

Indeed, it is common to treat cancer by double or triple therapy. It may be useful especially to combine the molecules of the invention with one or more anticancer compounds, thus allowing the treatment of cancer, on the one hand, and the prevention of the appearance of resistant cancer cells, on the other hand.

In particular, this/these active principle(s) may be anticancer agents used conventionally in the treatment of cancer. These anticancer agents may be selected in particular from cisplatin and the derivatives thereof such as carboplatin and oxaliplatin; taxanes such as taxol, taxotere, paclitaxel and docetaxel; vinca alkaloids such as vinblastine, vincristine and vinorelbine; purine analogues such as mercaptopurine, thioguanine, pentostatin and 2-chlorodeoxyadenosine; topoisomerase I inhibitors such as compounds of camptothecin, like irinotecan and topotecan; topoisomerase II inhibitors such as epipodophyllotoxin, podophyllotoxin and the derivatives thereof like etoposide and teniposide; antitumoural nucleoside derivatives such as 5-fluorouracil, leucovorin, gemcitabine or capecitabine; alkylating agents such as nitrogen mustards like cyclophosphamide, mechlorethamine, chlorambucil and melphalan, nitrosoureas like carmustine, lomustine and streptozocin, alkyl sulphonates like busulphan, ethyleneimines and methylmelamines like thiotepa and hexamethylmelamine, and tetrazines like dacarbazine antitumoural anthracycline derivatives such as daunorubicin, adriamycin, doxil, idarubicin and mitoxantrone; molecules targeting the IGF-I receptor such as picropodophyllin tetracarcin derivatives such as tetrocarcin A; corticosteroids such as prednisone; antibodies such as trastuzumab (anti-HER2 antibody), rituximab (anti-CD20 antibody), gemtuzamab, cetuximab, pertuzumab and bevacizumab; selective oestrogen receptor antagonists or modulators such as tamoxifen, fulvestrant, toremifene, droloxifene, faslodex and raloxifene; aromatase inhibitors such as exemestane, anastrozole, letrozole and vorozole; differentiating agents such as retinoids like retinoic acid and vitamin D and retinoic acid metabolism blocking agents such as accutane; DNA methyltransferase inhibitors such as azacytidine and decitabine; antifolates such as disodium permetrexed; antibiotics such as actinomycin D, bleomycin, mitomycin C, actinomycin D, caminomycin, daunomycin and plicamycin; antimetabolites such as chlofarabine, aminopterin, cytosine arabinoside, floxuridine and methotrexate; apoptosis inducing agents and Bcl-2 inhibitor antiangiogenic agents such as YC 137, BH 312, ABT 737, gossypol, HA 14-1, TW 37 and decanoic acid; agents binding to tubulin such as combrestatin, colchicine derivatives and nocodazole; kinase inhibitors such as flavoperidol, imatinib mesylate, erlotinib and gefitinib; farnesyltransferase inhibitors such as tipifarnib; histone deacetylase inhibitors such as sodium butyrate, suberoylanilide hydroxamic acid, depsipeptide, NVP-LAQ824, R306465, JNJ-26481585 and trichostatin A; inhibitors of the ubiquitin proteasome system such as MLN 0.41, bortezomib and yondelis; and telomerase inhibitors such as telomestatin.

The present invention also concerns a pharmaceutical composition as defined hereinbefore, for use thereof as a medicament intended to treat or to prevent cancer, in particular a cancer which is resistant to chemotherapy.

The present invention also relates to the use of a pharmaceutical composition comprising:
(i) at least one compound of formula (I) as defined hereinbefore,
(ii) at least one other active principle, and in particular the active principle(s) cited hereinbefore,
as combination products for use simultaneously, separately or spread over time, for the production of a medicament intended to treat cancer, and in particular a cancer resistant to chemotherapy.

The present invention also relates to a process for preparing a compound of formula (I) as defined hereinbefore for which R2 represents a hydrogen atom, according to the following steps:
  reacting a ketone of formula R3-CO—R4 with an amine of formula R5-NH$_2$, a carboxylic acid of formula R6-COOH and an isonitrile of formula R1-NC, R1, R3, R4, R5 and R6 being as defined hereinbefore, to produce the compound of formula (I), and
  separating the compound of formula (I) obtained in the preceding step from the reaction medium.

The first step of this process corresponds to a multicomponent reaction known as an Ugi reaction (U-4MCRs), the conditions for the implementation of which are well known to a person skilled in the art.

Each of the four reagents used for this reaction (ketone, amine, carboxylic acid and isonitrile) can be either commercially available or prepared using organic synthesis methods well known to a person skilled in the art.

Advantageously, the four reagents are introduced in the following order: ketone, amine, carboxylic acid and isonitrile.

Advantageously, the reaction is carried out in methanol as a solvent, and advantageously at ambient temperature.

The ketone used will be an aldehyde where R3 represents a hydrogen atom.

Moreover, additional protection/deprotection and/or molecule functionalisation steps, well known to a person skilled in the art, are conceivable in the preceding process for the preparation of compounds of formula (I).

Other processes for the preparation of the compounds of the invention may be used as described below in examples 2 to 5.

The present invention also concerns compounds of general formula (I):

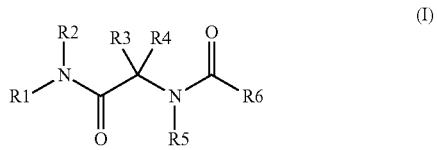

as well as the pharmaceutically acceptable salts thereof, the isomers or isomer mixtures thereof in all proportions, in particular an enantiomer mixture, and especially a racemic mixture,
for which R1, R2, R3, R4, R5 and R6 are as defined hereinbefore,
provided that:
  if R1 represents a cyclopentyl or cyclohexyl group or a benzyl group optionally substituted by a fluorine atom, R2 and R3 represent a hydrogen atom and R6 represents a —C≡CH group, then R4 does not represent a thiophenyl, furyl or furylmethyl group or a phenyl group optionally substituted by a fluorine atom, a chlorine atom or a methoxy group, and
  if R1 represents a tert-butyl group, R2 and R3 represent a hydrogen atom, R4 represents a phenyl group substituted by a chlorine atom or an OH group and R6 represents a —CH$_2$Cl group, then R5 does not represent a furylmethyl or 1,3-benzodioxolylmethyl group.

Compounds 3 and 158 to 184 of the present invention are in fact commercially available from Asinex.

The subject of the present invention is more particularly compounds of the general formula (I):

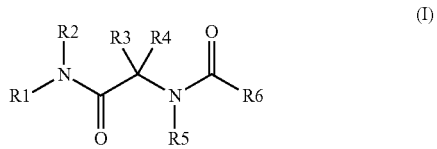

as well as the pharmaceutically acceptable salts thereof, the isomers or isomer mixtures thereof in all proportions, in particular an enantiomer mixture, and especially a racemic mixture,
for which R1, R2, R3, R4, R5 and R6 are as defined hereinbefore,
provided that:
  if R6=—C≡CR$^{38}$ with R$^{38}$ as defined hereinbefore,
then R1 does not represent an optionally substituted 1,3-thiazol-2-yl group,
  if R1 represents a cyclopentyl or cyclohexyl or a benzyl group optionally substituted by a fluorine atom, R2 and R3 represent a hydrogen atom and R6 represents a —C≡CH group,
then R4 does not represent a thiophenyl or furyl group or a phenyl group optionally substituted by a fluorine atom, a chlorine atom or a methoxy group,
  if when R1 represents a hydrogen atom, a tort-butyl, sec-butyl, cyclohexyl, hexyl, ethyl or methyl group, or a phenyl group optionally substituted by one or more groups selected from F, ethoxy and CF$_3$, R2 represents a hydrogen atom or a methyl group, or R1 and R2 together form, with the nitrogen atom carrying them, a morpholine or piperidine group, R3 represents a hydrogen atom, and R4 represents a hydrogen atom, a methyl or ethyl group, or a phenyl group optionally substituted by one or more groups selected from Cl, OH, methoxy, $NO_2$ or $NMe_2$, or R3 and R4 together form, with the carbon atom carrying them, a cyclopentane or a cyclohexane, and R6 represents a —$CH_2Cl$ group, then R5 does not represent a prop-2-yne, $(C_1-C_8)$alkyl, furylmethyl, tetrahydropyrane, thiopyrane ou 1,3-benzodioxolylmethyl group; or a benzyl group optionally substituted by a chlorine atom or $NO_2$; or a phenyl group optionally substituted by one or more Br, ethyl or methyl groups, and if R1 represents a tert-butyl or benzyl group, R2 and R3 each represent a hydrogen atom, R4 represents a furyl or pyrrole group substituted on the nitrogen atom by a —$SO_2Me$ group, and R6 represents a —C≡CMe or —C≡CPh group, then R5 does not represent a tert-butyl group or a benzyl group optionally substituted by a bromine atom or a phenyl.

Derivates of formula (I) are in fact described, without any biological activity not being reported elsewhere, in: WO 008/008 022, U.S. Pat. No. 4,944,796, U.S. Pat. No. 4,205,168, Neo et al. *Tetrahedron Lett.* 2005, 7977-7979 and Wright et al. *Tetrahedron Lett.* 2002, 943-946.

Subject to the same limitations as set out hereinbefore, the compounds of the invention will be advantageously characterised as follows.

When the NR1R2 group represents a heteroaryl or heterocycle, it is of course possible for said cycle to comprise one or more other heteroatoms, preferably zero or one another, heteroatom(s) in addition to the nitrogen atom carrying R1 and R2 which is already present, said heteroaryl or heterocycle advantageously having 5 to 6 members. Said heteroatom will therefore be advantageously selected from O, S and N, and preferably from O and N. Advantageously, it will be a piperidine, morpholine or piperazine group, and preferably piperazine.

The same comment also applies to the groups $NR^{19}R^{20}$ and $NR^{85}R^{86}$, when they form heterocycles.

Advantageously, R1 does not represent a hydrogen atom.
Advantageously, R1 and/or R4 do(es) not represent a hydrogen atom.
Even more advantageously, R1 and R4 do not represent a hydrogen atom.

According to a particular embodiment of the invention, $R^1$:
represents a hydrogen atom or a $(C_1-C_6)$alkyl, $(C_3-C_{10})$cycloalkyl, $(C_3-C_{10})$cycloalkenyl, aryl, heteroaryl, aryl-$(C_1-C_6)$alkyl, heteroaryl-$(C_1-C_6)$alkyl group,
said group being optionally substituted by one or more groups selected from a halogen atom, a $(C_1-C_6)$alkoxy, —$NH_2$, —COOH, —CN, —OH, —$NR^7R^8$, —O—$(C_1-C_6)$alkyl-$NR^7R^8$, benzyloxy, —C(O)O—$(C_1-C_6)$alkyl, —NH—C(O)O—$(C_1-C_6)$alkyl, —C(O)$NH_2$, —C(O)$NR^9R^{10}$, —S—$(C_1-C_6)$alkyl, —S(O)—$(C_1-C_6)$alkyl, —$SO_2$—$(C_1-C_6)$alkyl, —$SO_2NH_2$, —$SO_2NR^{11}R^{12}$, —$NR^{13}SO_2R^{14}$ radical and a $(C_1-C_6)$alkyl group optionally substituted by one or more halogen atoms, or
forms, with R2 and the nitrogen atom carrying them, a 3 to 7-membered heterocycloalkyl, said heterocycloalkyl being optionally substituted by one or more groups selected from a halogen atom and a $(C_1-C_6)$alkyl group optionally substituted by one or more halogen atoms.

Advantageously, R1 represents a hydrogen atom or a $(C_1-C_6)$alkyl, aryl, heteroaryl, aryl-$(C_1-C_6)$alkyl, heteroaryl-$(C_1-C_6)$alkyl, $(C_1-C_{10})$cycloalkyl group, said group being optionally substituted by one or more groups selected from —$NH_2$, —COOH, benzyloxy, aryloxy, —C(O)O(($C_1-C_6$)alkyl), —NHC(O)O(($C_1-C_6$)alkyl).

Also advantageously, R1 represents a $(C_1-C_6)$alkyl, aryl, acyl-$(C_1-C_6)$alkyl, $(C_1-C_{10})$cycloalkyl group, said group being optionally substituted by one or more groups selected from —$NH_2$, —COOH, benzyloxy, aryloxy, —C(O)O(($C_1$-$C_6$)alkyl), —NHC(O)O(($C_1$-$C_6$)alkyl), and advantageously from benzyloxy and —C(O)O(($C_1$-$C_6$)alkyl).

Also advantageously, R1 represents a $(C_1-C_6)$alkyl group optionally substituted by a —C(O)O(($C_1$-$C_6$)alkyl) group; an aryl group optionally substituted by a —C(O)O(($C_1$-$C_6$)alkyl) or benzyloxy group; an aryl-$(C_1-C_6)$alkyl group; or a $(C_3-C_{10})$cycloalkyl group.

Even more advantageously, R1 represents a cyclohexyl, cyclopentyl, benzyl, —$C_6H_4$—C(O)OMe, —$C_6H_4$—OAr (with Ar=aryl), —$C_6H_4$—OBn, —$CH_2CH_2$—$CO_2Me$ or —$CH_2CH_2$—$CO_2tBu$ group.

Also advantageously, R1 represents a cyclohexyl, cyclopentyl or benzyl, and also advantageously cyclohexyl group.

In one particular embodiment, R2 represents a hydrogen atom.

According to a first preferred embodiment of the invention, R1 represents a $(C_3-C_{10})$cycloalkyl or aryl-$(C_1-C_6)$alkyl group, and preferably cyclohexyl, cyclopentyl or benzyl, said group being optionally substituted by one or more groups selected from a halogen atom, a $(C_1-C_6)$alkoxy, —$NH_2$, —COOH, —CN, —OH, —$NR^7R^8$, —O—$(C_1-C_6)$alkyl-$NR^7R^8$, benzyloxy, aryloxy, —C(O)O—$(C_1-C_6)$alkyl, —NH—C(O)O—$(C_1-C_6)$alkyl, —C(O)$NH_2$, —C(O)$NR^9R^{10}$, —S—$(C_1-C_6)$alkyl, —S(O)—$(C_1-C_6)$alkyl, —$SO_2$—$(C_1-C_6)$alkyl, —$SO_2NH_2$, —$SO_2NR^{11}R^{12}$, —$NR^{13}SO_2R^{14}$ radical and a $(C_1-C_6)$alkyl group optionally substituted by one or more groups selected from a halogen atom, a $(C_1-C_6)$alkoxy, —$NH_2$, —COOH, benzyloxy, aryloxy, —C(O)O(($C_1-C_6$)alkyl), —NHC(O)O(($C_1-C_6$)alkyl) group.

Advantageously, R1 represents a $(C_3-C_{10})$cycloalkyl or aryl-$(C_1-C_6)$alkyl group, preferably cyclohexyl, cyclopentyl or benzyl, said group being optionally substituted by one or more groups from a halogen atom, —OH and $(C_1-C_6)$alkoxy.

In this case, R1 advantageously represents a $(C_3-C_{10})$cycloalkyl group, and preferably cyclohexyl, preferably unsubstituted, and R2 advantageously represents a hydrogen atom.

According to a second preferred embodiment of the invention, R1 forms, with R2 and the nitrogen atom carrying them, a 3 to 7-membered heterocycle optionally substituted by one or more groups selected from a halogen atom, a $(C_3-C_{10})$cycloalkyl, $(C_3-C_{10})$cycloalkenyl, aryl, heteroaryl, aryl-$(C_1-C_6)$alkyl, heteroaryl-$(C_1-C_6)$alkyl, heterocycloalkyl-$(C_1-C_6)$alkyl, —OH, —$NH_2$, —C(O)OH, —C(O)$NH_2$, —C(S)$NH_2$, —$OR^{50}$, —OC(O)$R^{51}$, —C(O)$R^{52}$, —C(O)$OR^{53}$, —NHC(O)$R^{54}$, —NHC(O)$OR^{55}$, —$SO_2R^{56}$—$(C_1-C_6)$alkyl-C(O)$OR^{57}$, —$NR^{58}R^{59}$, —C(O)$NR^{60}R^{61}$, —C(O)N($R^{62}$)(aryl), C(O)N($R^{63}$)(heteroaryl), —C(O)NHN$R^{64}R^{65}$, —C(S)$NR^{66}R^{67}$, —C(S)N($R^{68}$)(aryl), —C(S)N($R^{69}$)(heteroaryl), —C(S)NHN$R^{76}R^{71}$, —OC(O)—$NR^{72}R^{73}$, —$(C_1-C_6)$alkyl-C(O)—$NR^{74}R^{75}$, —$(C_1-C_6)$alkyl-$NR^{103}$—C(O)—$OR^{104}$, —$(C_1-C_6)$alkyl-$NR^{76}R^{77}$, —C(NO$R^{78}$)-aryl radical, and a $(C_1-C_6)$alkyl group optionally substituted by one or more halogen atoms,
the aryl and heteroaryl unit of said radical, when present, being optionally substituted by one or more groups selected from a halogen atom, a —CN, —OH, $(C_1-C_6)$alkyl, $(C_1-C_6)$alkoxy, —$NR^{79}R^{80}$, —$(C_1-C_6)$alkyl-$NR^{81}R^{82}$ and —O—$(C_1-C_6)$alkyl-$NR^{83}R^{84}$ group.

In this case the heterocycle will advantageously be 5 or 6-membered and preferably saturated. It will advantageously be piperazine.

Thus, —NR1R2 will advantageously represent the following piperazine cycle:

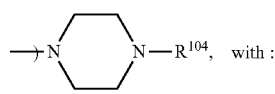 with:

$R^{104}$ representing a hydrogen atom, a $(C_3-C_{10})$cycloalkyl, $(C_3-C_{10})$cycloalkenyl, aryl, heteroaryl, aryl-$(C_1-C_6)$alkyl, heteroaryl-$(C_1-C_6)$alkyl, heterocycloalkyl-$(C_1-C_6)$alkyl, —C(O)$R^{52}$, —C(O)O$R^{53}$, —C(O)OH, —C(O)NH$_2$, —C(S)NH$_2$, —C(O)N$R^{60}R^{61}$, —C(S)N$R^{66}R^{67}$, —SO$_2R^{56}$, —C(O)NHN$R^{64}R^{65}$, —C(S)NHN$R^{70}R^{71}$ radical, and a $(C_1-C_6)$alkyl group optionally substituted by one or more halogen atoms, the aryl and heteroaryl unit of said radical, when present, being optionally substituted with one or more groups selected from a halogen atom, a —CN, —OH, $(C_1-C_6)$alkoxy, —N$R^{79}R^{80}$, and —O—$(C_1-C_6)$alkyl-N$R^{83}R^{84}$ group.

Advantageously, $R^{104}$ represents a $(C_3-C_{10})$cycloalkyl, aryl-$(C_1-C_6)$alkyl, heteroaryl-$(C_1-C_6)$alkyl, —C(O)$R^{52}$, —C(O)O$R^{53}$, —C(O)NH$_2$, —C(O)N$R^{60}R^{61}$, —SO$_2R^{56}$ or —C(O)NHN$R^{64}R^{65}$ group, and preferably a represents a $(C_3-C_{10})$cycloalkyl, aryl-$(C_1-C_6)$alkyl, heteroaryl-$(C_1-C_6)$alkyl, —C(O)$R^{52}$, —C(O)O$R^{53}$, —C(O)N$R^{60}R^{61}$ or —SO$_2R^{56}$ group.

According to a particular embodiment of the invention, R4:
represents a hydrogen atom or a $(C_1-C_6)$alkyl, $(C_3-C_{10})$ cycloalkyl, aryl advantageously phenyl, or heteroaryl, advantageously thiophenyl, group, said group being optionally substituted by one or more groups selected from a halogen atom, a —C(CF$_3)_2$OH, —CN, —NH$_2$, —OPO$_3$H$_2$, —N$R^{17}R^{18}$, —NO$_2$, —COOH, —OH, —O—$(C_1-C_6)$alkyl-O—$(C_1-C_6)$alkyl, —O$(C_1-C_6)$alkyl-N$R^{19}R^{20}$ (with $R^{19}$ and $R^{20}$ each representing a $(C_1-C_6)$alkyl), benzyloxy, —C(O)O—$(C_1-C_6)$alkyl, —NHC(O)O—$(C_1-C_6)$alkyl, —C(O)NH$_2$, —C(O)N$R^{21}R^{22}$, —S—$(C_1-C_6)$alkyl, —S(O)—$(C_1-C_6)$alkyl, —SO$_2$—$(C_1-C_6)$alkyl, —SO$_2$NH$_2$, —SO$_2$N$R^{23}R^{24}$, —N$R^{25}$SO$_2R^{26}$ group, a 3 to 7-membered heterocycloalkyl, aryloxy radical, a $(C_1-C_6)$alkyl optionally substituted by one or more halogen atoms, and a $(C_1-C_6)$alkoxy optionally substituted by one or more fluorine atoms, and said group, when it is an aryl or heteroaryl, being optionally fused to a 5 or 6-membered heterocycle, or forms, with R3 and the carbon carrying them, a ring selected from a $(C_1-C_{10})$cycloalkyl and a 3 to 7-membered heterocycloalkyl, said cycle being optionally substituted by a $(C_1-C_6)$alkyl, —C(O)—$(C_1-C_6)$alkyl, —C(O)O—$(C_1-C_6)$alkyl group.

Advantageously, R3 represents a hydrogen atom or a methyl, and advantageously a hydrogen atom, and R4 represents a hydrogen atom or a $(C_1-C_6)$alkyl, aryl, advantageously phenyl, or heteroaryl, advantageously thiophenyl, group, said group being optionally substituted by one or more groups selected from a halogen atom, a —CF$_3$, —B(OH)$_2$, —CN, —OH, —N$R^{17}R^{18}$ ($R^{17}$ and $R^{18}$ being as defined hereinbefore), —NO$_2$, —COOH, 3 to 7-membered heterocycloalkyl, $(C_1-C_6)$alkyl, —S—$(C_1-C_6)$alkyl, aryloxy radical and a $(C_1-C_6)$alkoxy optionally substituted by one or more fluorine atoms, and said group, if it is an aryl or heteroaryl, being optionally fused to a 5 or 6-membered heterocycle, or R3 and R4 form with the carbon carrying them a ring selected from a $(C_3-C_{10})$cycloalkyl and a 3 to 7-membered heterocycloalkyl, said ring being optionally substituted by a —C(O)O($(C_1-C_6)$alkyl group).

Also advantageously, R3 represents a hydrogen atom or a methyl, and advantageously a hydrogen atom, and R4 represents a hydrogen atom or an aryl, advantageously phenyl, or heteroaryl, advantageously thiophenyl group, said group being optionally substituted by one or more groups selected from a halogen atom, a —CF$_3$, —B(OH)$_2$, —CN, —OH, —N$R^{17}R^{18}$, —NO$_2$, —COOH, 3 to 7-membered heterocycloalkyl, $(C_1-C_6)$alkyl, —S—$(C_1-C_6)$alkyl, aryloxy radical and a $(C_1-C_6)$alkoxy optionally substituted by one or more fluorine atoms, and said group being optionally fused to a 5 or 6-membered heterocycle, or R3 and R4 form with the carbon carrying them a ring selected from a $(C_3-C_{10})$cycloalkyl and a 3 to 7-membered heterocycloalkyl, advantageously a 3 to 7-membered heterocycloalkyl, said ring being optionally substituted by a —C(O)O($(C_1-C_6)$alkyl) group, $R^{17}$ and $R^{18}$ being as defined hereinbefore.

Advantageously, R3 represents a hydrogen atom or a methyl, and advantageously a hydrogen atom, and R4 represents a hydrogen atom or an aryl, advantageously phenyl, or heteroaryl, advantageously thiophenyl group, said group being optionally substituted by one or more groups selected from a halogen atom, a —CF$_3$, —B(OH)$_2$, —CN, —OH, —N$R^{17}R^{18}$, —NO$_2$, —COOH, 3 to 7-membered heterocycloalkyl, $(C_1-C_6)$alkyl, —S—$(C_1-C_6)$alkyl, aryloxy radical and a $(C_1-C_6)$alkoxy optionally substituted by one or more fluorine atoms, and said group being optionally fused to a 5 or 6-membered heterocycle, $R^{17}$ and $R^{18}$ being as defined hereinbefore.

Advantageously, R3 represents a hydrogen atom or a methyl, and advantageously a hydrogen atom, and R4 represents a hydrogen atom; a heteroaryl, preferably thiophenyl, group optionally substituted by a $(C_1-C_6)$alkyl group; or an aryl, preferably phenyl, group optionally fused to a 5 or 6-membered heterocycle comprising preferably two oxygen atoms, and optionally substituted by one or more groups selected from a halogen atom and a —CN, —N$R^{17}R^{18}$, —NO$_2$, $(C_1-C_6)$alkyl, $(C_1-C_6)$alkoxy, $(C_5-C_6)$heterocycloalkyl, —S—$(C_1-C_6)$alkyl and aryloxy group, or R3 and R4 form with the carbon carrying them a $(C_5-C_6)$ cycloalkyl or 5 or 6-membered heterocycloalkyl ring, advantageously a 5 or 6-membered heterocycloalkyl, said ring being optionally substituted by a —C(O)O($(C_1-C_6)$alkyl) group, $R^{17}$ and $R^{18}$ being as defined hereinbefore.

Advantageously, R3 represents a hydrogen atom or a methyl, and advantageously a hydrogen atom, and R4 represents a hydrogen atom; or a heteroaryl, preferably, thiophenyl, group optionally substituted by a $(C_1-C_6)$alkyl group; or an aryl, preferably phenyl, group optionally fused to a 5 or 6-membered heterocycle comprising preferably two oxygen atoms, and optionally substituted by one or more groups selected from a halogen atom and a —CN, —N$R^{17}R^{18}$, —NO$_2$, $(C_1-C_6)$alkyl, $(C_1-C_6)$alkoxy, $(C_5-C_6)$heterocycloalkyl, —S—$(C_1-C_6)$alkyl and aryloxy group, $R^{17}$ and $R^{18}$ being as defined hereinbefore.

Even more advantageously, R4 does not represent a hydrogen atom.

Advantageously, R3 represents a hydrogen atom or a methyl, and advantageously a hydrogen atom.

Also advantageously, R3 represents a hydrogen atom or a methyl, and advantageously a hydrogen atom, and R4 represents a thiophenyl group optionally substituted by a methyl, a 1,3-benzodioxolyl group or a phenyl group optionally substituted by one or more groups selected from a halogen atom and a —CN, —NR$^{17}$R$^{18}$, preferably —NMe$_2$, —NO$_2$, (C$_1$-C$_6$)alkyl, preferably methyl or isopropyl, (C$_1$-C$_6$)alkoxy, preferably methoxy, pyrrolidinyl, —S—(C$_1$-C$_6$)alkyl, preferably thiomethoxy, and phenoxy group, or R3 and R4 form with the carbon carrying them a ring of formula

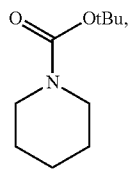

R$^{17}$ and R$^{18}$ being as defined hereinbefore.

Also advantageously, R3 represents a hydrogen atom or a methyl, and advantageously a hydrogen atom, and R4 represents a thiophenyl group optionally substituted by a methyl; a 1,3-benzodioxolyl group; or a phenyl group optionally substituted by one or more groups selected from a halogen atom and a —CN, —NR$^{17}$R$^{18}$, preferably —NMe$_2$, —NO$_2$, (C$_1$-C$_6$)alkyl, preferably methyl or isopropyl, (C$_1$-C$_6$)alkoxy, preferably methoxy, pyrrolidinyl, —S—(C$_1$-C$_6$)alkyl, preferably thiomethoxy, and phenoxy group, R$^7$ and R$^8$ being as defined hereinbefore.

Also advantageously, R3 represents a hydrogen atom or a methyl, and advantageously a hydrogen atom, and R4 represents a thiophenyl, advantageously thiophen-2-yl group.

According to a first preferred embodiment of the invention, R3 and R4 each represent, independently of each other, a (C$_1$-C$_6$)alkyl group, such as methyl.

According to a second preferred embodiment of the invention, R3 represents a hydrogen atom, and R4 represents an aryl, advantageously phenyl or heteroaryl, advantageously thiophenyl, group, said group being optionally substituted by one or more groups selected from a halogen atom, a —C(CF$_3$)$_2$OH, —CN, —NH$_2$, —OPO$_3$H$_2$, —NR$^{17}$R$^{18}$, —NO$_2$, —COOH, —OH, —O(C$_1$-C$_6$)alkyl-OPO$_3$H$_2$, —O—(C$_1$-C$_6$)alkyl-O—(C$_1$-C$_6$)alkyl, —O(C$_1$-C$_6$)alkyl-NR$^{19}$R$^{20}$, —NR$^{81}$(C$_1$-C$_6$)alkyl-NR$^{85}$R$^{86}$, benzyloxy, —C(O)O—(C$_1$-C$_6$)alkyl, NHC(O)O—(C$_1$-C$_6$)alkyl, —C(O)NH$_2$, —C(O)NR$^{21}$R$^{22}$, —S—(C$_1$-C$_6$)alkyl, —S(O)—(C$_1$-C$_6$)alkyl, —SO$_2$—(C$_1$-C$_6$)alkyl, —SO$_2$NH$_2$, —SO$_2$NR$^{23}$R$^{24}$, NR$^{25}$SO$_2$R$^{26}$, 3 to 7-membered heterocycloalkyl, aryloxy radical, a (C$_1$-C$_6$)alkyl optionally substituted by one or more halogen atoms, and a (C$_1$-C$_6$)alkoxy optionally substituted by one or more fluorine atoms, and said group being optionally fused to a 5 or 6-membered heterocycle.

In this case, R4 advantageously represents an aryl, advantageously phenyl, or heteroaryl, advantageously thiophenyl, group, said group being optionally substituted by one or more groups selected from a halogen atom, a —CF$_3$, —B(OH)$_2$, —CN, —OH, —NR$^{17}$R$^{18}$ (R$^{17}$ and R$^{18}$ being as defined above), —NO$_2$, —COOH, 3 to 7-membered heterocycloalkyl, (C$_1$-C$_6$)alkyl, —S—(C$_1$-C$_6$)alkyl, aryloxy, —O(C$_1$-C$_6$)alkyl-NR$^{19}$R$^{20}$ radical and a (C$_1$-C$_6$)alkoxy optionally substituted by one or more fluorine atoms, and said group being optionally fused to a 5 or 6-membered heterocycle R4 preferably represents an unsubstituted thiophenyl group, preferably thiophen-2-yl; or a phenyl group optionally substituted by one or more groups selected from a halogen atom and a —CF$_3$, —B(OH)$_2$, —CN, —OH, —NR$^{17}$R$^{18}$ group (R$^{17}$ and R$^{18}$ being as defined above), —NO$_2$, —COOH, 3 to 7-membered heterocycloalkyl, (C$_1$-C$_6$)alkyl, —S—(C$_1$-C$_6$)alkyl, aryloxy, —O(C$_1$-C$_6$)alkyl-NR$^{19}$R$^{20}$ radical and a (C$_1$-C$_6$)alkoxy optionally substituted by one or more fluorine atoms, and optionally fused to

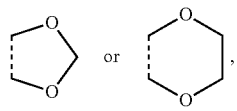

the bond shown as a dotted line representing the bond common with phenyl.

Advantageously, R5 represents a (C$_1$-C$_6$)alkyl, aryl, heteroaryl, aryl-(C$_1$-C$_6$)alkyl, heteroaryl-(C$_1$-C$_6$)alkyl, (C$_3$-C$_{10}$)cycloalkyl-(C$_1$-C$_6$)alkyl, (3 to 7-membered heterocycloalkyl)-(C$_1$-C$_6$)alkyl group, said group being optionally substituted by one or more groups selected from a halogen atom, a —CF$_3$, —CN, —OH, —NR$^{29}$R$^{30}$, —NO$_2$, —C(CF$_3$)$_2$OH, (C$_1$-C$_6$)alkoxy, aryloxy, —S—(C$_1$-C$_6$)alkyl, —C(O)O((C$_1$-C$_6$)alkyl), (C$_2$-C$_6$)alkynyl, aryl, heteroaryl, (C$_1$-C$_6$)alkyl-heteroaryl, 3 to 7-membered heterocycloalkyl, (3 to 7-membered heterocycloalkyl)-(C$_1$-C$_6$)alkoxy radical and a (C$_1$-C$_6$)alkyl optionally substituted by one or more fluorine atoms, and the aryl or heteroaryl core of said group, when present, being optionally fused to a 5 or 6-membered heterocycle, R$^{29}$ and R$^{30}$ being as defined hereinbefore.

Also advantageously, R5 represents a (C$_1$-C$_6$)alkyl, heteroaryl, (C$_1$-C$_{10}$)cycloalkyl-(C$_1$-C$_6$)alkyl, aryl-(C$_1$-C$_6$)alkyl, or aryl group, the aryl core of the aryl or aryl-(C$_1$-C$_6$)alkyl group being optionally fused to a 5 or 6-membered heterocycle, comprising preferably two oxygen atoms, and being optionally substituted by one or more groups selected from a halogen atom, a —CF$_1$, —CN, —OH, —NR$^{29}$R$^{30}$, —NO$_2$, —C(CF$_3$)$_2$OH, (C$_1$-C$_6$)alkoxy, aryloxy, —S—(C$_1$-C$_6$)alkyl, —C(O)O((C$_1$-C$_6$)alkyl), (C$_2$-C$_6$)alkynyl, aryl, heteroaryl, (C$_1$-C$_6$)alkylheteroaryl, 3 to 7-membered heterocycloalkyl, (3 to 7-membered heterocycloalkyl)-(C$_1$-C$_6$)alkoxy radical, and a (C$_1$-C$_6$)alkyl optionally substituted by one or more fluorine atoms, R$^{29}$ and R$^{30}$ being as defined hereinbefore.

Advantageously, R5 represents a (C$_1$-C$_6$)alkyl, heteroaryl, (C$_3$-C$_{10}$)cycloalkyl-(C$_1$-C$_6$)alkyl, aryl-(C$_1$-C$_6$)alkyl, or aryl group, the aryl core of the aryl or aryl-(C$_1$-C$_6$)alkyl group being optionally fused to a 5 or 6-membered heterocycle, comprising preferably two oxygen atoms, and being optionally substituted by one or more groups selected from a halogen atom, a —CF$_3$, —CN, —NR$^{29}$R$^{30}$, —NO$_2$, —C(CF$_3$)$_2$OH, (C$_1$-C$_6$)alkoxy, aryloxy, (C$_1$-C$_6$)alkyl, (C$_2$-C$_6$)alkynyl, aryl and 5 or 6-membered heterocycloalkyl group, R$^{29}$ and being as defined hereinbefore.

Also advantageously, R5 represents a (C$_1$-C$_6$)alkyl, preferably methyl or isobutyl; indazolyl; phenyl-(C$_1$-C$_6$)alkyl, preferably benzyl; cyclopropyl-(C$_1$-C$_6$)alkyl, preferably, cyclopropylmethyl; 1,3-benzodioxolyl; 1,3-benzodioxolyl-methyl; naphthyl; or phenyl group, said phenyl group being optionally substituted by one or more groups selected from a halogen atom, preferably a fluorine or chlorine atom, a —CF$_3$, —CN, —NR$^{29}$R$^{30}$, preferably —NMe$_2$ or —NEt$_2$, —NO$_2$, —C(CF$_3$)$_2$OH, (C$_1$-C$_6$)alkoxy, preferably methoxy, phenoxy, $(C_1-C_6)$alkyl, preferably methyl, isopropyl or tertbutyl, $(C_2-C_6)$alkynyl, preferably —C≡CH, phenyl and morpholinyl group, $R^{29}$ and $R^{30}$ being as defined hereinbefore.

Also advantageously, R5 represents a phenyl group, being optionally fused to a 5 or 6-membered heterocycle, comprising preferably two oxygen atoms, and being optionally substituted by one or more groups selected from a halogen atom, a —$NH_2$, —COOH, —CN, —OH, —$NO_2$, —$B(OH)_2$, $(C_1-C_6)$alkoxy, —O—$(C_1-C_6)$alkyl-$NR^{27}R^{28}$, —O—$(C_1-C_6)$alkyl-O—$(C_1-C_6)$alkyl, aryloxy, —C(O)O—$(C_1-C_6)$alkyl, $(C_2-C_6)$alkynyl, —$NR^{29}R^{30}$, —NHC(O)O—$(C_1-C_6)$alkyl, —C(O)$NH_2$, —C(O)$NR^{31}R^{32}$, —S—$(C_1-C_6)$alkyl, —S(O)—$(C_1-C_6)$alkyl, —$SO_2$—$(C_1-C_6)$alkyl, —$SO_2NH_2$, —$SO_2NR^{33}R^{34}$, —$NR^{35}SO_2R^{36}$, aryl, heteroaryl, $(C_1-C_6)$alkylheteroaryl, 3 to 7-membered heterocycloalkyl, (3 to 7-membered heterocycloalkyl)-$(C_1-C_6)$alkoxy radical and a $(C_1-C_6)$alkyl group optionally substituted by one or more halogen atoms, $R^{29}$ to $R^{36}$ being as defined hereinbefore.

Even more advantageously, R5 represents a 1,3-benzodioxolyl or phenyl group, said phenyl group being optionally substituted by one or more groups selected from a halogen atom, preferably a fluorine or chlorine atom, a —$CF_3$, —CN, —$NR^{29}R^{30}$, preferably —$NMe_2$ or —$NEt_2$, —$NO_2$, —$C(CF_3)_2OH$, $(C_1-C_6)$alkoxy, preferably methoxy, phenoxy, $(C_1-C_6)$alkyl, preferably methyl, isopropyl or tertbutyl, $(C_2-C_6)$alkynyl, preferably —C≡CH, phenyl and morpholinyl group, $R^{29}$ and $R^{30}$ being as defined hereinbefore.

Also advantageously, R6 represents a —$CH_2$Hal or —C≡$CR^{12}$ group, with Hal and $R^{12}$ as defined hereinbefore.

Even more advantageously, R6 is selected from —$CH_2$Cl, —$CH_2$Br, —$CH_2$F, —C≡CH, —C≡CMe and —C≡CPh, and advantageously R6 is selected from —$CH_2$Cl and —C≡CH.

In one particular embodiment, R6 represents the —$CH_2$Cl group.

In another particular embodiment, R6 represents the —C≡CH group.

In one particular embodiment, the compounds according to the invention will be selected from the compounds of formula (I) for which R1 represents a cyclohexyl, R2 and R3 represent a hydrogen atom, R4 represents a thiophenyl, R6 represents a —$CH_2$Cl or —C≡CH group and R5 represents a phenyl group, said phenyl group being optionally fused to a 5 or 6-membered heterocycle, comprising preferably two oxygen atoms, and being optionally substituted by one or more groups selected from a halogen atom, a —$NH_2$, —COOH, —CN, —OH, —$NO_2$, —$B(OH)_2$, $(C_1-C_6)$alkoxy, —O—$(C_1-C_6)$alkyl-$NR^{27}R^{28}$, —C—$(C_1-C_6)$alkyl-O—$(C_1-C_6)$alkyl, aryloxy, —C(O)O—$(C_1-C_6)$alkyl, $(C_2-C_6)$alkynyl, —$NR^{29}R^{30}$, —NHC(O)O—$(C_1-C_6)$alkyl, —C(O)$NH_2$, —C(O)$NR^{31}R^{32}$, —S—$(C_1-C_6)$alkyl, —S(O)—$(C_1-C_6)$alkyl, —$SO_2$—$(C_1-C_6)$alkyl, —$SO_2NH_2$, —$SO_2NR^{33}R^{34}$, —$NR^{35}SO_2R^{36}$, aryl, heteroaryl, $(C_1-C_6)$alkylheteroaryl, 3 to 7-membered heterocycloalkyl, (3 to 7-membered heterocycloalkyl)-$(C_1-C_6)$alkoxy radical and a $(C_1-C_6)$alkyl group optionally substituted by one or more halogen atoms, $R^{29}$ to $R^{36}$ being as defined hereinbefore.

In another particular embodiment, the compounds according to the invention will be selected from the compounds of formula (I) for which R1 represents a cyclohexyl, R2 and R3 represent a hydrogen atom, R4 represents a thiophenyl, R6 represents a —$CH_2$Cl or —C≡CH group and R5 represents a 1,3-benzodioxolyl or phenyl group, said phenyl group being optionally substituted by one or more groups selected from a halogen atom, preferably a fluorine or chlorine atom, a —$CF_3$, —CN, —$NR^{29}R^{30}$, preferably —$NMe_2$ or —$NEt_2$, —$NO_2$, —$C(CF_3)_2OH$, $(C_1-C_6)$alkoxy, preferably methoxy, phenoxy, $(C_1-C_6)$alkyl, preferably methyl, isopropyl or tertbutyl, $(C_2-C_6)$alkynyl, preferably —C≡CH, phenyl and morpholinyl group, $R^{29}$ and $R^{30}$ being as defined hereinbefore.

In one particular embodiment, the compound of the invention is selected from the molecules cited hereinbefore of number 1, 2, 4-6, 8-157, and also 185-206.

The invention will be better understood on reading the following examples, these examples serving merely to illustrate the invention.

EXAMPLES

Compounds Nos. 3 and 158 to 184 are sold by Asinex.

Example 1

Synthesis of the Compounds of the Invention by an Ugi Reaction

The compounds of formula (I) for which R2=H can be prepared via the multicomponent reaction known as the Ugi reaction (U-4MCRs) as described in reaction scheme II.

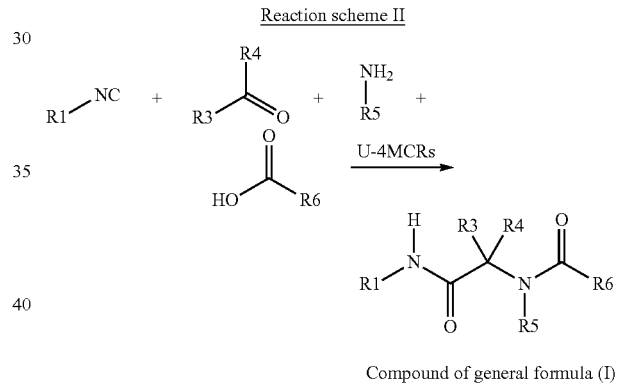

Reaction scheme II

Compound of general formula (I)

The reaction conventionally uses four chemical reagents which are an isonitrile (R1-NC), an aldehyde or a ketone (R3-CO—R4), an amine (R5-$NH_2$) and a carboxylic acid (R6-COOH), but can also use three chemical reagents, one of the reagents then being bifunctionalised. Each of the reagents can be commercially available or be prepared beforehand by methods known to a person skilled in the art. The product obtained is in the form of a racemic mixture. The groups R1, R3, R4, R5 and R6 can be aliphatic, aromatic and also functionalised by any additional synthesis steps. The functions R1 and COR6 can be protective groups which can be cleaved using suitable synthesis methods or else reactive functions which can give rise to additional synthesis steps.

Experimental Part

General Method E

The amine R5-$NH_2$ (1 eq.) was added to a millimolar aldehyde or ketone R3-CO—R4 (1 eq) solution in methanol. The solution was stirred at ambient temperature for 0.5 hours. After the addition of carboxylic acid R6-COOH (1 eq) the reaction medium was stirred for 10 minutes. The isonitrile R1-NC (1 eq) was then added. The reaction medium was stirred for 2 hours. Once it had reacted, the reaction medium was concentrated then taken up in dichloromethane. The organic phase, in accordance with the nature of the groups R1, R3, R4, R5 and R6, was washed with a 1M HCl aqueous solution, a 1M NaHCO$_3$ aqueous solution and with water. After drying on MgSO$_4$ and filtration, the solvent was evaporated to recover the crude product either in the form of a solid or in the form of an oil. The solid was washed with a little organic solvent (usually diisopropyl ether, also pentane or diethyl ether). If necessary, the solid can be recrystallised, or purified on silica gel. If there is no precipitation, the oil is also purified on silica gel.

Synthesis of Example 1

Propynoic Acid (benzylcarbamoylthiophen-2-yl-methyl)-(3-trifluoromethylphenyl)amide Example 1 was obtained in the form of a white solid using general method E.
Yield=50: C$_{23}$H$_{17}$F$_3$N$_2$O$_2$S: MS [M+H]=443; [M+Na]=465.
NMR H$^1$ (CDCl$_3$, 300): δ=2.89 (s, 1H, ═CH); 4.50 (AB, 1H, J=15.0 6.1 Hz, CH$_2$); 4.57 (AB, 1H, J=15.0 5.7 Hz, CH$_2$); 6.25 (s, 1H, CH); 6.29 (br, 1H, NH); 6.90 (dd, 1H, J=5.1 3.6 Hz, CH); 6.97 (dl, 1H, J=2.7 Hz, CH); 7.25-7.47 (m, 8H, CH); 7.51 (d, 1H, J=8.4 Hz, CH); 7.59 (d, 1H, J=7.5 Hz, CH).

Synthesis of Example 2

Propynoic Acid (cyclohexylcarbamoylthiophen-2-yl-methyl)-(4-trifluoromethylphenyl)amide Example 2 was obtained in the form of a white solid using general method E.
Yield=55%; C$_{22}$H$_{21}$F$_3$N$_2$O$_2$S; MS [M+H]=435; [M+Na]=457.
NMR H$^1$ (CDCl$_3$, 300): δ=1.10-1.24 (m, 3H, CH$_2$); 1.26-1.46 (m, 2H, CH$_2$); 1.55-1.77 (m, 3H, CH$_2$); 1.86-2.01 (m, 2H, CH$_2$); 2.88 (s, 1H, ═CH); 3.75-3.90 (m, 1H, CH—NH); 5.84 (dl, 1H, J=5.1 Hz, NH); 6.23 (s, 1H, CH); 6.91 (dd, 1H, J=5.4 3.6 Hz, CH); 6.97 (d, 1H, J=2.7 Hz, CH); 7.29 (d, 1H, J=5.4 Hz, CH); 7.38 (d, 2H, J=8.1 Hz, CH); 7.54 (d, 2H, J=8.1 Hz, CH).

Synthesis of Example 3

Propynoic Acid (cyclohexylcarbamoylthiophen-2-yl-methyl)-(3-trifluoromethylphenyl)amide Example 3 was obtained in the form of a white solid using general method E.
Yield=47%; C$_{22}$H$_{21}$F$_3$N$_2$O$_2$S; MS [M+H]=435; [M+Na]=457.
NMR H$^1$ (CDCl$_3$, 300): δ=1.10-1.24 (m, 3H, CH$_2$); 1.27-1.46 (m, 2H, CH$_2$); 1.60-1.78 (m, 3H, CH$_2$); 1.87-2.02 (m, 2H, CH$_2$); 2.87 (s, 1H, ═CH); 3.75-3.90 (m, 1H, CH—NH); 5.84 (d, 1H, J=7.8 Hz, NH); 6.25 (s, 1H, CH); 6.90 (dd, 1H, J=5.1 3.6 Hz, CH); 6.96 (d, 1H, J=2.7 Hz, CH); 7.29 (dd, 1H, J=4.8 1.2 Hz, CH); 7.39-7.46 (m, 2H, CH); 7.53 (d, 2H, J=7.8 Hz, CH); 7.57 (d, 2H, J=8.4 Hz, CH).

Synthesis of Example 4

Propynoic Acid (benzylcarbamoylthiophen-2-yl-methyl)-(4-trifluoromethylphenyl)amide Example 4 was obtained in the form of a white solid using general method E.
Yield=63%; C$_{23}$H$_{17}$F$_3$N$_2$O$_2$S; MS [M+H]=443; [M+Na]=465.
NMR H$^1$ (CDCl$_3$, 300): δ=2.89 (s, 1H, ═CH); 4.50 (AB, 1H, J=155.7 Hz, CH$_2$); 4.57 (AB, 1H, J=155.7 Hz, CH$_2$); 6.23 (s, 1H, CH); 6.28 (br, 1H, NH); 6.90 (dd, 1H, J=5.1 3.6 Hz, CH); 6.98 (d, 1H, J=3.0 Hz, CH); 7.26-7.41 (m, 8H, CH); 7.55 (d, 2H, J=8.1 Hz, CH).

Synthesis of Example 5

Propynoic Acid (phenylcarbamoylthiophen-2-yl-methyl)-(3-trifluoromethylphenyl)amide Example 5 was obtained in the form of lightly coloured oil using general method E.
Yield=11%; C$_{25}$H$_{15}$F$_3$N$_2$O$_2$S; MS [M+H]=429; [M+Na]=451.
NMR H$^1$ (CDCl$_3$, 300): δ=2.91 (s, 1H, ═CH); 6.46 (s, 1H, CH); 6.94 (dd, 1H, J=4.8 3.6 Hz, CH); 7.05 (d, 1H, J=3.0 Hz, CH); 7.16 (t, 1H, J=7.5 Hz, CH); 7.31-7.62 (m, 9H, CH); 7.84 (s, 1H, NH)

Synthesis of Example 6

Propynoic Acid (phenylcarbamoylthiophen-2-yl-methyl)-(4-trifluoromethylphenyl)amide Example 6 was obtained in the form of lightly coloured oil using general method E.
Yield=8%; C$_{25}$H$_{15}$F$_3$N$_2$O$_2$S; MS [M+H]=429; [M+Na]=451.
NMR H$^1$ (CDCl$_3$, 300): δ=2.90 (s, 1H, ═CH); 6.48 (s, 1H, CH); 6.93 (dd, 1H, J=5.1 3.6 Hz, CH); 7.04 (d, 1H, J=3.3 Hz, CH); 7.16 (t, 1H, J=7.5 Hz, CH); 7.30-7.42 (m, 5H, CH); 7.49-7.58 (m, 4H, CH); 7.97 (s, 1H, NH)

Synthesis of Example 8

Propynoic Acid (benzylcarbamoylthiophen-2-yl-methyl)-((S)-1-phenylethyl)amide

Example 8 was obtained in the form of a white solid using general method E.
Yield=9%; C$_{24}$H$_{22}$N$_2$O$_2$S; MS [M+H]=403; [M+Na]=425.
NMR H$^1$ (CDCl$_3$, 300): δ=1.54 (d, 3H, J=7.2 Hz, CH), 3.24 (s, 1H, ═CH), 4.14 (dd, 1H, J=15.0 5.1 Hz, CH), 4.52 (dd, 1H, J=15.0 6.6 Hz, CH), 4.92 (s, 1H, CH), 5.91-6.01 (m, 2H, CH—CH$_3$+NH), 6.95 (dd, 1H, J=5.1 3.6 Hz, CH), 6.96 (d, 1H, J=3.3 Hz, CH), 7.17-7.47 (m, 9H, CH), 7.55-7.60 (m, 2H, CH).

Synthesis of Example 9

Propynoic Acid (benzylcarbamoylthiophen-2-yl-methyl)-((R)-1-phenylethyl)amide

Example 9 was obtained in the form of a white solid using general method E.
Yield=33%; C$_{24}$H$_{22}$N$_2$O$_2$S; MS [M+H]=403; [M+Na]=425.
NMR H$^1$ (CDCl$_3$, 300): δ=1.86 (d, 3H, J=6.9 Hz, CH), 3.25 (s, 1H, ═CH), 4.28 (dd, 1H, J=15.0 5.1 Hz, CH), 4.62 (dd, 1H, J=15.0 6.6 Hz, CH), 4.84 (s, 1H, CH), 5.92 (q, 1H, J=7.2 Hz, CH), 6.21-6.26 (m, 2H, CH—CH$_3$+NH), 6.62 (dd, 1H, J=5.1 3.6 Hz, CH), 7.11 (dd, 1H, J=5.1 1.2 Hz, CH), 7.20-7.33 (m, 10H, CH).

Synthesis of Example 10

3-Phenylpropynoic acid (cyclohexylcarbamoyl thiophen-2-yl-methyl)-(4-trifluoromethylphenyl) amide Example 10 was obtained in the form of a white solid using general method E.

Yield=49%; $C_{28}H_{25}F_3N_2O_2S$; MS [M+H]=511; [M+Na]=533.

NMR $H^1$ (CDCl$_3$, 300): δ=1.10-1.28 (m, 3H, CH$_2$); 1.29-1.47 (m, 2H, CH$_2$); 1.53-1.77 (m, 3H, CH$_2$); 1.85-2.03 (m, 2H, CH$_2$); 3.77-3.93 (m, 1H, CH—NH); 5.91-6.06 (l, 1H, NH); 6.34 (s, 1H, CH); 6.91 (dd, 1H, J=5.2 3.6 Hz, CH); 6.96-7.07 (m, 3H, CH); 7.16-7.49 (m, 4H, CH); 7.44 (d, 2H, l=8.2 Hz, CH), 7.58 (d, 2H, J=8.2 Hz, CH).

Synthesis of Example 11

3-Phenylpropynoic acid (benzylcarbamoylthiophen-2-yl-methyl)-(3-trifluoromethylphenyl)amide Example 11 was obtained in the form of a white solid using general method E.

Yield=53%; $C_{29}H_{21}F_3N_2O_2S$; MS [M+H]=519; [M+Na]=541.

NMR $H^1$ (CDCl$_3$, 300): δ=4.51 (AB, 1H, J=14.6 5.5 Hz, CH$_2$); 4.58 (AB, 1H, J=14.6 5.5 Hz, CH$_2$); 6.35 (s, 1H, CH); 6.41-6.54 (l, 1H, NH); 6.90 (t, 2H, J=4.3 Hz, CH), 6.98-7.14 (m, 3H, CH); 7.17-7.69 (m, 13H, CH).

Synthesis of Example 12

Propynoic Acid (cyclohexylcarbamoylthiophen-2-yl-methyl)isobutylamide

Example 12 was obtained in the form of a white solid using general method E.

Yield=7%; $C_{19}H_{26}N_2O_2S$; MS [M+H]=347; [M+Na]=369.

NMR $H^1$ (CDCl$_3$, 300): δ=0.84 (d, 3H, J=6.6 Hz, CH$_3$), 0.87 (d, 3H, J=6.7 Hz, CH$_3$), 1.06-1.26 (m, 3H, CH$_2$); 1.26-1.44 (m, 2H, CH$_2$); 1.59-1.77 (m, 3H, CH$_2$); 1.77-1.99 (m, 3H, CH+CH$_2$); 3.18 (s, 1H, ≡CH), 3.29 (AB, 1H, J=14.6 6.5 Hz, CH$_2$); 3.49 (AB, 1H, J=14.5 8.4 Hz, CH$_2$), 3.69-3.87 (m, 1H, CH—NH); 5.83 (s, 1H, CH); 6.27-6.38 (l, 1H, NH), 7.02, (dd, 1H, J=5.1 3.6 Hz, CH); 7.18 (d, 1H, J=2.9 Hz, CH), 7.39 (d, 1H, J=4.3 Hz, CH).

Synthesis of Example 13

3-Phenylpropynoic Acid (cyclohexylcarbamoyl thiophen-2-yl-methyl)-(3-trifluoromethylphenyl) amide Example 13 was obtained in the form of a white solid using general method E.

Yield=37%; $C_{28}H_{25}F_3N_2O_2S$; MS [M+H]=511; [M+Na]=533.

NMR $H^1$ (CDCl$_3$, 300): δ=1.08-1.30 (m, 3H, CH$_2$); 1.30-1.49 (m, 2H, CH$_2$); 1.54-1.78 (m, 3H, CH$_2$); 1.86-2.05 (m, 2H, CH$_2$); 3.77-3.94 (m, 1H, CH—NH); 5.90-6.07 (l, 1H, NH); 6.34 (s, 1H, CH); 6.91 (dd, 1H, J=5.0 3.7 Hz, CH); 6.97-7.13 (m, 3H, CH); 7.17-7.39 (m, 4H, CH); 7.40-7.53 (m, 2H, CH); 7.53-7.65 (m, 2H, CH).

Synthesis of Example 14

3-Phenylpropynoic Acid (cyclohexylcarbamoyl thiophen-2-yl-methyl)isobutylamide

Example 14 was obtained in the form of a white solid using general method E.

Yield=28%; $C_{25}H_{30}N_2O_2S$; MS [M+H]=423; [M+Na]=445.

NMR $H^1$ (CDCl$_3$, 300): δ=0.88 (d, 3H, J=6.8 Hz, CH$_3$), 0.91 (d, 3H, J=6.8 Hz, CH$_3$), 1.07-1.27 (m, 3H, CH$_2$); 1.27-1.45 (m, 2H, CH$_2$); 1.51-1.75 (m, 3H, CH$_2$); 1.83-1.99 (m, 3H, CH+CH$_2$); 3.36 (AB, 1H, J=14.6 6.6 Hz, CH$_2$); 3.56 (AB, 1H, J=14.6 8.5 Hz, CH$_2$), 3.71-3.88 (m, 1H, CH—NH); 5.94 (s, 1H, CH); 6.45 (dl, 1H, J=6.3 Hz, NH); 7.02 (dd, 1H, J=5.1 3.5 Hz, CH); 7.21 (d, 1H, J=−2.8 Hz, CH), 7.32-7.48 (m, 4H, CH); 7.50-7.59 (m, 2H, CH).

Synthesis of Example 15

3-Phenylpropynoic Acid (cyclohexylcarbamoyl thiophen-2-yl-methyl)cyclopropylmethylamide Example 15 was obtained in the form of a white solid using general method E.

Yield=30%; $C_{25}H_{28}N_2O_2S$; MS [M+H]=421; [M+Na]=443.

NMR $H^1$ (CDCl$_3$, 300): δ=0.07-0.22 (m, 1H, CH$_2$); 0.26-0.56 (m, 3H, CH$_2$), 0.90-1.08 (m, 1H, CH), 1.09-1.28 (m, 3H, CH$_2$); 1.28-1.47 (m, 2H, CH$_2$); 1.52-1.75 (m, 3H, CH$_2$); 1.82-1.99 (m, 2H, CH$_2$); 3.52 (AB, 1H, J=15.2 6.6 Hz, CH$_2$); 3.62 (AB, 1H, J=15.3 7.4 Hz, CH$_2$), 3.73-3.92 (m, 1H, CH—NH); 6.18 (s, 1H, CH); 6.40 (dl, 1H, J=7.0 Hz, NH); 7.02 (dd, 1H, J=5.0 3.6 Hz, CH); 7.24 (d, 1H, J=3.1 Hz, CH), 7.31-7.49 (m, 4H, CH); 7.49-7.59 (m, 2H, CH).

Synthesis of Example 16

Propynoic Acid (benzylcarbamoylthiophen-2-yl-methyl)isobutylamide

Example 16 was obtained in the form of a white solid using general method E.

Yield=39%; $C_{20}H_{22}N_2O_2S$; MS [M+H]=355; [M+Na]=377.

NMR $H^1$ (CDCl$_3$, 300): δ=0.80 (d, 3H, J=6.6 Hz, CH$_3$), 0.90 (d, 3H, J=6.6 Hz, CH$_3$), 1.69-1.91 (m, 1H, CH); 3.18 (s, 1H, ≡CH), 3.38 (AB, 1H, J=14.6 6.8 Hz, CH$_2$); 3.53 (AB, 1H, J=14.7 8.2 Hz, CH$_2$), 4.38 (AB, 1H, J=15.0 5.44 Hz, CH$_2$); 4.55 (AB, 1H, J=15.0 6.2 Hz, CH$_2$), 5.74 (s, 1H, CH); 6.53-6.66 (l, 1H, NH), 7.00, (dd, 1H, J=5.2 3.6 Hz, CH); 7.15-7.41 (m, 7H, CH).

Synthesis of Example 17

Propynoic Acid (cyclohexylcarbamoylthiophen-2-yl-methyl)cyclopropylmethylamide

Example 17 was obtained in the form of a white solid using general method E.

Yield=48%; $C_{19}H_{24}N_2O_2S$; MS [M+H]=345; [M+Na]=367.

NMR $H^1$ (CDCl$_3$, 300): δ=0.03-0.15 (m, 1H, CH$_2$); 0.18-0.53 (m, 3H, CH$_2$), 0.85-1.01 (m, 1H, CH), 1.06-1.25 (m, 3H, CH$_2$); 1.25-1.44 (m, 2H, CH$_2$); 1.50-1.75 (m, 3H, CH$_2$); 1.79-2.01 (m, 2H, CH$_2$); 3.16 (s, 1H, ≡CH), 3.45 (AB, 1H, J=15.4 6.8 Hz, CH$_2$); 3.54 (AB, 1H, J=15.4 7.5 Hz, CH$_2$), 3.69-3.85 (m, 1H, CH—NH); 6.06 (s, 1H, CH); 6.19-6.34 (l, 1H, NH); 7.01 (dd, 1H, J=5.1 3.6 Hz, CH); 7.18-7.22 (m, 1H, CH); 7.36 (dd, 1H, J=5.1 1.2 Hz, CH).

Synthesis of Example 18

Propynoic Acid (benzylcarbamoylthiophen-2-yl-methyl)cyclopropylmethylamide

Example 18 was obtained in the form of a white solid using general method E.
Yield=26%; $C_{20}H_{20}N_2O_2S$; MS [M+H]=353; [M+Na]=375.
NMR $H^1$ (CDCl$_3$, 300): δ=0.03-0.14 (m, 1H, CH$_2$); 0.23-0.52 (m, 3H, CH$_2$), 0.83-0.99 (m, 1H, CH), 3.13 (s, 1H, 1H, ≡CH), 3.50 (AB, 1H, J=15.3 6.7 Hz, CH$_2$); 3.58 (AB, 1H, J=15.3 7.5 Hz, CH$_2$), 4.43 (AB, 1H, J=15.0 5.6 Hz, CH$_2$); 4.53 (AB, 1H, J=14.8 5.6 Hz, CH$_2$), 6.04 (s, 1H, CH); 6.53-6.68 (l, 1H, NH); 7.01 (dd, 1H, J=5.2 3.6 Hz, CH); 7.12-7.43 (m, 7H, CH).

Synthesis of Example 19

Propynoic Acid [cyclohexylcarbamoyl-(5-methylthiophen-2-yl)-methyl]-(3-trifluoromethylphenyl)amide Example 19 was obtained in the form of a white solid using general method E.
Yield=16%; $C_{23}H_{23}F_3N_2O_2S$; MS [M+H]=449.
NMR $H^1$ (CDCl$_3$, 300): δ=1.03-1.27 (m, 3H, CH$_2$); 1.27-1.47 (m, 2H, CH$_2$); 1.52-1.80 (m, 3H, CH$_2$); 1.82-2.02 (m, 2H, CH$_2$); 2.39 (s, 3H, CH$_3$); 2.85 (s, 1H, ≡CH); 3.72-3.93 (m, 1H, CH—NH); 5.81 (dl, 1H, J=7.1 Hz, NH); 6.10 (s, 1H, CH); 6.53 (dd, 1H, J=3.5 1.0 Hz, CH); 7.71 (d, 1H, J=3.4 Hz, CH), 7.37-7.47 (m, 2H, CH); 7.51-7.63 (m, 2H, CH).

Synthesis of Example 20

But-2-ynoic acid (cyclohexylcarbamoylthiophen-2-yl-methyl)-(3-trifluoromethylphenyl)amide Example 20 was obtained in the form of a white solid using general method E.
Yield=51%; $C_{23}H_{23}F_3N_2O_2S$; MS [M+H]=349; [M+Na]=371.
NMR $H^1$ (CDCl$_3$, 300): δ=1.04-1.27 (m, 3H, CH$_2$); 1.27-1.48 (m, 2H, CH$_2$); 1.55-1.76 (m, 6H, CH$_3$+CH$_2$); 1.84-2.01 (m, 2H, CH$_2$); 3.75-3.91 (m, 1H, CH—NH); 5.93 (dl, 1H, J=6.8 Hz, NH); 6.26 (s, 1H, CH); 6.88 (dd, 1H, J=5.1 3.8 Hz, CH); 6.96 (d, 1H, J=3.3 Hz, CH), 7.25 (dd, 1H, J=5.2 1.0 Hz, CH); 7.35-7.43 (m, 2H, CH); 7.44-7.57 (m, 2H, CH).

Synthesis of Example 21

Propynoic Acid [benzylcarbamoyl-(5-methylthiophen-2-yl)-methyl]-(3-trifluoromethylphenyl)amide Example 21 was obtained in the form of a white solid using general method E.
Yield=5%; $C_{24}H_{29}F_3N_2O_2S$; MS [M+Na]=479.
NMR $H^1$ (CDCl$_3$, 300): δ=2.38 (s, 3H, CH$_3$); 2.86 (s, 1H, ≡CH); 4.48 (AB, 1H, J=15.2 5.4 Hz, CH$_2$), 4.55 (AB, 1H, J=14.7 5.8 Hz, CH$_2$), 6.20-6.34 (m, 1H, NH); 6.46-6.59 (m, 1H, CH); 6.73 (d, 1H, J=3.1 Hz, CH), 7.22-7.39 (m, 5H, CH), 7.39-7.66 (m, 4H, CH).

Synthesis of Example 22

But-2-ynoic acid (benzylcarbamoylthiophen-2-yl-methyl)-(3-trifluoromethylphenyl)amide Example 22 was obtained in the four of a white solid using general method E.
Yield=65%; $C_{24}H_{19}F_3N_2O_2S$; MS [M+H]=457; [M+Na]=479.
NMR $H^1$ (CDCl$_3$, 300): δ=1.71 (s, 3H, CH$_3$); 4.48 (AB, 1H, J=14.9 4.9 Hz, CH$_2$); 4.56 (AB, 1H, J=14.5 5.5 Hz, CH$_2$), 6.25 (s, 1H, CH); 6.31-6.46 (l, 1H, NH); 6.88 (dd, 1H, J=5.1 3.6 Hz, CH); 6.93-7.01 (l, 1H, CH); 7.25-7.60 (m, 10H, CH).

Synthesis of Example 23

2-(Benzylpropynoylamino)-4,4-dimethylpentanoic acid cyclohexylamide

Example 23 was obtained in the form of a white solid using general method E.
Yield=68%; $C_{23}H_{32}N_2O_2$; MS [M+H]=369; [M+Na]=391.
NMR $H^1$ (CDCl$_3$, 300): δ=0.82 (s, 9H, CH$_3$), 1.00-1.87 (m, 10H, CH$_2$), 1.28 (dd, 1H, J=14.1 3.6 Hz, CH$_2$), 2.20 (dd, 1H, J=13.9 8.8 Hz, CH$_2$), 3.12 (s, 1H, ≡CH), 3.42-3.59 (m, 1H, CH), 4.73 (dd, 1H, J=9.0 3.6 Hz, CH), 4.82 (sys AB, 1H, J=16.5 Hz, CH$_2$), 4.89 (sys AB, 1H, J=16.5 Hz, CH$_2$), 6.29 (dl, 1H, J=7.8 Hz, NH), 7.20-7.37 (m, 5H, CH).

Synthesis of Example 24

2-(Benzylpropynoylamino)-4,4-dimethylpentanoic acid benzylamide

Example 24 was obtained in the form of a white solid using general method E.
Yield=33%; $C_{24}H_{28}N_2O_2$; MS [M+H]=377; [M+Na]=399.
NMR $H^1$ (CDCl$_3$, 300): δ=0.83 (s, 9H, CH$_3$), 1.34 (dd, 1H, J=14.1 3.6 Hz, CH$_2$), 1.23 (sys dd, 1H, J=14.1 8.4 Hz, CH$_2$), 3.13 (s, 1H, ≡CH); 4.10 (sys AB, 1H, J=14.7 5.4 Hz, CH$_2$), 4.33 (sys AB, 1H, J=14.7 6.3 Hz, CH$_2$), 4.79-4.95 (m, 3H, CH$_2$+CH), 6.78 (tl, 1H, J=5.4 Hz, NH), 7.10-7.35 (m, 10H, CH).

Synthesis of Example 25

1-[Propynoyl-(4-trifluoromethylphenyl)amino]cyclohexane carboxylic acid cyclohexylamide Cyclohexanecarbaldehyde, 4-trifluoromethylphenylamine, propargylic acid and isocyanocyclohexane were reacted as described in general method E. Compound 25 was obtained in the form of a yellow oil.
Yield=50%; $C_{23}H_{27}F_3N_2O_2$; MS [M+H]=421
NMR $H^1$ (CDCl$_3$, 300): δ=1.15-1.78 (m, 16H); 1.95-2.04 (m, 2H); 2.25-2.29 (m, 2H); 2.77 (s, 1H); 3.17 (s, 1H); 3.75-3.91 (m, 1H); 6.26 (d, J=7.8 Hz, 1H); 7.58 (d, J=8.4 Hz, 2H); 7.66 (d, =8.4 Hz, 2H).

Synthesis of Example 26

1-[Propynoyl-(3-trifluoromethylphenyl)amino]cyclohexane carboxylic acid cyclohexylamide Cyclohexanecarbaldehyde, 3-trifluoromethylphenylamine, propargylic acid and isocyanocyclohexane were reacted as described in general method E. The compound from Example 26 was obtained in the form of a white solid.
Yield=28%; $C_{23}H_{27}N_3N_2O_2$; MS [M+H]=421.
NMR H$^1$ (CDCl$_3$, 300): δ=1.19-1.78 (m, 16H); 1.95-2.00 (m, 2H); 2.15-2.39 (m, 2H); 2.77 (s, 1H); 2.76 (s, 1H); 3.78-3.92 (m, 1H); 6.24 (d, J=7.8 Hz, 1H); 7.52 (t, J=7.8 Hz, 1H); 7.63-7.69 (m, 2H); 7.72 (s, 1H).

Synthesis of Example 27

Propynoic Acid (cyclohexylcarbamoylthiophen-2-yl-methyl)-(3-nitrophenyl)amide

Example 27 was obtained in the form of a brown solid using general method E.
Yield=63%; $C_{21}H_{21}N_3O_4S$; MS [M+H]=412; [M+Na]=434.

Synthesis of Example 28

Propynoic Acid (cyclohexylcarbamoylthiophen-2-yl-methyl)-(4-[1,2,3]thiadiazol-4-yl-phenyl)amide Example 28 was obtained in the form of a brown foam using general method E.
Yield=63%; $C_{23}H_{22}N_4O_2S_2$; MS [M+H]=451; [M+Na]=473.

Synthesis of Example 29

Propynoic Acid (cyclohexylcarbamoylthiophen-2-yl-methyl)-[4-(2,2,2-trifluoro-1-hydroxy-1-trifluoromethylethyl)phenyl]amide Example 29 was obtained in the form of an orange foam using general method E.
Yield=27%; $C_{24}H_{22}N_4F_6O_2S$; MS [M+H]=533; [M+Na]=555.

Synthesis of Example 30

Propynoic Acid (cyclohexylcarbamoylthiophen-2-yl-methyl)-(4-hydroxyphenyl)amide

Example 30 was obtained in the form of a white solid using general method E.
Yield=27%; $C_{21}H_{22}N_2O_3S$; MS [M+H]=383; [M+Na]=405.

Synthesis of Example 31

Propynoic Acid (3-cyanophenyl)(cyclohexyl carbamoylthiophen-2-yl-methyl)amide

Example 31 was obtained in the form of a brown oil using general method E.
Yield=90%; $C_{22}H_{21}N_3O_2S$; MS [M+H]=392; [M+Na]=414.

Synthesis of Example 32

Propynoic Acid (cyclohexylcarbamoylthiophen-2-yl-methyl)-(4-diethylaminophenyl)amide Example 32 was obtained in the form of a brown foam using general method E.
Yield=44%; $C_{25}H_{31}N_3O_2S$; MS [M+H]=438.

Synthesis of Example 33

Propynoic Acid (2-chlorophenyl)(cyclohexyl carbamoylthiophen-2-yl-methyl)amide

Example 33 was obtained in the form of a red oil using general method E.
Yield=26%; $C_{21}H_{21}ClN_2O_2S$; MS [M+H]=401.

Synthesis of Example 34

Propynoic Acid (cyclohexylcarbamoylthiophen-2-yl-methyl)-(2-methylsulphanylphenyl)amide Example 34 was obtained in the form of a brown oil using general method E.
Yield=22%; $C_{22}H_{24}N_2O_2S_2$; MS [M+H]=413.

Synthesis of Example 35

Propynoic Acid (cyclohexylcarbamoylthiophen-2-yl-methyl)-(2-phenoxyphenyl)amide

Example 35 was obtained in the form of a brown oil using general method E.
Yield=25%; $C_{27}H_{26}N_2O_3S$; MS [M+H]=459; [M+Na]=481.

Synthesis of Example 36

Propynoic Acid benzo[1,3]dioxol-5-yl-(cyclohexyl carbamoylthiophen-2-yl-methyl)amide Example 36 was obtained in the form of a brown oil using general method E.
Yield=61%; $C_{22}H_{22}N_2O_4S$; MS [M+H]=411; [M+Na]=433.

Synthesis of Example 37

Propynoic Acid (cyclohexylcarbamoylthiophen-2-yl-methyl)-(3,4-difluorophenyl)amide Example 37 was obtained in the form of a white solid using general method E.
Yield=71%; $C_{21}H_{20}F_2N_2O_2S$; MS [M+H]=403; [M+Na]=425.

Synthesis of Example 38

Propynoic Acid (cyclohexylcarbamoylthiophen-2-yl-methyl)-[3-(2-methylpyrimidin-4-yl)-phenyl]amide Example 38 was obtained in the form of a red foam using general method E.
Yield=65%; $C_{26}H_{26}N_4O_2S$; MS [M+H]=459.

Synthesis of Example 39

Propynoic Acid (cyclohexylcarbamoylthiophen-2-yl-methyl)-(3-methylsulphanylphenyl)amide Example 39 was obtained in the form of a brown oil using general method E.
Yield=47%; $C_{22}H_{24}N_2O_2S_2$; MS [M+H]=413.

Synthesis of Example 40

Propynoic Acid (cyclohexylcarbamoylthiophen-2-yl-methyl)-(2-methoxyphenyl)amide

Example 40 was obtained in the form of a brown oil using general method E.
Yield=22%; $C_{22}H_{24}N_2O_1S_2$; MS [M+H]=397.

Synthesis of Example 41

Propynoic Acid (4-chlorophenyl)(cyclohexyl carbamoylthiophen-2-yl-methyl)amide

Example 41 was obtained in the form of a white solid using general method E.
Yield=67%; $C_{21}H_{21}ClN_2O_2S$; MS [M+H]=401.

Synthesis of Example 42

Propynoic Acid (cyclohexylcarbamoylthiophen-2-yl-methyl)-(2-hydroxyphenyl)amide

Example 42 was obtained in the form of a yellow foam using general method E.
Yield=66%; $C_{21}H_{22}N_2O_1S$; MS [M+H]=383; [M+Na]=405.

Synthesis of Example 43

2-[(Cyclohexylcarbamoylthiophen-2-yl-methyl)propynoylamino]benzoic acid methyl ester Example 43 was obtained in the form of an orange oil using general method E.
Yield=54%; $C_{23}H_{24}N_2O_4S$; MS [M+H]=425.

Synthesis of Example 44

Propynoic Acid (cyclohexylcarbamoylthiophen-2-yl-methyl)-(2,6-dimethylphenyl)amide Example 44 was obtained in the form of a brown oil using general method E.
Yield=27%; $C_{23}H_{26}N_2O_2S$; MS [M+H]=395.

Synthesis of Example 45

Propynoic Acid (cyclohexylcarbamoylthiophen-2-yl-methyl)-p-tolylamide

Example 45 was obtained in the form of a white solid using general method E.
Yield=86%; $C_{22}H_{24}N_2O_2S$; MS [M+H]=381; [M+Na]=403.

Synthesis of Example 46

Propynoic Acid (cyclohexylcarbamoylthiophen-2-yl-methyl)-(3-methoxyphenyl)amide

Example 46 was obtained in the form of an orange oil using general method E.
Yield=65%; $C_{22}H_{24}N_2O_3S$; MS [M+H]=397; [M+Na]=419.

Synthesis of Example 47

Propynoic Acid (cyclohexylcarbamoylthiophen-2-yl-methyl)-(2-trifluoromethyl-1H-benzoimidazol-5-yl)-amide Example 47 was obtained in the form of a white solid using general method E.
Yield=83%; $C_{23}H_{21}F_3N_4O_2S$; MS [M+H]=475.

Synthesis of Example 48

Propynoic Acid (cyclohexylcarbamoylthiophen-2-yl-methyl)-(4-morpholin-4-yl-phenyl)amide Example 48 was obtained in the form of a white solid using general method E.
Yield=73%; $C_{25}H_{29}N_3O_3S$; MS [M+H]=452; [M+Na]=474.

Synthesis of Example 49

Propynoic Acid (cyclohexylcarbamoylthiophen-2-yl-methyl)-(1H-indazol-5-yl)-amide Example 49 was obtained in the form of a white solid using general method E.
Yield=84%; $C_{22}H_{22}N_4O_2S$; MS [M+H]=407.

Synthesis of Example 50

Propynoic Acid (cyclohexylcarbamoylthiophen-2-yl-methyl)-(2,4-difluorophenyl)amide Example 50 was obtained in the form of a white solid using general method E.
Yield=28%; $C_{21}H_{20}F_2N_2O_2S$; MS [M+H]=403; [M+Na]=425.

Synthesis of Example 51

Propynoic Acid (cyclohexylcarbamoylthiophen-2-yl-methyl)-(2,4-dimethylphenyl)amide Example 51 was obtained in the form of a yellow solid using general method E.
Yield=61%; $C_{23}H_{26}N_2O_2S$; MS [M+H]=395; [M+Na]=417.

Synthesis of Example 52

Propynoic Acid (4-tert-butylphenyl)(cyclohexyl carbamoylthiophen-2-yl-methyl)amide Example 52 was obtained in the form of a white solid using general method E.
Yield=49%; $C_{25}H_{30}N_2O_2S$; MS [M+H]=423; [M+Na]=445.

Synthesis of Example 53

Propynoic Acid (4-cyanophenyl)(cyclohexyl carbamoylthiophen-2-yl-methyl)amide

Example 53 was obtained in the form of a white solid using general method E.

Yield=79%; $C_{22}H_{21}N_3O_2S$; MS [M+H]=392; [M+Na]=414.

Synthesis of Example 54

Propynoic Acid (2-cyanophenyl)(cyclohexyl carbamoylthiophen-2-yl-methyl)amide

Example 54 was obtained in the form of a brown oil using general method E.
Yield=18%; $C_{22}H_{21}N_3O_2S$; MS [M+H]=392; [M+Na]=414.

Synthesis of Example 55

Propynoic Acid (cyclohexylcarbamoylthiophen-2-yl-methyl)-(4-phenoxyphenyl)amide

Example 55 was obtained in the form of a white solid using general method E.
Yield=84%; $C_{27}H_{26}N_2O_3S$; MS [M+H]=459; [M+Na]=481.

Synthesis of Example 56

Propynoic Acid (cyclohexylcarbamoylthiophen-2-yl-methyl)-(3-ethynylphenyl)amide

Example 56 was obtained in the form of a brown foam using general method E.
Yield=59%; $C_{23}H_{22}N_2O_2S$; MS [M+H]=391; [M+Na]=413.

Synthesis of Example 57

Propynoic Acid (cyclohexylcarbamoylthiophen-2-yl-methyl)-(4-isopropylphenyl)amide Example 57 was obtained in the form of a yellow solid using general method E.
Yield=58%; $C_{24}H_{28}N_2O_2S$; MS [M+H]=409; [M+Na]=431.

Synthesis of Example 58

Propynoic acid biphenyl-3-yl-(cyclohexylcarbamoylthiophen-2-yl-methyl)amide

Example 58 was obtained in the form of a brown foam using general method E.
Yield=84%; $C_{27}H_{26}N_2O_2S$; MS [M+H]=443; [M+Na]=465.

Synthesis of Example 59

Propynoic Acid (cyclohexylcarbamoylthiophen-2-yl-methyl)-(2-fluorophenyl)amide

Example 59 was obtained in the form of an orange solid using general method E.
Yield=49%; $C_{21}H_{21}FN_2O_2S$; MS [M+H]=385; [M+Na]=407.

Synthesis of Example 60

Propynoic Acid (cyclohexylcarbamoylthiophen-2-yl-methyl)-o-tolylamide

Example 60 was obtained in the form of a white solid using general method E.
Yield=68%; $C_{22}H_{24}N_2O_2S$; MS [M+H]=381.

Synthesis of Example 61

Propynoic Acid biphenyl-4-yl-(cyclohexylcarbamoylthiophen-2-yl-methyl)amide

Example 61 was obtained in the form of a white solid using general method E.
Yield=80%; $C_{1-27}H_{26}N_2O_2S$; MS [M+H]=443; [M+Na]=465.

Synthesis of Example 62

Propynoic Acid (cyclohexylcarbamoylthiophen-2-yl-methyl)-(3-pyrimidin-5-yl-phenyl)amide Example 62 was obtained in the form of an orange solid using general method E.
Yield=88%; $C_{25}H_{24}N_4O_2S$; MS [M+H]=445.

Synthesis of Example 63

Propynoic Acid (benzo[1,3]dioxol-5-yl-cyclohexyl carbamoylmethyl)-(3-trifluoromethylphenyl)amide Example 63 was obtained in the form of a white solid using general method E.
Yield=58%; $C_{25}H_{23}F_3N_2O_4$; MS [M+H]=473; [M+Na]=495.

Synthesis of Example 64

Propynoic Acid [cyclohexylcarbamoyl-(3-fluorophenyl)methyl]-(3-trifluoromethylphenyl)amide Example 64 was obtained in the form of a white solid using general method E.
Yield=26%; $C_{24}H_{22}F_4N_2O_2$; MS [M+H]=447; [M+Na]=469.

Synthesis of Example 65

Propynoic Acid [cyclohexylcarbamoyl-(3,4-dimethoxyphenyl)methyl]-(3-trifluoromethylphenyl)amide Example 65 was obtained in the form of a white solid using general method E.
Yield=96%; $C_{26}H_{27}F_3N_2O_4$; MS [M+H]=489; [M+Na]=411.

Synthesis of Example 66

Propynoic Acid (cyclohexylcarbamoyl phenylmethyl)-(3-trifluoromethylphenyl)amide Example 66 was obtained in the form of a white solid using general method E.
Yield=24%; $C_{24}H_{23}F_3N_2O_2$; MS [M+H]=429; [M+Na]=451.

Synthesis of Example 67

Propynoic Acid [cyclohexylcarbamoyl-(4-hydroxyphenyl)methyl]-(3-trifluoromethylphenyl)amide Example 67 was obtained in the form of a white solid using general method E.

Yield=97%; $C_{24}H_{23}F_3N_2O_3$; MS [M+H]=445; [M+Na]=467.

Synthesis of Example 68

Propynoic Acid [cyclohexylcarbamoyl-(4-difluoromethoxyphenyl)methyl]-(3-trifluoromethylphenyl)amide Example 68 was obtained in the form of a white solid using general method E.
Yield=44%; $C_{25}H_{23}F_5N_2O_1$; MS [M+H]=495; [M+Na]=517.

Synthesis of Example 69

Propynoic Acid (cyclohexylcarbamoyl-p-tolylmethyl)-(3-trifluoromethylphenyl)amide Example 69 was obtained in the form of a white solid using general method E.
Yield=62%; $C_{25}H_{25}F_3N_2O_2$; MS [M+H]=443; [M+Na]=465.

Synthesis of Example 70

Propynoic Acid (cyclohexylcarbamoyl-o-tolylmethyl)-(3-trifluoromethylphenyl)amide Example 70 was obtained in the form of a white solid using general method E.
Yield=42%; $C_{25}H_{25}F_3N_2O_2$; MS [M+H]=443; [M+Na]=465.

Synthesis of Example 71

Propynoic Acid [(2-chlorophenyl)cyclohexyl-carbamoylmethyl]-(3-trifluoromethylphenyl)amide Example 71 was obtained in the form of a white solid using general method E.
Yield=45%; $C_{24}H_{22}ClF_3N_2O_2$; MS [M+H]=463; [M+Na]=485.

Synthesis of Example 72

Propynoic Acid [cyclo hexylcarbamoyl-(2-fluorophenyl)methyl]-(3-trifluoromethylphenyl)amide Example 72 was obtained in the form of a white solid using general method E.
Yield=71%; $C_{24}H_{22}F_4N_2O_2$; MS [M+H]=447; [M+Na]=469.

Synthesis of Example 73

Propynoic Acid [cyclohexylcarbamoyl-(3,4-difluorophenyl)methyl]-(3-trifluoromethylphenyl)amide Example 73 was obtained in the form of a white solid using general method E.
Yield=35%; $C_{24}H_2F_5N_2O_2$; MS [M+H]=465; [M+Na]=487.

Synthesis of Example 74

Propynoic Acid [cyclohexylcarbamoyl-(4-fluorophenyl)methyl]-(3-trifluoromethylphenyl)amide Example 74 was obtained in the form of a white solid using general method E.
Yield=30%; $C_{24}H_{22}F_4N_2O_2$; MS [M+H]=447; [M+Na]=469.

Synthesis of Example 75

Propynoic Acid [cyclohexylcarbamoyl-(4-hydroxy-3-methoxyphenyl)methyl]-(3-trifluoromethylphenyl)amide Example 75 was obtained in the form of a white solid using general method E.
Yield=98%; $C_{25}H_{25}F_3N_2O_4$; MS [M+H]=475; [M+Na]=497.

Synthesis of Example 76

Propynoic Acid [cyclohexylcarbamoyl-(4-dimethylaminophenyl)methyl]-(3-trifluoromethylphenyl)amide Example 76 was obtained in the form of a white solid using general method E.
Yield=53%; $C_{26}H_{28}F_3N_3O_2$; MS [M+H]=472.

Synthesis of Example 77

Propynoic Acid [cyclohexylcarbamoyl-(3-nitrophenyl)methyl]-(3-trifluoromethylphenyl)amide Example 77 was obtained in the form of a white solid using general method E.
Yield=72%; $C_{24}H_{22}F_3N_3O_4$ MS [M+H]=474.

Synthesis of Example 78

Propynoic Acid [(2-chloro-5-trifluoromethyl phenyl)cyclohexylcarbamoylmethyl]-(3-trifluoromethylphenyl)amide Example 78 was obtained in the form of a white solid using general method E.
Yield=39%; $C_{25}H_{21}ClF_6N_2O_2$; MS [M+H]=531; [M+Na]=553.

Synthesis of Example 79

Propynoic Acid [(3-chlorophenyl)cyclohexylcarbamoylmethyl]-(3-trifluoromethylphenyl)amide Example 79 was obtained in the form of a white solid using general method E.

Synthesis of Example 80

Propynoic Acid [cyclohexylcarbamoyl-(4-trifluoromethoxyphenyl)methyl]-(3-trifluoromethylphenyl)amide Example 80 was obtained in the form of a white solid using general method E.
Yield=50%; $C_{25}H_{22}F_6N_2O_3$; MS [M+H]=513.

Synthesis of Example 81

Propynoic Acid [(4-cyanophenyl)cyclohexyl carbamoylmethyl]-(3-trifluoromethylphenyl)amide Example 81 was obtained in the form of a white solid using general method E.
Yield=66%; $C_{25}H_{22}F_3N_3O_2$; MS [M+H]=454; [M+Na]=476.

Synthesis of Example 82

Propynoic Acid [cyclohexylcarbamoyl-(4-methoxyphenyl)methyl]-(3-trifluoromethylphenyl)amide Example 82 was obtained in the form of a white solid using general method E.
Yield=62%; $C_{25}H_{25}F_3N_2O_3$; MS [M+H]=459.

Synthesis of Example 83

Propynoic Acid [cyclohexylcarbamoyl-(4-nitrophenyl)methyl]-(3-trifluoromethylphenyl)amide Example 83 was obtained in the form of a white solid using general method E.
Yield=70%; $C_{2=1}H_{22}F_3N_3O_4$; MS [M+H]=474; [M+Na]=496.

Synthesis of Example 84

Propynoic Acid (benzo[1,3]dioxol-4-yl-cyclohexylcarbamoylmethyl)-(3-trifluoromethyl-phenyl)amide Example 84 was obtained in the form of a white solid using general method E.
Yield=33%; $C_{25}H_{23}F_3N_2O_4$; MS [M+H]=473; [M+Na]=495.

Synthesis of Example 85

Propynoic Acid [cyclohexylcarbamoyl-(2-nitrophenyl)methyl]-(3-trifluoromethylphenyl)amide Example 85 was obtained in the form of a white solid using general method E.
Yield=87%; $C_{24}H_{22}F_3N_3O_4$; MS [M+H]=474; [M+Na]=496.

Synthesis of Example 86

Propynoic Acid [cyclohexylcarbamoyl-(2,4-dichlorophenyl)methyl]-(3-trifluoromethylphenyl)amide Example 86 was obtained in the form of a pink solid using general method E.
Yield=62%; $C_{24}H_{21}Cl_2F_3N_2O_2$; MS [M+H]=497.

Synthesis of Example 87

Propynoic Acid [(4-chloro-3-fluorophenyl)cyclohexylcarbamoylmethyl]-(3-trifluoromethylphenyl)

Example 87 was obtained in the form of a white solid using general method E.
Yield=52%; $C_{24}H_{21}ClF_4N_2O_2$; MS [M+H]=481; [M+Na]=503.

Synthesis of Example 88

Propynoic Acid [cyclohexylcarbamoyl-(4-methylsulphanylphenyl)methyl]-(3-trifluoromethylphenyl)amide Example 88 was obtained in the form of a white solid using general method E.
Yield=73%; $C_{25}H_{25}F_3N_2O_2S$; MS [M+H]=475; [M+Na]=497.

Synthesis of Example 89

Propynoic Acid [cyclo hexylcarbamoyl-(4-isopropylphenyl)methyl]-(3-trifluoromethylphenyl)amide Example 89 was obtained in the form of a white solid using general method E.
Yield=32%; $C_{27}H_{29}F_3N_2O_2$; MS [M+H]=471; [M+Na]=493.

Synthesis of Example 90

Propynoic Acid [cyclohexylcarbamoyl-(3-phenoxyphenyl)methyl]-(3-trifluoromethylphenyl)amide Example 90 was obtained in the form of a yellow solid using general method E.
Yield=32%; $C_{30}H_{27}F_3N_2O_3$; MS [M+H]=521; [M+Na]=543.

Synthesis of Example 91

Propynoic Acid [cyclohexylcarbamoyl-(2,3-dihydrobenzo[1,4]dioxin-6-yl)-methyl]-(3-trifluoromethylphenyl)amide Example 91 was obtained in the form of a white solid using general method E.
Yield=47%; $C_{26}H_{25}F_3N_2O_4$; MS [M+H]=487; [M+Na]=509.

Synthesis of Example 92

Propynoic Acid [cyclohexylcarbamoyl-(2,6-dichlorophenyl)methyl]-(3-trifluoromethylphenyl)amide Example 92 was obtained in the form of a yellow solid using general method E.
Yield=46%; $C_{24}H_2Cl_2F_3N_2O_2$; MS [M+H]=497.

Synthesis of Example 93

Propynoic Acid [cyclohexylcarbamoyl-(2,4-difluorophenyl)methyl]-(3-trifluoromethylphenyl)amide Example 93 was obtained in the form of a white solid using general method E.

Yield=72%; $C_{24}H_{21}F_5N_2O_2$, MS [M+H]=465; [M+Na]=487.

Synthesis of Example 94

Propynoic Acid (cyclohexylcarbamoyl-m-tolylmethyl)-(3-trifluoromethylphenyl)amide Example 94 was obtained in the form of a white solid using general method E.
Yield=26%; $C_{25}H_{25}F_3N_2O_2$; MS [M+H]=443; [M+Na]=465.

Synthesis of Example 95

Propynoic Acid [(3-cyanophenyl)-cyclohexyl carbamoylmethyl]-(3-trifluoromethylphenyl)amide Example 95 was obtained in the form of a pink solid using general method E.
Yield=89%; $C_{25}H_{22}F_3N_3O_2$; MS [M+H]=454; [M+Na]=476.

Synthesis of Example 96

Propynoic Acid [cyclohexylcarbamoyl-(2-methoxyphenyl)methyl]-(3-trifluoromethylphenyl)amide Example 96 was obtained in the form of a white solid using general method E.
Yield=73%; $C_{25}H_{25}F_3N_2O_3$; MS [M+H]=459; [M+Na]=481.

Synthesis of Example 97

Propynoic Acid [cyclo hexylcarbamoyl-(3-methoxyphenyl)methyl]-(3-trifluoromethylphenyl)amide Example 97 was obtained in the form of a white solid using general method E.
Yield=85%; $C_{25}H_{25}F_3N_2O_3$; MS [M+H]=459; [M+Na]=481.

Synthesis of Example 98

Propynoic Acid [cyclohexylcarbamoyl-(4-boronic acid-phenyl)methyl]-(3-trifluoromethylphenyl)amide Example 98 was obtained in the form of a yellow solid using general method E.
Yield=72%; $C_{24}H_{24}BF_3N_2O_4$; MS [M+H]=473.

Synthesis of Example 99

Propynoic Acid [cyclohexylcarbamoyl-(3-boronic acid-phenyl)methyl]-(3-trifluoromethylphenyl)amide Example 99 was obtained in the form of a yellow solid using general method E.
Yield=73%; $C_{24}H_{24}BF_3N_2O_4$; MS [M+H]=473; [M+Na]=495.

Synthesis of Example 100

Propynoic Acid [cyclohexylcarbamoyl-(2,4-dimethylphenyl)methyl]-(3-trifluoromethylphenyl)amide Example 100 was obtained in the form of a white solid using general method E.
Yield=82%; $C_{26}H_{27}F_3N_2O_2$, MS [M+H]=457; [M+Na]=480.

Synthesis of Example 101

Propynoic Acid [cyclohexylcarbamoyl-(4-pyrrolidin-1-yl-phenyl)methyl]-(3-trifluoromethylphenyl)amide Example 101 was obtained in the form of a pink solid using general method E.
Yield=83%; $C_{28}H_{30}F_3N_3O_2$; MS [M+H]=498.

Synthesis of Example 102

Propynoic Acid [cyclohexylcarbamoyl-(3,4-dichlorophenyl)methyl]-(3-trifluoromethylphenyl)amide Example 102 was obtained in the form of a pink solid using general method E.
Yield=74%; $C_{24}H_{21}Cl_2F_3N_2O_2$; MS [M+H]=497; [M+Na]=520.

Synthesis of Example 103

Propynoic Acid [cyclohexylcarbamoyl-(4-trifluoromethylphenyl)methyl]-(3-trifluoromethylphenyl)amide Example 103 was obtained in the form of a white solid using general method E.
Yield=32%; $C_{25}H_{22}F_6N_2O_2$; MS [M+H]=497.

Synthesis of Example 104

Propynoic Acid (cyclohexylcarbamoylthiophen-2-yl-methyl)-[3-(1H-tetrazol-5-yl)-phenyl]amide Example 104 was obtained in the form of a pink solid using general method E.
Yield=90%; $C_{22}H_{22}N_6O_2S$; MS [M+H]=435.

Synthesis of Example 105

Propynoic Acid (1H-benzotriazol-5-yl)-(cyclohexylcarbamoylthiophen-2-yl-methyl)amide Example 105 was obtained in the form of a pink solid using general method E.
Yield=74%; $C_{21}H_{21}N_5O_2S$; MS [M+H]=408; [M+Na]=430.

Synthesis of Example 106

Propynoic Acid [cyclohexylcarbamoyl-(2,3-difluorophenyl)methyl]-(3-trifluoromethylphenyl)amide Example 106 was obtained in the form of a white solid using general method E.
Yield=69%; $C_{24}H_{21}F_5N_2O_2$; MS [M+H]=465; [M+Na]=487.

Synthesis of Example 107

2-[(2-Bromoacetyl)-(3-trifluoromethylphenyl)amino]-N-cyclohexyl-2-thiophen-2-yl-acetamide Example 107 was obtained in the form of a white solid using general method E.
Yield=80%; $C_{21}H_{22}BrF_3N_2O_2S$; MS [M+H]=503.

Synthesis of Example 108

2-[(2-bromoacetyl)-(4-methoxyphenyl)amino]-N-cyclohexyl-2-thiophen-2-yl-acetamide

Example 108 was obtained in the form of a white solid using general method E.

Yield=77%; $C_{21}H_{25}BrN_2O_3S$; MS [M+H]=466.

NMR $H^1$ (CDCl$_3$, 300): δ=1.10-1.25 (m, 3H, CH$_2$), 1.25-1.45 (m, 2H, CH$_2$), 1.55-1.77 (m, 3H, CH$_2$), 1.85-2.07 (m, 2H, CH$_2$), 3.65 (s, 2H, CH$_2$), 3.78 (s, 2H, CH$_2$), 3.80 (m, 1H, CH), 6.02 (d, 1H, J=7.8 Hz, NH), 6.19 (s, 1H, CH), 6.50-7.50 (l, 4H, CH), 6.88 (dd, 1H, J=5.1 3.6 Hz, CH), 6.95 (m, 1H, CH), 7.25 (dd, 1H, J=5.1 1.2 Hz, CH).

NMR $C^{13}$ (CDCl$_3$, 300): δ=167.2 159.7 154.8 135.3 131.3 130.7 129.8 128.1 126.2 114.3 60.4 55.4 48.8 32.7 27.5 25.4 24.7.

Synthesis of Example 109

2-[(2-Chloroacetyl)-(4-methoxyphenyl)amino]-N-cyclohexyl-2-thiophen-2-yl-acetamide

Thiophene-2-carbaldehyde, 4-methoxyphenylamine, chloroacetic acid and isocyanocyclohexane were reacted as described in general method E. Example 109 was obtained in the form of a grey solid.

Yield=38%; $C_{21}H_{25}ClN_2O_3S$; MS [M+H]=421

NMR $H^1$ (DMSO D$_6$, 300): δ=0.96-1.29 (m, 5H); 1.50-1.78 (m, 5H); 3.5-3.61 (m, 1H); 3.69 (s, 3H); 3.90 (sys AB, 2H); 6.23 (s, 1H); 6.75-7.36 (m, 7H); 8.06 (d, J=7.8 Hz, 1H)

Synthesis of Example 110

2-[(2-Chloroacetyl)-(3-trifluoromethylphenyl)amino]-N-cyclo hexyl-2-thiophen-2-yl-acetamide

Thiophene-2-carbaldehyde, 3-trifluoromethylphenylamine, chloroacetic acid and isocyanocyclohexane were reacted as described in general method E. Example 110 was obtained in the form of a white solid.

Yield=52%; $C_{21}H_{22}ClF_3N_2O_2S$ MS [M+H]=559; [M−H]=557.

NMR $H^1$ (acetone D$_6$, 300): δ=1.08-1.42 (m, 5H); 1.56-1.92 (m, 5H); 3.67-3.79 (m, 1H); 3.96 (s, 2H); 6.40 (s, 1H); 6.83 (dd, J=3.6 Hz, J=5.1 Hz, 1H), 6.91-6.92 (m, 1H); 7.31-7.90 (m, 5H.

Synthesis of Example 111

2-[(2-Chloroacetyl)isobutylamino]-N-cyclo hexyl-2-thiophen-2-yl-acetamide

Thiophene-2-carbaldehyde, isobutylamine, chloroacetic acid and isocyanocyclohexane were reacted as described in general method E. Example 111 was obtained in the form of an orange solid.

Yield=48%; $C_{18}H_{22}ClN_2O_2S$; MS [M+H]=371; [M−H]=399.

NMR $H^1$ (CDCl$_3$, 300): δ=0.75-084 (m, 6H); 1.12-1.39 (m, 5H); 1.51-1.83 (m, 6H); 3.08-3.35 (m, 2H); 3.65-3.75 (m, 1H); 4.10-4.35 (m, 2H); 5.84 (s, 1H); 6.82-6.84 (m, 1H); 7.20-7.21 (m, 1H); 7.49 (d, J=4.5 Hz, 1H).

Synthesis of Example 112

Propynoic Acid [(2-benzyloxyphenylcarbamoyl)thiophen-2-yl-methyl]-(3-trifluoromethylphenyl)amide

Example 112 was obtained in the form of a white solid using general method E.

Yield=30%; $C_{29}H_{21}F_3N_2O_1S$; MS [M+H]=535; [M+Na]=557; [M+K]=573.

NMR $H^1$ (CDCl$_3$, 300): δ=2.86 (s, 1H, ≡CH), 5.00 (s, 2H, CH$_2$), 6.37 (s, 1H, CH), 6.76 (dd, J=5.2 3.6 Hz, 1H, CH); 6.89-7.10 (m, 4H, CH), 7.20 (dd, J=5.2 1.0 Hz, 1H, CH); 7.22-7.27 (m, 2H, CH), 7.30-7.50 (m, 5H, CH), 7.54-7.63 (m, 2H, CH), 8.27 (s, 1H, NH), 8.39 (dd, J=7.8 1.8 Hz, 1H, CH).

NMR $C^{13}$ (CDCl$_3$, 300): δ=165.2 153.0 147.4 139.8 136.1 134.1 133.8 131.6 130.6 129.5 128.7 128.5 128.2 127.7 127.4 126.8 125.7 12 4.4 121.4 120.9 120.1 111.6 81.4 70.7 61.1.

Synthesis of Example 113

N-Cyclohexyl-2-[(2-fluoroacetyl)-(3-trifluoromethylphenyl)amino]-2-thiophen-2-yl-acetamide

Example 113 was obtained in the form of a white solid using general method E.

Yield=60%; $C_{21}H_{22}F_4N_2O_2S$; MS [M+H]=443.

NMR $H^1$ (CDCl$_3$, 300): δ=1.03-1.27 (m, 3H, CH$_2$); 1.27-1.48 (m, 2H, CH$_2$); 1.53-1.78 (m, 3H, CH$_2$); 1.82-2.05 (m, 2H, CH$_2$); 3.73-3.90 (m, 1H, CH—NH); 4.59 (d, J=46.6 Hz, 2H, CH$_2$), 5.87 (d, J=7.0 Hz, 1H, NH), 6.25 (s, 1H, CH), 6.83-6.97 (m, 2H, CH); 7.20-7.31 (m, 2H, CH), 7.37-7.66 (m, 3H, CH).

Synthesis of Example 114

N-Cyclo hexyl-2-[(2-fluoroacetyl)isobutylamino]-2-thiophen-2-yl-acetamide

Example 114 was obtained in the form of a white solid using general method E.

Yield=25%; $C_{18}H_{27}FN_2O_2S$; MS [M+H]=355.

NMR $H^1$ (CDCl$_3$, 300): δ=0.81 (d, J=6.7 Hz, 3H, CH$_3$); 0.88 (d, J=6.7 Hz, 3H, CH$_3$); 1.04-1.24 (m, 3H, CH$_2$); 1.25-1.44 (m, 2H, CH$_2$); 1.51-1.75 (m, 3H, CH$_2$); 1.78-2.00 (m, 3H, CH+CH$_2$); 2.89-3.09 (m, 2H, CH$_2$); 3.69-3.88 (m, 1H, CH—NH); 5.03 (d, J=46.6 Hz, 2H, CH$_2$), 5.63 (s, 1H, CH); 6.16-6.35 (l, 1H, NH), 7.03 (dd, J=5.2 3.6 Hz, 1H, CH), 7.18 (d, J=3.2 Hz, 1H, CH), 7.38 (dd, J=5.2 1.2 Hz, 1H, CH).

Synthesis of Example 115

N-Cyclohexyl-2-[(2-fluoroacetyl)-(4-methoxyphenyl)amino]-2-thiophen-2-yl-acetamide

Example 115 was obtained in the form of a white solid using general method E.

Yield=74%; $C_{21}H_{25}FN_2O_3S$; MS [M+H]=405.

NMR $H^1$ (CDCl$_3$, 300): δ=1.02-1.50 (m, 5H, CH$_2$); 1.50-1.82 (m, 3H, CH$_2$); 1.83-2.05 (m, 2H, CH$_2$); 3.71-3.91 (m, 1H, CH—NH); 3.79 (s, 3H, CH$_3$), 4.59 (d, J=46.9 Hz, 2H, CH$_2$), 5.96 (d, J=7.5 Hz, 1H, NH), 6.25 (s, 1H, CH); 6.66-6.84 (m, 2H, CH), 6.88 (dd, J=5.2 3.6 Hz, 1H, CH), 6.92-6.97 (m, 1H, CH), 7.25 (dd, J=5.1 1.1 Hz, 1H, CH), 5.90-7.65 (m, 2H, CH).

Synthesis of Example 116

Propynoic Acid (cyclohexylcarbamoylthiophen-2-yl-methyl)methylamide

Thiophene-2-carbaldehyde, methylamine, propargylic acid and isocyanocyclohexane were reacted as described in general method E. Example 116 was obtained in the form of a white solid.

Yield=20%; $C_{16}H_{20}N_2O_2S$; MS [M+H]=305; [M−H]=303.

NMR $H^1$ (CDCl$_3$, 300): δ=1.09-1.40 (m, 5H); 1.55-1.71 (m, 3H); 1.86-1.92 (m, 2H); 2.90 and 3.14 (2s, 3H); 3.20 and 3.26 (2s, 1H); 3.70-3.75 (m, 1H); 65.95-6.12 (m, 1H); 6.34 and 6.36 (2s, 1H); 7.00-7.03 (m, 1H, CH); 7.11-7.16 (m, 1H); 7.34-7.37 (m, 1H).

Synthesis of Example 117

Propynoic Acid (cyclohexylcarbamoylmethyl-(3-trifluoromethylphenyl)amide)

Formaldehyde, 3-trifluoromethylphenylamine, propargylic acid and isocyanocyclohexane were reacted as described in general method E. Example 117 was obtained in the form of a white solid.

Yield=26%; $C_{18}H_{19}F_3N_2O_2$; MS [M+H]=353.

NMR $H^1$ (CDCl$_3$, 300): δ=1.02-1.25 (m, 5H); 1.49-1.66 (m, 5H); 3.40-3.44 (m, 1H); 4.29 and 4.32 (2s, 2H); 4.51 and 4.69 (2s, 1H); 7.59-8.11 (m, 5H).

Synthesis of Example 118

Propynoic Acid (carbamoylthiophen-2-yl-methyl)-(3-trifluoromethylphenyl)amide

Example 118 was obtained in the form of a white solid using general method E.

Yield=52%; $C_{16}H_{11}F_3N_2O_2S$; [M+Na]=375.

NMR $H^1$ (CDCl$_3$, 300): δ=2.87 (s, 1H, ≡CH), 5.85-6.22 (l, 2H, NH$_2$); 6.32 (s, 1H, CH), 6.88 (dd, J=5.1 1.2 Hz, 1H, CH), 6.92-6.98 (m, 1H, CH); 7.25-7.60 (m, 5H, CH), 7.17-7.70 (l, 1H, CH).

Synthesis of Example 119

Propynoic acid cyclohexylcarbamoylmethyl methylamide

Example 119 was obtained in the form of a white solid using general method E.

Yield=32%; $C_{12}H_{18}N_2O_2$ MS [M+H]=223; [M+Na]=245.

NMR $H^1$ (CDCl$_3$, 300): δ=1.05-1.26 (m, 3H, CH$_2$), 1.26-1.48 (m, 2H, CH$_2$); 1.53-1.80 (m, 3H, CH$_2$); 1.82-1.99 (m, 2H, CH$_2$); 3.03 (s, 1.04H, CH$_3$ form 1), 3.16 (s, 0.33H, ≡CH form 1), 3.22 (s, 0.59H, ≡CH form 2), 3.33 (s, 1.88H, CH$_3$ form 2), 3.64-3.92 (m, 1H, CH—NH); 4.00 (s, 1.26H, CH$_2$ form 2), 4.23 (s, 0.71H, CH$_2$ form 1), 5.60-5.80 (l, 0.32H, NH form 1), 5.85-6.08 (l, 0.57H, NH form 2).

Synthesis of Example 120

2-[(2-Chloroacetyl)-(2-cyanophenyl)amino]-N-cyclohexyl-2-thiophen-2-yl-acetamide Thiophene-2-carbaldehyde, 2-aminobenzonitrile, chloroacetic acid and isocyanocyclohexane were reacted as described in general method E. Example 120 was obtained in the form of a white solid.

Yield=5%; $C_{21}H_{22}ClN_3O_2S$ MS [M+H]=416.

NMR $H^1$ (CDCl$_3$, 300): δ=1.08-2.05 (m, 10H); 3.75-3.93 (m, 3H); 5.86 (dl, 1H); 6.42 (s, 1H); 6.85 (dd, J=3.6 Hz, J=5.4 Hz, 1H); 7.07 (dd, J=3.6 Hz, J=0.6 Hz, 1H); 7.018 (dd, J=0.6 Hz, J=5.4 Hz, 1H); 7.35-7.73 (m, 3H); 8.08 (d, J=7.8 Hz, 1H).

Synthesis of Example 121

2-[(2-Chloroacetyl)-(3-cyanophenyl)amino]-N-cyclohexyl-2-thiophen-2-yl-acetamide Thiophene-2-carbaldehyde, 3-aminobenzonitrile, chloroacetic acid and isocyanocyclohexane were reacted as described in general method E. Example 121 was obtained in the form of a beige solid.

Yield=67%; $C_{21}H_{22}ClN_3O_2S$; MS [M+H]=416; [M−H]=414.

NMR $H^1$ (CDCl$_3$, 300): δ=1.08-1.24 (m, 3H); 1.29-1.42 (m, 2H); 1.58-1.72 (m, 3H); 1.87-1.98 (m, 2H); 3.78-3.86 (m, 3H); 5.81 (dl, J=6.6 Hz, 1H); 6.21 (s, 1H); 6.87-6.91 (m, 2H); 7.10-7.90 (m, 5H).

Synthesis of Example 122

2-[(2-Chloroacetyl)-(4-cyanophenyl)amino]-N-cyclohexyl-2-thiophen-2-yl-acetamide Thiophene-2-carbaldehyde, 4-aminobenzonitrile, chloroacetic acid and isocyanocyclohexane were reacted as described in general method E. Example 122 was obtained in the form of a beige solid.

Yield=41%; $C_{21}H_{22}ClN_3O_2S$ MS [M+H]=416; [M−H]=414.

NMR $H^1$ (CDCl$_3$, 300): δ=1.05-1.21 (m, 3H); 1.29-1.42 (m, 2H); 1.57-1.72 (m, 3H); 1.85-1.98 (m, 2H); 3.77-3.85 (m, 3H); 5.82 (dl, J=8.1 Hz, 1H); 6.21 (s, 1H); 6.87-6.91 (m, 2H); 7.10-7.90 (m, 5H).

Synthesis of Example 123

2-[1,3-Benzodioxol-5-yl-methyl-(2-chloroacetyl) amino]-N-benzyl-2-(2-fluorophenyl)acetamide 2-Fluorobenzaldehyde, C-1,3-benzodioxol-5-yl-methylamine, chloroacetic acid and isocyanomethylbenzene were reacted as described in general method E.

Example 123 was obtained in the form of a white solid.

Yield=70%; $C_{25}H_{22}ClFN_2O_4$ MS [M+Na]=491; [M−H]=467.

NMR $H^1$ (CDCl$_3$, 300): δ=3.98-4.13 (m, 2H); 4.50-4.74 (m, 4H); 5.89 (s, 2H); 6.21 (sl, 2H); 6.51-6.64 (m, 3H); 6.97 (t, J=9.3 Hz, 1H); 7.10 (t, J=7.5 Hz, 1H); 7.25-7.32 (m, 6H); 7.54 (tl, 1H).

Synthesis of Example 124

2-[(2-Chloroacetyl)-(2-methoxyphenyl)amino]-N-cyclohexyl-2-thiophen-2-yl-acetamide Example 124 was obtained in the form of a white solid using general method E.

Yield=69%; $C_{21}H_{25}ClN_2O_3S$; MS [M+H]=421.

Synthesis of Example 125

2-[(2-Chloroacetyl)-(3-methoxyphenyl)amino]-N-cyclohexyl-2-thiophen-2-yl-acetamide Example 125 was obtained in the form of a white solid using general method E.

Yield=57%; $C_{21}H_{25}ClN_2O_3S$; MS [M+H]=421.

Synthesis of Example 126

2-[(2-Chloroacetyl)phenylamino]-N-cyclo hexyl-2-thiophen-2-yl-acetamide

Example 126 was obtained in the form of a white solid using general method E.
Yield=80%; $C_{20}H_{23}ClN_2O_2S$; MS [M+H]=391; [M+Na]=413.

Synthesis of Example 127

2-[(2-Chloroacetyl)-(4-diethylaminophenyl)amino]-N-cyclohexyl-2-thiophen-2-yl-acetamide Example 127 was obtained in the form of a white solid using general method E.
Yield=39%; $C_{24}H_{32}ClN_3O_2S$; MS [M+H]=462.

Synthesis of Example 128

2-[(2-Chloroacetyl)-(4-hydroxyphenyl)amino]-N-cyclohexyl-2-thiophen-2-yl-acetamide Example 128 was obtained in the form of a white solid using general method E.
Yield=27%; $C_{20}H_{23}ClN_2O_3S$; MS [M+H]=407; [M+Na]=429.

Synthesis of Example 129

2-[(2-Chloroacetyl)-(4-trifluoromethylphenyl)amino]-N-cyclohexyl-2-thiophen-2-yl-acetamide Example 129 was obtained in the form of a white solid using general method E.
Yield=65%; $C_{21}H_{22}ClF_3N_2O_2S$; MS [M+H]=459; [M+Na]=481.

Synthesis of Example 130

2-Chloro-N-cyclohexylcarbamoylmethyl-N-(3-trifluoromethylphenyl)acetamide

Formaldehyde (37% in water), 4-trifluoromethylphenylamine, chloroacetic acid and isocyanocyclohexane were reacted as described in general method E.
Example 130 was obtained in the form of a white solid.
Yield=31%; $C_{17}H_{20}ClF_3N_2O_2$; MS [M+H]=377; [M−H+$HCO_2$H]=421.
NMR $H^1$ (CDCl$_3$, 300): δ=1.11-1.45 (m, 5H); 1.69-1.76 (m, 3H); 1.89-1.96 (m, 2H); 3.72-3.84 (m, 1H); 3.88 (s, 2H); 4.26 (s, 2H); 5.92 (d, J=7.8 Hz, 1H); 7.58-7.68 (m, 4H).

Synthesis of Example 131

2-[(2-Chloroacetyl)-(3-trifluoromethylphenyl)amino]-N-cyclohexyl-2-phenylacetamide Benzaldehyde, 4-trifluoromethylphenylamine, chloroacetic acid and isocyanocyclohexane were reacted as described in general method E. Example 131 was obtained in the form of a white solid.
Yield=74%; $C_{23}H_{24}ClF_3N_2O_2$; MS [M+H]=453; [M−H]=451.
NMR $H^1$ (CDCl$_3$, 300): δ=0.90-1.99 (m, 10H); 3.75-3.87 (m, 3H); 5.49 (d, J=7.8 Hz, 1H); 6.08 (s, 1H); 7.04-7.50 (m, 9H).

Synthesis of Example 132

2-[(2-Chloroacetyl)-(3-trifluoromethylphenyl)amino]-N-cyclohexyl-3-methylbutyramide Isobutyraldehyde, 4-trifluoromethylphenylamine, chloroacetic acid and isocyanocyclohexane were reacted as described in general method E. Example 132 was obtained in the form of a white solid.
Yield=62%; $C_{20}H_{26}ClF_3N_2O_2$; MS [M+H]=419; [M−H+$HCO_2$H]=463.
NMR $H^1$ (CDCl$_3$, 300): δ=0.93 (d, J=8.1 Hz, 3H); 1.1 (d, J=8.1 Hz, 3H); 1.15-1.55 (m, 5H); 1.49-1.75 (m, 3H); 1.89-1.94 (m, 2H); 2.10-2.21 (m, 1H); 3.72-3.83 (m, 3H); 4.34 (d, J=11.1 Hz, 1H); 6.46 (d, J=6.6 Hz, 1H); 7.58-7.71 (m, 4H).

Synthesis of Example 133

2-[(2-Chloroacetyl)-(3-trifluoromethylphenyl)amino]-4,4-dimethylpentanoic acid cyclohexylamide 3,3-dimethylbutyraldehyde, 4-trifluoromethylphenylamine, chloroacetic acid and isocyanocyclohexane were reacted as described in general method E. Example 133 was obtained in the form of a beige solid.
Yield=41%; $C_{22}H_{30}ClF_3N_2O_2$; MS [M+H]=447.
NMR $H^1$ (CDCl$_3$, 300): δ=0.89 (s, 9H); 1.09-1.91 (m, 12H); 3.67-3.80 (m, 3H); 5.09 (dd, J=3 Hz, J=9.3 Hz, 1H); 6.45 (d, J=7.8 Hz, 1H); 7.48-7.61 (m, 3H); 7.68-7.71 (m, 1H).

Synthesis of Example 134

2-[(2-Chloroacetyl)naphthalen-1-yl-amino]-N-cyclohexyl-2-thiophen-2-yl-acetamide Example 134 was obtained in the form of a white solid using general method E.
Yield=75%; $C_{24}H_{25}ClN_2O_2S$; MS [M+H]=441.

Synthesis of Example 135

2-[1,3-Benzodioxol-5-yl-(2-chloroacetyl)amino]-N-cyclo hexyl-2-thiophen-2-yl-acetamide Example 135 was obtained in the form of a white solid using general method E.
Yield=57%; $C_{21}H_{23}ClN_2O_4S$; MS [M+H]=435; [M+Na]=457.

Synthesis of Example 136

2-[(2-Chloroacetyl)-(3-trifluoromethylphenyl)amino]-N-cyclohex-1-enyl-2-thiophen-2-yl-acetamide Example 136 was obtained in the form of a white solid using general method E.
Yield=43%; $C_{21}H_{20}ClF_3N_2O_2S$; MS [M+Na]=479.
NMR $H^1$ (CDCl$_3$, 300): δ=1.52-1.63 (m, 2H, CH$_2$), 1.64-1.74 (m, 2H, CH$_2$); 1.79-1.92 (m, 1H, CH$_2$); 2.07-2.17 (m, 3H, CH$_2$); 3.82 (s, 2H, ClCH$_2$), 6.05-6.13 (m, 1H, CH); 6.22

(s, 1H, CH), 6.78-6.99 (m, 3H, NH+CH); 7.27 (dd, J=5.1 1.1 Hz, 1H, CH), 7.40-7.53 (m, 1H, CH); 7.59 (d, J=7.6 Hz, 1H, CH), 7.05-7.90 (l, 2H, CH).

NMR $C^{13}$ (CDCl$_3$, 300): δ=166.4 166.1 138.8 134.3 133.8 132.3 130.4 129.9 128.5 127.2 126.8 125.9 114.5 61.0 42.1 27.8 24.0 22.4 21.8.

Synthesis of Example 137

2-[(2-Chloroacetyl)-(3-trifluoromethylphenyl)amino]-2-thiophen-2-yl-acetamide

Example 137 had been generated from Example 136 (390 mg, 0.902 mmol) dissolved in 5 mL of a 5% v/v THF-HCl mixture. The reaction medium was stirred for 1 hour then was extracted in dichloromethane. The organic phase was washed in water then dried on MgSO$_4$. After evaporation, the white solid recovered was washed in a little diisopropyl ether and was recovered by filtration.

Example 137 was obtained in the form of a white solid.
Yield=79%; C$_{15}$H$_{12}$ClF$_4$N$_2$O$_2$S; MS [M+Na]=399.
NMR H$^1$ (CDCl$_3$, 300): δ=3.82 (s, 2H, ClCH$_2$), 5.73 (l, 1H, NH); 6.00 (l, 1H, NH); 6.28 (s, 1H, CH), 6.84-6.94 (m, 2H, CH); 7.28 (dd, J=5.1 1.2 Hz, 1H, CH), 7.40-7.65 (m, 3H, CH), 7.17-7.70 (l, 1H, CH).

Synthesis of Example 138

(S)-2-Chloro-N-(cyclohexylcarbamoylthiophen-2-yl-methyl)-N-(3-trifluoromethylphenyl)propionamide Thiophenecarboxaldehyde, 4-trifluoromethylphenylamine, (S)-2-chloropropanoic acid and isocyanocyclohexane were reacted as described in general method E.

Example 138 was obtained in the form of a white solid.
Yield=47%; C$_{22}$H$_{24}$ClF$_3$N$_2$O$_2$S; MS [M+H]=473; [M+Na]=471.
NMR H$^1$ (CDCl$_3$, 300): δ=1.06-1.39 (m, 5H); 1.58 (d, J=6.6 Hz, 3H); 1.59-1.70 (m, 3H); 1.85-1.96 (m, 2H); 3.77-3.91 (m, 1H); 4.03-4.12 (m, 1H); 6.00-6.33 (m, 2H); 6.81-8.00 (m, 7H).

Synthesis of Example 139

3-{2-[(2-Chloroacetyl)-(3-trifluoromethylphenyl)amino]-2-thiophen-2-yl-acetylamino}propionic acid methyl ester Thiophenecarboxaldehyde, 4-trifluoromethylphenylamine, chloroacetic acid and methyl 3-isocyanopropanoate were reacted as described in general method E.

Example 139 was obtained in the form of a yellow solid.
Yield=55% C$_{19}$H$_{18}$ClF$_3$N$_2$O$_4$S; MS [M+H]=463; [M+Na]=461.
NMR H$^1$ (CDCl$_3$, 300): δ=2.58 (t, J=6.0 Hz, 2H); 3.58 (quint, J=6.1 Hz, 2H); 3.66 (s, 3H); 3.82 (s, 2H); 6.15 (s, 1H); 4.50 (tl, 1H); 6.87-6.89 (m, 2H); 7.26-7.28 (m, 2H); 7.51-7.61 (m, 3H).

Synthesis of Example 140

(R)-2-Chloro-N-(cyclohexylcarbamoylthiophen-2-yl-methyl)-N-(3-trifluoromethylphenyl) propionamide Thiophenecarboxaldehyde, 4-trifluoromethylphenylamine, (R)-2-chloropropanoic acid and isocyanocyclohexane were reacted as described in general method E.

Example 140 was obtained in the form of a beige solid.
Yield=77%; C$_{22}$H$_{24}$ClF$_3$N$_2$O$_2$S; MS [M+H]=473; [M+Na]=471.
NMR H$^1$ (CDCl$_3$, 300): δ=1.09-1.99 (m, 13H); 3.74-3.89 (m, 1H); 4.05-4.17 (m, 1H); 5.77-6.31 (m, 2H); 6.83-6.98 (m, 2H); 7.26 (m, 1H); 7.35 (m, 5H).

Synthesis of Example 141

2-Chloro-N-(2-cyanophenyl)-N-cyclohexyl carbamoylmethylacetamide

Formaldehyde (37% in water), 2-cyanophenylamine, chloroacetic acid and isocyanocyclohexane were reacted as described in general method E. Example 141 was obtained in the form of a white solid.
Yield=70%;
C$_{17}$H$_{20}$ClN$_3$O$_2$; MS [M+H]=334; [M−H+HCO$_2$H]=378.
NMR H$^1$ (CDCl$_3$, 300): δ=1.11-1.99 (m, 10H); 3.70-3.81 (m, 1H); 3.83-3.97 (m, 3H); 4.71 (d de AB, 1H); 5.99 (dl, 1H); 7.53-7.62 (m, 1H); 7.73-7.81 (m, 3H).

Synthesis of Example 142

(4-{2-[(2-Chloroacetyl)-(3-trifluoromethylphenyl)amino]-2-thiophen-2-yl-acetylamino}cyclohexyl) carbamic acid test-butyl ester Example 142 was obtained in the form of a white solid using general method E.
Yield=83%; C$_{26}$H$_{31}$ClF$_3$N$_3$O$_4$S; [M+Na]=596.
NMR H$^1$ (CDCl$_3$, 300): δ=1.14-1.32 (m, 4H, CH$_2$), 1.44 (s, 9H, CH$_3$), 1.92-2.13 (m, 4H, CH$_2$), 3.28-3.50 (m, 1H, CH), 3.71-3.87 (m, 1H, CH), 4.29-4.48 (m, 1H, NH), 5.79 (d, 1H, J=8.0 Hz, NH), 6.15 (s, 1H, CH), 6.84-6.94 (m, 2H, CH), 7.03-7.93 (m, 5H, CH).

Synthesis of Example 143

N-(4-Aminocyclohexyl)-2-[(2-chloroacetyl)-(3-trifluoromethylphenyl)amino]-2-thiophen-2-yl-acetamide hydrochloride Example 143 had been generated from Example 142 using the method described for Example 125.
Example 143 was obtained in the form of a white solid.
Yield=65%; C$_{21}$H$_{24}$Cl$_2$F$_3$N$_3$O$_2$S; [M−H]=472.
NMR H$^1$ (DMSO, 300): δ=1.02-1.49 (m, 4H), 1.71-2.05 (m, 4H), 2.87-3.02 (m, 1H), 3.43-3.62 (m, 1H), 3.88-4.10 (m, 2H), 6.28 (s, 1H), 6.78-6.86 (m, 2H), 7.37 (dd, J=5.0 1.3 Hz, 1H), 7.43-7.51 (m, 1H), 7.60 (d, J=7.6 Hz, 1H), 7.90-8.10 (l, 3H), 8.30 (d, J=7.1 Hz, 1H).

Synthesis of Example 144

2-[(2-Chloroacetyl)-(3-trifluoromethylphenyl)amino]-N-cyclohexyl-2-pyridin-3-yl-acetamide Example 144 was obtained in the form of a white solid using general method E.
Yield=82%; C$_{22}$H$_{23}$ClF$_3$N$_3$O$_2$; [M+H]=454.
NMR H$^1$ (CDCl$_3$, 300): δ=0.96-1.45 (m, 5H, CH$_2$), 1.52-2.04 (m, 5H, CH$_2$), 3.69-3.88 (m, 1H, CH), 3.81 (s, 2H, ClCH$_2$), 6.21 (s, 1H, CH), 6.30 (d, J=7.0 Hz, 1H, NH), 6.65-8.40 (m, 2H, CH), 7.18 (d, J=7.7 5.0 Hz, 1H, CH), 7.32-7.63 (m, 3H, CH), 8.51 (d, J=4.2 Hz, 1H, CH), 8.55-8.68 (l, 1H, CH).

Synthesis of Example 185

2-[(2-Chloroacetyl)-(4-fluoro-phenyl)-amino]-N-(4-fluoro-benzyl)-2-methyl-propionamide Example 185 was obtained in the form of a white solid using general method E.
Yield=71%; $C_{19}H_{19}ClF_2N_2O_2$; [M+H]=381.
NMR $H^1$ (CDCl$_3$, 300): δ=1.45 (s, 3H), 1.61 (s, 3H), 3.72 (s, 2H), 4.51 (s, 2H), 6.12 (m, 1H), 7.06 (t, J=6.7 Hz, 2H), 7.16 (t, J=6.7 Hz, 2H), 7.34 (d, J=6.7 Hz, 1H), 7.36 (d, J=6.7 Hz, 1H), 7.43 (d, J=6.7 Hz, 1H), 7.45 (d, J=6, 7 Hz, 1H).

Synthesis of Example 186

2-[(2-Chloro-acetyl)-(4-fluoro-phenyl)-amino]-N-(4-methoxy-benzyl)-2-methyl-propionamide Example 186 was obtained in the form of a colourless gum using general method E.
Yield=31%; $C_{20}H_{22}ClFN_2O_3$; [M+H]=393.
NMR $H^1$ (CDCl$_3$, 300): δ=1.40 (s, 6H), 3.72 (s, 2H), 3.82 (s, 3H), 4.46 (m, 2H), 6.04 (m, 1H), 6.90 (m, 2H), 7.16 (m, 2H), 7.28 (m, 2H), 7.42 (m, 2H).

Synthesis of Example 187

2-[(2-Chloro-acetyl)-(2-methyl-4-phenoxy-phenyl)-amino]-N-(4-methoxy-benzyl)-2-methyl-propionamide Example 187 was obtained in the form of a colourless gum using general method E.
Yield=37%; $C_{27}H_{29}ClN_2O_4$; [M+H]=481.
NMR $H^1$ (CDCl$_3$, 300): δ=1.38 (s, 3H), 1.51 (s, 3H), 2.42 (s, 3H), 3.73 (q, J=10.4 Hz, 2H), 3.82 (s, 3H), 4.48 (d, J=4.3 Hz, 2H), 6.13 (m, 1H), 6.84-6.97 (m, 4H), 7.08 (d, J=67 Hz, 2H), 7.20 (t, J=5.0 Hz, 1H), 7.31 (d, J=6.7 Hz, 2H), 7.38-7.47 (m, 3H).

Synthesis of Example 188

2-[(2-Chloro-acetyl)-(3-chloro-2-methyl-phenyl)-amino]-N-(4-fluoro-benzyl)-2-methyl-propionamide Example 188 was obtained in the form of a colourless gum using general method E.
Yield=18%; $C_{20}H_{21}Cl_2FN_2O_2$; [M+H]=411.
NMR $H^1$ (CDCl$_3$, 300): δ=1.38 (s, 3H), 1.51 (s, 3H), 2.55 (s, 3H), 3.68 (m, 2H), 4.52 (d, J=4.3 Hz, 2H), 6.24 (m, 1H), 7.07 (t, J=6.7 Hz, 2H), 7.21-7.32 (m, 1H), 7.37 (dd, J=6.7 Hz et J=4.8 Hz, 2H), 7.49 (t, J=5.2 Hz, 2H).

Synthesis of Example 189

2-[(3-tert-Butyl-phenyl)-(2-chloro-acetyl)-amino]-N-cyclohexyl-2-[4-[3-(4-methyl-piperazin-1-yl)-propoxy]-phenyl]-acetamide Example 189 was obtained using general method E for implementation of the synthesis. After reaction, the reaction medium is simply concentrated to then obtain an oil, directly purified by semi-preparative HPLC using a binary water-acetonitrile mixture buffered to a pH of 9.2 with ammonium formate. Example 189 is recovered following lyophilisation in the form of white powder.
Yield=42%; $C_{34}H_{49}ClN_4O_3$; MS [M+H]=598.
NMR $^1$H (CDCl$_3$, 300): δ=0.85-2.44 (m, 21H, 6CH$_2$+3CH$_3$); 2.31 (s, 3H, NCH$_3$); 2.36-2.84 (m, 10H, NCH$_2$); 3.74-3.90 (m, 3H, CH—NH+CH$_2$Cl); 3.91 (t, 2H, J=6.3 Hz, OCH$_2$); 5.53 (d, 1H, J=8.0 Hz, NH); 5.79-6.16 (l, 1H, CH); 6.24-6.77 (m, 3H, CH); 6.79-7.81 (m, 5H, CH).

Synthesis of Example 190

2-[(4-Butyl-2-methyl-phenyl)-(2-chloro-acetyl)-amino]-N-cyclohexyl-2-{4-[3-(4-methyl-piperazin-1-yl)-propoxy]-phenyl}-acetamide Example 190 was obtained in the form of a white powder using general method E.
Yield=46%; $C_{34}H_{49}ClN_4O_3$; MS [M+H]=612.
NMR $^1$H (CDCl$_3$, 300): δ=0.78-2.10 (m, 21H, 9CH$_2$+1CH$_3$); 2.29 (s, 3H, NCH$_3$); 2.17-2.83 (m, 13H, 5NCH$_2$+1CH$_3$); 3.61-4.10 (m, 5H, CH—NH+CH$_2$Cl+CH$_2$O); 5.63 (d, 1H, J=8.0 Hz, NH); 5.83 (s, 1H, CH); 6.50-7.15 (m, 6H, CH); 7.20-7.58 (m, 1H, CH).

Synthesis of Example 191

2-[(2-Chloro-acetyl)-(2-methyl-3-trifluoromethyl-phenyl)-amino]-N-cyclohexyl-2-{4-[3-(4-methyl-piperazin-1-yl)-propoxy]-phenyl}-acetamide Example 191 was obtained in the form of a white powder using general method E.
Yield=30%; $C_{32}H_{42}ClF_3N_4O_3$; MS [M+H]=624.
NMR $^1$H (CDCl$_3$, 300): δ=0.91-1.22 (m, 3H, CH$_2$); 1.23-1.47 (m, 2H, CH$_2$); 1.50-1.75 (m, 3H, CH$_2$); 1.76-2.06 (m, 8H, CH$_2$+CH$_3$); 2.32 (s, 3H, NCH$_3$); 2.38-2.75 (m, 10H, NCH$_2$); 3.63-4.08 (m, 5H, CH—NH+CH$_2$Cl+CH$_2$O); 5.45 (d, 1H, J=8.1 Hz, NH); 5.90 (s, 1H, CH); 6.65 (d, 2H, J=8.7 Hz, CH); 6.93 (d, 2H, J=8.7 Hz, CH); 6.28-6.68 (m, 2H, CH); 8.00 (d, 1H, J=7.8 Hz, CH).

Synthesis of Example 192

2-[(2-Chloro-acetyl)-(2-fluoro-4-isopropyl-phenyl)-amino]-N-cyclohexyl-2-{4-[3-(4-methyl-piperazin-1-yl)-propoxy]-phenyl}-acetamide Example 192 was obtained in the form of a white powder using general method E.
Yield=22%; $C_{33}H_{46}ClF_1N_4O_3$; MS [M+H]=621.
NMR $^1$H (CDCl$_3$, 300): δ=1.00-1.05 (m, 18H, CH$_2$+CH$_3$); 2.31 (s, 3H, NCH$_3$); 2.37-2.70 (m, 10H, NCH$_2$); 2.72-2.95 (m, 1H, CH); 3.70-4.03 (m, 5H, CH—NH+CH$_2$Cl+CH$_2$O); 5.50 (d, 1H, J=8.0 Hz, NH); 5.65-6.05 (m, 1H, CH); 6.55-7.07 (m, 6H, CH); 7.20-7.84 (m, 1H, CH).

Synthesis of Example 193

2-[(2-Chloro-acetyl)-(2-ethyl-4-isopropyl-phenyl)-amino]-N-cyclohexyl-2-{4-[3-(4-methyl-piperazin-1-yl)-propoxy]-phenyl}-acetamide Example 193 was obtained in the form of a white powder using general method E.
Yield=61%; $C_{35}H_{51}ClN_4O_1$; MS [M+14]=612.
NMR $^1$H (CDCl$_3$, 300): δ=0.69-1.39 (m, 14H, CH$_2$+CH$_3$); 1.43-1.66 (m, 3H, CH$_2$); 1.68-2.11 (m, 6H, CH$_2$); 2.22 (s, 3H, NCH$_3$); 2.19-2.63 (m, 10H, NCH$_2$); 2.78 (sep, 1H, J=6.7 Hz, CH); 3.60-4.00 (m, 5H, CH—NH+CH$_2$Cl+CH$_2$O); 5.55 (d, 1H, J=7.7 Hz, NH); 5.61 (s, 1H, CH); 6.52-6.80 (m, 2H, CH); 6.83-7.39 (m, 5H, CH).

Synthesis of Example 194

2-[(2-Chloro-acetyl)-(3-isopropyl-2-methoxy-phenyl)-amino]-N-cyclohexyl-2-{4-[3-(4-methyl-piperazin-1-yl)-propoxy]-phenyl}-acetamide Example 194 was obtained in the form of a white powder using the method described for Example 149.
Yield=52%; C$_{54}$H$_{49}$ClN$_4$O$_4$; MS [M+H]=614.
NMR $^1$H (CDCl$_3$, 300): δ=0.90-1.30 (m, 9H, CH$_2$+CH$_3$); 1.30-1.50 (m, 2H, CH$_2$); 1.54-1.77 (m, 3H, CH$_2$); 1.78-2.01 (m, 4H, CH$_2$); 2.30 (s, 3H, NCH$_3$); 2.36-2.70 (m, 10H, NCH$_2$); 3.00-3.37 (m, 1H, CH); 3.45-3.63 (m, 3H, CH$_3$O); 3.70-3.87 (m, 4H, CH$_2$Cl+CH$_2$O); 5.68 (s, 1H, CH); 5.79 (d, 1H, J=8.3 Hz, NH); 6.63-6.82 (m, 2H, CH); 6.91-7.40 (m, 5H, CH).

Synthesis of Example 195

2-[(2-Chloro-acetyl)-(2-cyclopropyl-4-isopropyl-phenyl)-amino]-N-cyclohexyl-2-{4-[3-(4-methyl-piperazin-1-yl)-propoxy]-phenyl}-acetamide Example 195 was obtained in the form of a white powder using general method E.
Yield=38%; C$_{36}$H$_{51}$ClN$_4$O$_3$; MS [M+14]=624.
NMR $^1$H (CDCl$_3$, 300): δ=0.34-0.76 (m, 4H, CH$_2$); 0.76-2.04 (m, 19H, CH$_2$+CH$_3$); 2.30 (s, 3H, NCH$_3$); 2.35-2.70 (m, 10H, NCH$_2$); 2.78 (sep, 1H, J=6.9 Hz, CH); 3.71-4.04 (m, 5H, CH—NH+CH$_2$Cl+CH$_2$O); 5.60 (d, 1H, J=8.1 Hz, NH); 5.69 (s, 1H, CH); 6.28-6.54 (m, 1H, CH); 6.61-6.85 (m, 2H, CH); 6.87-7.00 (m, 1H, CH); 7.00-7.17 (m, 2H, CH); 7.28-7.42 (m, 1H, CH).

Synthesis of Example 196

2-[(2-Chloro-acetyl)-(2-methyl-3-trifluoromethyl-phenyl)-amino]-N-cyclohexyl-2-{3-[3-(4-methyl-piperazin-1-yl)-propoxy]-phenyl}-acetamide Example 196 was obtained in the form of a white powder using general method E.
Yield=20%; C$_{32}$H$_{42}$ClF$_3$N$_4$O$_1$; MS [M+11]=624.
NMR $^1$H (CDCl$_3$, 300): δ=0.92-1.21 (m, 3H, CH$_2$); 1.22-1.46 (m, 2H, CH$_2$); 1.50-1.75 (m, 3H, CH$_2$); 1.77-2.16 (m, 7H, CH$_2$+CH$_1$); 2.33 (s, 3H, NCH$_3$), 2.36-2.74 (m, 10H, NCH$_2$); 3.64-3.99 (m, 5H, CH—NH+CH$_2$Cl+CH$_2$O); 5.50 (d, 1H, J=8.1 Hz, NH); 5.88 (s, 1H, CH); 6.48-6.57 (m, 1H, CH); 6.64 (d, 1H, J=7.6 Hz, CH); 6.72-6.89 (m, 1H, CH); 7.06 (t, 1H, J=8.0 Hz, CH); 7.33 (t, 1H, J=8.0 Hz, CH); 7.53-7.67 (m, 1H, CH); 8.00 (d, 1H, J=7.8 Hz, CH).
Compounds 145 to 184 were similarly prepared using general method E.

Example 2

Synthesis of the Compounds of the Invention from a Trifluoroacetate Derivative

The compounds of formula (I) can also be prepared in accordance with reaction scheme III.

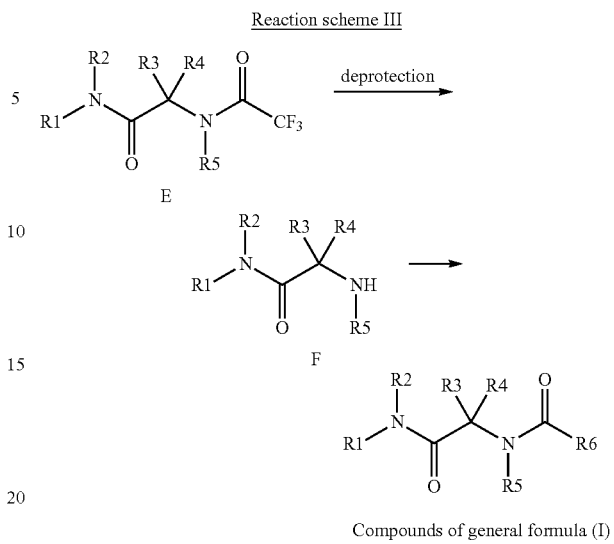

Reaction scheme III

Compounds of general formula (I)

Starting from the compound of general formula E, the first step consists in releasing the amine by eliminating the trifluoroacetate to obtain the compound of general formula F. The CO—R6 group is subsequently introduced onto this amine. For this step, a person skilled in the art is capable of adapting the method used in order to introduce the CO—R6 group as a function of the nature of R6, which can be for example a peptide coupling, a Mitsunobu reaction, a nucleophilic substitution or else a reductive amination. Similarly, the R6 group can also be functionalised or modified subsequently by any synthesis methods known to a person skilled in the art.

The compounds of formula E which R2=H can be obtained by an Ugi reaction according to Example 1 using trifluoroacetic acid as carboxylic acid or else can be prepared in accordance with reaction scheme IV.

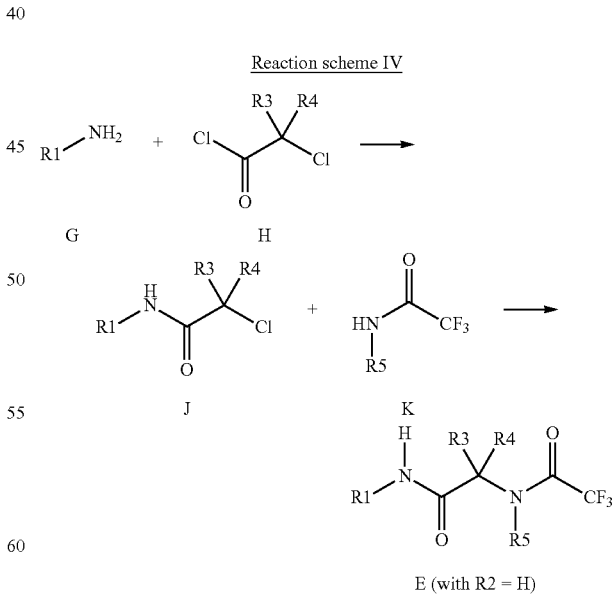

Reaction scheme IV

The first step consists in condensing the amine G on the acid chloride H in order to obtain the compound of general formula J. The second step consists in carrying out a nucleophilic substitution of a trifluoroacetamide derivative K on the chlorinated derivative of general formula J in order to obtain the desired compound of general formula F.

Experimental Part

1. Synthesis of the Compounds of General Formula E

Synthesis of Intermediate 1

N-(Cyclohexylcarbamoylthiophen-2-yl-methyl)-2,2,2-trifluoro-N-(3-trifluoromethylphenyl)acetamide Intermediate 1 was obtained in the form of a white solid using general method E from Example 1.
Yield=60% $C_{21}H_{20}F_6N_2O_2S$; MS [M+H]=479; [M+Na]=501.
NMR $H^1$ (CDCl$_3$, 300): δ=1.03-1.24 (m, 3H, CH$_2$); 1.28-1.47 (m, 2H, CH$_2$); 1.55-1.76 (m, 3H, CH$_2$); 1.85-2.02 (m, 2H, CH$_2$); 3.75-3.91 (m, 1H, CH—NH); 5.68 (d, 1H, J=6.3 Hz, NH); 5.96-6.21 (l, 1H, CH); 6.85-6.94 (m, 2H, CH); 6.96-7.19 (l, 1H, CH); 7.29-7.34 (m, 1H, CH); 7.37-7.54 (l, 1H, CH); 7.59 (d, 1H, J=7.6 Hz, CH); 7.72-7.99 (l, 1H, CH).

Synthesis of Intermediate 2

N-(Cyclohexylcarbamoylthiophen-2-yl-methyl)-2,2,2-trifluoro-N-(4-methoxyphenyl)acetamide 2-Thiophenecarboxaldehyde, 4-methoxyphenylamine, trifluoroacetic acid and isocyanocyclohexane were reacted as described in general method E from Example 1. Intermediate 2 was obtained in the form of a white solid.
Yield=70%; $C_{21}H_{23}F_3N_2O_3S$; [M+NH]=441.

Synthesis of Intermediate 3

N-(Cyclohexylcarbamoylthiophen-2-yl-methyl)-2,2,2-trifluoro-N-isobutylacetamide

2-Thiophenecarboxaldehyde, isobutylamine, trifluoroacetic acid and isocyanocyclohexane were reacted as described in general method E from Example 2. Intermediate 3 was obtained in the form of a white solid.
Yield=56%; $C_{18}H_{25}F_3N_2O_2S$; [M+NH]=391.

2. Synthesis of the Compounds of General Formula F

General Method F

A solution of the compound of general formula E (1 eq.), and of $K_2CO_3$ (1.5 eq.) in ethanol was stirred under reflux until the reaction was completed. The medium was subsequently concentrated under vacuum, taken up with ethyl acetate, and washed with brine. The organic phase was dried on MgSO$_4$, then concentrated under vacuum. The compound of general formula F could then be purified on a silica gel column or precipitated.

Synthesis of Intermediate 4

N-Cyclo hexyl-2-thiophen-2-yl-2-(3-trifluoromethylphenylamino)acetamide

Intermediate 4 was generated from intermediate 1 using general method F. The oil obtained was subsequently precipitated with pentane in order to obtain a white powder.
Yield=81%; $C_{19}H_{21}F_3N_2OS$; MS [M+H]=383

NMR $H^1$ (CDCl$_3$, 300) δ=0.99-1.22 (m, 3H); 1.24-1.43 (m, 2H); 1.53-1.72 (m, 3H); 1.75-1.94 (m, 2H); 3.72-3.86 (m, 1H); 5.15-5.23 (m, 1H); 6.45 (d, 1H, J=7.2 Hz); 6.90-7.07 (m, 3H); 7.09-7.17 (m, 1H); 7.18-7.20 (m, 1H); 7.25-7.33 (m, 2H).

Synthesis of Intermediate 5

N-Cyclohexyl-2-thiophen-2-yl-2-isobutylaminoacetamide

Intermediate 5 was generated from intermediate 2 using general method F. The product was subsequently purified on a silica gel column (EtOAc/cyclohexane, 1/9) and obtained in the form of a white solid.
Yield=85%; $C_{16}H_{26}N_2OS$
NMR $H^1$ (CDCl$_3$, 300) δ=0.85 (d, J=3.6 Hz, 3H); 0.88 (d, J=3.6 Hz, 3H); 1.17-1.36 (m, 3H); 1.61-1.73 (m, 3H); 1.81-1.85 (m, 2H); 1.80-2.14 (m, 3H); 2.83 (dd, J=6.9 Hz, J=14.1 Hz, 1H); 3.32 (dd, J=8.4 Hz, J=14.1 Hz, 1H); 3.93 (tt, J=12.3 Hz, J=3.9 Hz, 1H); 7.00-7.02 (m, 2H); 7.35-7.36 (m, 1H).

Synthesis of Intermediate 6

N-Cyclohexyl-2-(4-methoxyphenylamino)-2-thiophen-2-yl-acetamide

Intermediate 6 was generated from intermediate 3 using general method F. The product was subsequently purified on a silica gel column (EtOAc/cyclohexane, 0.5/9.5) and obtained in the form of a colourless oil.
Yield=81%; $C_{19}H_{24}N_2O_2S$
NMR $H^1$ (CDCl$_3$, 300) δ=1.00-1.25 (m, 3H); 1.25-1.44 (m, 2H); 1.52-1.74 (m, 3H); 1.76-1.96 (m, 2H); 3.73-3.96 (m, 1H); 3.75 (s, 3H), 4.98-5.07 (br, 1H); 6.66-6.90 (m, 4H); 6.99 (dd, 1H, J=5.2 3.5 Hz); 7.14-7.18 (m, 1H); 7.28 (dd, 1H, J=cached by CDCl$_3$, J=1.2 Hz).

Example 3

Synthesis of Compounds of the Invention from a Carboxylic Acid Derivative

The compounds of formula (I) where R4=H can similarly be prepared in accordance with reaction scheme V, from a carboxylic acid derivative L, which latter may be prepared in accordance with reaction scheme VI.

Reaction Scheme V

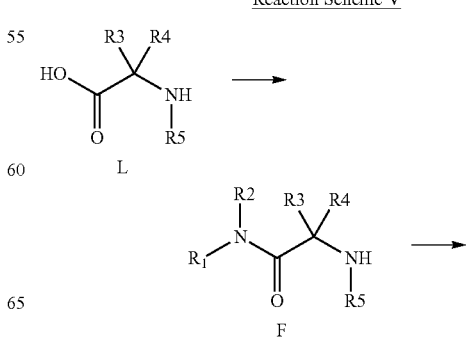

-continued

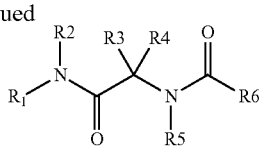

Compounds of general formula (I)
Reaction scheme VI

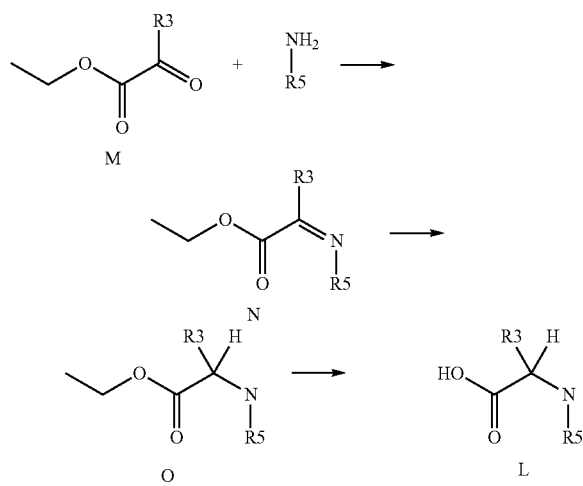

Experimental Part

1. Synthesis of Compounds of General Formula N

General Method G

A solution of the compound of general formula M (1 eq.) and of the amine of general formula R5NH$_2$ (1.2 eq.) in toluene is subjected to magnetic stirring, under nitrogen, in a three-necked flask fitted with a Dean-Stark. Para-toluenesulphonic acid (PTSA) (2%) is added at ambient temperature and the mixture is heated to 125° C. for 48 h. The medium is then allowed to return to ambient temperature, and the toluene phase is washed successively with a saturated NaHCO$_3$ solution, then with brine. After drying on MgSO$_4$ and filtration, the organic phase is concentrated under vacuum. The compound of general formula M can then be purified on a column of silica gel.

Synthesis of Intermediate 7

Thiophen-2-yl-(3-trifluoromethyl-phenylimino)-acetic acid ethyl ester

Intermediate 7 was generated from ethyl thienylglyoxylate and 3-aminobenzo-trifluoride using general method G. The product was then purified on a column of silica gel (heptane/diisopropyl ether) and obtained in the form of a yellow oil.
Yield=66%; C$_{15}$H$_{12}$F$_3$NO$_2$S; MS [M+H]=328.

2. Synthesis of Compounds of General Formula O

General method H

Under a nitrogen stream and with magnetic stirring, the compound of general formula N (1 eq.) is solubilised in methanol (27 Vol.), in the presence of acetic acid (2.7 Vol.). The solution is cooled to 0° C. and sodium cyanoborohydride (1.5 eq.) is added portionwise within 5 min. The mixture is allowed to return to ambient temperature. The mixture is then sealed under a nitrogen atmosphere and stirred at ambient temperature for 18 h. The medium is then poured on to a mixture of ice/NaHCO$_3$ (saturated solution). After decantation, the mixture is extracted with ethyl acetate. The organic phases are washed with a saturated solution of NaHCO$_3$, then with brine. After drying on MgSO$_4$ and filtration, the organic phases are concentrated. The compound O obtained is used as it is in the following reaction.

Synthesis of Intermediate 8

Thiophen-2-yl-(3-trifluoromethyl-phenylamino)-acetic acid ethyl ester

Intermediate 8 was generated from intermediate 7 using general method H. No purification is necessary and the product is obtained in the form of a colourless oil.
Yield=96%; C$_{15}$H$_{14}$F$_3$NO$_2$S; MS [M+H]=330.

3. Synthesis of Compounds of General Formula L

General Method I

The ethyl ester derivative O (1 eq) is solubilised in tetrahydrofuran (10 Vol.). A sodium hydroxide solution (3 eq.) is then added at 0° C. and the mixture is allowed to return to ambient temperature with stirring overnight. The aqueous phase is acidified then extracted with ethyl acetate (twice). The organic phases are combined and then washed successively with water, with a saturated solution of NH$_4$Cl, then with brine. After drying on MgSO$_4$ and filtration, the organic phase is concentrated in a vacuum.

Synthesis of Intermediate 9

Thiophen-2-yl-(3-trifluoromethyl-phenylamino)-acetic acid

Intermediate 9 was generated from intermediate 8 using General method I the product was obtained in the form of a yellow solid.
Yield=96%; C$_{13}$H$_{10}$F$_3$NO$_2$S; MS [M−H]=300.

4. Synthesis of Compounds of General Formula F

General method J

The carboxylic acid derivative L (1 eq.) was dissolved in dichloromethane (10 Vol) with the amine R1R2NH (1.5 eq.). 2-(7-aza-1H-benzotriazole-1-yl)-1,1,3,3-tetramethyluronium hexafluorophosphate (HATU) (2 eq.) was added and the reaction medium was heated to 55° C. for 3 h. R1R2NH (0.2 eq.) amine and HATU (0.3 eq.) may be added to render the reaction total.

The medium is allowed to return to ambient temperature, then taken up in ethyl acetate. The organic phase is washed with a saturated NH$_4$Cl solution and then with brine. After drying on MgSO₄ and filtration, the organic phase is concentrated under vacuum. The crude product obtained is purified on silica gel.

Synthesis of Intermediate 10

1-(4-Cyclohexyl-piperazin-1-yl)-2-thiophen-2-yl-2-(3-trifluoromethyl-phenylamino)-ethanone Intermediate 10 was generated from intermediate 9 and cyclohexylpiperazine using general method J. The product was then purified on a silica gel column (dichloromethane/methanol) and obtained in the form of a yellow solid.

Yield=53%; $C_{23}H_{25}F_3N_3OS$.

Synthesis of Intermediate 11

4-[2-thiophen-2-yl-2-(3-trifluoromethyl-phenylamino)-acetyl]-piperazine-1-carboxylic acid benzyl ester Intermediate 11 was generated from intermediate 9 and 1-Z-piperazine using general method J. The product was then purified on a silica gel column (heptane/ethyl acetate) and obtained in the form of a pale yellow solid.

Yield=62%; $C_{25}H_{24}F_3N_3O_3S$; MS [M−H]=502

5. Synthesis of Compounds of General Formula (I)

General Method K

The compound of general formula F (1 eq.) is dissolved in dichloromethane (10 Vol.). The mixture is cooled to 0° C. and the NaHCO₃ base (2 eq.) is added along with the chloroacetic acid chloride (2 eq.). After 4 h to 1 night of stirring at ambient temperature, the reaction medium is hydrolysed with water. After decantation and extraction with ethyl acetate, the organic phases are washed with a saturated NH₄Cl solution, dried on MgSO₄, filtered and concentrated under vacuum. The crude product may be in the form either of a solid or of an oil. The solid is washed with a little organic solvent (usually diisopropyl ether, also pentane or diethyl ether). If necessary the solid may be recrystallised or else is purified on silica gel. In the absence of precipitation, the oil is similarly purified on silica gel.

Synthesis of Example 197

2-Chloro-N-[2-(4-cyclohexyl-piperazin-1-yl)-2-oxo-1-thiophen-2-yl-ethyl)]-N-(3-trifluoromethyl-phenyl)-acetamide Compound 197 was prepared from intermediate 10 using general method K. It was obtained in the form of a white solid following trituration in a pentane/isopropyl ether mixture, then crystallisation in a dichloromethane/diethyl ether mixture.

Yield=70%; $C_{25}H_{29}ClF_{11}N_3O_2S$; MS [M+H]=528; [M+Na]=550.

NMR H¹ (CDCl₃, 300 MHz) δ=1.10-1.60 (m, 6H); 1.71 (m, 2H); 1.94 (m, 2H); 2.27 (m, 2H); 3.03 (m, 2H); 3.18-3.58 (m, 2H); 3.82 (m, 2H); 4.07 (m, 2H); 4.45-4.90 (m, 1H); 6.62 (s, 1H); 6.68-6.85 (m, 2H), 6.94 (m, 1H), 7.19 (m, 1H), 7.54 (m, 2H), 8.09-8.30 (m, 1H).

Synthesis of Example 198

4-{2-[(2-chloro-acetyl)-(3-trifluoromethyl-phenyl)-amino]-2-thiophen-2-yl-acetyl}-piperazine-1-carboxylic acid benzyl ester The compound 198 was generated from intermediate 11 using general method K.

It was obtained in the form of a white solid following purification on a silica column (heptane/ethyl acetate), then taken up several times in a pentane/isopropyl ether mixture.

Yield=42%; $C_{27}H_{25}ClF_3N_3O_4S$; [M+Na]=602.

NMR H¹ (CDCl₃, 300 MHz) δ=3.03 (m, 1H); 3.38 (m, 2H); 3.46-3.90 (m, 7H); 5.11 (s, 2H); 6.65-6.81 (m, 3H); 6.86-6.98 (m, 1H); 7.15-7.41 (m, 6H); 7.51 (m, 2H); 8.26 (m, 1H).

Example 4

Synthesis of Compounds of the Invention from an Imine Derivative

The compounds of formula (I) with R4=H can be prepared similarly according to reaction scheme VII from an imine derivative P, which latter may be prepared according to reaction scheme VIII.

Reaction scheme VII

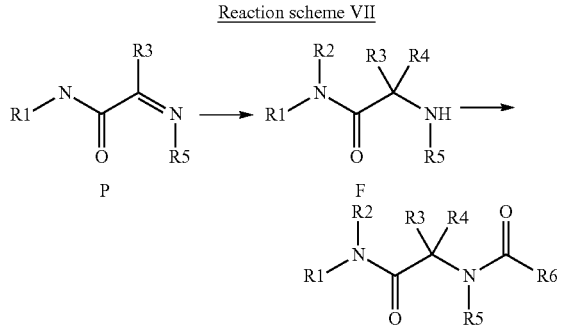

Compounds of general formula (I)

Reaction scheme VIII

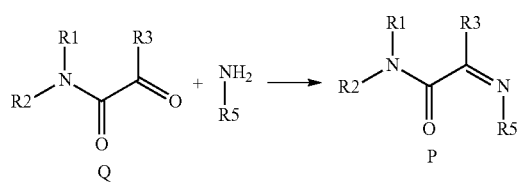

To form the compound Q, the person skilled in the art is capable of adapting the method used to introduce the R1R2NH group as a function of the nature of R1 and R2, such as for example a peptide coupling on a carboxylic acid, or an animation on an ester. Similarly, the R1 and R2 groups can also be subsequently functionalised or modified by any method of synthesis known to the person skilled in the art.

Experimental Part

1. Synthesis of Compounds of General Formula P

General Method L

The compound of general formula P was generated from compound of general formula Q and aniline of general formula R5NH$_2$ using the general method G.

The difference in synthesis resides in the number of equivalents (1.2 eq.) of APTS.

Synthesis of Intermediate 12

1-(4-Cyclohexyl-piperazin-1-yl)-2-[3-isopropyl-phenylimino]-2-thiophen-2-yl-ethanone Intermediate 12 was generated from 1-(4-cyclohexyl-piperazin-1-yl)-2-thiophen-2-yl-ethane-1,2-dione and 3-isopropylaniline using general method L.

Following purification on a column of silica (dichloromethane/methanol eluent), Intermediate 12 is engaged directly in the next reaction.

Synthesis of Intermediate 13

2-[2-Methyl-3-trifluoromethyl-phenylimino]-1-piperazin-1-yl-2-thiophen-2-yl-ethanone Intermediate 13 was generated from 1-piperazin-1-yl-2-thiophen-2-yl-ethane-1,2-dione and 2-methyl-3-(trifluoromethyl)aniline using general method L.

After purification on a silica column (dichloromethane/methanol eluent), Intermediate 13 was obtained in the form of a yellow gel.

Yield=78%; C$_{18}$H$_{18}$F$_3$N$_3$OS; MS [M+H]=382.

Synthesis of Intermediate 14

4-[2-(2-methyl-3-trifluoromethyl-phenylimino)-2-thiophen-2-yl-acetyl]-piperazine-1-carboxylic acid tert-butyl ester Intermediate 14 was generated from intermediate 13 according to the following protocol:

Intermediate 13 (1 eq.) is dissolved in dichloromethane. Di-tert-butyl dicarbonate (1.2 eq.) and triethylamine (1.5 eq.) are added to the solution and the reaction medium is subjected to magnetic stirring overnight at ambient temperature. The organic phase is washed with water, and then with brine. After drying on MgSO$_4$ and filtration, the organic phase is concentrated under vacuum. Intermediate 14 is obtained in the form of a yellow-orange gel.

Yield=quantitative; C$_{23}$H$_{26}$F$_3$N$_3$O$_3$S; MS [M+H]=482.

2. Synthesis of Compounds of General Formula F

General method M

The compound of general formula P (1 eq.) is dissolved in tetrahydrofurane, under nitrogen. The mixture is cooled to 0° C. and a solution of DIBALH in THF (3 eq.) is added dropwise. The medium is allowed to return to ambient temperature. After 1 h30 of stirring, the reaction medium is hydrolysed with Glauber salts. The medium is then filtered on Celiac and the solvent evaporated. The raw product can be used as it is in the following reaction or purified on silica gel.

Synthesis of Intermediate 15

1-(4-Cyclohexyl-piperazin-1-yl)-2-(3-isopropyl-phenylamino]-2-thiophen-2-yl-ethanone Intermediate 15 was prepared from intermediate 12 using general method M. The product was then purified on a silica gel column (dichloromethane/methanol) and obtained in the form of a yellow oil.

Yield=21% (in 2 stages); C$_{25}$H$_{35}$N$_3$OS; MS [M+14]=426.

Synthesis of Intermediate 16

4-[2-(2-methyl-3-trifluoromethyl-phenylamino)-2-thiophen-2-yl-acetyl]-piperazine-1-carboxylic acid tert-butyl ester Intermediate 16 was prepared from Intermediate 14 using general method M. The product was obtained without purification in the form of a yellow gel. It is used as it is in the following reaction.

C$_{23}$H$_{28}$F$_3$N$_3$O$_3$S; MS [M+H]=484.

3. Synthesis of compounds of general formula (I)

Synthesis of Example 199

2-Chloro-N-[2-(4-cyclohexyl-piperazin-1-yl)-2-oxo-1-thiophen-2-yl-ethyl)]-N-(3-isopropyl-phenyl)-acetamide The compound 199 was obtained from intermediate 15 using general method K.

The product was obtained following purification on a silica gel column (dichloromethane/methanol) in the form of a colourless gum.

Yield=92%; C$_{27}$H$_{36}$ClN$_3$O$_2$S; MS [M+H]=502.

NMR H$^1$ (CDCl$_3$, 300 MHz) δ=1.03 (t, J=5.2 Hz, 3H), 1.07-1.32 (m, 8H); 1.63 (m, 2H); 1.78 (m, 3H); 2.20 (m, 2H); 2.31-2.99 (m, 4H); 3.38 (m, 1H); 3.49-3.75 (m, 3H); 3.76-3.99 (m, 2H); 6.40-6.52 (m, 1H); 6.65-6.82 (m, 2H), 6.97-7.30 (m, 4H), 7.65-7.80 (m, 1H).

Synthesis of Example 200

4-{2-[(2-chloro-acetyl)-(2-methyl-3-trifluoro-methyl-phenyl)-amino]-2-thiophen-2-yl-acetyl}-piperazine-1-carboxylic acid tert-butyl ester The compound 200 was obtained from intermediate 15 using general method K.

The product was obtained following purification on a silica gel column (heptane/ethyl acetate) in the form of a white powder.

Yield=55%; C$_{25}$H$_{29}$ClF$_3$N$_3$O$_4$S; MS [M+H]=560.

NMR H$^1$ (CDCl$_3$, 300 MHz) δ=1.46 (s, 9H); 2.17 (s, 3H); 2.95 (m, 1H); 3.25-3.71 (m, 7H); 3.76 (q, J=10.4 Hz, 2H); 6.71 (s, 1H); 6.78 (dd, J=3.8 Hz et J=2.7 Hz, 1H); 6.86 (d,

J=3.8 Hz, 1H); 7.17 (d, J=3.8 Hz, 1H); 7.35 (t, J=5.7 Hz, 1H); 7.58 (d, J=5.7 Hz, 1H); 8.32 (d, J=5.7 Hz, 1H).

Example 5

Synthesis of Compounds of the Invention from a Derivative Protected by a Boc Group The compounds of the invention of formula T may be prepared in accordance with the following reaction scheme IX Reaction scheme IX

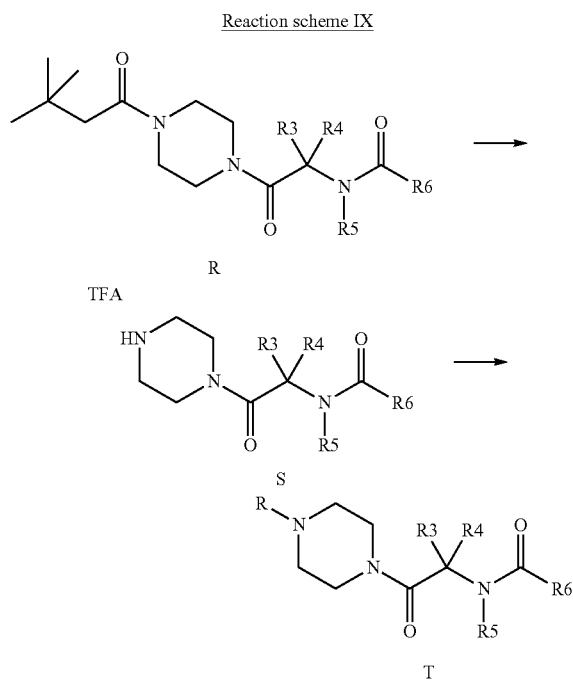

Experimental Part

1. Synthesis of Compounds of General Formula S

General method N

To a solution of the compound of general formula R (1 eq.) in dichloromethane (20 Vol.) is added slowly trifluoroacetic acid (TFA) (15 eq.). After 2 h30 of agitation at ambient temperature, the medium is concentrated under vacuum. The medium is taken up again in methyl tert-butyl ether (MTBE) several times in order to obtain the compound of general formula S in crystalline form.

Synthesis of Intermediate 17

2-chloro-N-(2-methyl-3-trifluoromethyl-phenyl)-N-(2-oxo-2-piperazin-1-yl-1-thiophen-2-yl-ethyl)-acetamide trifluoroacetic acid salt Intermediate 17 was generated from Example 200 using general method N of Example 5. It was obtained in the form of a white powder.
Yield=quantitatif; MS [M+H]=460.

2. Synthesis of the compounds of the invention of general formula T

General Method O

Triethylamine (2.5 eq.) was added to a solution of the compound of general formula S (1 eq) in dichloromethane (20 Vol.) at 0° C. The compound of general formula R—Cl (1.3 eq.) was then added slowly at 0° C. The reaction medium was subjected to stirring overnight at ambient temperature. The organic phase was washed with water, then with brine. After drying on MgSO$_4$ and filtration, the organic phase was concentrated under vacuum. The product obtained was purified on silica gel.

General Method P

Triethylamine (1.1 eq.) is added to a solution of the compound of general formula S (1 eq.) in dichloromethane. The compound of general formula R—CHO (1.1 eq.) and sodium triacetoxyborohydride (1.5 eq.) are then added to the reaction medium. After one night of stirring at ambient temperature, a 1N solution of sodium bicarbonate is poured into the mixture and the product is extracted with dichloromethane (twice). The organic phases are combined, dried on MgSO$_4$, filtered and concentrated under vacuum. The product obtained is purified on silica gel Synthesis of Example 201

4-{2-[(2-chloro-acetyl)-(2-methyl-3-trifluoromethyl-phenyl)-amino]-2-thiophen-2-yl-acetyl}-piperazine-1-carboxyli c acid benzyl ester The compound 201 was obtained from intermediate 17 using general method O.
The product was obtained following purification on a silica gel column (heptane/ethyl acetate) in the form of a gel which crystallises into a white solid.
Yield=58%; $C_{28}H_{27}ClF_3N_3O_4S$; MS [M+H]=594.
NMR H$^1$ (CDCl$_3$, 300 MHz) δ=2.16 (s, 3H); 3.01 (m, 1H); 3.42 (m, 1H); 3.56-3.70 (m, 6H); 3.77 (q, J=10.2 Hz, 2H); 5.13 (s, 2H); 6.70 (s, 1H); 6.78 (dd, J=3.4 Hz and J=2.8 Hz, 1H); 6.86 (m, 1H); 7.17 (d, J=3.4 Hz, 1H); 7.31-7.44 (m, 6H); 7.58 (d, J=5.6 Hz, 1H); 8.31 (d, J=5.6 Hz, 1H).

Synthesis of Example 202

2-Chloro-N-{2-[4-(3,3-dimethyl-butyl)-piperazin-1-yl]-2-oxo-1-thiophen-2-yl-ethyl}-N-(2-methyl-3-trifluoromethyl-phenyl)-acetamide The compound 202 was obtained from intermediate 17 using general method P.
The product was obtained following purification on a silica gel column (ethyl acetate) in the form of a white solid.
Yield=79%; $C_{26}H_{33}ClF_3N_3O_2S$; MS [M+H]=544.
NMR H$^1$ (CDCl$_3$, 300 MHz) δ=0.89 (s, 9H); 1.37 (t, J=6.4 Hz, 2H); 1.66 (m, 1H); 2.01 (m, 1H); 2.16 (s, 3H); 2.32 (m, 3H); 2.52 (m, 2H); 3.44 (m, 1H); 3.60-3.72 (m, 2H); 3.77 (q, J=10.2 Hz, 2H); 6.73 (s, 1H); 6.77 (dd, J=3.6 Hz et J=2.4 Hz, 1H); 6.83 (d, J=2.4 Hz, 1H); 7.17 (d, J=3.6 Hz, 1H); 7.34 (t, J=5.6 Hz, 1H); 7.57 (d, J=5.6 Hz, 1H); 8.34 (d, J=5.6 Hz, 1H).

Synthesis of Example 203

2-Chloro-N-{2-[4-(3,3-dimethyl-butyl)-piperazin-1-yl]-2-oxo-1-thiophen-2-yl-ethyl}-N-(trifluoromethyl-phenyl)-acetamide The compound 203 was obtained from intermediate 17 using general method O.

The product was obtained following purification on a silica gel column (dichloromethane/ethyl acetate) in the form of a pale brown gum.

Yield=82%; $C_{25}H_{29}ClF_3N_3O_3S$; MS [M+H]=544.

NMR $H^1$ (CDCl$_3$, 300 MHz) δ=1.04 (s, 9H); 2.22 (m, 2H); 3.10-3.30 (m, 1H); 3.31-3.50 (m, 2H); 3.51-3.78 (m, 5H); 3.83 (m, 2H); 6.72 (s, 1H); 6.78 (m, 2H); 6.92 (m, 1H); 7.23 (m, 1H); 7.53 (m, 2H); 8.15-8.37 (m, 1H).

Synthesis of Example 204

4-{2-[(2-Chloroacetyl)-(3-trifluoromethylphenyl)-amino]-2-thiophen-2-yl-acetyl}piperazine-1-carboxylic acid methylphenyl-amide The compound 204 was obtained from intermediate 17 using general method O.

The product was obtained after purification on a silica gel column (dichloromethane/ethyl acetate) in the form of colourless gum.

Yield=74%; $C_{27}H_{26}ClF_3N_4O_3S$; MS [M+H]=579.

NMR $H^1$ (CDCl$_3$, 300 MHz) δ=2.83 (m, 1H); 3.12 (m, 1H); 3.22 (s, 3H); 3.25 (m, 3H); 3.41 (m, 2H); 3.53 (m, 1H); 3.79 (m, 2H); 6.63 (s, 1H); 6.69 (m, 1H); 6.76 (m, 1H); 6.85-6.94 (m, 1H); 7.09 (d, J=5.5 Hz, 2H); 7.17 (m, 2H); 7.35 (t, J=5.5 Hz, 2H); 7.51 (m, 2H); 8.15-8.31 (m, 1H).

Synthesis of Example 205

2-Chloro-N-{2-oxo-1-thiophen-2-yl-2-[4-(toluene-4-sulfonyl)-piperazin-1-yl]-ethyl}-N-(3-trifluoromethyl-phenyl)-acetamide The compound 205 was obtained from intermediate 17 using general method O.

The product was obtained after purification on a silica gel column (heptane/ethyl acetate) in the form of a white solid.

Yield=76%; $C_{26}H_{25}ClF_3N_3O_4S_2$; MS [M+H]=600.

NMR $H^1$ (CDCl$_3$, 300 MHz) δ=2.47 (s, 3H); 2.79 (m, 1H); 2.95 (m, 2H); 3.10 (m, 1H); 3.35 (m, 1H); 3.60 (m, 1H); 3.65 (m, 1H); 3.78 (m, 2H); 3.92 (m, 1H); 6.60-6.66 (m, 2H); 6.71 (m, 1H); 6.84-6.92 (m, 1H); 7.14-7.25 (m, 1H); 7.34 (d, J=6.2 Hz, 2H); 7.50 (t, J=6.2 Hz, 2H); 7.59 (d, J=6.2 Hz, 2H); 8.11-8.28 (m 1H).

Example 6

Biological Tests

The effects of the compounds of the invention on the proliferation of cancer cells were studied on various human cancer cell lines of various tissue origins (MCF-7: breast cancer, MCF-7/adr adriamycin-resistant breast cancer, ARH-77: myeloma, ARH-77/Dox: doxorubicin (other name for adriamycin)-resistant myeloma, HL-60: acute promyelocytic leukaemia, HL-60/R10: doxorubicin-resistant acute promyelocytic leukaemia). The cancer cells used for this study were incubated at 37° C. in the presence of one of the compounds of the invention added to the culture medium at various concentrations.

The cancer cell lines originate from the ATCC (American Type Culture Collection) in the case of MCF-7, ARH-77 and HL-60, from Pharmacell (Paris, France) for HL-60/R10, from Oncodesign (Dijon, France) for ARH-77/Dox and from the Pitié Salpetrière Hospital for MCF-7/adr. They were cultivated in a RPMI 1640 medium containing 2 mM L-glutamine and supplemented with 10% foetal calf serum. All the cell lines were maintained in culture at 37° C. in a moist atmosphere containing 5% $CO_2$. Cell proliferation was evaluated using the "CellTiter 96® AQ$_{ueous}$" reagent (Promega, Wis., USA) while adhering to the manufacturer's instructions. The cells were seeded in 96-well culture plates in a proportion of from 5,000 to 10,000 cells per well in 200 μl of culture medium. After 24 hours of preincubation at 37° C., the compounds of the invention dissolved in dimethyl sulphoxide (DMSO) were added individually to each of the wells in a proportion of 2 μl per well. After 72 hours of incubation at 37° C. in a moist atmosphere containing 5% $CO_2$, 40 μL of a MTS/PMS ([3-(4,5-dimethylthiazol-2-yl)-5-(3-carboxymethoxyphenyl)-2-(4-sulphophenyl)-2H-tetrazolium phenazine methosulphate) solution were added to each well. After 1 to 4 hours of incubation at 37° C., the absorbance was measured at 490 nm with the aid of a plate reader and then the data thus obtained was processed by computer to give the value of the concentration of each of the compounds that induces the death of 50% of the cells ($CI_{50}$).

The results obtained are presented in the following Tables 1 and 2.

TABLE 1

Results obtained with the MCF-7 and MCF-7/adr cell lines

| Compound of the invention | $CI_{50}$ for various cell lines (nM) | |
|---|---|---|
| | MCF-7/adr | MCF-7 |
| 1 | 1.6 | 224 |
| 2 | 0.7 | 150 |
| 3 | 2.6 | 275 |
| 4 | 0.9 | — |
| 7 | 0.5 | — |
| 8 | 30 | — |
| 9 | 30 | — |
| 12 | 30 | — |
| 16 | 1 | — |
| 18 | 30 | — |
| 19 | 1.4 | 340 |
| 27 | 0.8 | 110 |
| 28 | 2.2 | 70 |
| 29 | 18 | 877 |
| 32 | 2.9 | 1,260 |
| 33 | 2.7 | 736 |
| 38 | 1.9 | 272 |
| 41 | 3.2 | 158 |
| 48 | 1 | — |
| 49 | 1 | 220 |
| 50 | 2 | 282 |
| 52 | 3.5 | 708 |
| 53 | 2.8 | 372 |
| 54 | 2.9 | 224 |
| 55 | 2.4 | 694 |
| 56 | 1.4 | 640 |
| 57 | 8.1 | 599 |
| 58 | 2.4 | 580 |
| 60 | 3.5 | 357 |
| 63 | 2 | 401 |
| 66 | 1 | — |
| 71 | 3.4 | 402 |
| 72 | 3 | 619 |

TABLE 1-continued

Results obtained with the MCF-7 and MCF-7/adr cell lines

| Compound of the invention | CI$_{50}$ for various cell lines (nM) | |
|---|---|---|
| | MCF-7/adr | MCF-7 |
| 74 | 2.9 | 506 |
| 76 | 1.5 | — |
| 81 | 1.6 | 269 |
| 84 | 1.6 | 250 |
| 85 | 1.6 | 177 |
| 86 | 0.8 | 216 |
| 88 | 1.4 | 334 |
| 89 | 2.2 | 825 |
| 90 | 2.2 | 820 |
| 94 | 2 | 599 |
| 95 | 1.4 | 243 |
| 100 | 0.5 | 308 |
| 101 | 1.1 | 416 |
| 102 | 1 | 428 |
| 106 | 1 | 260 |
| 107 | 0.5 | 267 |
| 109 | 1 | 100 |
| 110 | 1 | 70 |
| 112 | 1.8 | 200 |
| 121 | 70 | 252 |
| 122 | 4 | 300 |
| 124 | 27 | >2,000 |
| 127 | 7.5 | 77 |
| 128 | 86 | 133 |
| 129 | 3.6 | 77 |
| 130 | 34 | 203 |
| 134 | 74 | >1,000 |
| 135 | 19 | 285 |
| 139 | 63 | 468 |
| 145 | 1.7 | 82 |
| 147 | 1.1 | 92 |
| 150 | 0.6 | 230 |
| 153 | 1.3 | 79 |
| 154 | 3.5 | 88 |
| 176 | 1.9 | — |
| 181 | 0.2 | — |
| 185 | 127 | 2792 |
| 187 | 99 | 1134 |
| 189 | 72 | 360 |
| 197 | 37 | 1378 |
| 198 | 55 | 1079 |
| 199 | 23 | 1861 |
| 204 | 89 | 741 |
| 206 | 38 | 2500 |

— means that the CI$_{50}$ was not measured

TABLE 2

Result obtained with the ARH-77, ARH-77/Dox, HL-60 and HL-60/R10 cell lines

| N° of the tested compound of the invention | CI$_{50}$ for various cell lines (nM) | | | |
|---|---|---|---|---|
| | ARH-77 | ARH-77/Dox | HL-60 | HL-60/R10 |
| 1 | 46 | 12 | 1,343 | 32 |
| 2 | 92 | 6 | 2,082 | 95 |
| 3 | 58 | 5 | 2,959 | 46 |
| 4 | 103 | 25 | 1,632 | 76 |
| 21 | 60 | 6 | 2,024 | 43 |
| 186 | — | — | 362 | 78 |
| 188 | — | — | 2500 | 176 |
| 192 | — | — | 524 | 140 |

Moreover, the compound BADLG of the following formula

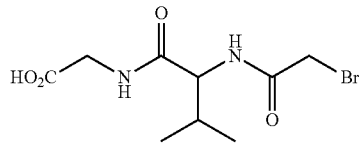 [SMILES: CC(C)C(NC(=O)CBr)C(=O)NCC(=O)O]

described in U.S. Pat. No. 5,200,426 as potentially having anticancer activity was tested on cell lines MCF7 and MCF7/adr, as well as HL60 and HL60/R10, under the same conditions as described above, without any cytotoxic activity being detected for concentrations below 10 μM, clearly demonstrating the importance of substituting R5 for the nitrogen of the compounds of the invention.

The invention claimed is:

1. A pharmaceutical composition comprising at least one compound of formula (I):

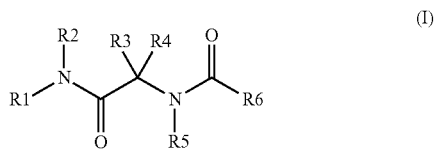

or a pharmaceutically acceptable salt thereof, an isomer or isomer mixture thereof in all proportions, for which:

R1 represents a hydrogen atom or a ($C_1$-$C_6$)alkyl, ($C_3$-$C_{10}$)cycloalkyl, ($C_3$-$C_{10}$)cycloalkenyl, aryl, heteroaryl, aryl-($C_1$-$C_6$)alkyl, heteroaryl-($C_1$-$C_6$)alkyl group, said group being optionally substituted by one or more groups selected from a halogen atom, ($C_1$-$C_6$)alkoxy, —NH$_2$, —COOH, —CN, —OH, —NR$^7$R$^8$, —O—($C_1$-$C_6$)alkyl-NR$^7$R$^8$, benzyloxy, aryloxy, —C(O)O—($C_1$-$C_6$)alkyl, —NH—C(O)O—($C_1$-$C_6$)alkyl, —C(O)NH$_2$, —C(O)NR$^9$R$^{10}$, —S—($C_1$-$C_6$)alkyl, —S(O)—($C_1$-$C_6$)alkyl, —SO$_2$—($C_1$-$C_6$)alkyl, —SO$_2$NH$_2$, —SO$_2$NR$^{11}$R$^{12}$, NR$^{13}$SO$_2$R$^{14}$ and a ($C_1$-$C_6$)alkyl group optionally substituted by one or more halogen atoms, R2 represents a hydrogen atom or a ($C_1$-$C_6$)alkyl, or R1 and R2 together form, with the nitrogen atom carrying them:

a heteroaryl optionally substituted by one or more groups selected from a halogen atom, a —CN, —NH$_2$, —NR$^{40}$R$^{41}$, NO$_2$, OH, ($C_1$-$C_6$)alkoxy, aryloxy, benzyloxy, —O($C_1$-$C_6$)alkyl-NR$^{42}$R$^{43}$, —C(O)O—($C_1$-$C_6$)alkyl, —NHC(O)O—($C_1$-$C_6$)alkyl, —C(O)NH$_2$, —C(O)NR$^{44}$R$^{45}$, —SO$_2$NH$_2$, —SO$_2$NR$^{46}$R$^{47}$ and —NR$^{48}$SO$_2$R$^{49}$ group, or a 3 to 7-membered heterocycle optionally substituted by one or more groups selected from a halogen atom, a ($C_3$-$C_{10}$)cycloalkyl, ($C_3$-$C_{10}$)cycloalkenyl, aryl, heteroaryl, aryl-($C_1$-$C_6$)alkyl, heteroaryl-($C_1$-$C_6$)alkyl, heterocycloalkyl-($C_1$-$C_6$)alkyl, —OH, —NH$_2$, —C(O)OH, —C(O)NH$_2$, —C(S)NH$_2$, —OR$^{50}$, —OC(O)R$^{51}$, —C(O)R$^{52}$, —C(O)OR$^{53}$, —NHC(O)R$^{54}$, —NHC(O)OR$^{55}$, —SO$_2$R$^{56}$—($C_1$-$C_6$)alkyl-C(O)OR$^{57}$, —NR$^{58}$R$^{59}$, —C(O)NR$^{60}$R$^{61}$, —C(O)N(R$^{62}$)(aryl), C(O)N(R$^{63}$)(heteroaryl), —C(O)NHNR$^{64}$R$^{65}$, —C(S)NR$^{66}$R$^{67}$, —C(S)N(R$^{68}$)(aryl), —C(S)N(R$^{69}$)(heteroaryl), —C(S)NHNR$^{70}$R$^{71}$, —OC(O)—NR$^{72}$R$^{73}$—($C_1$-$C_6$)alkyl-C(O)—NR$^{74}$R$^{75}$, —($C_1$-$C_6$)alkyl- $NR^{103}$—C(O)—$OR^{104}$, —($C_1$-$C_6$)alkyl-$NR^{76}R^{77}$, —C($NOR^{78}$)-aryl radical, and a ($C_1$-$C_6$)alkyl group optionally substituted by one or more halogen atoms, the aryl and heteroaryl unit of said radical, when present, being optionally substituted by one or more groups selected from a halogen atom, a —CN, —OH, ($C_1$-$C_6$)alkyl, ($C_1$-$C_6$)alkoxy, —$NR^{79}R^{80}$, —($C_1$-$C_6$)alkyl-$NR^{81}R^{82}$ and —O—($C_1$-$C_6$)alkyl-$NR^{83}R^{84}$ group, R3 represents a hydrogen atom or a ($C_1$-$C_6$)alkyl, or —($C_1$-$C_4$)alkyl-$NR^{15}R^{16}$ group, R4 represents a ($C_1$-$C_6$)alkyl, ($C_3$-$C_{10}$)cycloalkyl, aryl, or heteroaryl group, said group being optionally substituted by one or more groups selected from a halogen atom, a —($CF_3$)$_2$OH, —CN, —$NH_2$, —$OPO_3H_2$, —$NR^{17}R^{18}$, —$NO_2$, —COOH, —OH, —O($C_1$-$C_6$)alkyl-$OPO_3H_2$, —O—($C_1$-$C_6$)alkyl-O—($C_1$-$C_6$)alkyl, —O($C_1$-$C_6$)alkyl-$NR^{19}R^{20}$, —$NR^{81}$ ($C_1$-$C_6$)alkyl-$NR^{85}R^{86}$, benzyloxy, —C(O)O—($C_1$-$C_6$)alkyl, —NHC(O)O—($C_1$-$C_6$)alkyl, —C(O)$NH_2$, —C(O)$NR^{21}R^{22}$, —S—($C_1$-$C_6$)alkyl, —S(O)—($C_1$-$C_6$)alkyl, —$SO_2$—($C_1$-$C_6$)alkyl, —$SO_2NH_2$, —$SO_2NR^{23}R^{24}$, —$NR^{25}SO_2R^{26}$, 3 to 7-membered heterocycloalkyl, aryloxy radical, a ($C_1$-$C_6$)alkyl group optionally substituted by one or more halogen atoms and a ($C_1$-$C_6$)alkoxy optionally substituted by one or more fluorine atoms, and the aryl and heteroaryl unit of said radical, when present, being optionally fused to a 5 or 6-membered heterocycle, or R3 and R4 form with the carbon carrying them a ring selected from a ($C_3$-$C_{10}$)cycloalkyl and a 3 to 7-membered heterocycloalkyl, said ring being optionally substituted by a ($C_1$-$C_6$)alkyl, —C(O)—($C_1$-$C_6$)alkyl, —C(O)O—($C_1$-$C_6$)alkyl group, R5 represents a ($C_1$-$C_6$)alkyl, ($C_3$-$C_{10}$)cycloalkyl, ($C_3$-$C_{10}$)cycloalkenyl, aryl, heteroaryl, aryl-($C_1$-$C_6$)alkyl, heteroaryl-($C_1$-$C_6$)alkyl, ($C_3$-$C_{10}$)cycloalkyl-($C_1$-$C_6$)alkyl, (3 to 7-membered heterocycloalkyl)-($C_1$-$C_6$)alkyl group, said group being optionally substituted by one or more groups selected from a halogen atom, a —$NH_2$, —COOH, —CN, —OH, —$NO_2$, —B(OH)$_2$, ($C_1$-$C_6$)alkoxy, —O—($C_1$-$C_6$)alkyl-$NR^{27}R^{28}$, —O—($C_1$-$C_6$)alkyl-O—($C_1$-$C_6$)alkyl, aryloxy, —C(O)O—($C_1$-$C_6$)alkyl, ($C_2$-$C_6$)alkynyl, —$NR^{29}R^{30}$, —NHC(O)O—($C_1$-$C_6$)alkyl, —C(O)$NH_2$, —C(O)$NR^{31}R^{32}$, —S—($C_1$-$C_6$)alkyl, —S(O)—($C_1$-$C_6$)alkyl, —$SO_2$—($C_1$-$C_6$)alkyl, —$SO_2NH_2$, —$SO_2NR^{33}R^{34}$, —$NR^{35}SO_2R^{36}$, aryl, heteroaryl, ($C_1$-$C_6$)alkylheteroaryl, 3 to 7-membered heterocycloalkyl, (3 to 7-membered heterocycloalkyl)-($C_1$-$C_6$)alkoxy radical and a ($C_1$-$C_6$)alkyl group optionally substituted by one or more halogen atoms, the aryl or heteroaryl unit of said radical, when present, being optionally fused to a 5 or 6-membered heterocycle, and R6 represents —$CHR^{37}$Hal, with Hal representing a halogen atom, wherein:

$R^7$ to $R^{13}$, $R^{15}$ to $R^{18}$, $R^{21}$ to $R^{25}$, $R^{27}$ to $R^{35}$, $R^{37}$, $R^{40}$ to $R^{48}$, $R^{58}$ to $R^{84}$, $R^{89}$ to $R^{102}$ represent, independently of one another, a hydrogen atom or a ($C_1$-$C_6$)alkyl group, or, if two groups are carried by the same nitrogen, the two groups form with the nitrogen atom carrying them a 3 to 7-membered heterocycloalkyl, $R^{14}$, $R^{26}$, $R^{36}$ and $R^{49}$ represent, independently of one another, a ($C_1$-$C_6$)alkyl group, $R^{50}$ to $R^{57}$, $R^{87}$ and $R^{88}$ represent, independently of one another, a ($C_1$-$C_6$)alkyl, aryl, heteroaryl, aryl-($C_1$-$C_6$)alkyl, heteroaryl-($C_1$-$C_6$)alkyl, ($C_1$-$C_6$)alkyl-aryl or ($C_1$-$C_6$)alkyl-heteroaryl group, and $R^{19}$, $R^{20}$, $R^{85}$ et $R^{86}$ represent, independently of one another, a ($C_1$-$C_6$)alkyl group, or ($R^{19}$ and $R^{20}$) and/or ($R^{85}$ and $R^{86}$) together form, with the nitrogen atom carrying them, a 3 to 7-membered heterocycloalkyl optionally substituted by one or more groups selected from a halogen atom, a ($C_3$-$C_{10}$)cycloalkyl, aryl, heteroaryl, aryl-($C_1$-$C_6$)alkyl, heteroaryl-($C_1$-$C_6$)alkyl, —C(O)$OR^{87}$, —$SO_2R^{88}$, —OH, ($C_1$-$C_6$)alkoxy, —OC(O)—($C_1$-$C_6$)alkyl, —OC(O)—$NR^{89}R^{90}$, —NHC(O)O—($C_1$-$C_6$)alkyl, —C(O)$NH_2$, —C(O)$NR^{91}R^{92}$, —C(S)$NR^{93}R^{94}$, —C(O)NH$NR^{95}R^{96}$, —C(S)NH$NR^{97}R^{98}$ radical and a ($C_1$-$C_6$)alkyl group optionally substituted by one or more halogen atoms, the aryl and heteroaryl unit of said radical, when present, being optionally substituted by one or more groups, selected from a halogen atom and a ($C_1$-$C_6$)alkyl, —CN, —OH, $NR^{99}R^{100}$, ($C_1$-$C_6$)-alkoxy, —O—($C_1$-$C_6$)alkyl-$NR^{101}R^{102}$ group, in association with one or more pharmaceutically acceptable excipients.

2. The pharmaceutical composition according to claim 1, wherein the isomer mixture is an enantiomer mixture.

3. The pharmaceutical composition according to claim 2, wherein the enantiomer mixture is a racemic mixture.

4. The pharmaceutical composition according to claim 1, wherein $R^2$ represents a hydrogen atom, and $R^1$ represents a ($C_3$-$C_{10}$)cycloalkyl or aryl-($C_1$-$C_6$)alkyl group, said group being optionally substituted by one or more groups selected from a halogen atom, a ($C_1$-$C_6$)alkoxy, —$NH_2$, —COOH, —CN, —OH, —$NR^7R^8$, —O—($C_1$-$C_6$)alkyl-$NR^7R^8$, benzyloxy, aryloxy, —C(O)O—($C_1$-$C_6$)alkyl, —NH—C(O)O—($C_1$-$C_6$)alkyl, —C(O)$NH_2$, —C(O)$NR^9R^{10}$, —S—($C_1$-$C_6$)alkyl, —S(O)—($C_1$-$C_6$)alkyl, —$SO_2$—($C_1$-$C_6$)alkyl, —$SO_2NH_2$, —$SO_2NR^{11}R^{12}$, —$NR^{13}SO_2R^{14}$ radical and a ($C_1$-$C_6$) alkyl group optionally substituted by one or more halogen atoms.

5. The pharmaceutical composition according to claim 4, wherein $R^1$ represents a cyclohexyl, cyclopentyl or benzyl group, said group being optionally substituted by one or more groups selected from a halogen atom, a ($C_1$-$C_6$)alkoxy, —$NH_2$, —COOH, —CN, —OH, —$NR^7R^8$, —O—($C_1$-$C_6$)alkyl-$NR^7R^8$, benzyloxy, aryloxy, —C(O)O—($C_1$-$C_6$)alkyl, —NH—C(O)O—($C_1$-$C_6$)alkyl, —C(O)$NH_2$, —C(O)$NR^9R^{10}$, —S—($C_1$-$C_6$)alkyl, —S(O)—($C_1$-$C_6$)alkyl, —$SO_2$—($C_1$-$C_6$)alkyl, —$SO_2NH_2$, —$SO_2NR^{11}R^{12}$, —$NR^{13}SO_2R^{14}$ radical and a ($C_1$-$C_6$) alkyl group optionally substituted by one or more halogen atoms.

6. The pharmaceutical composition according to claim 5, wherein $R^1$ represents a cyclohexyl, cyclopentyl or benzyl group, said group being optionally substituted by one or more groups selected from a halogen atom and a ($C_1$-$C_6$) alkoxy, —$NH_2$, —COOH, benzyloxy, aryloxy, —C(O)O(($C_1$-$C_6$)alkyl), —NHC(O)O(($C_1$-$C_6$)alkyl) group.

7. The pharmaceutical composition according to claim 1, wherein —NR1R2 represents the following piperazine ring:

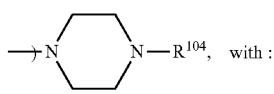

R$^{104}$ representing a hydrogen atom, a (C$_3$-C$_{10}$)cycloalkyl, (C$_3$-C$_{10}$)cycloalkenyl, aryl, heteroaryl, aryl-(C$_1$-C$_6$) alkyl, heteroaryl-(C$_1$-C$_6$)alkyl, heterocycloalkyl-(C$_1$-C$_6$)alkyl, —C(O)R$^{52}$, —C(O)OR$^{53}$, —C(O)OH, —C(O)NH$_2$, —C(S)NH$_2$, —C(O)NR$^{60}$R$^{61}$, —C(S)NR$^{66}$R$^{67}$, —SO$_2$R$^{56}$, —C(O)NHNR$^{64}$R$^{65}$, —C(S)NHNR$^{70}$R$^{71}$ radical, and a (C$_1$-C$_6$)alkyl group optionally substituted by one or more halogen atoms, the aryl and heteroaryl unit of said radical, when present, being optionally substituted by one or more groups selected from a halogen atom, a —CN, —OH, (C$_1$-C$_6$) alkoxy, —NR$^{79}$R$^{80}$, and —O—(C$_1$-C$_6$)alkyl-NR$^{83}$R$^{84}$ group.

8. The pharmaceutical composition according to claim 1, wherein R4 represents a (C$_1$-C$_6$)alkyl, (C$_3$-C$_{10}$)cycloalkyl, phenyl, or thiophenyl group, said group being optionally substituted by one or more groups selected from a halogen atom, a —(CF$_3$)$_2$OH, —CN, —NH$_2$, —OPO$_3$H$_2$, —NR$^{17}$R$^{18}$, —NO$_2$, —COOH, —OH, —O(C$_1$-C$_6$)alkyl-OPO$_3$H$_2$, —O—(C$_1$-C$_6$)alkyl-O—(C$_1$-C$_6$)alkyl, —O(C$_1$-C$_6$)alkyl-NR$^{19}$R$^{20}$, —NR$^{81}$(C$_1$-C$_6$)alkyl-NR$^{85}$R$^{86}$, benzyloxy, —C(O)O—(C$_1$-C$_6$)alkyl, —NHC(O)O—(C$_1$-C$_6$)alkyl, —C(O)NH$_2$, —C(O)NR$^{21}$R$^{22}$, —S—(C$_1$-C$_6$)alkyl, —S(O)—(C$_1$-C$_6$)alkyl, —SO$_2$—(C$_1$-C$_6$)alkyl, —SO$_2$NH$_2$, —SO$_2$NR$^{23}$R$^{24}$, —NR$^{25}$SO$_2$R$^{26}$, 3 to 7-membered heterocycloalkyl, aryloxy radical, a (C$_1$-C$_6$)alkyl group optionally substituted by one or more halogen atoms and a (C$_1$-C$_6$)alkoxy optionally substituted by one or more fluorine atoms, and the aryl and heteroaryl unit of said radical, when present, being optionally fused to a 5 or 6-membered heterocycle.

9. The pharmaceutical composition according to claim 1, wherein R$^3$ represents a hydrogen atom and R$^4$ represents an aryl or heteroaryl group said group being optionally substituted by one or more groups selected from a halogen atom, a —CF$_3$, —B(OH)$_2$, —CN, —OH, —NR$^{17}$R$^{18}$, —NO$_2$, —COOH, 3 to 7-membered heterocycloalkyl, (C$_1$-C$_6$) alkyl, —S— (C$_1$-C$_6$)alkyl, aryloxy, —O(C$_1$-C$_6$)alkyl-NR$^{19}$R$^{20}$ radical and a (C$_1$-C$_6$)alkoxy optionally substituted by one or more fluorine atoms, and said group being optionally fused to a 5 or 6-membered heterocycle.

10. The pharmaceutical composition according to claim 9, wherein R4 represents a phenyl or thiophenyl group said group being optionally substituted by one or more groups selected from a halogen atom, a —CF$_3$, —B(OH)$_2$, —CN, —OH, —NR$^{17}$R$^{18}$, —NO$_2$, —COOH, 3 to 7-membered heterocycloalkyl, (C$_1$-C$_6$) alkyl, —S— (C$_1$-C$_6$)alkyl, aryloxy, —O(C$_1$-C$_6$)alkyl-NR$^{19}$R$^{20}$ radical and a (C$_1$-C$_6$)alkoxy optionally substituted by one or more fluorine atoms, and said group being optionally fused to a 5 or 6-membered heterocycle.

11. The pharmaceutical composition according to claim 1, wherein R5 represents a (C$_1$-C$_6$)alkyl, heteroaryl, (C$_3$-C$_{10}$) cyclo alkyl-(C$_1$-C$_6$)alkyl, aryl-(C$_1$-C$_6$)alkyl or aryl group, the aryl core of the aryl or aryl-(C$_1$-C$_6$)alkyl group being optionally fused to a 5 or 6-membered heterocycle, and being optionally substituted by one or more groups selected from a halogen atom, a —CF$_3$, —CN, —NR$^{29}$R$^{30}$, —NO$_2$, —C(CF$_3$)$_2$OH, (C$_1$-C$_6$)alkoxy, aryloxy, (C$_1$-C$_6$)alkyl, (C$_2$-C$_6$)alkynyl, aryl and 5 or 6-membered heterocycloalkyl group.

12. The pharmaceutical composition according to claim 11, wherein the 5 or 6-membered heterocycle comprises two oxygen atoms.

13. The pharmaceutical composition according to claim 1, wherein the compound of formula (I) is selected from:

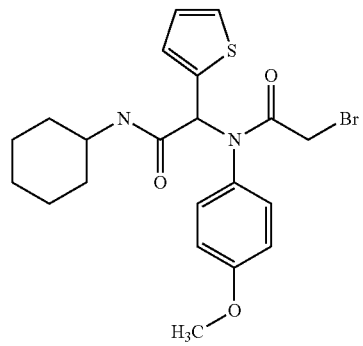

108

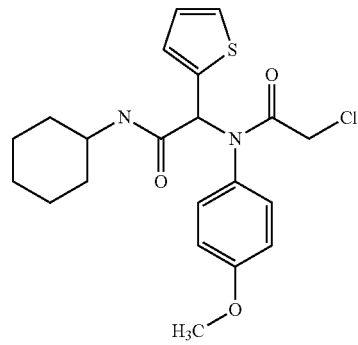

109

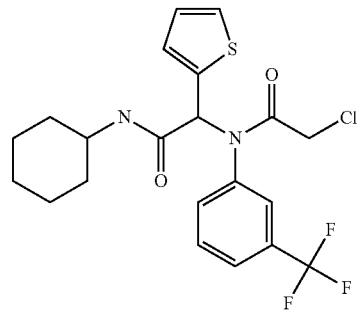

110

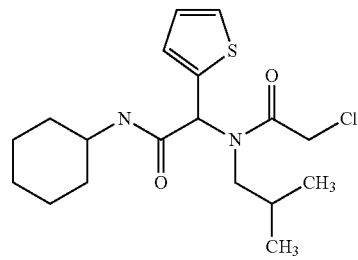

111

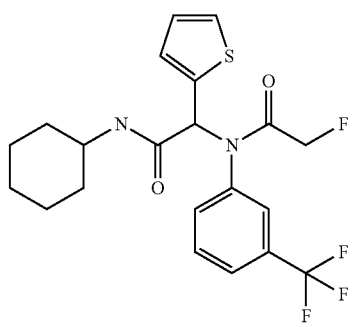
113
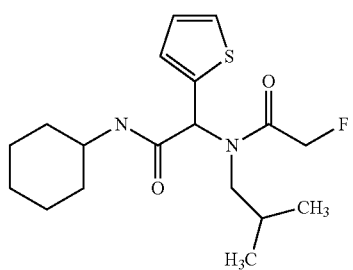
114
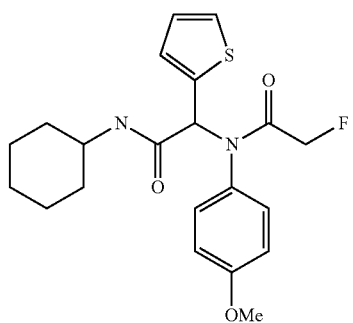
115
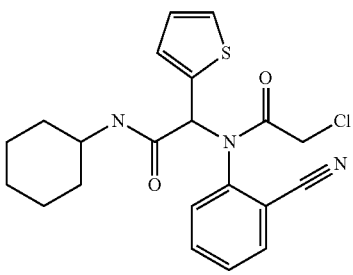
120
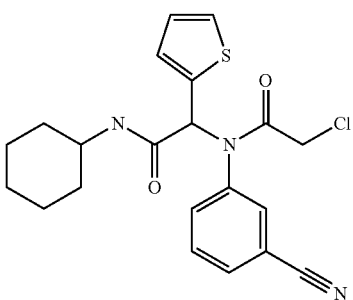
121
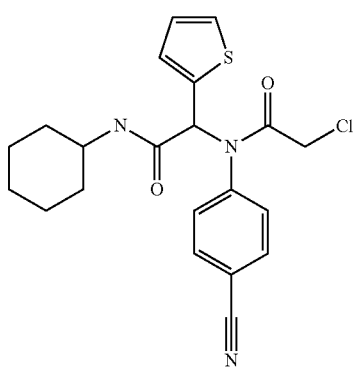
122
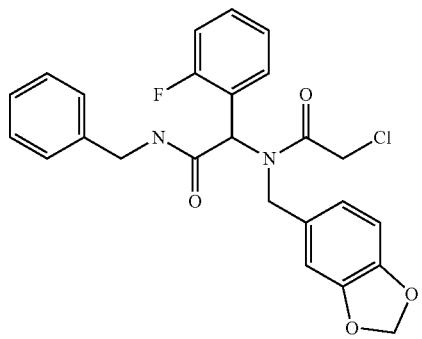
123
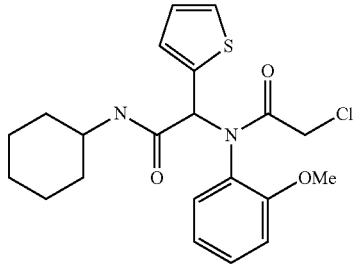
124
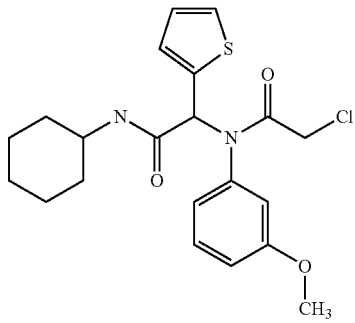
125
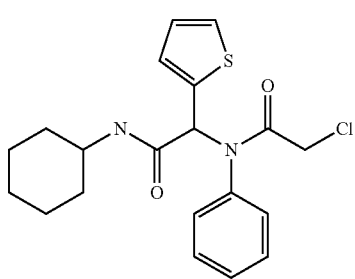
126

127 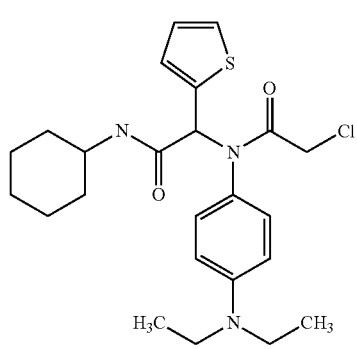
128 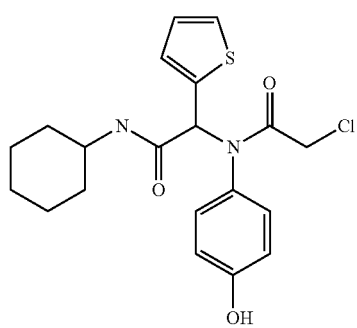
129 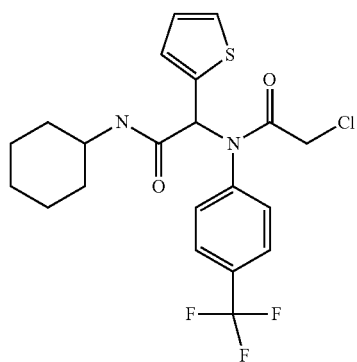
131 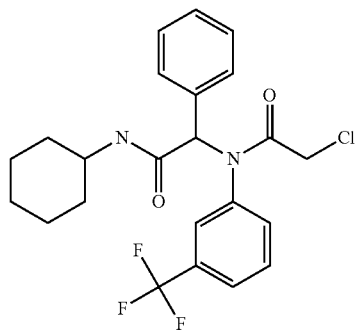
132 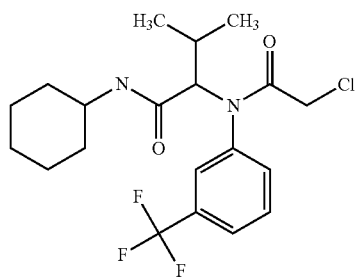
133 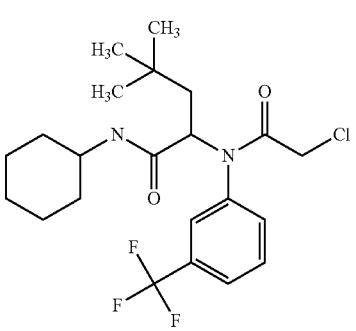
134 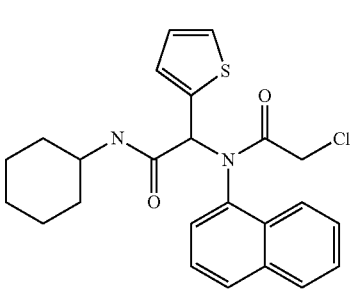
135 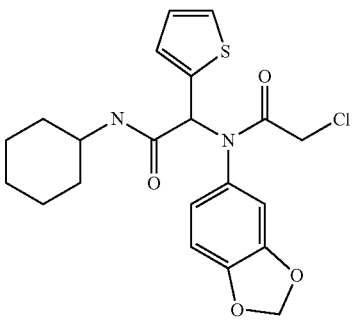
136 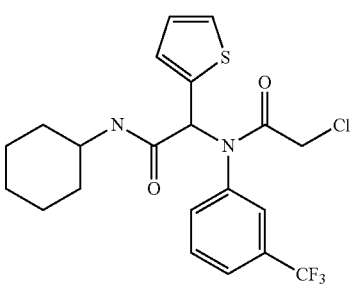
137 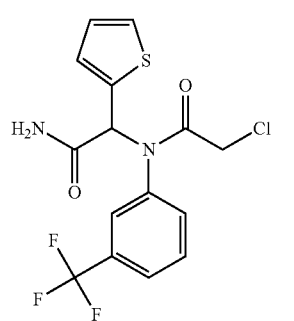

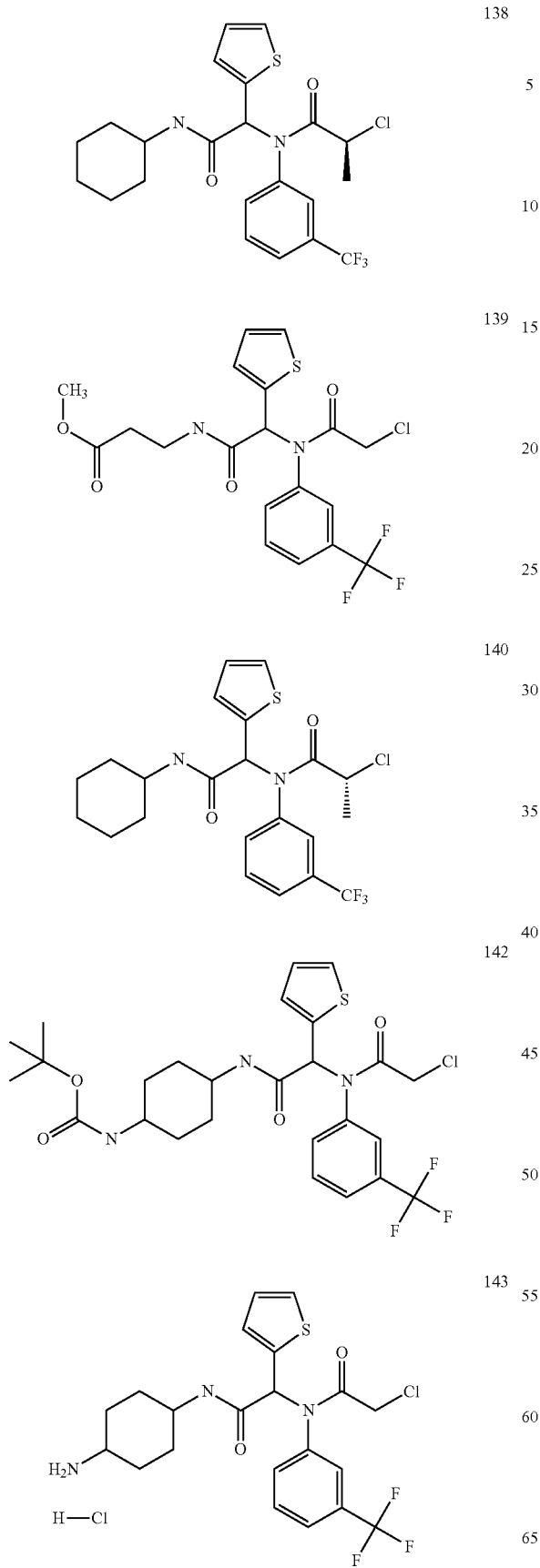
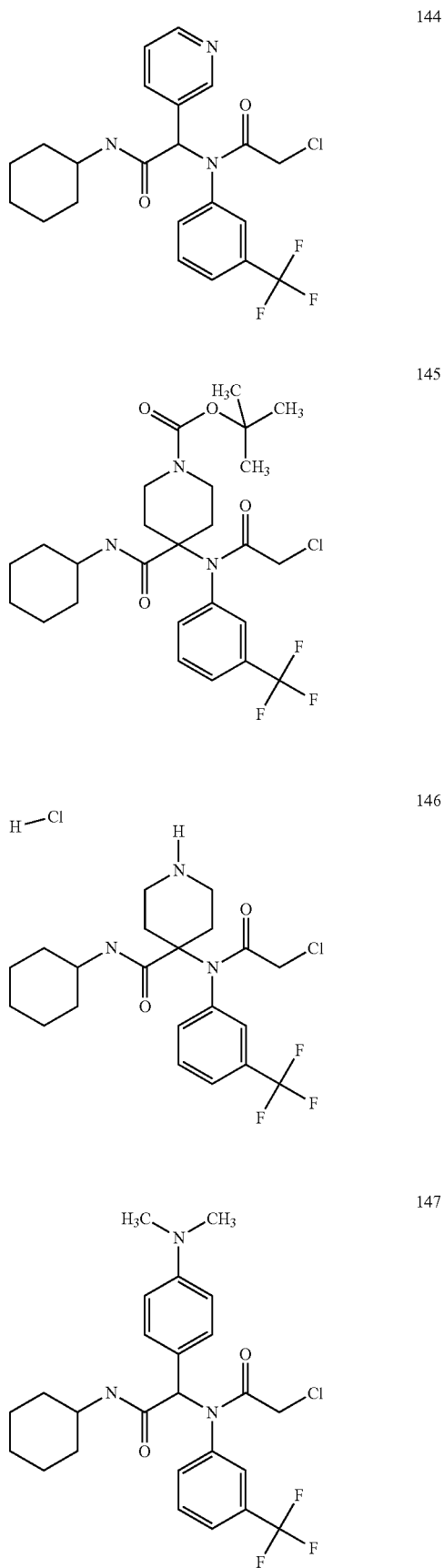

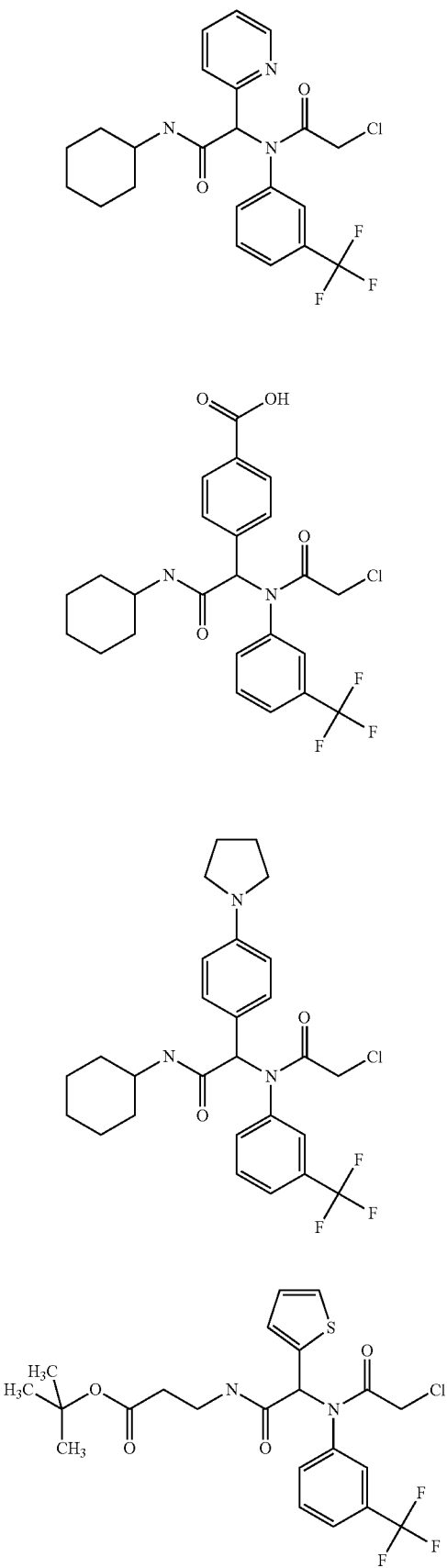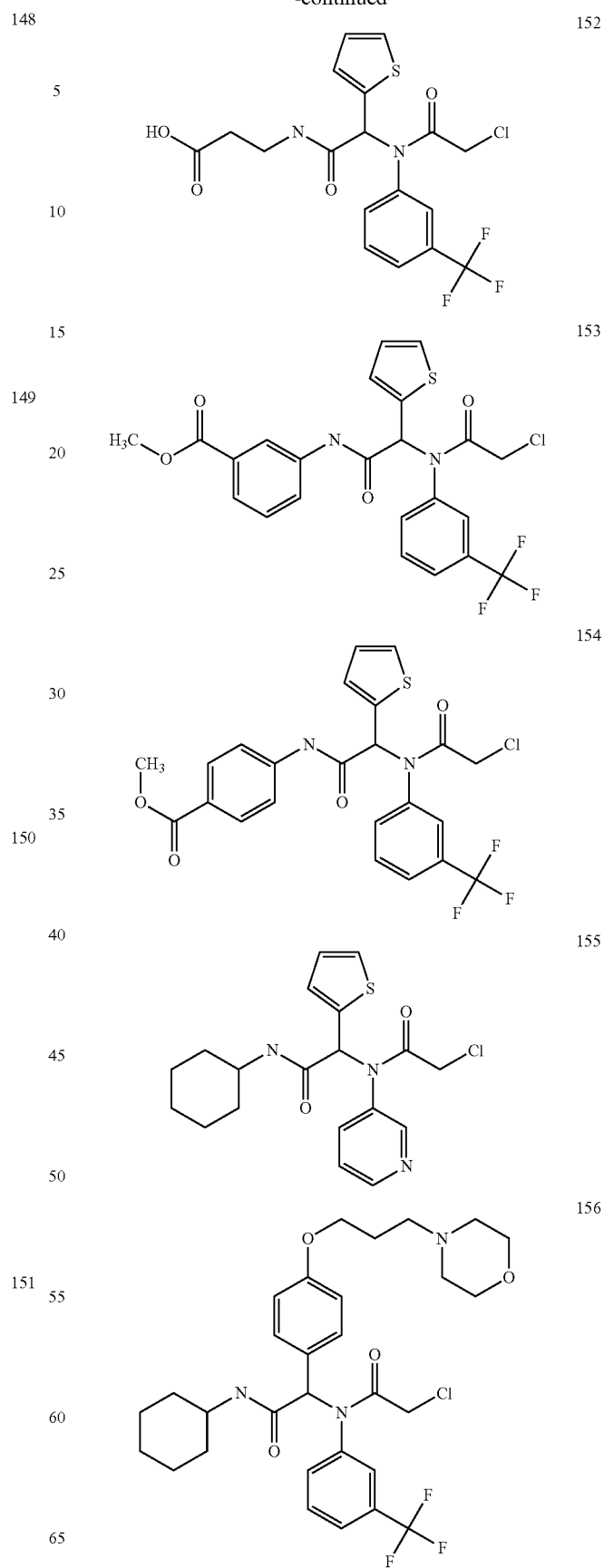

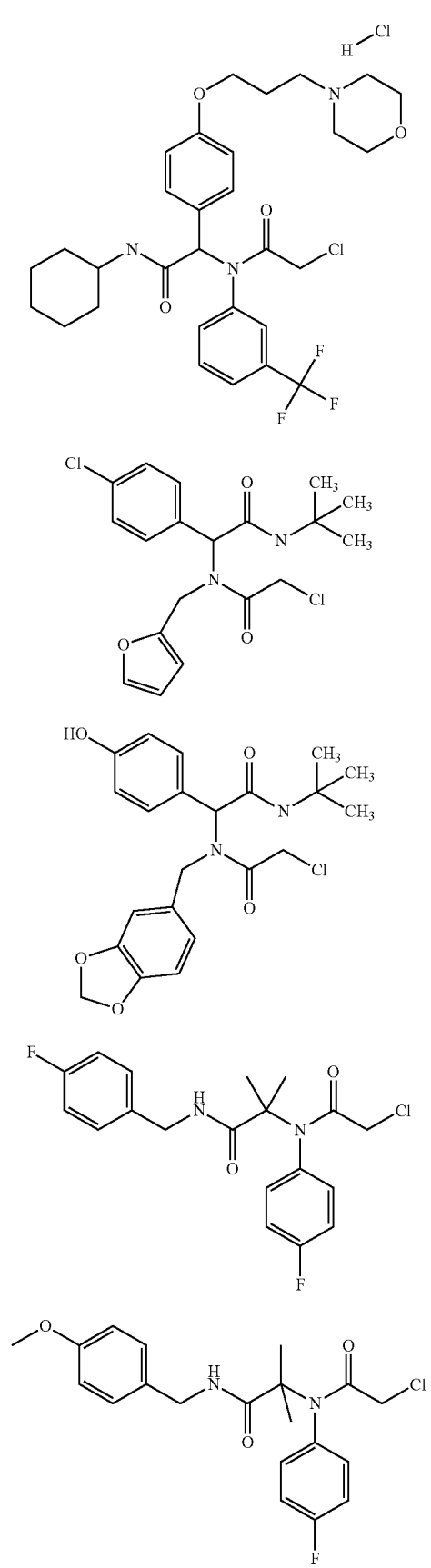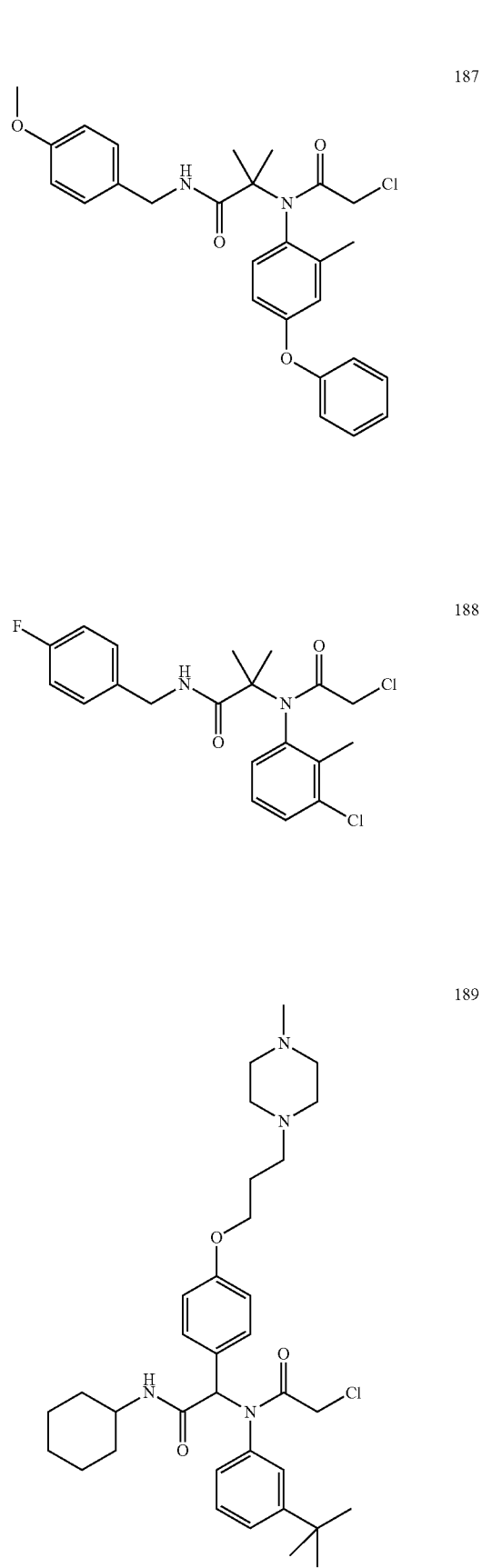

131
-continued
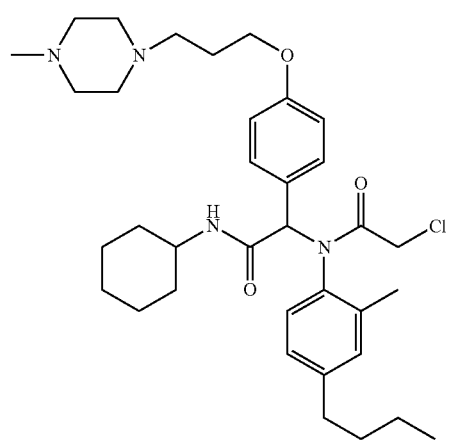
190
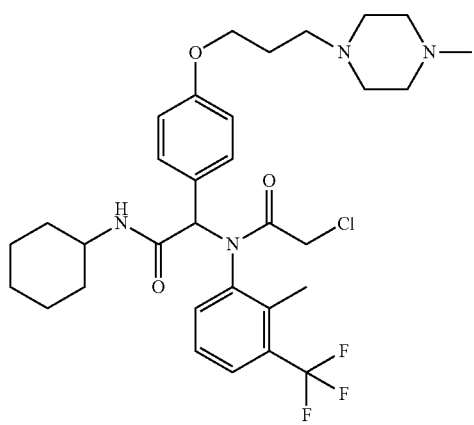
191
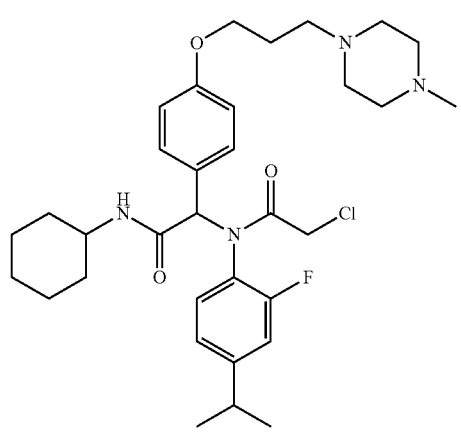
192
132
-continued
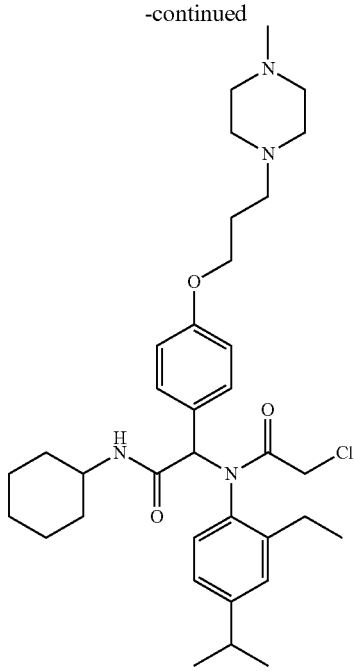
193
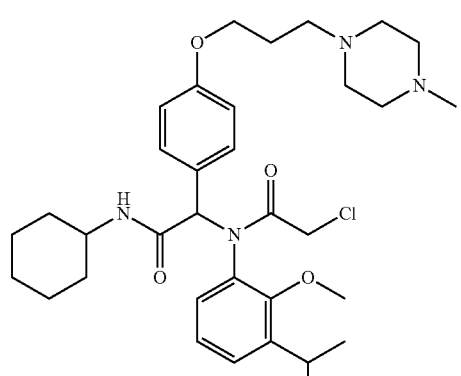
194
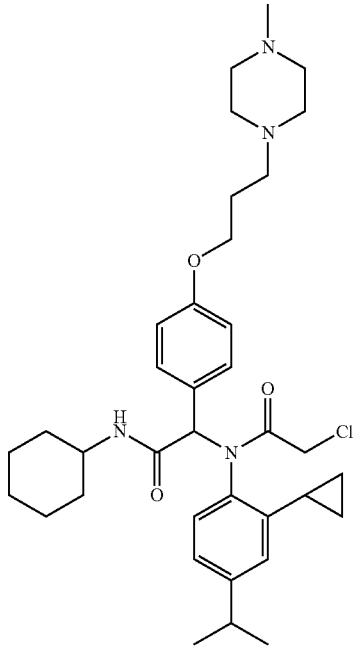
195

133
-continued
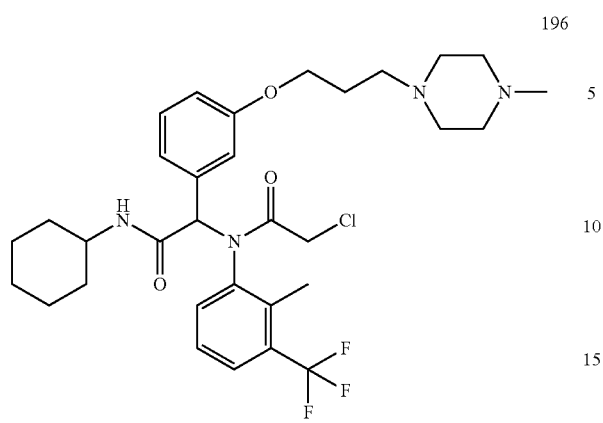
196
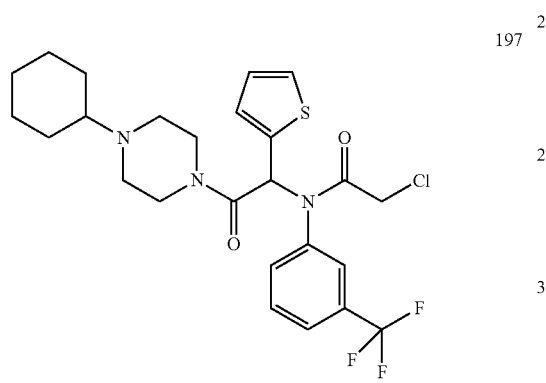
197
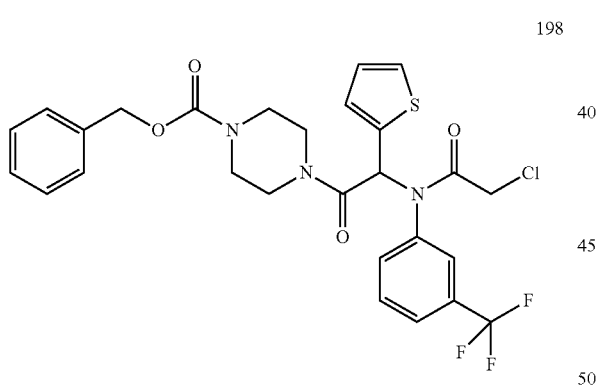
198
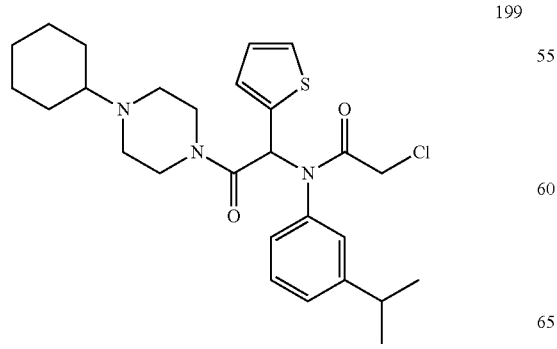
199
134
-continued
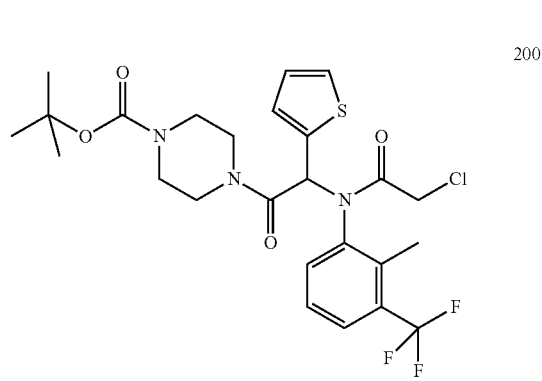
200
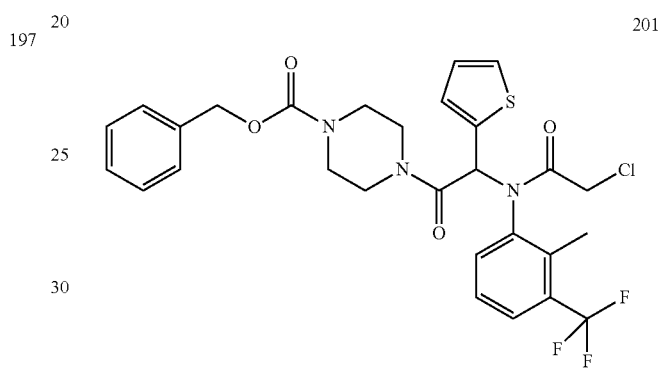
201
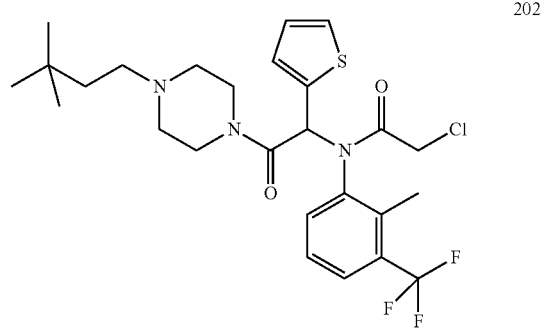
202
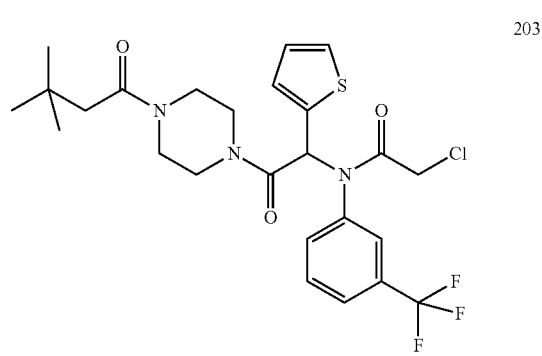
203

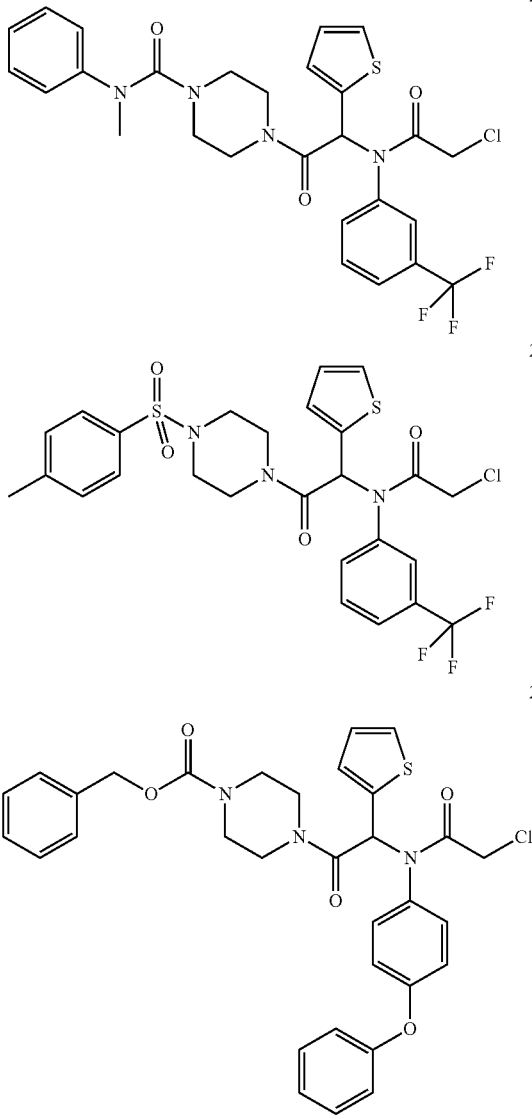

14. The pharmaceutical composition according to claim 1, further comprising at least one other active principle.

15. A pharmaceutical composition comprising:
(i) at least one compound of formula (I) as defined in claim 1, and
(ii) at least one other active principle,
as combination products for use simultaneously, separately or spread over time.

16. The pharmaceutical composition according to claim 14, wherein the at least one active principle is selected from cisplatin and the derivatives thereof; vinca alkaloids; purine analogues; topoisomerase I inhibitors; topoisomerase II inhibitors; antitumoural nucleoside derivatives; alkylating agents; antitumoural anthracycline derivatives; molecules targeting the IGF-I receptor; tetracarcin derivatives; corticosteroids; antibodies; selective oestrogen receptor antagonists or modulators; aromatase inhibitors; differentiating agents; DNA methyltransferase inhibitors; antifolates; antibiotics; antimetabolites; apoptosis inducing agents and Bcl-2 inhibitor antiangiogenic agents; agents binding to tubulin; kinase inhibitors; farnesyltransferase inhibitors; histone deacetylase inhibitors; inhibitors of the ubiquitin proteasome system; and telomerase inhibitors.

17. The pharmaceutical composition according to claim 15, wherein the at least one active principle is selected from cisplatin and the derivatives thereof; vinca alkaloids; purine analogues; topoisomerase I inhibitors; topoisomerase II inhibitors; antitumoural nucleoside derivatives; alkylating agents; antitumoural anthracycline derivatives; molecules targeting the IGF-I receptor; tetracarcin derivatives; corticosteroids; antibodies; selective oestrogen receptor antagonists or modulators; aromatase inhibitors; differentiating agents; DNA methyltransferase inhibitors; antifolates; antibiotics; antimetabolites; apoptosis inducing agents and Bcl-2 inhibitor antiangiogenic agents; agents binding to tubulin; kinase inhibitors; farnesyltransferase inhibitors; histone deacetylase inhibitors; inhibitors of the ubiquitin proteasome system; and telomerase inhibitors.

18. The pharmaceutical composition according to claim 16, wherein the cisplatin derivatives are selected from carboplatin and oxaliplatin; the taxanes are selected from taxol, taxotere, paclitaxel and docetaxel; the vinca alkaloids are selected from vinblastine, vincristine and vinorelbine; the purine analogues are selected from mercaptopurine, thioguanine, pentostatin and 2-chlorodeoxyadenosine; the topoisomerase I inhibitors are selected from compounds of camptothecin; the topoisomerase II inhibitors are selected from epipodophyllotoxin, podophyllotoxin and the derivatives thereof; thz antitumoural nucleoside derivatives are selected from 5-fluorouracil, leucovorin, gemcitabine and capecitabine; the alkylating agents are selected from nitrogen mustards, nitrosoureas, alkyl sulphonates, ethyleneimines, methylmelamines, and tetrazines; the antitumoural anthracycline derivatives are selected from daunorubicin, adriamycin, doxil, idarubicin and mitoxantrone; the molecule targeting the IGF-I receptor is picropodophyllin; the tetracarcin derivatives is tetrocarcin A; the corticosteroid is prednisone; the antibodies are selected from trastuzumab (anti-HER2 antibody), rituximab (anti-CD20 antibody), gemtuzamab, cetuximab, pertuzumab and bevacizumab; the selective oestrogen receptor antagonists or modulators are selected from tamoxifen, fulvestrant, toremifene, droloxifene, faslodex and raloxifene; the aromatase inhibitors are selected from exemestane, anastrozole, letrozole and vorozole; the differentiating agents are selected from retinoids and retinoic acid metabolism blocking agents; the DNA methyltransferase inhibitors are selected from azacytidine and decitabine; the antifolate is disodium permetrexed; the antibiotics are selected from antinomycin D, bleomycin, mitomycin C, actinomycin D, camimomycin, daunomycin and plicamycin; the antimetabolites are selected from chlofarabine, aminopterin, cytosine arabinoside, floxuridine and methotrexate; the apoptosis inducing agents and Bcl-2 inhibitor antiangiogenic agents are selected from YC 137, BH 312, ABT 737, gossypol, HA 14-1, TW 37 and decanoic acid; the agents binding to tubulin are selected from combrestatin, colchicine derivatives and nocodazole; the kinase inhibitors are selected from flavoperidol, imatinib mesylate, erlotinib and gefitinib; the farnesyltransferase inhibitor is tipifarnib; the histone deacetylase inhibitors are selected from sodium butyrate, suberoylanilide hydroxamic acid, depsipeptide, NVP-LAQ824, R306465, JNJ-26481585 and trichostatin A; the inhibitors of the ubiquitin proteasome system are selected from MLN 0.41, bortezomib and yondelis; and the telomerase inhibitor is telomestatin.

19. The pharmaceutical composition according to claim 17, wherein the cisplatin derivatives are selected from carboplatin and oxaliplatin; the taxanes are selected from taxol, taxotere, paclitaxel and docetaxel; the vinca alkaloids are selected from vinblastine, vincristine and vinorelbine; the purine analogues are selected from mercaptopurine, thioguanine, pentostatin and 2-chlorodeoxyadenosine; the topoisomerase I inhibitors are selected from compounds of camptothecin; the topoisomerase II inhibitors are selected from epipodophyllotoxin, podophyllotoxin and the derivatives thereof; thz antitumoural nucleoside derivatives are selected from 5-fluorouracil, leucovorin, gemcitabine and capecitabine; the alkylating agents are selected from nitrogen mustards, nitrosoureas, alkyl sulphonates, ethyleneimines, methylmelamines, and tetrazines; the antitumoural anthracycline derivatives are selected from daunorubicin, adriamycin, doxil, idarubicin and mitoxantrone; the molecule targeting the IGF-I receptor is picropodophyllin; the tetracarcin derivatives is tetrocarcin A; the corticosteroid is prednisone; the antibodies are selected from trastuzumab (anti-HER2 antibody), rituximab (anti-CD20 antibody), gemtuzamab, cetuximab, pertuzumab and bevacizumab; the selective oestrogen receptor antagonists or modulators are selected from tamoxifen, fulvestrant, toremifene, droloxifene, faslodex and raloxifene; the aromatase inhibitors are selected from exemestane, anastrozole, letrozole and vorozole; the differentiating agents are selected from retinoids and retinoic acid metabolism blocking agents; the DNA methyltransferase inhibitors are selected from azacytidine and decitabine; the antifolate is disodium permetrexed; the antibiotics are selected from antinomycin D, bleomycin, mitomycin C, actinomycin D, caminomycin, daunomycin and plicamycin; the antimetabolites are selected from chlofarabine, aminopterin, cytosine arabinoside, floxuridine and methotrexate; the apoptosis inducing agents and Bcl-2 inhibitor antiangiogenic agents are selected from YC 137, BH 312, ABT 737, gossypol, HA 14-1, TW 37 and decanoic acid; the agents binding to tubulin are selected from combrestatin, colchicine derivatives and nocodazole; the kinase inhibitors are selected from flavoperidol, imatinib mesylate, erlotinib and gefitinib; the farnesyltransferase inhibitor is tipifarnib; the histone deacetylase inhibitors are selected from sodium butyrate, suberoylanilide hydroxamic acid, depsipeptide, NVP-LAQ824, R306465, JNJ-26481585 and trichostatin A; the inhibitors of the ubiquitin proteasome system are selected from MLN 0.41, bortezomib and yondelis; and the telomerase inhibitor is telomestatin.

20. The pharmaceutical composition according to claim 19, wherein the compounds of camptothecin are selected from irinotecan and topotecan; the podophyllotoxin derivatives are selected from etoposide and teniposide; the nitrogen mustards are selected from cyclophosphamide, mechlorethamine, chlorambucil and melphalan; the nitrosoureas are selected from carmustine, lomustine and streptozocin; the alkyl sulphonate is busulphan; the ethyleneimines and methylmelamines are selected from thiotepa and hexamethylmelamine; the tetrazine is dacarbazine; the retinoids are selected from retinoic acid and vitamin D; and the retinoic acid metabolism blocking agent is accutane.

21. The pharmaceutical composition according to claim 19, wherein the compounds of camptothecin are selected from irinotecan and topotecan; the podophyllotoxin derivatives are selected from etoposide and teniposide; the nitrogen mustards are selected from cyclophosphamide, mechlorethamine, chlorambucil and melphalan; the nitrosoureas are selected from carmustine, lomustine and streptozocin; the alkyl sulphonate is busulphan; the ethyleneimines and methylmelamines are selected from thiotepa and hexamethylmelamine; the tetrazine is dacarbazine; the retinoids are selected from retinoic acid and vitamin D; and the retinoic acid metabolism blocking agent is accutane.

22. A method for treating a cancer comprising administering to a person in need thereof of an effective amount of a compound of formula (I) as defined in claim 1, wherein the cancer is selected from the group consisting of breast cancer, myeloma, and leukaemia.

23. The method according to claim 22, wherein the cancer is a cancer resistant to chemotherapy.

24. A compound of general formula (I):

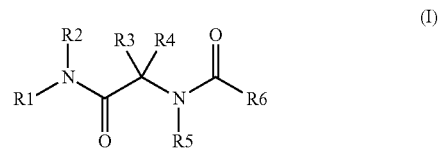

wherein R1, R2, R3, R4, R5 and R6 are as defined in claim 1, provided that:

if R1 represents a hydrogen atom, a tert-butyl, sec-butyl, cyclohexyl, hexyl, ethyl or methyl group, or a phenyl group, optionally substituted by one or more groups selected from F, ethoxy and $CF_3$, R2 represents a hydrogen atom or a methyl group, or R1 and R2 together form, with the nitrogen atom carrying them, a morpholine or piperidine group, R3 represents a hydrogen atom, and R4 represents a methyl or ethyl group or a phenyl group optionally substituted with one or more groups selected from Cl, OH, methoxy, $NO_2$ or $NMe_2$, or R3 and R4 together form, with the carbon atom carrying them, a cyclopentane or cyclohexane, and R6 represents a —$CH_2Cl$ group, then R5 does not represent a prop-2-yne, ($C_1$-$C_8$)alkyl, furylmethyl, tetrahydropyrane, thiopyrane or 1,3-benzodioxolyl-methyl group; or a benzyl group optionally substituted by a chlorine atom or $NO_2$; or a phenyl group optionally substituted by one or more Br, ethyl or methyl groups.

25. The compound according to claim 24, selected from:

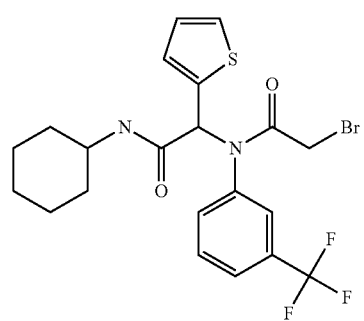

107

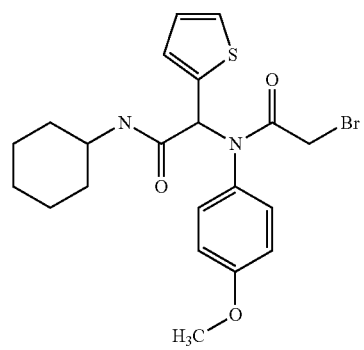

108

109 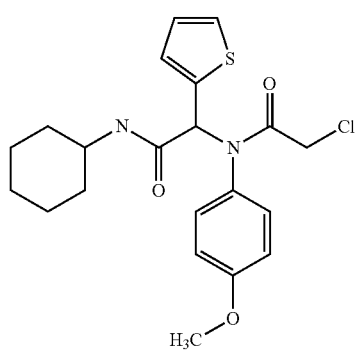
110 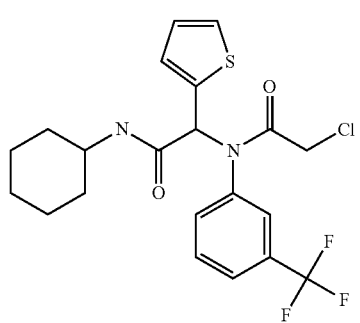
111 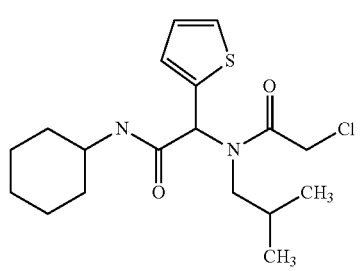
113 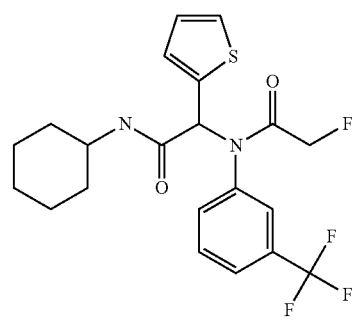
114 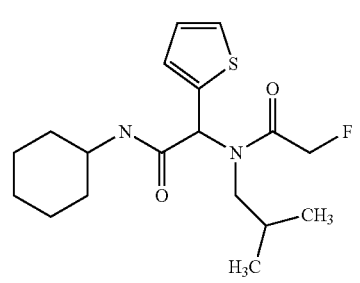
115 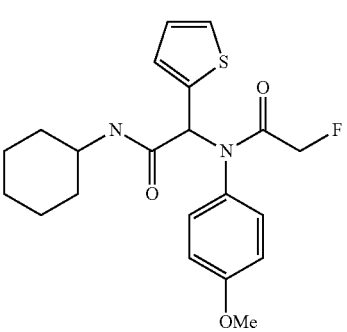
120 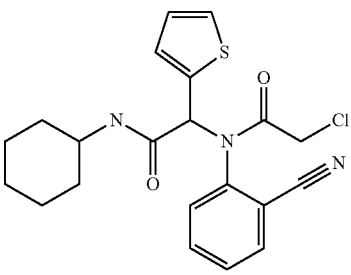
121 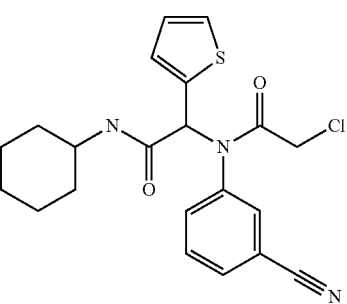
122 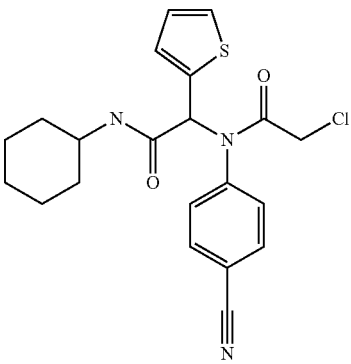
123 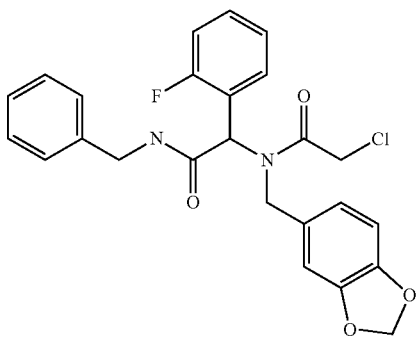

124 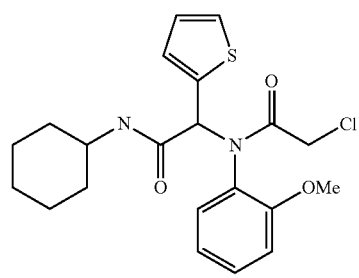
125 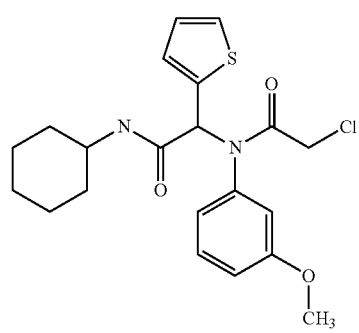
126 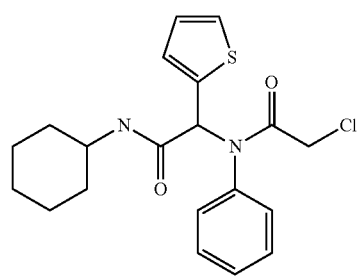
127 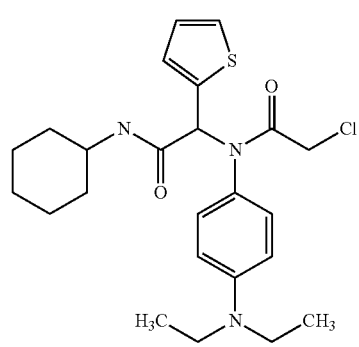
128 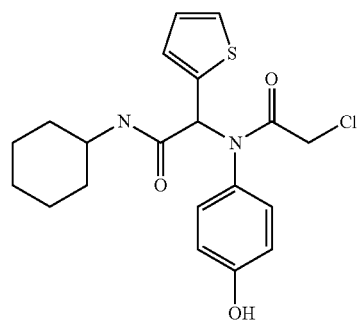
129 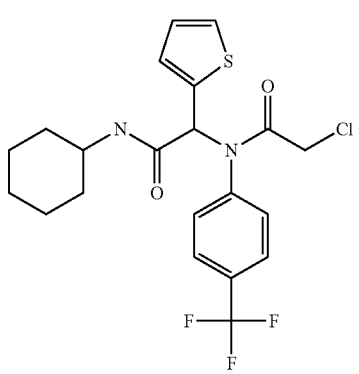
131 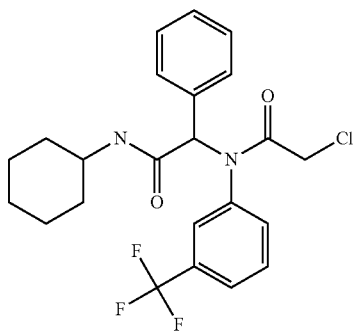
132 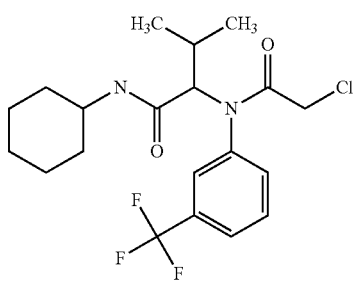
133 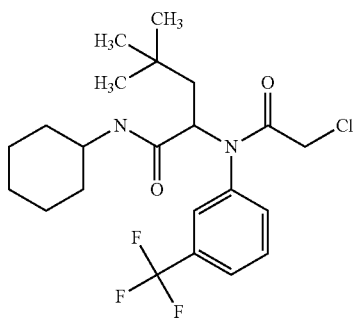
134 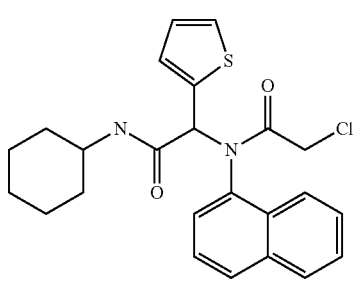

135
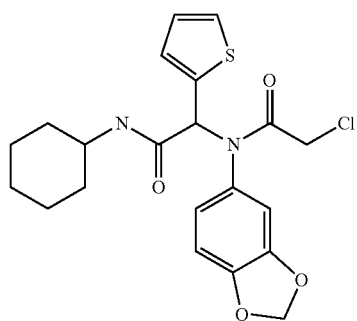
136
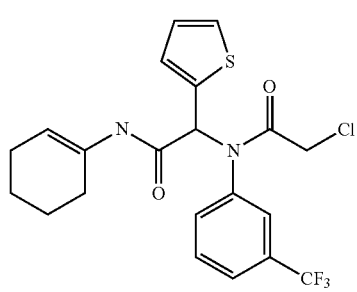
137
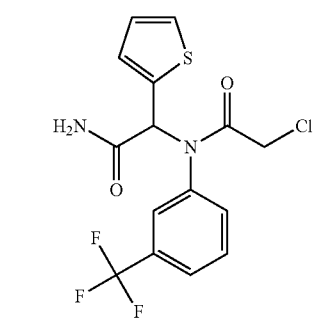
138
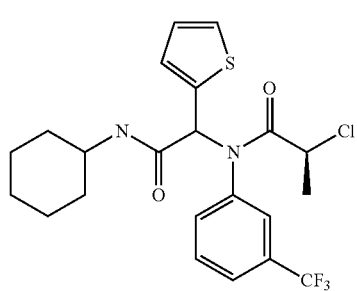
139
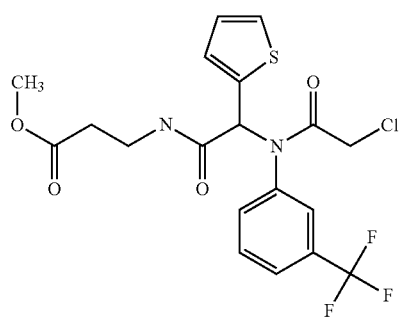
140
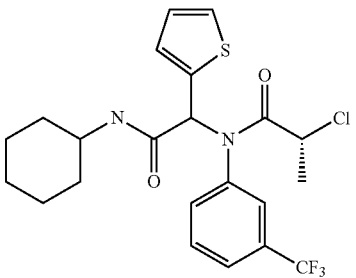
142
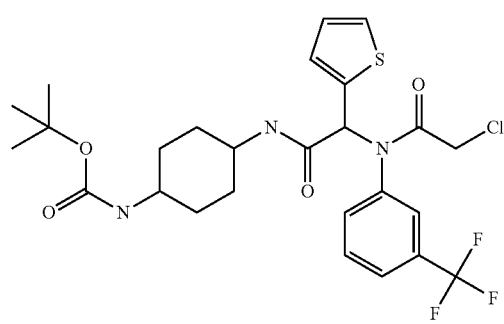
143
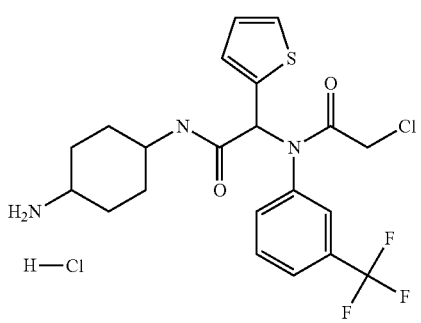
144
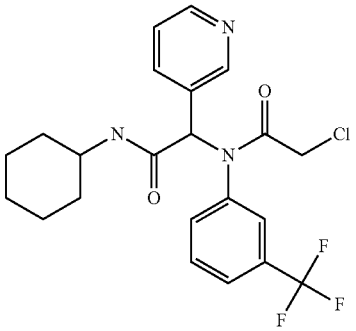

145
-continued
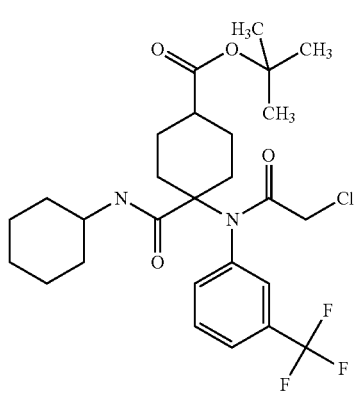
145
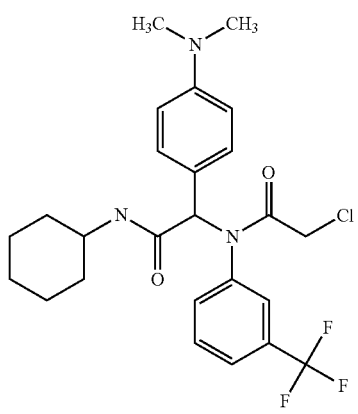
146
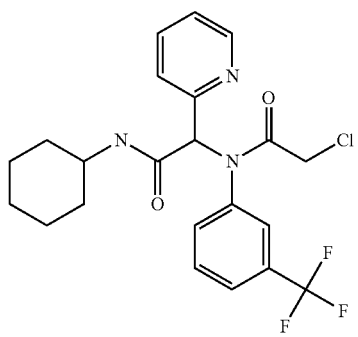
147
146
-continued
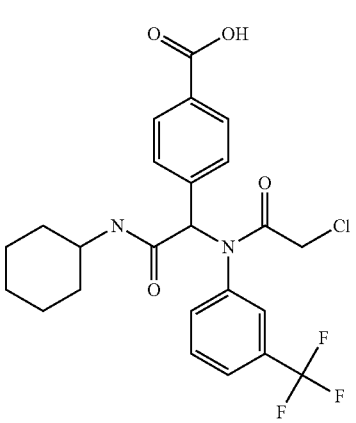
149
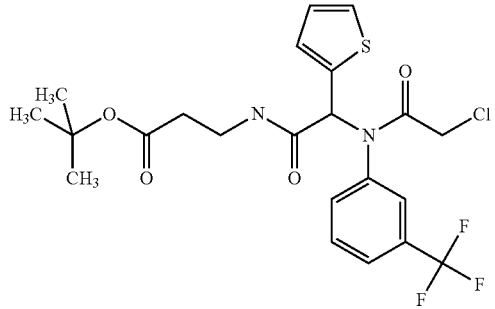
150
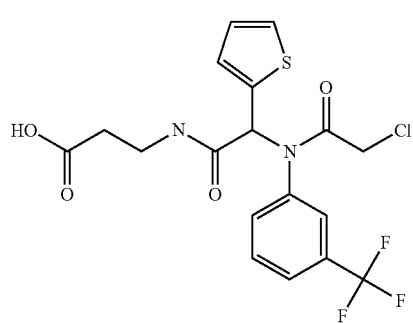
151
148
152

153 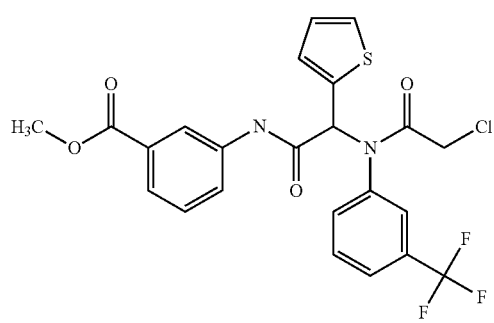
154 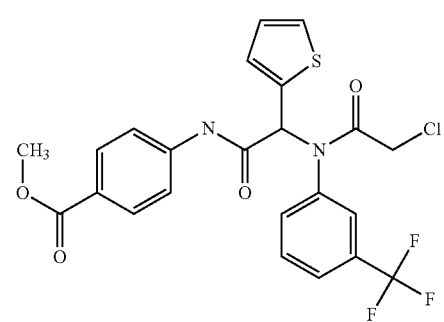
155 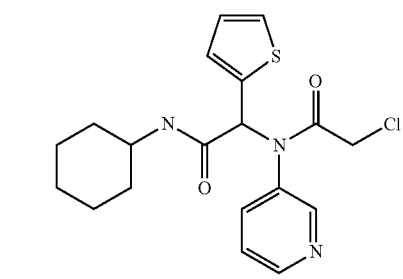
156 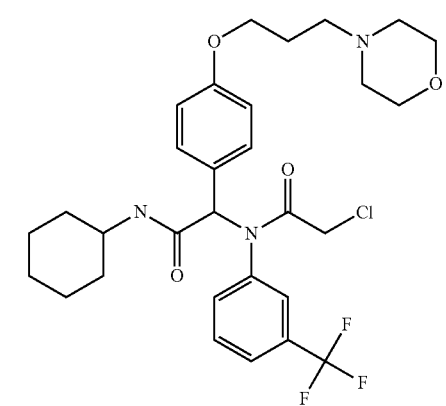
157 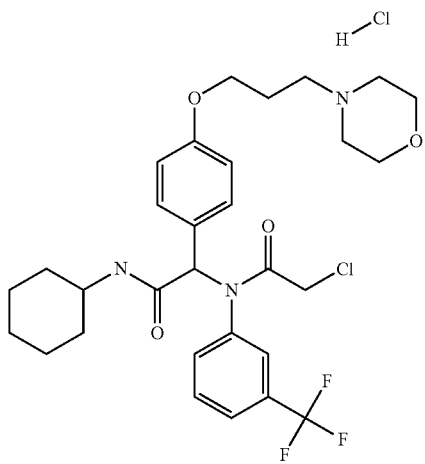
185 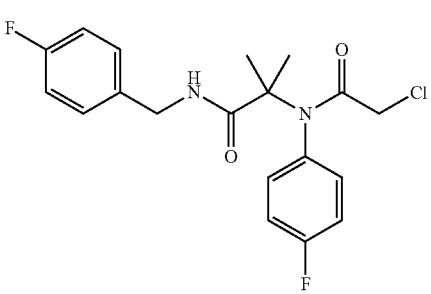
186 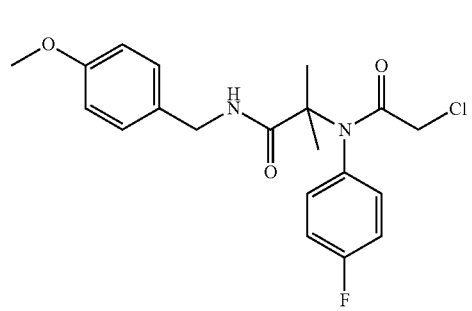
187 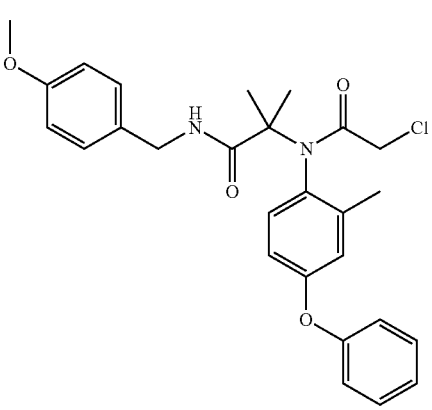

| 149 -continued | | 150 -continued | |
|---|---|---|---|
| 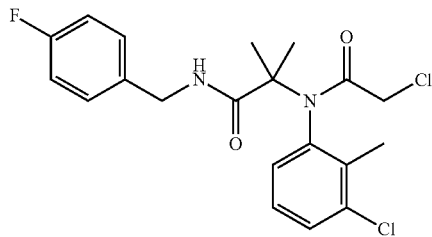 | 188 | 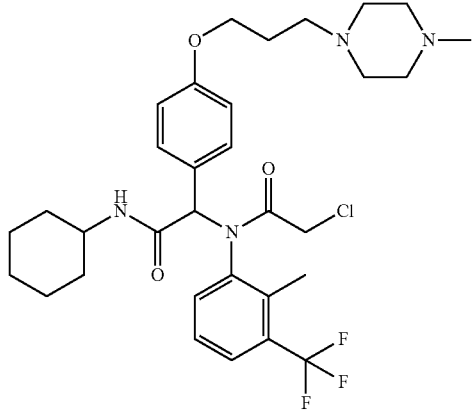 | 191 |
| 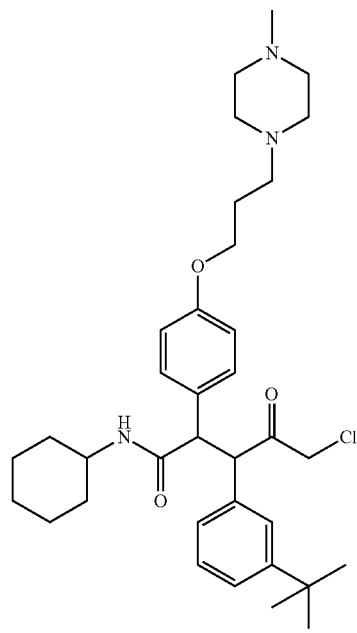 | 189 | 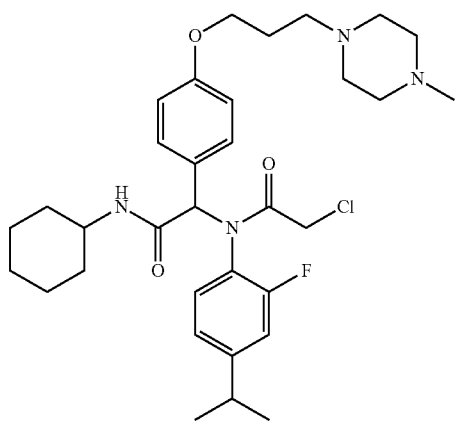 | 192 |
| 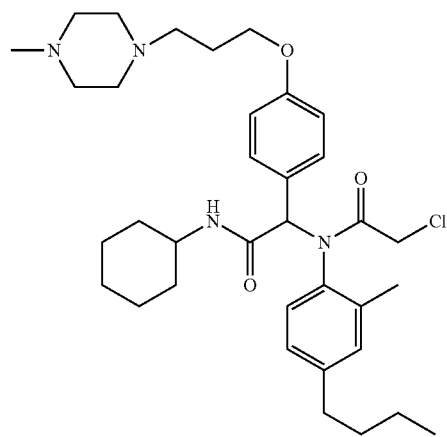 | 190 | 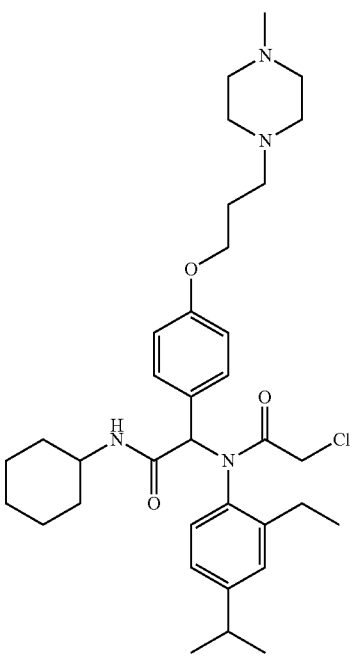 | 193 |

| 194 | 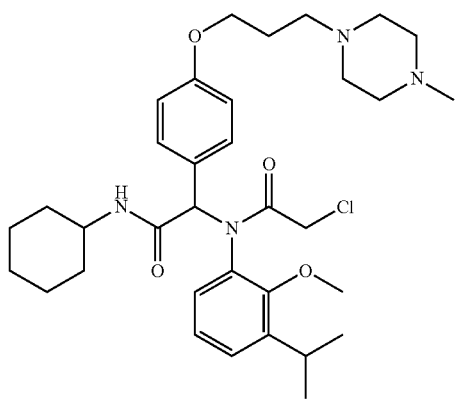 |
|---|---|
| 197 | 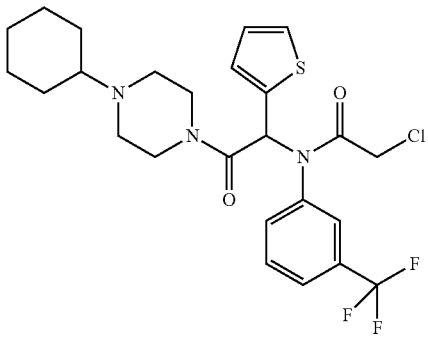 |
| 195 | 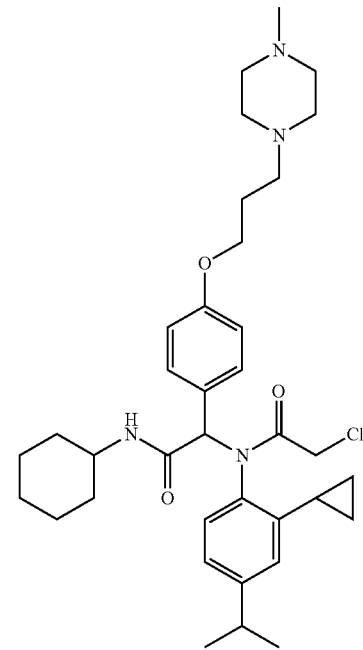 |
| 198 | 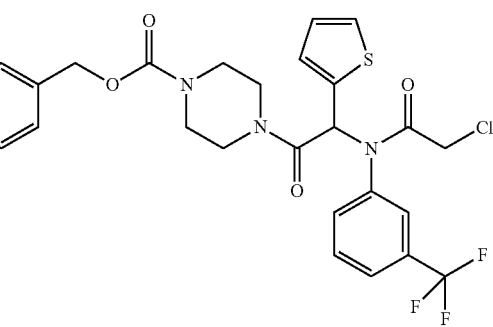 |
| 199 | 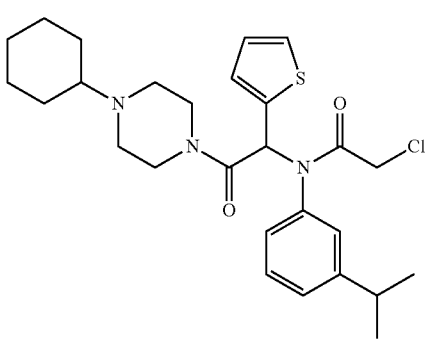 |
| 196 | 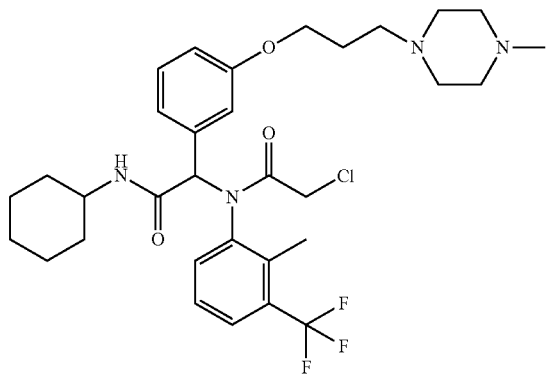 |
| 200 | 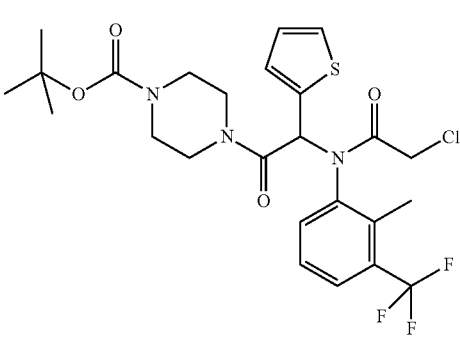 |

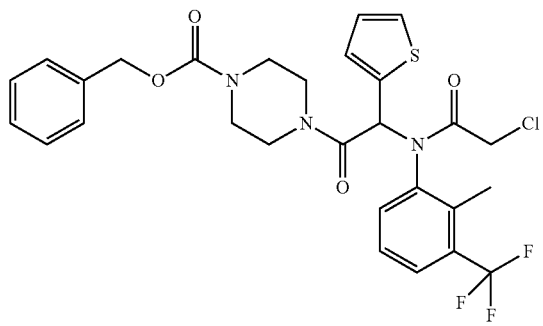

201

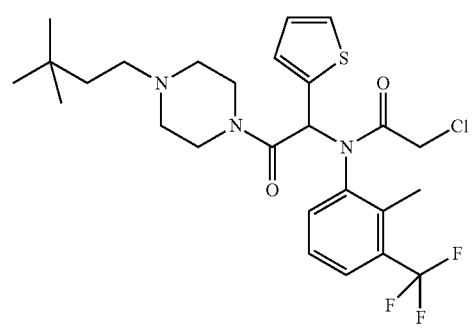

202

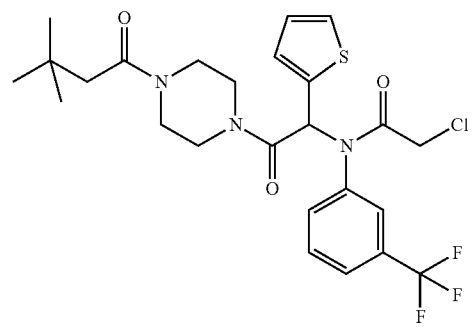

203

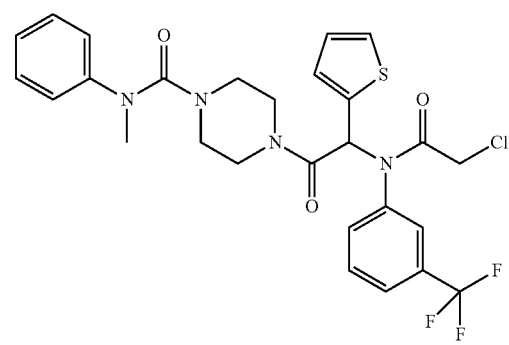

204

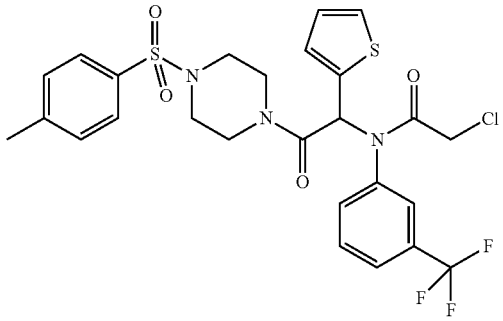

205

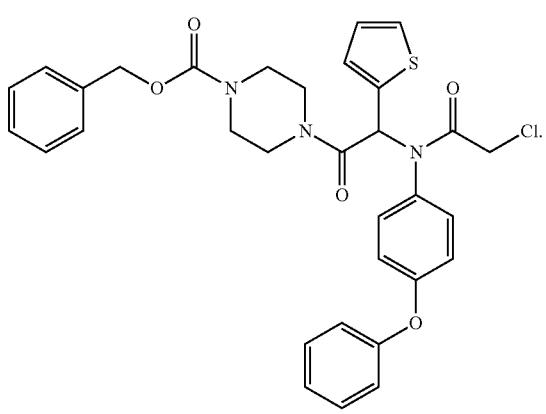

206

26. The method according to claim 23, wherein the cancer is resistant to adriamycin or doxorubicin.

27. A pharmaceutical composition comprising at least one compound of formula (I):

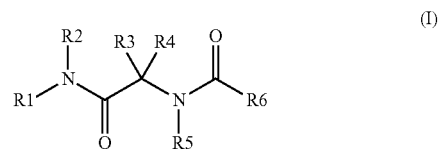

(I)

or a pharmaceutically acceptable salt thereof, an isomer or isomer mixture thereof in all proportions, for which:

R1 represents a hydrogen atom or a $(C_1$-$C_6)$alkyl, $(C_3$-$C_{10})$cycloalkyl, $(C_3$-$C_{10})$cycloalkenyl, aryl, aryl-$(C_1$-$C_6)$alkyl, heteroaryl-$(C_1$-$C_6)$alkyl group, said group being optionally substituted by one or more groups selected from a halogen atom, $(C_1$-$C_6)$alkoxy, —NH$_2$, —COOH, —CN, —OH, —NR$^7$R$^8$, —O—$(C_1$-$C_6)$alkyl-NR$^7$R$^8$, benzyloxy, aryloxy, —C(O)O—$(C_1$-$C_6)$alkyl, —NH—C(O)O—$(C_1$-$C_6)$alkyl, —C(O)NH$_2$, —C(O)NR$^9$R$^{10}$, —S$(C_1$-$C_6)$alkyl, —S(O)—$(C_1$-$C_6)$alkyl, —SO$_2$—$(C_1$-$C_6)$alkyl, —SO$_2$NH$_2$, —SO$_2$NR$^{11}$R$^{12}$, —NR$^{13}$SO$_2$R$^{14}$ and a $(C_1$-$C_6)$alkyl group optionally substituted by one or more halogen atoms, R2 represents a hydrogen atom or a $(C_1$-$C_6)$alkyl, or R1 and R2 together form, with the nitrogen atom carrying them:

a heteroaryl optionally substituted by one or more groups selected from a halogen atom, a —CN, —NH$_2$, —NR$^{40}$R$^{41}$, NO$_2$, OH, $(C_1$-$C_6)$alkoxy, aryloxy, benzyloxy, —O($C_1$-$C_6$)alkyl-$NR^{42}R^{43}$, —C(O)O—($C_1$-$C_6$)alkyl, —NHC(O)O—($C_1$-$C_6$)alkyl, —C(O)$NH_2$, —C(O)$NR^{44}R^{45}$, —$SO_2NH_2$, —$SO_2NR^{46}R^{47}$ and —$NR^{48}SO_2R^{49}$ group, or a 3 to 7-membered heterocycle optionally substituted by one or more groups selected from a halogen atom, a ($C_3$-$C_{10}$)cycloalkyl, ($C_3$-$C_{10}$)cycloalkenyl, aryl, heteroaryl, aryl-($C_1$-$C_6$)alkyl, hetero aryl-($C_1$-$C_6$)alkyl, heterocycloalkyl-($C_1$-$C_6$)alkyl, —OH, —$NH_2$, —C(O)OH, —C(O)$NH_2$, —C(S)$NH_2$, —$OR^{50}$, —OC(O)$R^{51}$, —C(O)$R^{52}$, —C(O)$OR^{53}$, —NHC(O)$R^{54}$, —NHC(O)$OR^{55}$, —$SO_2R^{56}$—($C_1$-$C_6$)alkyl-C(O)$OR^{57}$, $NR^{58}R^{59}$, —C(O)$NR^{60}R^{61}$, —C(O)N($R^{62}$)(aryl), C(O)N($R^{63}$)(heteroaryl), —C(O)NHN$R^{64}R^{65}$, —C(S)$NR^{66}R^{67}$, —C(S)N($R^{68}$)(aryl), —C(S)N($R^{69}$)(heteroaryl), —C(S)NHN$R^{70}R^{71}$, —OC(O)—$NR^{72}R^{73}$, —($C_1$-$C_6$)alkyl-C(O)—$NR^{74}R^{75}$, —($C_1$-$C_6$)alkyl-$NR^{103}$—C(O)—$OR^{104}$, —($C_1$-$C_6$)alkyl-$NR^{76}R^{77}$, —C($NOR^{78}$)-aryl radical, and a ($C_1$-$C_6$)alkyl group optionally substituted by one or more halogen atoms, the aryl and heteroaryl unit of said radical, when present, being optionally substituted by one or more groups selected from a halogen atom, a —CN, —OH, ($C_1$-$C_6$)alkyl, ($C_1$-$C_6$)alkoxy, —$NR^{79}R^{80}$, —($C_1$-$C_6$)alkyl-$NR^{81}R^{82}$ and —O—($C_1$-$C_6$)alkyl-$NR^{83}R^{84}$ group, R3 represents a hydrogen atom or a ($C_1$-$C_6$)alkyl, or —($C_1$-$C_4$)alkyl-$NR^{15}R^{16}$ group, R4 represents a hydrogen atom or a ($C_1$-$C_6$)alkyl, ($C_3$-$C_{10}$)cycloalkyl, aryl, or heteroaryl group, said group being optionally substituted by one or more groups selected from a halogen atom, a —($CF_3$)$_2$OH, —CN—$NH_2$, —$OPO_3H_2$, —$NR^{17}R^{18}$, —$NO_2$, —COOH, —OH, —O($C_1$-$C_6$)alkyl-$OPO_3H_2$, —O—($C_1$-$C_6$)alkyl-O—($C_1$-$C_6$)alkyl, —O($C_1$-$C_6$)alkyl-$NR^{19}R^{20}$, —$NR^{81}$($C_1$-$C_6$)alkyl-$NR^{85}R^{86}$, benzyloxy, —C(O)O—($C_1$-$C_6$)alkyl, —NHC(O)O—($C_1$-$C_6$)alkyl, —C(O)$NH_2$, —C(O)$NR^{21}R^{22}$, —S—($C_1$-$C_6$)alkyl, —S(O)—($C_1$-$C_6$)alkyl, —$SO_2$—($C_1$-$C_6$)alkyl, —$SO_2NH_2$, —$SO_2NR^{23}R^{24}$, —$NR^{25}SO_2R^{26}$, 3 to 7-membered heterocycloalkyl, aryloxy radical, a ($C_1$-$C_6$)alkyl group optionally substituted by one or more halogen atoms and a ($C_1$-$C_6$)alkoxy optionally substituted by one or more fluorine atoms, and the aryl and heteroaryl unit of said radical, when present, being optionally fused to a 5 or 6-membered heterocycle, or R3 and R4 form with the carbon carrying them a ring selected from a ($C_3$-$C_{10}$)cycloalkyl and a 3 to 7-membered heterocycloalkyl, said ring being optionally substituted by a ($C_1$-$C_6$)alkyl, —C(O)—($C_1$-$C_6$)alkyl, —C(O)O—($C_1$-$C_6$)alkyl group, R5 represents a ($C_1$-$C_6$)alkyl, ($C_3$-$C_{10}$)cycloalkyl, ($C_3$-$C_{10}$)cycloalkenyl, aryl, heteroaryl, aryl-($C_1$-$C_6$)alkyl, heteroaryl-($C_1$-$C_6$)alkyl, ($C_3$-$C_{10}$)cycloalkyl-($C_1$-$C_6$)alkyl, (3 to 7-membered heterocycloalkyl)-($C_1$-$C_6$)alkyl group, said group being optionally substituted by one or more groups selected from a halogen atom, a —$NH_2$, —COOH, —CN, —OH, —$NO_2$, —B(OH)$_2$, ($C_1$-$C_6$)alkoxy, —O—($C_1$-$C_6$)alkyl-$NR^{27}R^{28}$, —O— ($C_1$-$C_6$)alkyl-O—($C_1$-$C_6$)alkyl, aryloxy, —C(O)O—($C_1$-$C_6$)alkyl, ($C_2$-$C_6$)alkynyl, —$NR^{29}R^{30}$, —NHC(O)O—($C_1$-$C_6$)alkyl, —C(O)$NH_2$, —C(O)$NR^{31}R^{32}$, —S—($C_1$-$C_6$)alkyl, —S(O)—($C_1$-$C_6$)alkyl, —$SO_2$—($C_1$-$C_6$)alkyl, —$SO_2NH_2$, —$SO_2NR^{33}R^{34}$, —$NR^{35}SO_2R^{36}$, aryl, heteroaryl, ($C_1$-$C_6$)alkylheteroaryl, 3 to 7-membered heterocycloalkyl, (3 to 7-membered heterocycloalkyl)-($C_1$-$C_6$)alkoxy radical and a ($C_1$-$C_6$)alkyl group optionally substituted by one or more halogen atoms, the aryl or heteroaryl unit of said radical, when present, being optionally fused to a 5 or 6-membered heterocycle, and R6 represents —C≡$CR^{38}$, wherein:

$R^7$ to $R^{13}$, $R^{15}$ to $R^{18}$, $R^{21}$ to $R^{25}$, $R^{27}$ to $R^{35}$, $R^{40}$ to $R^{48}$, $R^{58}$ to $R^{84}$, $R^{89}$ to $R^{102}$ represent, independently of one another, a hydrogen atom or a ($C_1$-$C_6$)alkyl group, or, if two groups are carried by the same nitrogen, the two groups form with the nitrogen atom carrying them a 3 to 7-membered heterocycloalkyl, $R^{14}$, $R^{26}$, $R^{36}$, and $R^{49}$ represent, independently of one another, a ($C_1$-$C_6$)alkyl group, $R^{38}$ represents a hydrogen atom, a ($C_1$-$C_6$)alkyl group, or a phenyl group, $R^{50}$ to $R^{57}$, $R^{87}$ and $R^{88}$ represent, independently of one another, a ($C_1$-$C_6$)alkyl, aryl, heteroaryl, aryl-($C_1$-$C_6$)alkyl, heteroaryl-($C_1$-$C_6$)alkyl, ($C_1$-$C_6$)alkyl-aryl or ($C_1$-$C_6$)alkyl-heteroaryl group, and $R^{19}$, $R^{20}$, $R^{85}$ and $R^{86}$ represent, independently of one another, a ($C_1$-$C_6$)alkyl group, or ($R^{19}$ and $R^{20}$) and/or ($R^{85}$ and $R^{86}$) together form, with the nitrogen atom carrying them, a 3 to 7-membered heterocycloalkyl optionally substituted by one or more groups selected from a halogen atom, a ($C_3$-$C_{10}$)cycloalkyl, aryl, heteroaryl, aryl-($C_1$-$C_6$)alkyl, heteroaryl-($C_1$-$C_6$)alkyl, —C(O)$OR^{87}$, —$SO_2R^{88}$, —OH, ($C_1$-$C_6$)alkoxy, —OC(O)— ($C_1$-$C_6$)alkyl, —OC(O)—$NR^{89}R^{90}$, —NHC(O)O—($C_1$-$C_6$)alkyl, —C(O)$NH_2$, —C(O)$NR^{91}R^{92}$, —C(S)$NR^{93}R^{94}$, —C(O)NHN$R^{95}R^{96}$, —C(S)NHN$R^{97}R^{98}$ radical and a ($C_1$-$C_6$)alkyl group optionally substituted by one or more halogen atoms, the aryl and heteroaryl unit of said radical, when present, being optionally substituted by one or more groups, selected from a halogen atom and a ($C_1$-$C_6$)alkyl, —CN, —OH, $NR^{99}R^{100}$, ($C_1$-$C_6$)alkoxy, —O—($C_1$-$C_6$)alkyl-$NR^{101}R^{102}$ group, in association with one or more pharmaceutically acceptable excipients.

28. The pharmaceutical composition according to claim 27, wherein the compound of formula (I) is selected from:

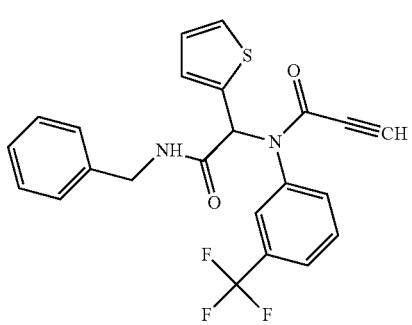

1

157
-continued
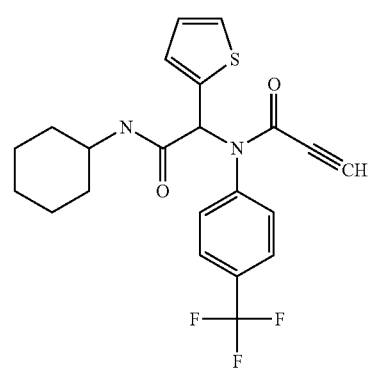
2
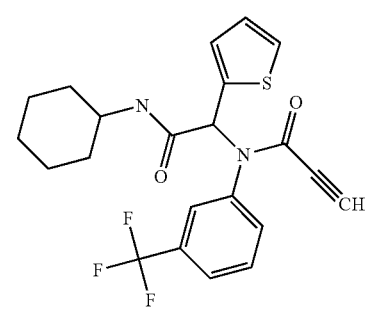
3
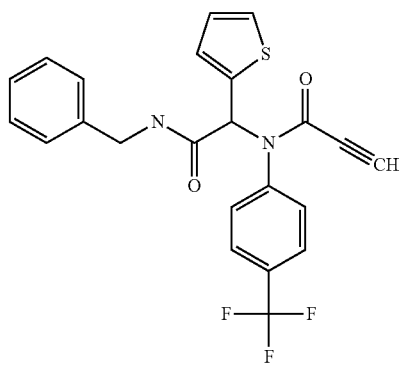
4
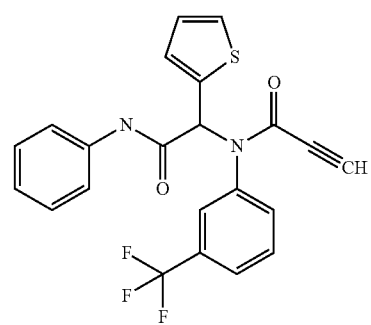
5
158
-continued
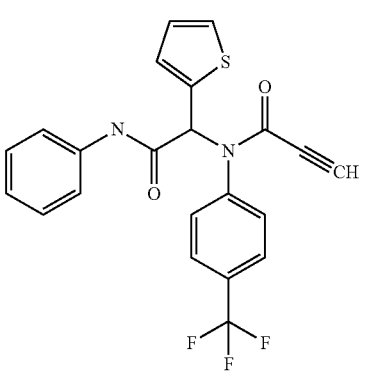
6
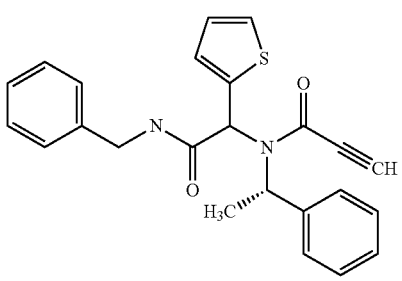
8
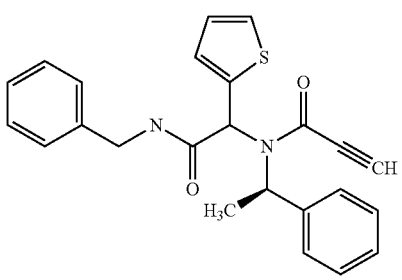
9
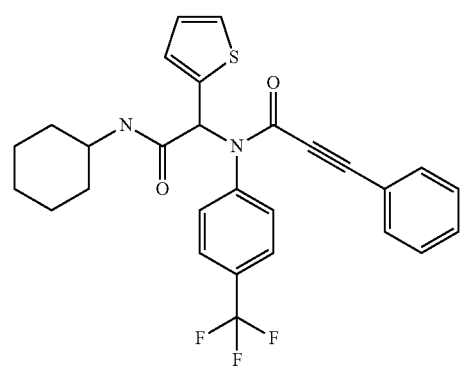
10
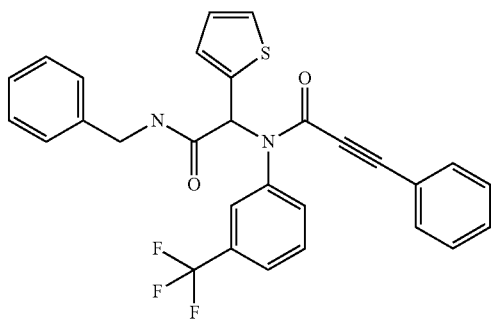
11

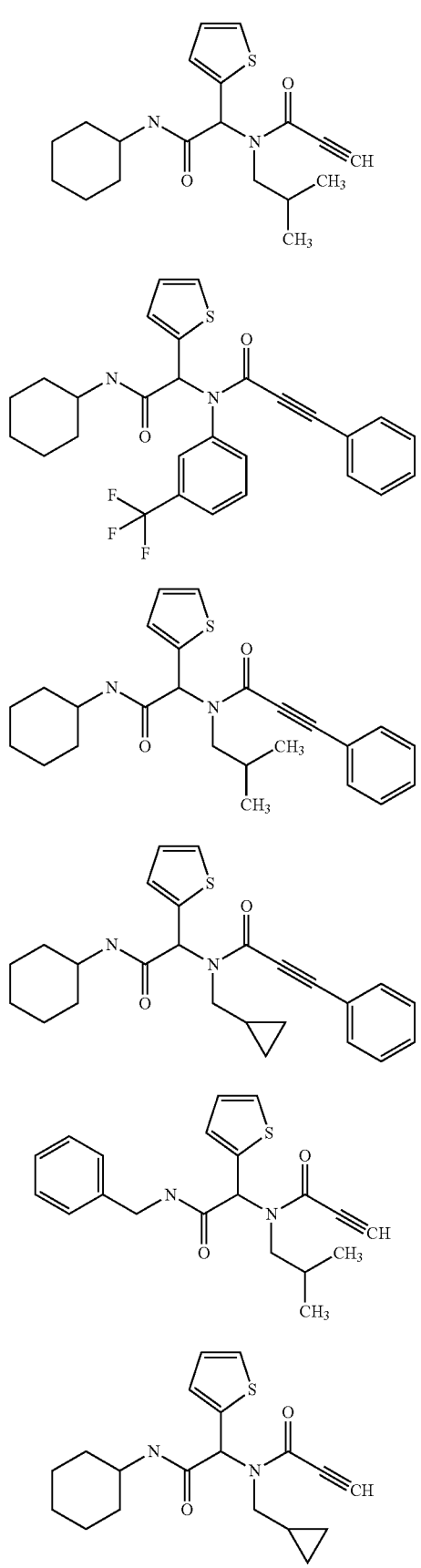
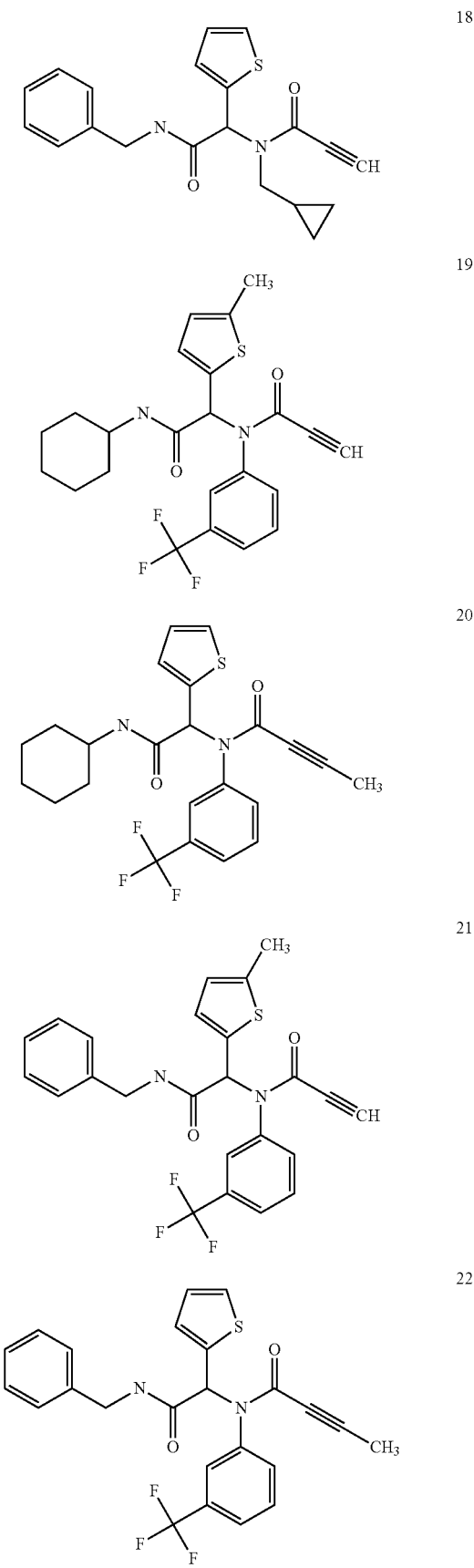

23
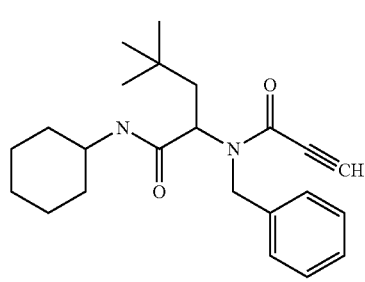
24
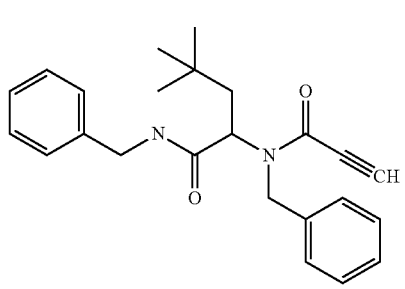
25
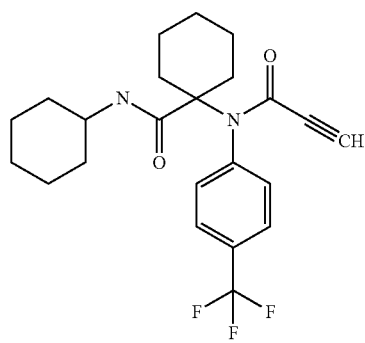
26
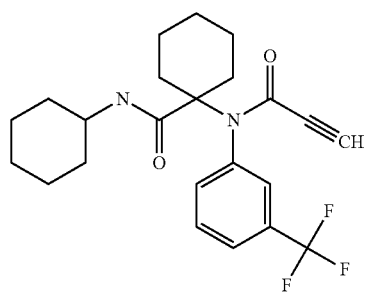
27
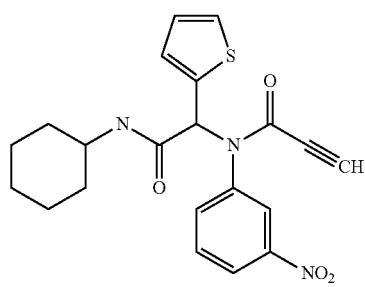
28
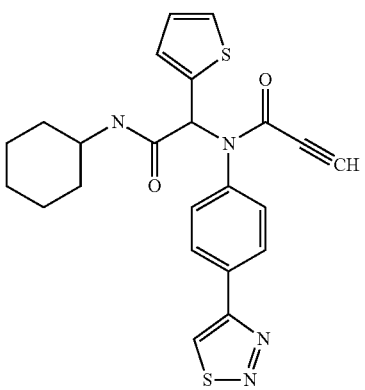
29
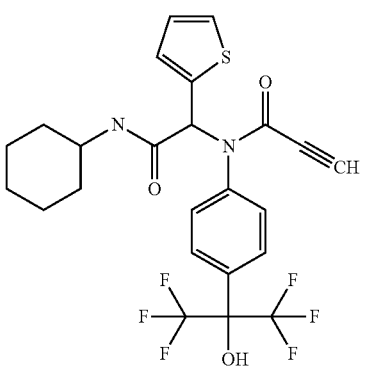
30
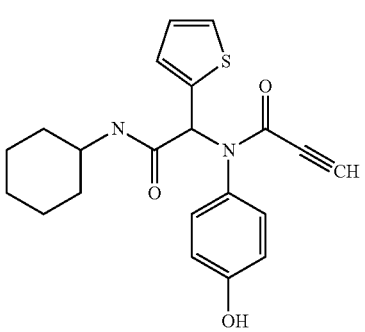
31
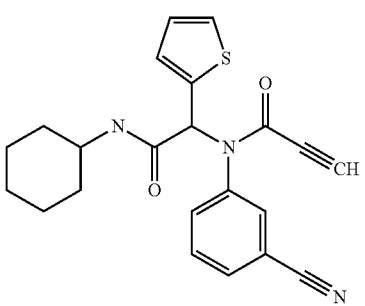

32
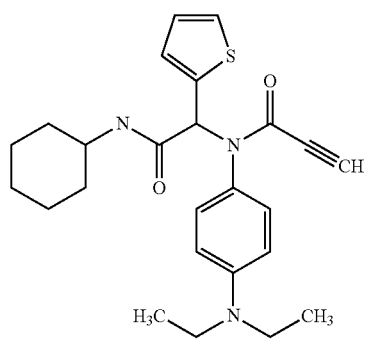
33
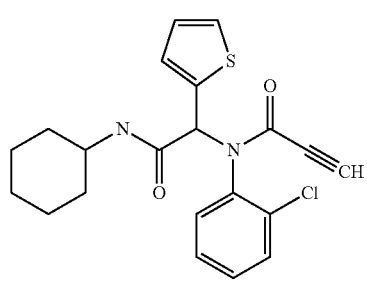
34
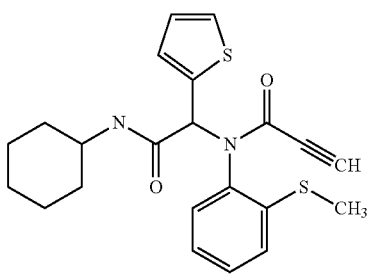
35
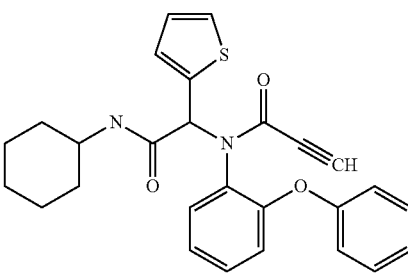
36
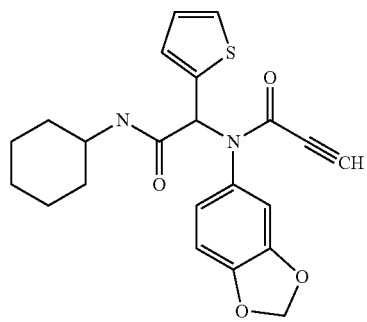
37
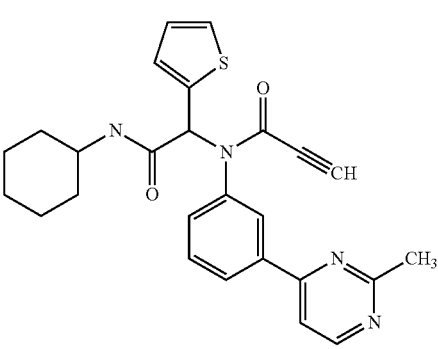
38
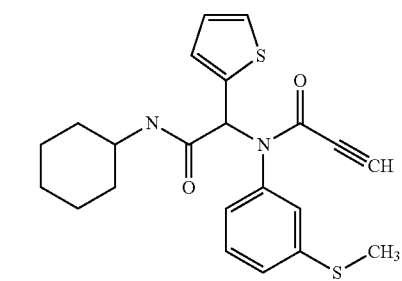
39
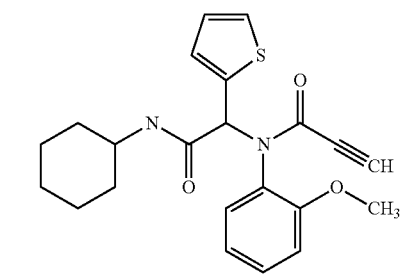
40
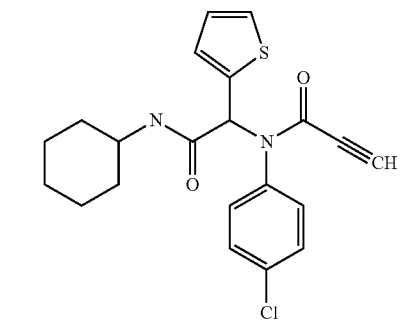
41

42
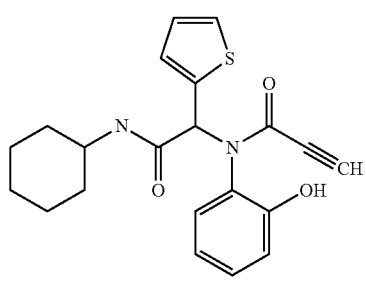
43
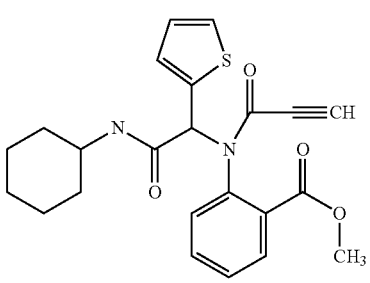
44
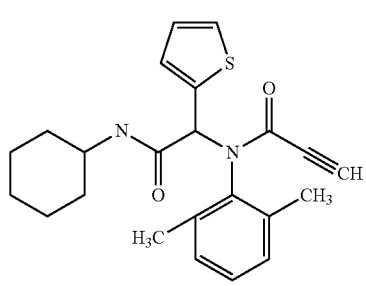
45
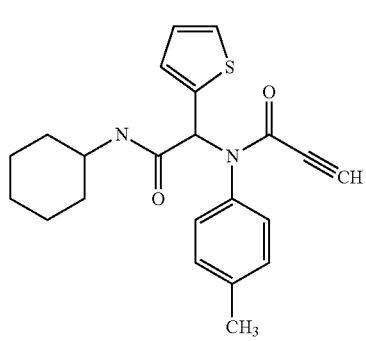
46
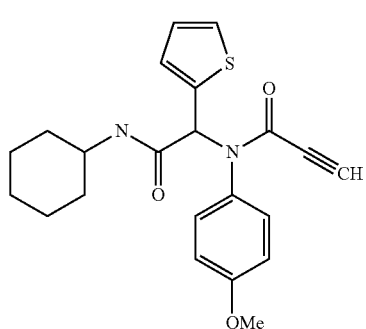
47
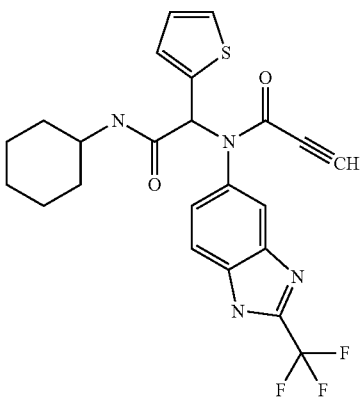
48
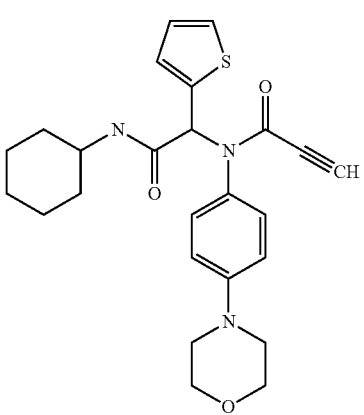
49
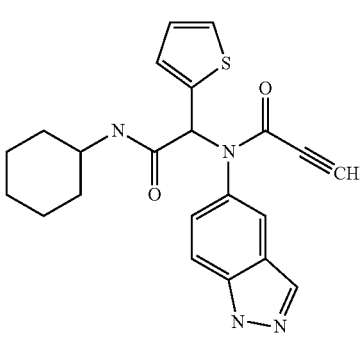
50
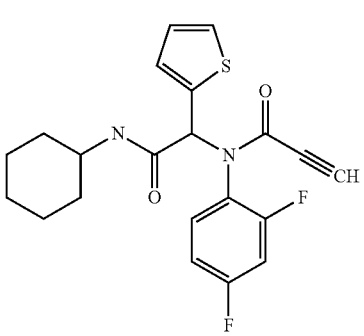

51
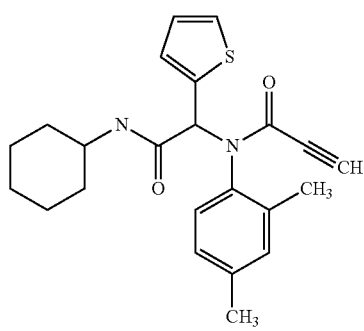
52
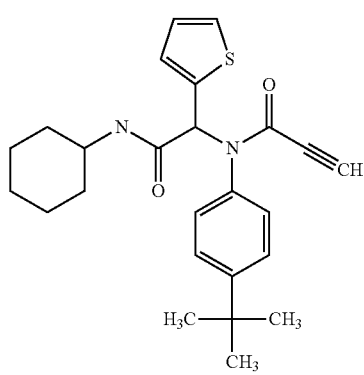
53
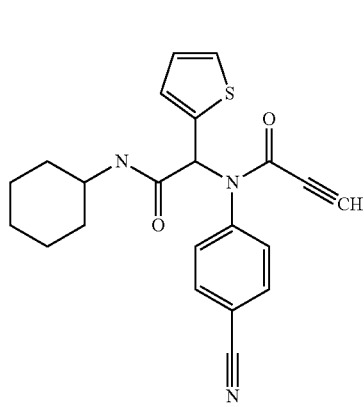
54
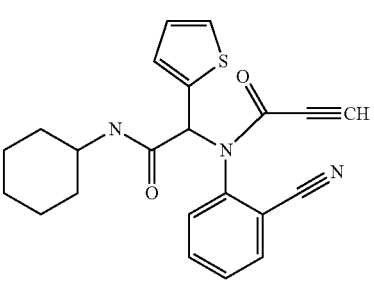
55
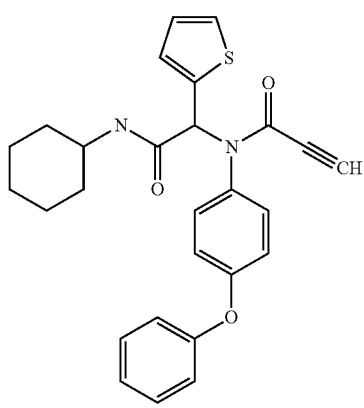
56
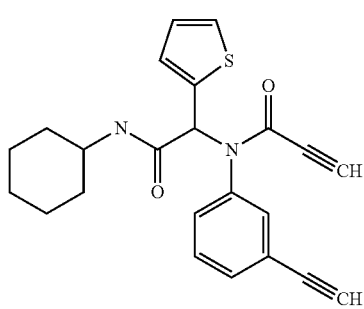
57
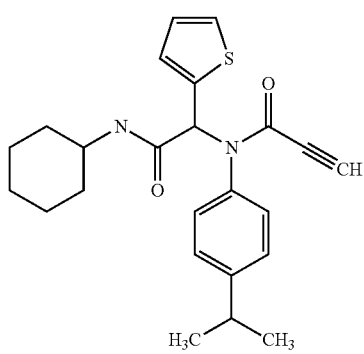
58
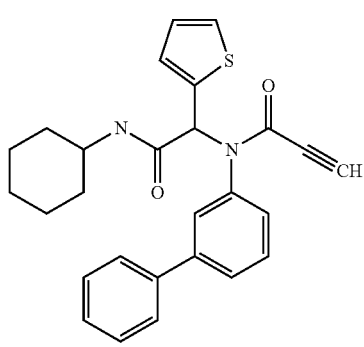

-continued
59
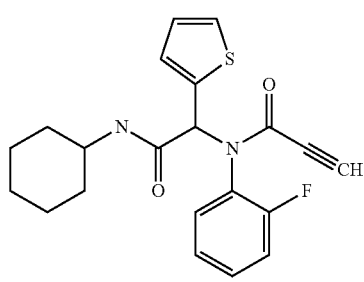
60
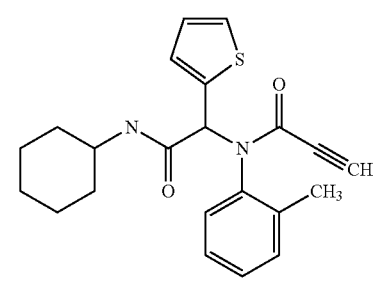
61
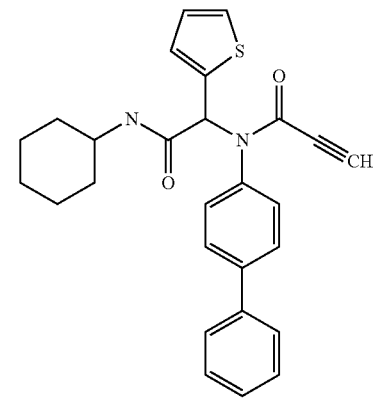
62
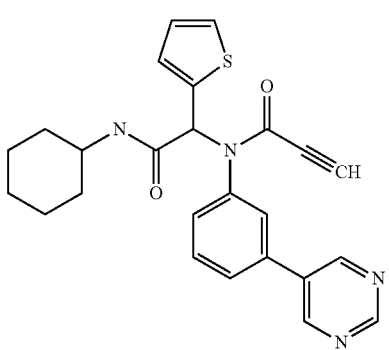
-continued
63
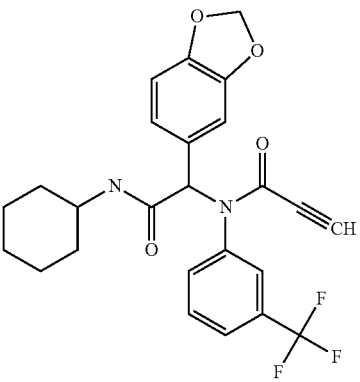
64
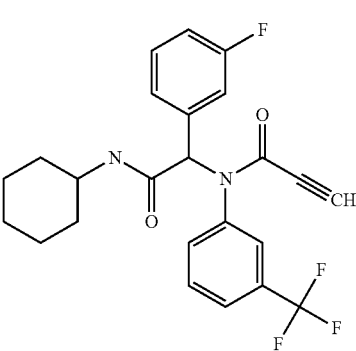
65
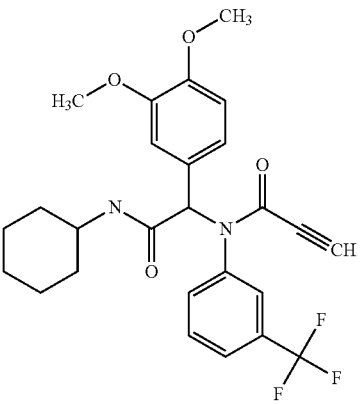
66
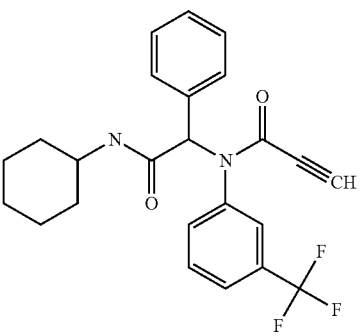

| | |
|---|---|
| 67 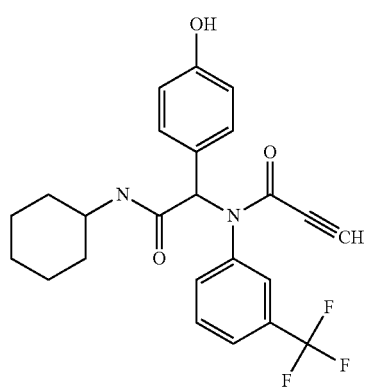 | 71 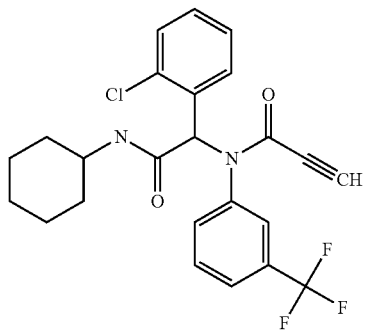 |
| 68 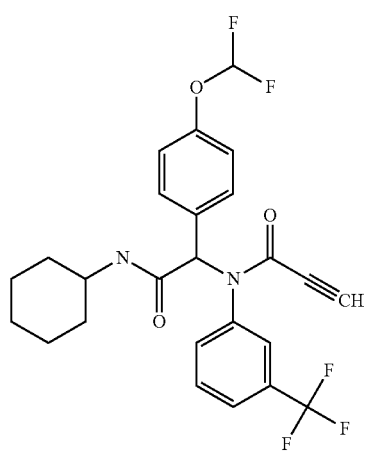 | 72 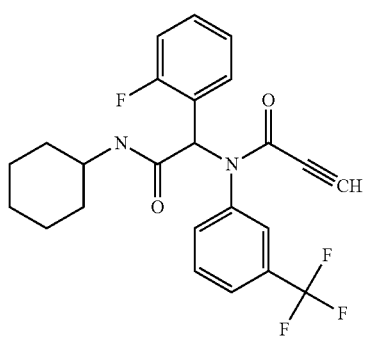 |
| 69 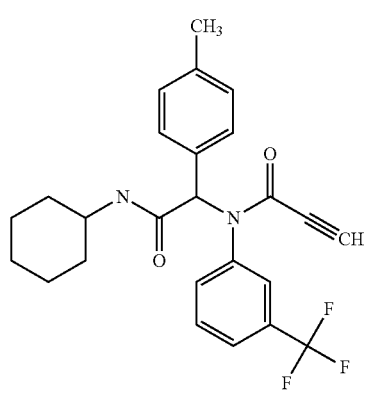 | 73 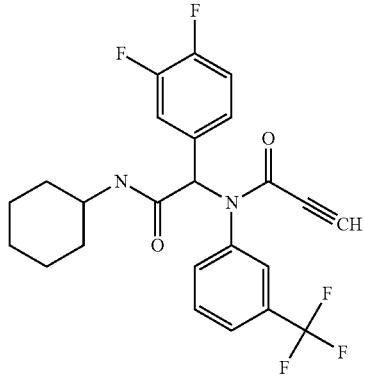 |
| 70 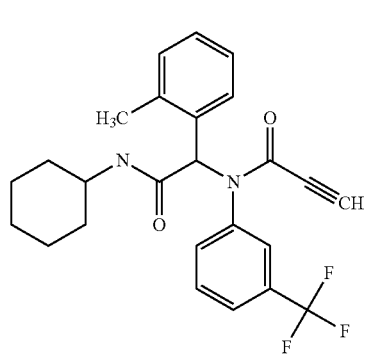 | 74 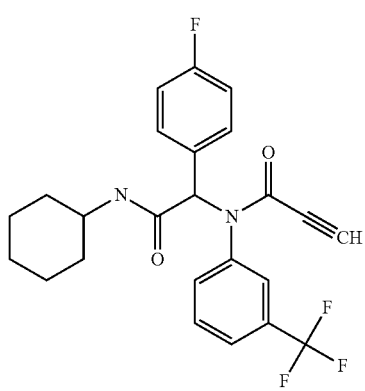 |

75 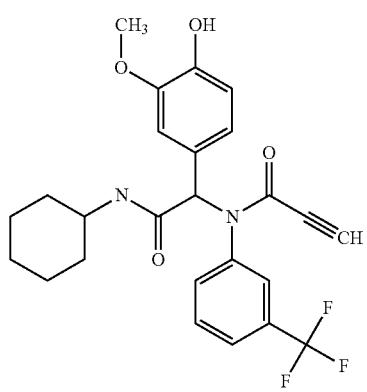
76 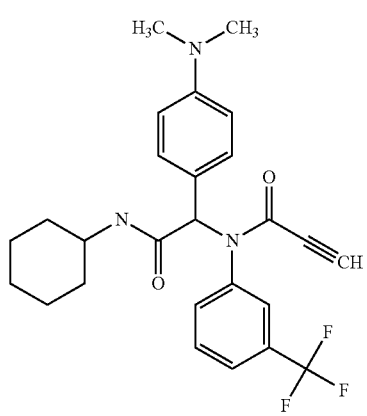
77 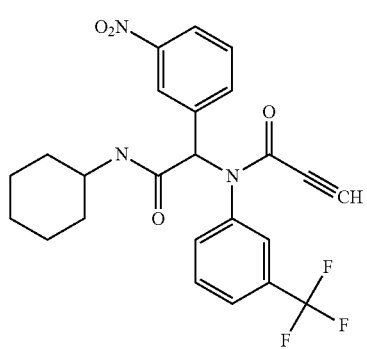
78 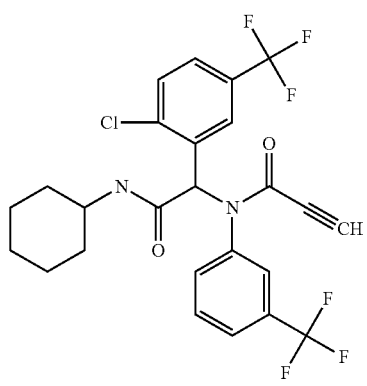
79 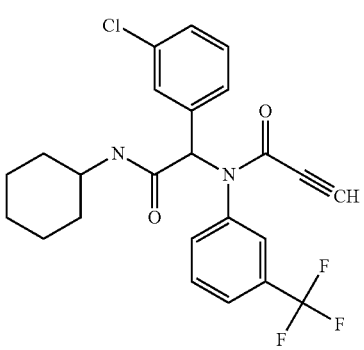
80 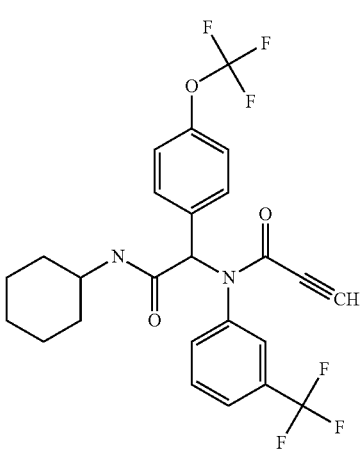
81 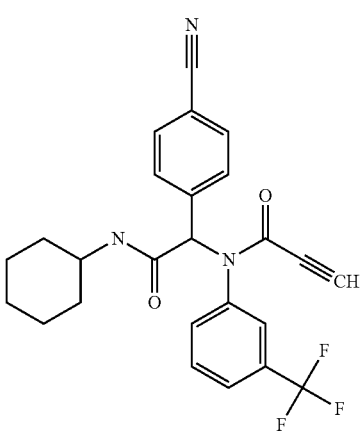
82 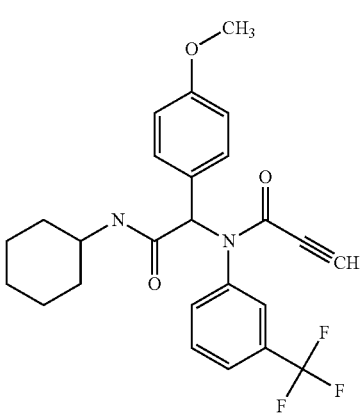

| 83 | 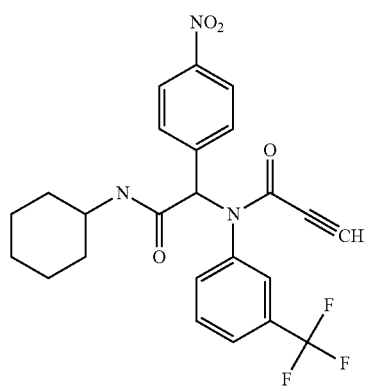 | 87 | 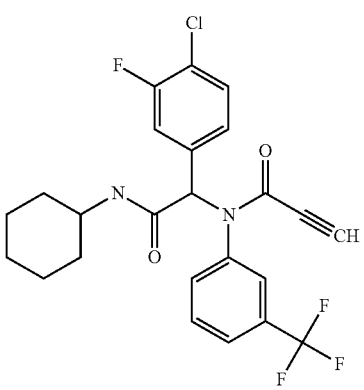 |
| 84 | 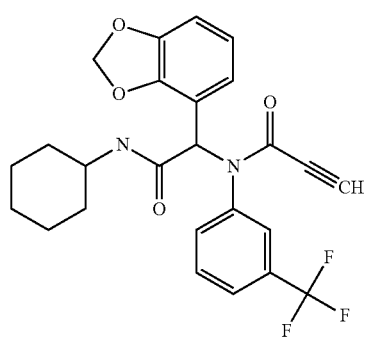 | 88 | 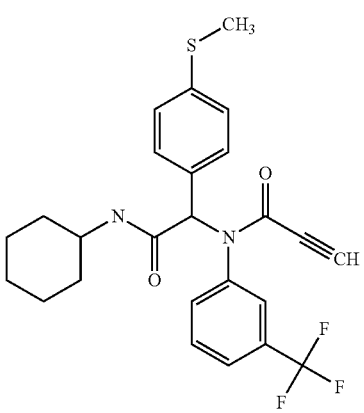 |
| 85 | 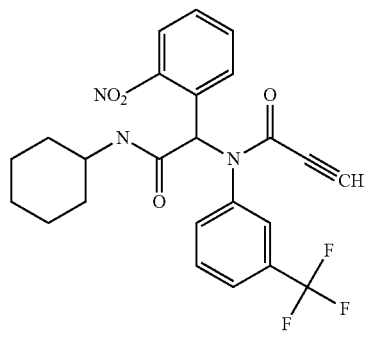 | 89 | 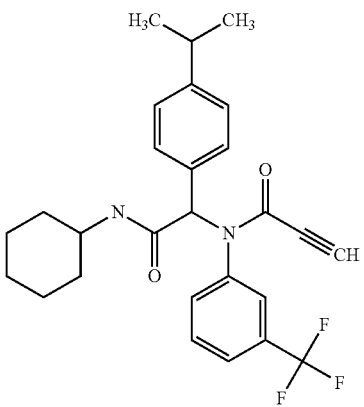 |
| 86 | 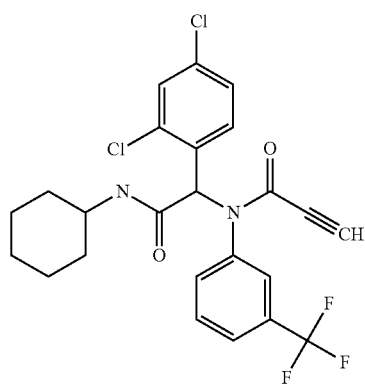 | 90 | 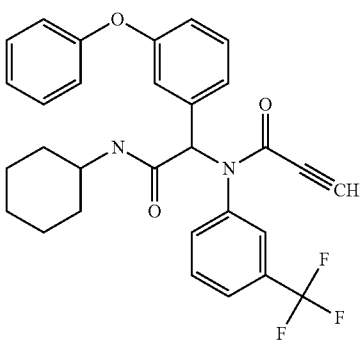 |

| 91 | 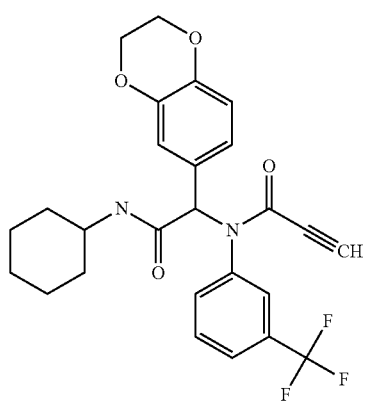 | 95 | 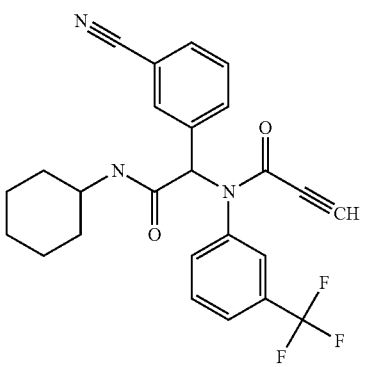 |
| 92 | 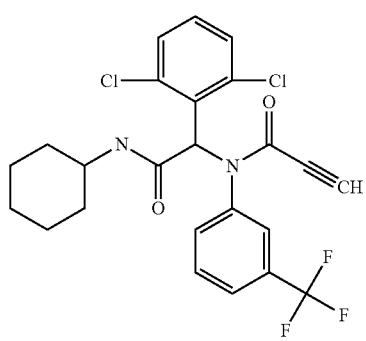 | 96 | 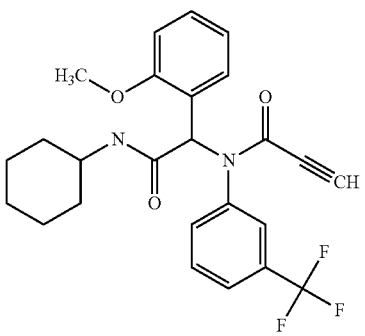 |
| 93 | 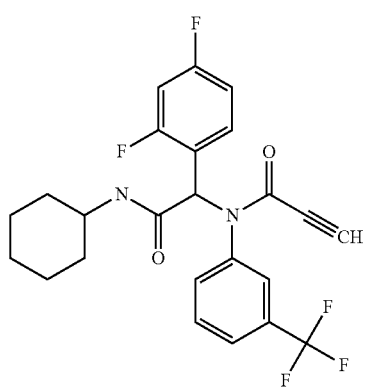 | 97 | 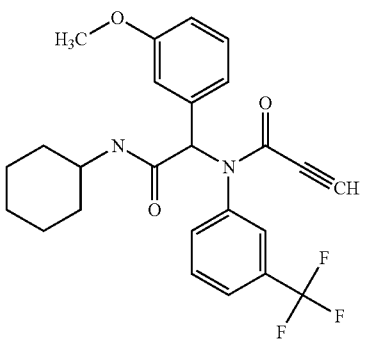 |
| 94 | 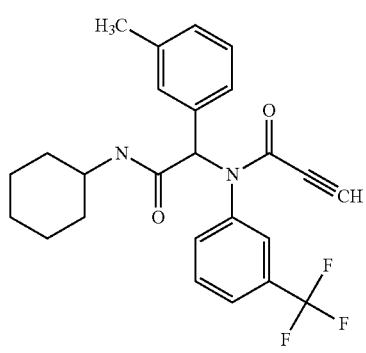 | 98 | 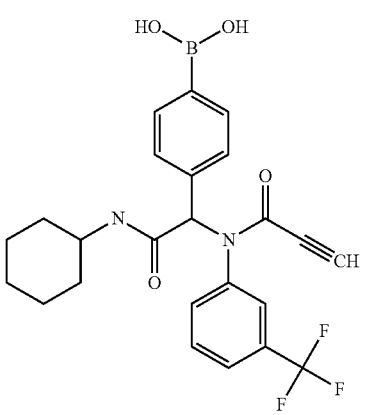 |

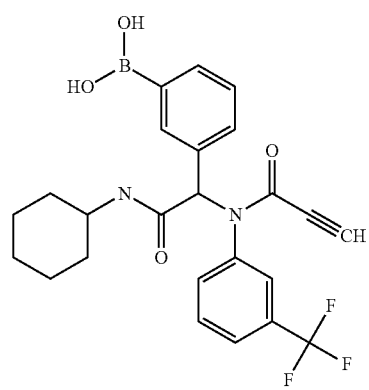
99
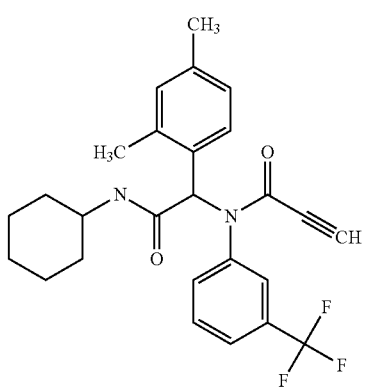
100
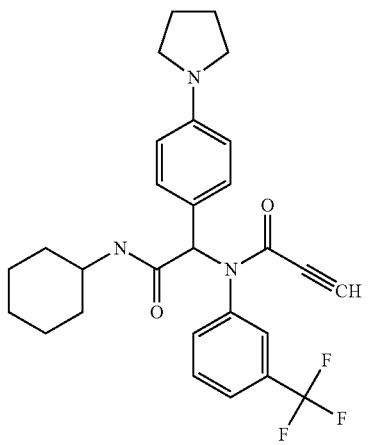
101
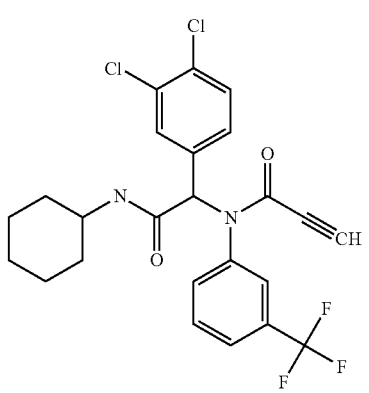
102
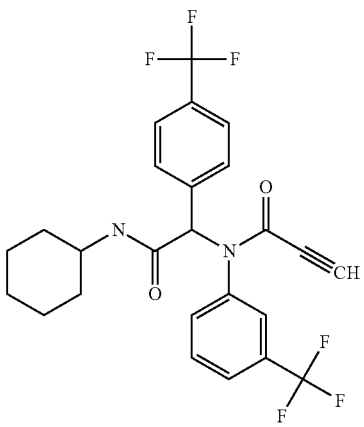
103
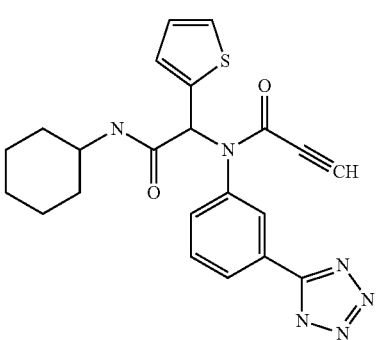
104
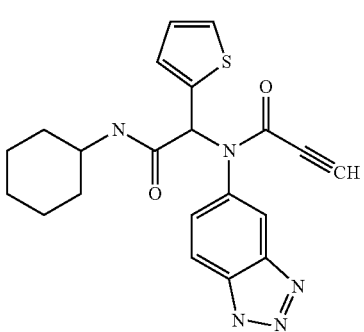
105
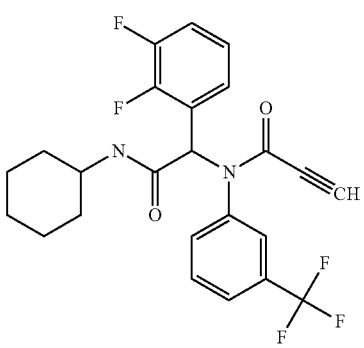
106

-continued
112
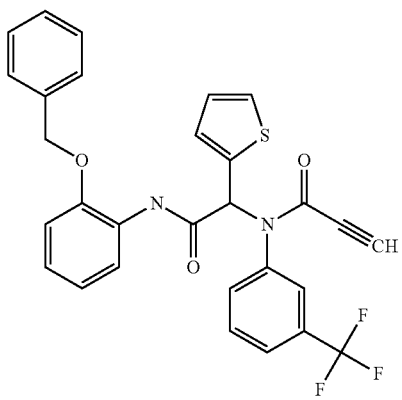
116
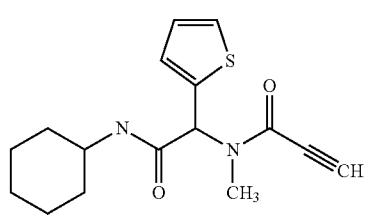
117
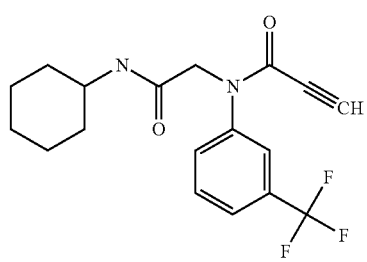
118
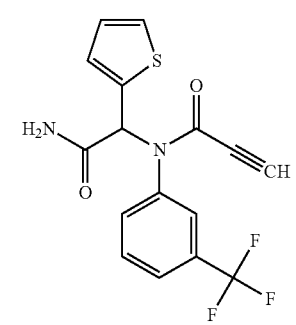
119
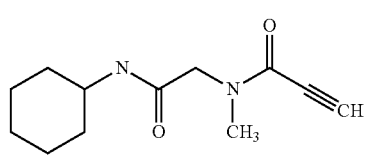
-continued
158
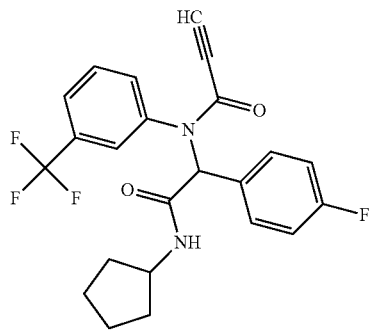
159
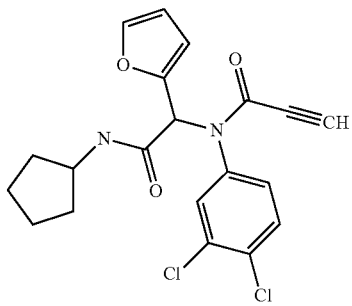
160
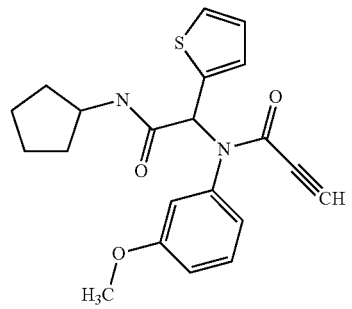
161
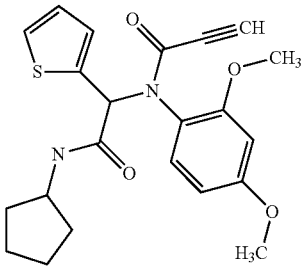
162
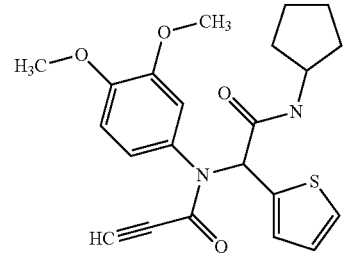

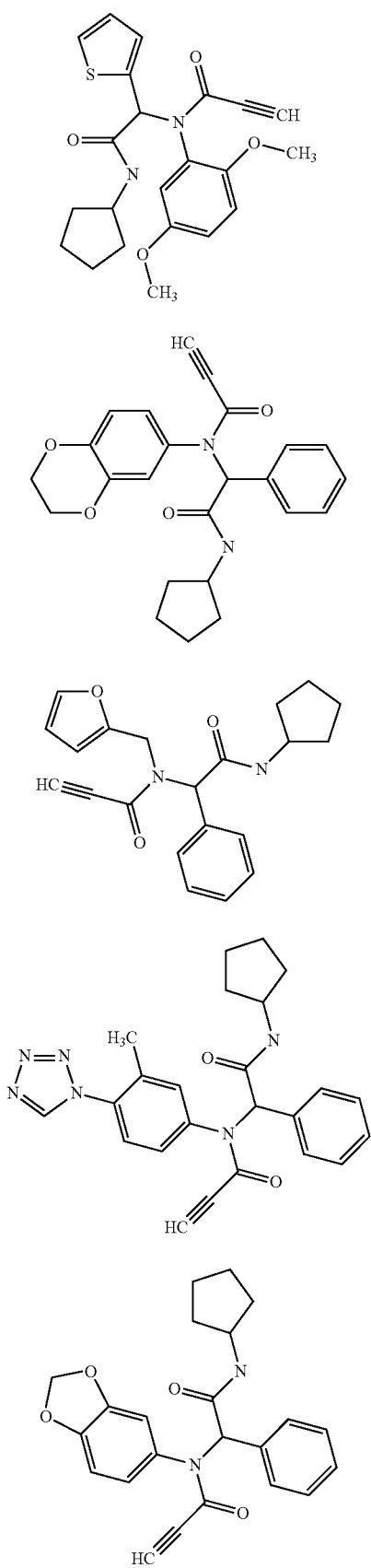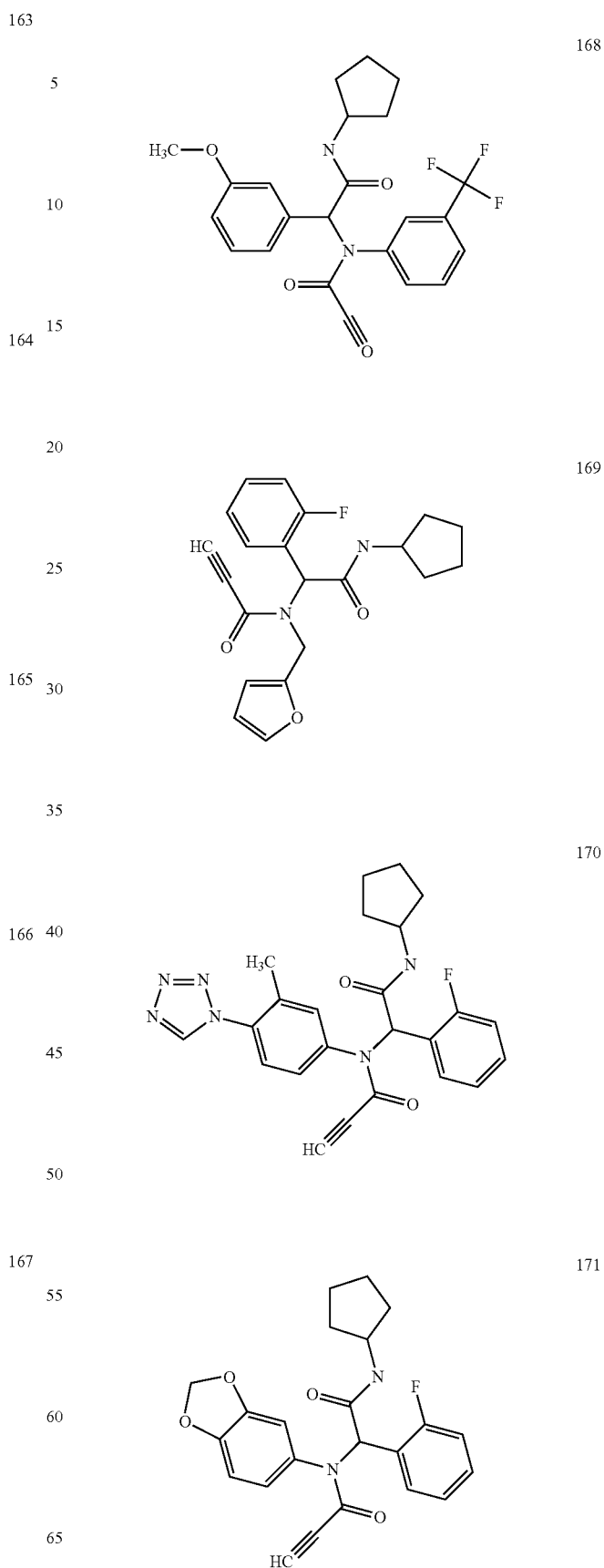

172 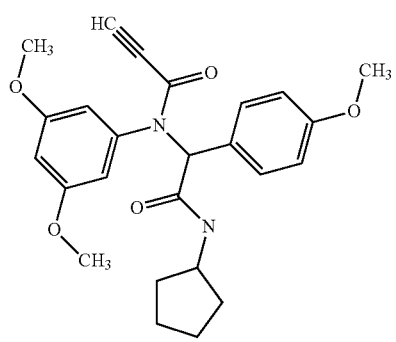
173 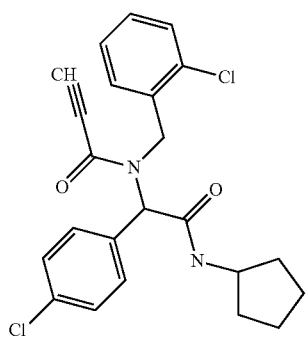
174 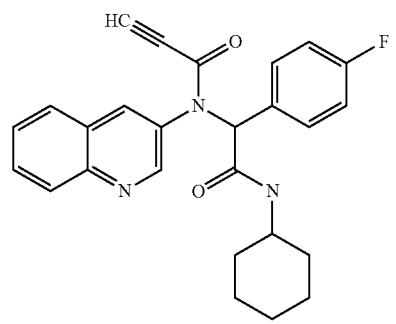
175 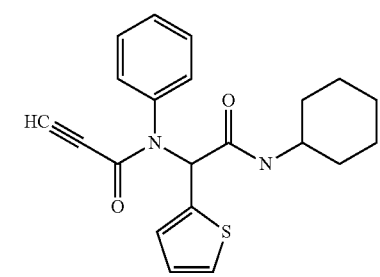
176 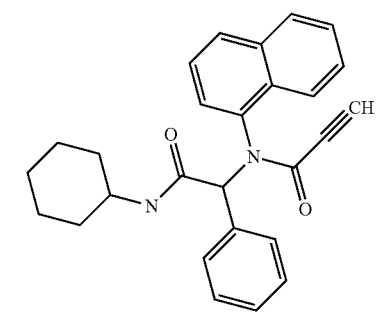
177 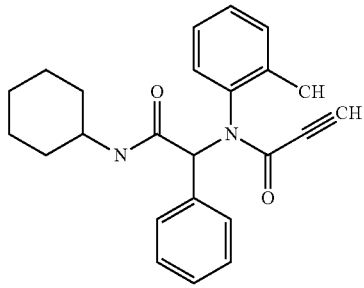
178 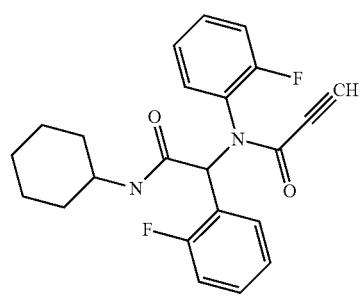
179 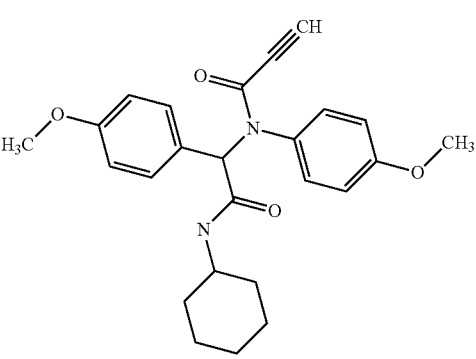
180 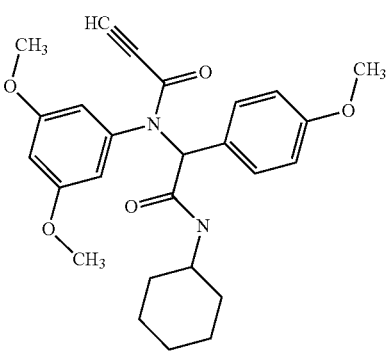
181 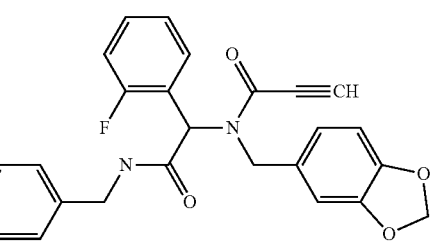

182
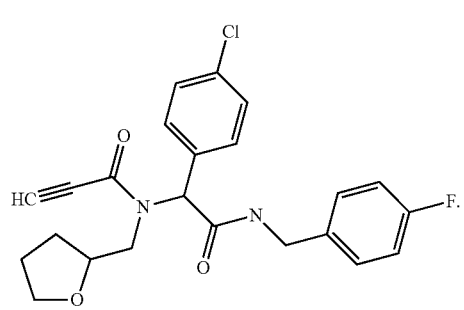
* * * * *